US012102677B2

(12) United States Patent
Moldt et al.

(10) Patent No.: US 12,102,677 B2
(45) Date of Patent: Oct. 1, 2024

(54) METHODS OF IDENTIFYING HIV PATIENTS SENSITIVE TO THERAPY WITH GP120 V3 GLYCAN-DIRECTED ANTIBODIES

(71) Applicant: Gilead Sciences, Inc., Foster City, CA (US)

(72) Inventors: Brian Moldt, San Carlos, CA (US); Craig S. Pace, Pacifica, CA (US)

(73) Assignee: GILEAD SCIENCES, INC., Foster City, CA (US)

( * ) Notice: Subject to any disclaimer, the term of this patent is extended or adjusted under 35 U.S.C. 154(b) by 654 days.

(21) Appl. No.: 16/877,292

(22) Filed: May 18, 2020

(65) Prior Publication Data
US 2020/0368347 A1 Nov. 26, 2020

Related U.S. Application Data

(60) Provisional application No. 62/850,994, filed on May 21, 2019.

(51) Int. Cl.
*A61K 39/21* (2006.01)
*A61K 31/4745* (2006.01)
*A61K 31/519* (2006.01)
*A61P 31/18* (2006.01)
*C07K 16/10* (2006.01)
*C12Q 1/70* (2006.01)

(52) U.S. Cl.
CPC .......... *A61K 39/21* (2013.01); *A61K 31/4745* (2013.01); *A61K 31/519* (2013.01); *A61P 31/18* (2018.01); *C07K 16/1063* (2013.01); *C12Q 1/703* (2013.01); *C07K 2317/34* (2013.01); *C07K 2317/76* (2013.01); *C07K 2317/92* (2013.01); *C12Q 2600/106* (2013.01); *C12Q 2600/156* (2013.01)

(58) Field of Classification Search
CPC .......................... A61K 39/21; C07K 16/1063
See application file for complete search history.

(56) References Cited

U.S. PATENT DOCUMENTS

| 10,047,146 | B2 | 8/2018 | Mouquet et al. | |
| 10,239,935 | B2 * | 3/2019 | Balakrishnan | C07K 16/1063 |
| 10,376,583 | B2 * | 8/2019 | Barouch | C07K 16/1045 |
| 2021/0079070 | A1 | 3/2021 | Lusso et al. | |

FOREIGN PATENT DOCUMENTS

| JP | 7126573 B2 | 8/2022 |
| TW | 201731870 A | 9/2017 |
| WO | WO-2012/030904 A2 | 3/2012 |
| WO | WO-2014/063059 A1 | 4/2014 |
| WO | WO-2017/106346 A2 | 6/2017 |
| WO | WO-2018/125813 A1 | 7/2018 |
| WO | WO-2018/237148 A1 | 12/2018 |
| WO | WO-2019/226829 A1 | 11/2019 |
| WO | WO-2020/010107 A1 | 1/2020 |
| WO | WO-2020/056145 A1 | 3/2020 |

OTHER PUBLICATIONS

Franchini, G., and M. L. Bosch, 1989, Genetic Relatedness of the Human Immunodeficiency Viruses Type 1 and 2 (HIV-1, HIV-2) and the Simian Immunodeficiency Virus (SIV), Annal NY Acad. Sci. 554(1):81-87.*
Li, Y., et al., Aug. 1991, Molecular Characterization of Human Immunodeficiency Virus Type 1 Cloned Directly from Uncultured Human Brain Tissue: Identification of Replication-Competent and -Defective Viral Genomes, J. Virol. 65(8):3973-3985.*
Gerhardt, M., et al., Jul. 2005, In-Depth, Longitudinal Analysis of Viral Quasispecies from an Individual Triply Infected with Late-Stage Human Immunodeficiency Virus Type 1, Using a Multiple PCR Primer Approach, J. Virol. 79(13):8249-8261.*
Barnes, C. O., et al., 2018, Structural characterization of a highly-potent V3-glycan broadly neutralizing antibody bound to natively-glycosylated HIV-1 envelope, Nat. Comm. 9:1251, pp. 1-12.*
Sela-Culang, I., et al., Oct. 2013, The structural basis of antibody-antigen recognition, Front. Immunol. 4:Article 302, pp. 1-13.*
Giles, I., et al., 2006, Arginine residues are important in determining the binding of human monoclonal antiphospholipid antibodies to clinically relevant antigens, J. Immunol. 177:1729-1736.*
Macleod D T et al. (2016), "Early Antibody Lineage Diversification and Independent Limb Maturation Lead to Broad HIV-1 Neutralization Targeting the Env High-Mannose Patch", Immunity 44, 1215-1226.
Office Action dated Nov. 30, 2022 for Japanese Appl. No. 2021-569063.
Intl. Search Report-Written Opinion dated Aug. 12, 2020 for Intl. Appl. No. PCT/US2020/033470.
Julg B et al. (2017), "Protection against a mixed SHIV challenge by a broadly neutralizing antibody cocktail", Sci Transl. Med. 9, eaao4235.
Julien J-P et al. (2013), "Broadly Neutralizing Antibody PGT121 Allosterically Modulates CD4 Binding via Recognition of the HIV-1 gp120 V3 Base and Multiple Surrounding Glycans", Plos Pathogens, vol. 9, No. 5, e1003342.
Julien J-P et al. (2013), "Crystal Structure of a Soluble Cleaved HIV-1 Envelope Trimer", Science, vol. 342, No. 6165, pp. 1477-1483.
Orwenyo J et al. (2017), "Systematic Synthesis and Binding Study of HIV V3 Glycopeptides Reveal the Fine Epitopes of Several Broadly Neutralizing Antibodies", ACS Chemical Biology, vol. 12, No. 6, pp. 1566-1575.
Perez De La Lastra et al. (1999), "Epitope mapping of 10 monoclonal antibodies against the pig analogue of human membrane cofactor protein (MCP)", Immunology, vol. 96, No. 4, pp. 663-670.
Sok D et al. (2016), "A Prominent Site of Antibody Vulnerability on HIV Envelope Incorporates a Motif Associated with CCR5 Binding and Its Camouflaging Glycans", Immunity, Elsevier, Amsterdam, NL, vol. 45, No. 1, pp. 31-45.

(Continued)

*Primary Examiner* — Jeffrey S Parkin

(57) ABSTRACT

Provided are methods for identifying patient populations infected with HIV that can be targeted by antibodies that bind to HIV gp120 V3 glycan region.

34 Claims, 4 Drawing Sheets

Specification includes a Sequence Listing.

(56) References Cited

OTHER PUBLICATIONS

Wang H et al. (2018), "Evaluation of susceptibility of HIV-1 CRF01_AE variants to neutralization by a panel of broadly neutralizing antibodies", Archives of Virology, Springer Wien, AT, vol. 163, No. 12, pp. 3303-3315.
Intl. Preliminary Report on Patentability-Written Opinion dated Dec. 2, 2021 for Intl. Appl. No. PCT/US2020/033470.
Moldt B (2021), "Evaluation of bNAb Sensitivity by Genotyping and Phenotyping for HIV Clinical Trials", Presentation for Conference on Retroviruses and Opportunistic Infections (CROI) 2021, Abst No. 45.
Moldt B et al. (2021), "Evaluation of Broadly Neutralizing Antibody Sensitivity by Genotyping and Phenotyping for Qualifying Participants to HIV Clinical Trials", J Acquir Immune Defic Syndr 2021, 88:61-69.
Moldt B et al. (2022), "Evaluation of HIV-1 reservoir size and broadly neutralizing antibody susceptibility in acute antiretroviral therapy-treated individuals", AIDS 2022, 36:205-214.
Notice of Allowance dated Jan. 17, 2022 for Taiwanese Appl. No. 109115301.
Office Action and Search Report dated Aug. 2, 2021 for Taiwanese Appl. No. 109115301.
Office Action dated Nov. 9, 2022 for Canadian Appl. No. 3134313.
Office Action dated Mar. 10, 2023 for Japanese Appl. No. 2021-569063.
Selzer L et al. (2023), "Susceptibility Screening to bNAbsTeropavimab(GS-5423) and Zinlirvimab(GS-2872) in ART-Suppressed Patients", Poster 580, Presented at CROI 2023, Feb. 19-22, 2023, Seattle, WA.
Examination Report dated Jun. 13, 2023 for European Appl. No. 20730900.6.
Summons to Attend Oral Proceedings dated Dec. 12, 2023 for European Appl. No. 20730900.6.
Caskey M et al. (2019), "Broadly neutralizing anti-HIV-1 monoclonal antibodies in the clinic", Nature Medicine, vol. 25, pp. 547-553.
ClinicalTrials.gov: "NCT04811040: Study to Evaluate the Safety and Efficacy of Teropavimab and Zinlirvimab in Combination With Lenacapavir (GS-6207) in Virologically Suppressed Adults With HIV-1 Infection", Gilead Sciences, Study first posted Mar. 2021, Last update posted Jun. 2023, Retrieved from the Internet: URL: https://www.clinicaltrials.gov/study/NCT04811040?term=NCT04811040&rank=1 [retrieved on Oct. 6, 2023].
ClinicalTrials.gov: "NCT05729568: A Study of GS-5423 and GS-2872 in Combination With Capsid Inhibitor Lenacapavir in Virologically Suppressed Adults With HIV-1 Infection", Gilead Sciences, Study first posted Feb. 2023, Last update posted Sep. 2023, Retrieved from the Internet: URL: https://www.clinicaltrials.gov/study/NCT05729568?term=NCT05729568&rank=1 [retrieved on Oct. 6, 2023].
Dashti A et al. (2019), "Broadly Neutralizing Antibodies against HIV: Back to Blood", Trends in Molecular Medicine, vol. 25, No. 3, pp. 228-240.
Eron J et al. (2023), "Lenacapavir with bNAbs GS-5423 and GS-2872 dosed every 6 months in people with HIV (Abstract 193)", Webcast from CROI 2023, Feb. 22, 10:00 AM-12:00 PM, downloadable from URL: https://www.croiwebcasts.org/p/2023croi/croi/193.
Eron J et al. (2023), "Lenacapavir with bNAbs GS-5423 and GS-2872 dosed every 6 months in people with HIV", CROI 2023, Seattle. Oral abstract 193.
Eron J et al. (2023), "Lenacapavir with bNAbs Teropavimab (GS-5423) and Zinlirvimab (GS-2872) Dosed Every 6 Months in People with HIV", CROI 2023, Feb. 19-22, Seattle, Washington, Oral 193 Presentation.
Garces F et al. (2014), "Structural Evolution of Glycan Recognition by a Family of Potent HIV Antibodies", Cell 159, 69-79.
Mccoy L E (2018), "The expanding array of HIV broadly neutralizing antibodies", Retrovirology 15:70, 1-12.
Mouquet H et al. (2012), "Complex-type N-glycan recognition by potent broadly neutralizing HIV antibodies", PNAS 109 (47) E3268-E3277.
Mouquet H et al. (2012), "Complex-type N-glycan recognition by potent broadly-neutralizing HIV antibodies", PNAS 109 (47) Supplementary Information, 54 pgs.
Notice of Allowance dated Sep. 20, 2023 for Japanese Appl. No. 2021-569063.
Possas C et al. (2018), "HIV cure: global overview of bNAbs' patents and related scientific publications", Expert Opinion on Therapeutic Patents, 28:7, 551-560.
Sok D et al. (2013), "The Effects of Somatic Hypermutation on Neutralization and Binding in the PGT121 Family of Broadly Neutralizing HIV Antibodies", PLoS Pathog 9(11): e1003754.
Sok D et al. (2018), "Recent progress in broadly neutralizing antibodies to HIV", Nature Immunology, vol. 19, 1179-1188.
Walker L M et al. (2011), "Broad neutralization coverage of HIV by multiple highly potent antibodies", Nature, vol. 477, 466-470.
Examination Report dated Feb. 14, 2024 for Australian Appl. No. 202027733.
Eron J J et al. (2024), "Safety of teropavimab and zinlirvimab with lenacapavir once every 6 months for HIV treatment: a phase 1b, randomised, proof-of-concept study", Lancet HIV 2024, vol. 11, Issue 3, E146-E155.
Office Action and Search Report dated Apr. 9, 2024 for Taiwanese Appl. No. 111111716.
Office Action dated Apr. 24, 2024 for Japanese Appl. No. 2023-008786.
Borducchi En et al. (2018), "Antibody and TLR7 agonist delay viral rebound in SHIV-infected monkeys", Nature, 563(7731):360-4.
Caskey M et al. (2017), "Antibody 10-1074 suppresses viremia in HIV-1-infected individuals", Nature Medicine, 23(2): 185-191.
Office Action dated Mar. 14, 2024 for Canadian Appl. No. 3134313.
Office Action dated Jul. 15, 2024 for Korean Application No. 10-2021-7041323.

* cited by examiner

SEQUENCE LISTING

```
<160> NUMBER OF SEQ ID NOS: 468

<210> SEQ ID NO 1
<211> LENGTH: 35
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Cys Thr Arg Pro Asn Asn Asn Thr Arg Lys Ser Ile His Ile Gly Pro
1               5                   10                  15

Gly Arg Ala Phe Tyr Thr Thr Gly Glu Ile Ile Gly Asp Ile Arg Gln
            20                  25                  30

Ala His Cys
        35

<210> SEQ ID NO 2
<211> LENGTH: 849
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Lys Val Met Gly Thr Lys Lys Asn Tyr Gln His Leu Trp Arg Trp
1               5                   10                  15

Gly Ile Met Leu Leu Gly Met Leu Met Ser Ser Ala Ala Glu Gln
            20                  25                  30

Leu Trp Val Thr Val Tyr Gly Val Pro Val Trp Arg Glu Ala Asn
        35                  40                  45
```

```
Thr Thr Leu Phe Cys Ala Ser Asp Ala Lys Ala Tyr Asp Thr Glu Val
 50                  55                  60

His Asn Val Trp Ala Thr His Ala Cys Val Pro Thr Asp Pro Asn Pro
 65                  70                  75                  80

Gln Glu Val Val Met Gly Asn Val Thr Glu Asp Phe Asn Met Trp Lys
                     85                  90                  95

Asn Asn Met Val Glu Gln Met His Glu Asp Ile Ile Ser Leu Trp Asp
                100                 105                 110

Gln Ser Leu Lys Pro Cys Val Lys Leu Thr Pro Leu Cys Val Thr Leu
                115                 120                 125

His Cys Thr Asn Val Thr Ile Ser Ser Thr Asn Gly Ser Thr Ala Asn
130                 135                 140

Val Thr Met Arg Glu Glu Met Lys Asn Cys Ser Phe Asn Thr Thr Thr
145                 150                 155                 160

Val Ile Arg Asp Lys Ile Gln Lys Glu Tyr Ala Leu Phe Tyr Lys Leu
                165                 170                 175

Asp Ile Val Pro Ile Glu Gly Lys Asn Thr Asn Thr Ser Tyr Arg Leu
                180                 185                 190

Ile Asn Cys Asn Thr Ser Val Ile Thr Gln Ala Cys Pro Lys Val Ser
                195                 200                 205

Phe Glu Pro Ile Pro Ile His Tyr Cys Ala Pro Ala Gly Phe Ala Ile
                210                 215                 220

Leu Lys Cys Asn Asn Lys Thr Phe Asn Gly Lys Gly Pro Cys Arg Asn
225                 230                 235                 240

Val Ser Thr Val Gln Cys Thr His Gly Ile Lys Pro Val Val Ser Thr
                245                 250                 255

Gln Leu Leu Leu Asn Gly Ser Leu Ala Glu Glu Asp Ile Ile Ile Arg
                260                 265                 270

Ser Glu Asn Phe Thr Asn Asn Gly Lys Asn Ile Ile Val Gln Leu Lys
                275                 280                 285

Glu Pro Val Lys Ile Asn Cys Thr Arg Pro Gly Asn Asn Thr Arg Arg
                290                 295                 300

Ser Ile Asn Ile Gly Pro Gly Arg Ala Phe Tyr Ala Thr Gly Ala Ile
305                 310                 315                 320

Ile Gly Asp Ile Arg Lys Ala His Cys Asn Ile Ser Thr Glu Gln Trp
                325                 330                 335

Asn Asn Thr Leu Thr Gln Ile Val Asp Lys Leu Arg Glu Gln Phe Gly
                340                 345                 350

Asn Lys Thr Ile Ile Phe Asn Gln Ser Ser Gly Gly Asp Pro Glu Val
                355                 360                 365

Val Met His Thr Phe Asn Cys Gly Gly Glu Phe Phe Tyr Cys Asn Ser
370                 375                 380

Thr Gln Leu Phe Asn Ser Thr Trp Phe Asn Asn Gly Thr Ser Thr Trp
385                 390                 395                 400

Asn Ser Thr Ala Asp Asn Ile Thr Leu Pro Cys Arg Ile Lys Gln Val
                405                 410                 415

Ile Asn Met Trp Gln Glu Val Gly Lys Ala Met Tyr Ala Pro Pro Ile
                420                 425                 430

Arg Gly Gln Ile Asp Cys Ser Ser Asn Ile Thr Gly Leu Ile Leu Thr
                435                 440                 445

Arg Asp Gly Gly Ser Asn Ser Ser Gln Asn Glu Thr Phe Arg Pro Gly
450                 455                 460

Gly Gly Asn Met Lys Asp Asn Trp Arg Ser Glu Leu Tyr Lys Tyr Lys
```

```
            465                 470                 475                 480
Val Val Lys Ile Glu Pro Leu Gly Ile Ala Pro Thr Arg Ala Lys Arg
                    485                 490                 495
Arg Val Val Gln Arg Glu Lys Arg Ala Val Thr Leu Gly Ala Val Phe
                500                 505                 510
Leu Gly Phe Leu Gly Ala Ala Gly Ser Thr Met Gly Ala Ala Ser Leu
            515                 520                 525
Thr Leu Thr Val Gln Ala Arg Leu Leu Leu Ser Gly Ile Val Gln Gln
        530                 535                 540
Gln Ser Asn Leu Leu Arg Ala Ile Glu Ala Gln Gln His Met Leu Gln
545                 550                 555                 560
Leu Thr Val Trp Gly Ile Lys Gln Leu Gln Ala Arg Val Leu Ala Ile
                565                 570                 575
Glu Arg Tyr Leu Lys Asp Gln Gln Leu Leu Gly Ile Trp Gly Cys Ser
                580                 585                 590
Gly Lys Leu Ile Cys Thr Thr Thr Val Pro Trp Asn Thr Ser Trp Ser
            595                 600                 605
Asn Lys Ser Tyr Asp Tyr Ile Trp Asn Asn Met Thr Trp Met Gln Trp
        610                 615                 620
Glu Arg Glu Ile Asp Asn Tyr Thr Gly Phe Ile Tyr Thr Leu Ile Glu
625                 630                 635                 640
Glu Ser Gln Asn Gln Gln Glu Lys Asn Glu Leu Glu Leu Leu Glu Leu
                645                 650                 655
Asp Lys Trp Ala Ser Leu Trp Asn Trp Phe Asn Ile Thr Asn Trp Leu
                660                 665                 670
Trp Tyr Ile Lys Leu Phe Ile Met Ile Ile Gly Gly Leu Val Gly Leu
            675                 680                 685
Arg Ile Val Cys Ala Val Leu Ser Ile Val Asn Arg Val Arg Gln Gly
        690                 695                 700
Tyr Ser Pro Leu Ser Phe Gln Thr Arg Leu Pro Asn Pro Arg Gly Pro
705                 710                 715                 720
Asp Arg Pro Glu Glu Thr Glu Gly Glu Gly Glu Arg Asp Arg Asp
                725                 730                 735
Arg Ser Ala Arg Leu Val Asn Gly Phe Leu Ala Ile Ile Trp Asp Asp
                740                 745                 750
Leu Arg Ser Leu Cys Leu Phe Ser Tyr His Arg Leu Arg Asp Leu Leu
            755                 760                 765
Leu Ile Val Ala Arg Val Glu Ile Leu Gly Arg Arg Gly Trp Glu
        770                 775                 780
Ile Leu Lys Tyr Trp Trp Asn Leu Leu Lys Tyr Trp Ser Gln Glu Leu
785                 790                 795                 800
Lys Asn Ser Ala Val Ser Leu Leu Asn Val Thr Ala Ile Ala Val Ala
                805                 810                 815
Glu Gly Thr Asp Arg Val Ile Glu Ile Val Gln Arg Ala Val Arg Ala
                820                 825                 830
Ile Leu His Ile Pro Thr Arg Ile Arg Gln Gly Phe Glu Arg Ala Leu
            835                 840                 845

Leu
```

<210> SEQ ID NO 3
<211> LENGTH: 856
<212> TYPE: PRT
<213> ORGANISM: Human immunodeficiency virus 1

```
<400> SEQUENCE: 3

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
                20                  25                  30

Lys Leu Trp Val Thr Val Tyr Tyr Gly Val Pro Val Trp Lys Glu Ala
                35                  40                  45

Thr Thr Thr Leu Phe Cys Ala Ser Asp Ala Lys Ala Tyr Asp Thr Glu
            50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
                100                 105                 110

Asp Gln Ser Leu Lys Pro Cys Val Lys Leu Thr Pro Leu Cys Val Ser
            115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Glu Val Val Ile
            260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
    290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350

Phe Gly Asn Asn Lys Thr Ile Ile Phe Lys Gln Ser Ser Gly Gly Asp
        355                 360                 365

Pro Glu Ile Val Thr His Ser Phe Asn Cys Gly Gly Glu Phe Phe Tyr
    370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Glu Gly Ser Asp Thr Ile Thr Leu
                405                 410                 415
```

```
Pro Cys Arg Ile Lys Gln Ile Ile Asn Met Trp Gln Lys Val Gly Lys
            420                 425                 430

Ala Met Tyr Ala Pro Pro Ile Ser Gly Gln Ile Arg Cys Ser Ser Asn
            435                 440                 445

Ile Thr Gly Leu Leu Leu Thr Arg Asp Gly Gly Asn Ser Asn Asn Glu
            450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
            485                 490                 495

Ala Pro Thr Lys Ala Lys Arg Arg Val Val Gln Arg Glu Lys Arg Ala
            500                 505                 510

Val Gly Ile Gly Ala Leu Phe Leu Gly Phe Leu Gly Ala Ala Gly Ser
            515                 520                 525

Thr Met Gly Ala Ala Ser Met Thr Leu Thr Val Gln Ala Arg Gln Leu
            530                 535                 540

Leu Ser Gly Ile Val Gln Gln Gln Asn Asn Leu Leu Arg Ala Ile Glu
545                 550                 555                 560

Ala Gln Gln His Leu Leu Gln Leu Thr Val Trp Gly Ile Lys Gln Leu
            565                 570                 575

Gln Ala Arg Ile Leu Ala Val Glu Arg Tyr Leu Lys Asp Gln Gln Leu
            580                 585                 590

Leu Gly Ile Trp Gly Cys Ser Gly Lys Leu Ile Cys Thr Thr Ala Val
            595                 600                 605

Pro Trp Asn Ala Ser Trp Ser Asn Lys Ser Leu Glu Gln Ile Trp Asn
            610                 615                 620

His Thr Thr Trp Met Glu Trp Asp Arg Glu Ile Asn Asn Tyr Thr Ser
625                 630                 635                 640

Leu Ile His Ser Leu Ile Glu Glu Ser Gln Asn Gln Gln Glu Lys Asn
            645                 650                 655

Glu Gln Glu Leu Leu Glu Leu Asp Lys Trp Ala Ser Leu Trp Asn Trp
            660                 665                 670

Phe Asn Ile Thr Asn Trp Leu Trp Tyr Ile Lys Leu Phe Ile Met Ile
            675                 680                 685

Val Gly Gly Leu Val Gly Leu Arg Ile Val Phe Ala Val Leu Ser Ile
            690                 695                 700

Val Asn Arg Val Arg Gln Gly Tyr Ser Pro Leu Ser Phe Gln Thr His
705                 710                 715                 720

Leu Pro Thr Pro Arg Gly Pro Asp Arg Pro Glu Gly Ile Glu Glu Glu
            725                 730                 735

Gly Gly Glu Arg Asp Arg Asp Arg Ser Ile Arg Leu Val Asn Gly Ser
            740                 745                 750

Leu Ala Leu Ile Trp Asp Asp Leu Arg Ser Leu Cys Leu Phe Ser Tyr
            755                 760                 765

His Arg Leu Arg Asp Leu Leu Leu Ile Val Thr Arg Ile Val Glu Leu
            770                 775                 780

Leu Gly Arg Arg Gly Trp Glu Ala Leu Lys Tyr Trp Trp Asn Leu Leu
785                 790                 795                 800

Gln Tyr Trp Ser Gln Glu Leu Lys Asn Ser Ala Val Ser Leu Leu Asn
            805                 810                 815

Ala Thr Ala Ile Ala Val Ala Glu Gly Thr Asp Arg Val Ile Glu Val
            820                 825                 830
```

```
Val Gln Gly Ala Cys Arg Ala Ile Arg His Ile Pro Arg Ile Arg
            835                 840                 845

Gln Gly Leu Glu Arg Ile Leu Leu
    850                 855

<210> SEQ ID NO 4
<211> LENGTH: 511
<212> TYPE: PRT
<213> ORGANISM: Human immunodeficiency virus 1

<400> SEQUENCE: 4

Met Arg Val Lys Glu Lys Tyr Gln His Leu Trp Arg Trp Gly Trp Arg
1               5                   10                  15

Trp Gly Thr Met Leu Leu Gly Met Leu Met Ile Cys Ser Ala Thr Glu
            20                  25                  30

Lys Leu Trp Val Thr Val Tyr Tyr Gly Val Pro Val Trp Lys Glu Ala
        35                  40                  45

Thr Thr Thr Leu Phe Cys Ala Ser Asp Ala Lys Ala Tyr Asp Thr Glu
    50                  55                  60

Val His Asn Val Trp Ala Thr His Ala Cys Val Pro Thr Asp Pro Asn
65                  70                  75                  80

Pro Gln Glu Val Val Leu Val Asn Val Thr Glu Asn Phe Asn Met Trp
                85                  90                  95

Lys Asn Asp Met Val Glu Gln Met His Glu Asp Ile Ile Ser Leu Trp
            100                 105                 110

Asp Gln Ser Leu Lys Pro Cys Val Lys Leu Thr Pro Leu Cys Val Ser
        115                 120                 125

Leu Lys Cys Thr Asp Leu Lys Asn Asp Thr Asn Thr Asn Ser Ser Ser
    130                 135                 140

Gly Arg Met Ile Met Glu Lys Gly Glu Ile Lys Asn Cys Ser Phe Asn
145                 150                 155                 160

Ile Ser Thr Ser Ile Arg Gly Lys Val Gln Lys Glu Tyr Ala Phe Phe
                165                 170                 175

Tyr Lys Leu Asp Ile Ile Pro Ile Asp Asn Asp Thr Thr Ser Tyr Lys
            180                 185                 190

Leu Thr Ser Cys Asn Thr Ser Val Ile Thr Gln Ala Cys Pro Lys Val
        195                 200                 205

Ser Phe Glu Pro Ile Pro Ile His Tyr Cys Ala Pro Ala Gly Phe Ala
    210                 215                 220

Ile Leu Lys Cys Asn Asn Lys Thr Phe Asn Gly Thr Gly Pro Cys Thr
225                 230                 235                 240

Asn Val Ser Thr Val Gln Cys Thr His Gly Ile Arg Pro Val Val Ser
                245                 250                 255

Thr Gln Leu Leu Leu Asn Gly Ser Leu Ala Glu Glu Val Val Ile
            260                 265                 270

Arg Ser Val Asn Phe Thr Asp Asn Ala Lys Thr Ile Ile Val Gln Leu
        275                 280                 285

Asn Thr Ser Val Glu Ile Asn Cys Thr Arg Pro Asn Asn Asn Thr Arg
    290                 295                 300

Lys Arg Ile Arg Ile Gln Arg Gly Pro Gly Arg Ala Phe Val Thr Ile
305                 310                 315                 320

Gly Lys Ile Gly Asn Met Arg Gln Ala His Cys Asn Ile Ser Arg Ala
                325                 330                 335

Lys Trp Asn Asn Thr Leu Lys Gln Ile Ala Ser Lys Leu Arg Glu Gln
            340                 345                 350
```

```
Phe Gly Asn Asn Lys Thr Ile Ile Phe Lys Gln Ser Ser Gly Gly Asp
            355                 360                 365

Pro Glu Ile Val Thr His Ser Phe Asn Cys Gly Gly Glu Phe Phe Tyr
        370                 375                 380

Cys Asn Ser Thr Gln Leu Phe Asn Ser Thr Trp Phe Asn Ser Thr Trp
385                 390                 395                 400

Ser Thr Glu Gly Ser Asn Asn Thr Gly Ser Asp Thr Ile Thr Leu
                405                 410                 415

Pro Cys Arg Ile Lys Gln Ile Ile Asn Met Trp Gln Lys Val Gly Lys
                420                 425                 430

Ala Met Tyr Ala Pro Pro Ile Ser Gly Gln Ile Arg Cys Ser Ser Asn
                435                 440                 445

Ile Thr Gly Leu Leu Leu Thr Arg Asp Gly Gly Asn Ser Asn Asn Glu
                450                 455                 460

Ser Glu Ile Phe Arg Pro Gly Gly Gly Asp Met Arg Asp Asn Trp Arg
465                 470                 475                 480

Ser Glu Leu Tyr Lys Tyr Lys Val Val Lys Ile Glu Pro Leu Gly Val
                485                 490                 495

Ala Pro Thr Lys Ala Lys Arg Arg Val Val Gln Arg Glu Lys Arg
                500                 505                 510

<210> SEQ ID NO 5
<211> LENGTH: 475
<212> TYPE: PRT
<213> ORGANISM: Human immunodeficiency virus 1

<400> SEQUENCE: 5

Ala Glu Gln Leu Trp Val Thr Val Tyr Tyr Gly Val Pro Val Trp Arg
1               5                   10                  15

Glu Ala Asn Thr Thr Leu Phe Cys Ala Ser Asp Ala Lys Ala Tyr Asp
                20                  25                  30

Thr Glu Val His Asn Val Trp Ala Thr His Ala Cys Val Pro Thr Asp
            35                  40                  45

Pro Asn Pro Gln Glu Val Val Met Gly Asn Val Thr Glu Asp Phe Asn
    50                  55                  60

Met Trp Lys Asn Asn Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Thr Leu His Cys Thr Asn Val Thr Ile Ser Ser Thr Asn Gly Ser
                100                 105                 110

Thr Ala Asn Val Thr Met Arg Glu Glu Met Lys Asn Cys Ser Phe Asn
            115                 120                 125

Thr Thr Thr Val Ile Arg Asp Lys Ile Gln Lys Glu Tyr Ala Leu Phe
    130                 135                 140

Tyr Lys Leu Asp Ile Val Pro Ile Glu Gly Lys Asn Asn Thr Asn Thr Ser
145                 150                 155                 160

Tyr Arg Leu Ile Asn Cys Asn Thr Ser Val Ile Thr Gln Ala Cys Pro
                165                 170                 175

Lys Val Ser Phe Glu Pro Ile Pro Ile His Tyr Cys Ala Pro Ala Gly
                180                 185                 190

Phe Ala Ile Leu Lys Cys Asn Asn Lys Thr Phe Asn Gly Lys Gly Pro
            195                 200                 205

Cys Arg Asn Val Ser Thr Val Gln Cys Thr His Gly Ile Lys Pro Val
```

```
            210                 215                 220
Val Ser Thr Gln Leu Leu Asn Gly Ser Leu Ala Glu Glu Asp Ile
225                 230                 235                 240

Ile Ile Arg Ser Glu Asn Phe Thr Asn Asn Gly Lys Asn Ile Ile Val
                    245                 250                 255

Gln Leu Lys Glu Pro Val Lys Ile Asn Cys Thr Arg Pro Gly Asn Asn
                260                 265                 270

Thr Arg Arg Ser Ile Asn Ile Gly Pro Gly Arg Ala Phe Tyr Ala Thr
            275                 280                 285

Gly Ala Ile Ile Gly Asp Ile Arg Lys Ala His Cys Asn Ile Ser Thr
        290                 295                 300

Glu Gln Trp Asn Asn Thr Leu Thr Gln Ile Val Asp Lys Leu Arg Glu
305                 310                 315                 320

Gln Phe Gly Asn Lys Thr Ile Ile Phe Asn Gln Ser Ser Gly Gly Asp
                    325                 330                 335

Pro Glu Val Val Met His Thr Phe Asn Cys Gly Gly Glu Phe Phe Tyr
                340                 345                 350

Cys Asn Ser Thr Gln Leu Phe Asn Ser Thr Trp Phe Asn Asn Gly Thr
            355                 360                 365

Ser Thr Trp Asn Ser Thr Ala Asp Asn Ile Thr Leu Pro Cys Arg Ile
        370                 375                 380

Lys Gln Val Ile Asn Met Trp Gln Glu Val Gly Lys Ala Met Tyr Ala
385                 390                 395                 400

Pro Pro Ile Arg Gly Gln Ile Asp Cys Ser Ser Asn Ile Thr Gly Leu
                    405                 410                 415

Ile Leu Thr Arg Asp Gly Gly Ser Asn Ser Ser Gln Asn Glu Thr Phe
                420                 425                 430

Arg Pro Gly Gly Gly Asn Met Lys Asp Asn Trp Arg Ser Glu Leu Tyr
            435                 440                 445

Lys Tyr Lys Val Val Lys Ile Glu Pro Leu Gly Ile Ala Pro Thr Arg
        450                 455                 460

Ala Lys Arg Arg Val Val Gln Arg Glu Lys Arg
465                 470                 475

<210> SEQ ID NO 6
<211> LENGTH: 481
<212> TYPE: PRT
<213> ORGANISM: Human immunodeficiency virus 1

<400> SEQUENCE: 6

Thr Glu Lys Leu Trp Val Thr Val Tyr Tyr Gly Val Pro Val Trp Lys
1               5                   10                  15

Glu Ala Thr Thr Thr Leu Phe Cys Ala Ser Asp Ala Lys Ala Tyr Asp
                20                  25                  30

Thr Glu Val His Asn Val Trp Ala Thr His Ala Cys Val Pro Thr Asp
            35                  40                  45

Pro Asn Pro Gln Glu Val Val Leu Val Asn Val Thr Glu Asn Phe Asn
        50                  55                  60

Met Trp Lys Asn Asp Met Val Glu Gln Met His Glu Asp Ile Ile Ser
65                  70                  75                  80

Leu Trp Asp Gln Ser Leu Lys Pro Cys Val Lys Leu Thr Pro Leu Cys
                85                  90                  95

Val Ser Leu Lys Cys Thr Asp Leu Lys Asn Asp Thr Asn Thr Asn Ser
                100                 105                 110
```

```
Ser Ser Gly Arg Met Ile Met Glu Lys Gly Glu Ile Lys Asn Cys Ser
    115                 120                 125

Phe Asn Ile Ser Thr Ser Ile Arg Gly Lys Val Gln Lys Glu Tyr Ala
    130                 135                 140

Phe Phe Tyr Lys Leu Asp Ile Pro Ile Asp Asn Asp Thr Thr Ser
145                 150                 155                 160

Tyr Lys Leu Thr Ser Cys Asn Thr Ser Val Ile Thr Gln Ala Cys Pro
                165                 170                 175

Lys Val Ser Phe Glu Pro Ile Pro Ile His Tyr Cys Ala Pro Ala Gly
                180                 185                 190

Phe Ala Ile Leu Lys Cys Asn Asn Lys Thr Phe Asn Gly Thr Gly Pro
                195                 200                 205

Cys Thr Asn Val Ser Thr Val Gln Cys Thr His Gly Ile Arg Pro Val
    210                 215                 220

Val Ser Thr Gln Leu Leu Leu Asn Gly Ser Leu Ala Glu Glu Glu Val
225                 230                 235                 240

Val Ile Arg Ser Val Asn Phe Thr Asp Asn Ala Lys Thr Ile Ile Val
                245                 250                 255

Gln Leu Asn Thr Ser Val Glu Ile Asn Cys Thr Arg Pro Asn Asn Asn
                260                 265                 270

Thr Arg Lys Arg Ile Arg Ile Gln Arg Gly Pro Gly Arg Ala Phe Val
    275                 280                 285

Thr Ile Gly Lys Ile Gly Asn Met Arg Gln Ala His Cys Asn Ile Ser
    290                 295                 300

Arg Ala Lys Trp Asn Asn Thr Leu Lys Gln Ile Ala Ser Lys Leu Arg
305                 310                 315                 320

Glu Gln Phe Gly Asn Asn Lys Thr Ile Ile Phe Lys Gln Ser Ser Gly
                325                 330                 335

Gly Asp Pro Glu Ile Val Thr His Ser Phe Asn Cys Gly Gly Glu Phe
                340                 345                 350

Phe Tyr Cys Asn Ser Thr Gln Leu Phe Asn Ser Thr Trp Phe Asn Ser
                355                 360                 365

Thr Trp Ser Thr Glu Gly Ser Asn Asn Thr Glu Gly Ser Asp Thr Ile
    370                 375                 380

Thr Leu Pro Cys Arg Ile Lys Gln Ile Ile Asn Met Trp Gln Lys Val
385                 390                 395                 400

Gly Lys Ala Met Tyr Ala Pro Pro Ile Ser Gly Gln Ile Arg Cys Ser
                405                 410                 415

Ser Asn Ile Thr Gly Leu Leu Leu Thr Arg Asp Gly Gly Asn Ser Asn
                420                 425                 430

Asn Glu Ser Glu Ile Phe Arg Pro Gly Gly Gly Asp Met Arg Asp Asn
                435                 440                 445

Trp Arg Ser Glu Leu Tyr Lys Tyr Lys Val Val Lys Ile Glu Pro Leu
    450                 455                 460

Gly Val Ala Pro Thr Lys Ala Lys Arg Val Val Gln Arg Glu Lys
465                 470                 475                 480

Arg

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 7

Asp Ser Tyr Trp Ser
1               5

<210> SEQ ID NO 8
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Tyr Val His Lys Ser Gly Asp Thr Asn Tyr Ser Pro Ser Leu Lys Ser
1               5                   10                  15

<210> SEQ ID NO 9
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Thr Leu His Gly Arg Arg Ile Tyr Gly Ile Val Ala Phe Asn Glu Trp
1               5                   10                  15

Phe Thr Tyr Phe Tyr Met Asp Val
            20

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gly Glu Lys Ser Leu Gly Ser Arg Ala Val Gln
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asn Asn Gln Asp Arg Pro Ser
1               5

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

His Ile Trp Asp Ser Arg Val Pro Thr Lys Trp Val
1               5                   10
```

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Tyr Val His Lys Ser Gly Asp Thr Asn Tyr Asn Pro Ser Leu Lys Ser
1               5                   10                  15

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Asn Tyr Tyr Trp Thr
1               5

<210> SEQ ID NO 15
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Tyr Ile Ser Asp Arg Glu Ser Ala Thr Tyr Asn Pro Ser Leu Asn Ser
1               5                   10                  15

<210> SEQ ID NO 16
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Arg Arg Gly Gln Arg Ile Tyr Gly Val Val Ser Phe Gly Glu Phe
1               5                   10                  15

Phe Tyr Tyr Tyr Ser Met Asp Val
            20

<210> SEQ ID NO 17
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Gly Arg Gln Ala Leu Gly Ser Arg Ala Val Gln
1               5                   10

<210> SEQ ID NO 18
<211> LENGTH: 12
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 18

His Met Trp Asp Ser Arg Ser Gly Phe Ser Trp Ser
1               5                   10

<210> SEQ ID NO 19
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Tyr Ile Ser Asp Arg Glu Thr Thr Thr Tyr Asn Pro Ser Leu Asn Ser
1               5                   10                  15

<210> SEQ ID NO 20
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Ala Arg Arg Gly Gln Arg Ile Tyr Gly Val Val Ser Phe Gly Glu Phe
1               5                   10                  15

Phe Tyr Tyr Tyr Tyr Met Asp Val
                20

<210> SEQ ID NO 21
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Arg Phe Trp Ser
1               5

<210> SEQ ID NO 22
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr Phe Ser Asp Thr Asp Arg Ser Glu Tyr Asn Pro Ser Leu Arg Ser
1               5                   10                  15

<210> SEQ ID NO 23
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Ala Gln Gln Gly Lys Arg Ile Tyr Gly Ile Val Ser Phe Gly Glu Phe

```
1               5                   10                  15

Phe Tyr Tyr Tyr Tyr Met Asp Ala
            20

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Gly Glu Arg Ser Arg Gly Ser Arg Ala Val Gln
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Asn Asn Gln Asp Arg Pro Ala
1               5

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

His Tyr Trp Asp Ser Arg Ser Pro Ile Ser Trp Ile
1               5                   10

<210> SEQ ID NO 27
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Gln Gln Gly Lys Arg Ile Tyr Gly Ile Val Ser Phe Gly Glu Leu
1               5                   10                  15

Phe Tyr Tyr Tyr Tyr Met Asp Ala
            20

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asp Asn Tyr Trp Ser
1               5
```

```
<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Tyr Val His Asp Ser Gly Asp Thr Asn Tyr Asn Pro Ser Leu Lys Ser
1               5                   10                  15

<210> SEQ ID NO 30
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Thr Lys His Gly Arg Arg Ile Tyr Gly Val Val Ala Phe Lys Glu Trp
1               5                   10                  15

Phe Thr Tyr Phe Tyr Met Asp Val
            20

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Glu Glu Ser Leu Gly Ser Arg Ser Val Ile
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asn Asn Asn Asp Arg Pro Ser
1               5

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

His Ile Trp Asp Ser Arg Arg Pro Thr Asn Trp Val
1               5                   10

<210> SEQ ID NO 34
<211> LENGTH: 5
<212> TYPE: PRT
<213> ORGANISM: Artificial Sequence
<220> FEATURE:
<223> OTHER INFORMATION: Description of Artificial Sequence: Synthetic
```

```
                          peptide

<400> SEQUENCE: 34

Asp Ala Tyr Trp Ser
1               5

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Tyr Val His His Ser Gly Asp Thr Asn Tyr Asn Pro Ser Leu Lys Arg
1               5                   10                  15

<210> SEQ ID NO 36
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Ala Leu His Gly Lys Arg Ile Tyr Gly Ile Val Ala Leu Gly Glu Leu
1               5                   10                  15

Phe Thr Tyr Phe Tyr Met Asp Val
            20

<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

Gly Lys Glu Ser Ile Gly Ser Arg Ala Val Gln
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

His Ile Tyr Asp Ala Arg Gly Gly Thr Asn Trp Val
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Ala Cys Thr Tyr Phe Trp Gly
1               5
```

<210> SEQ ID NO 40
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Ser Leu Ser His Cys Gln Ser Phe Trp Gly Ser Gly Trp Thr Phe His
1               5                   10                  15

Asn Pro Ser Leu Lys Ser
            20

<210> SEQ ID NO 41
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Phe Asp Gly Glu Val Leu Val Tyr Asn His Trp Pro Lys Pro Ala Trp
1               5                   10                  15

Val Asp Leu

<210> SEQ ID NO 42
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Asn Gly Thr Ala Thr Asn Phe Val Ser
1               5

<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gly Val Asp Lys Arg Pro Pro
1               5

<210> SEQ ID NO 44
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gly Ser Leu Val Gly Asn Trp Asp Val Ile
1               5                   10

<210> SEQ ID NO 45
<211> LENGTH: 7

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Cys Asp Tyr Phe Trp Gly
1               5

<210> SEQ ID NO 46
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gly Leu Ser His Cys Ala Gly Tyr Tyr Asn Thr Gly Trp Thr Tyr His
1               5                   10                  15

Asn Pro Ser Leu Lys Ser
            20

<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Phe Asp Gly Glu Val Leu Val Tyr His Asp Trp Pro Lys Pro Ala Trp
1               5                   10                  15

Val Asp Leu

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Thr Gly Thr Ser Asn Arg Phe Val Ser
1               5

<210> SEQ ID NO 49
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gly Val Asn Lys Arg Pro Ser
1               5

<210> SEQ ID NO 50
<211> LENGTH: 10
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 50

Ser Ser Leu Val Gly Asn Trp Asp Val Ile
1               5                   10

<210> SEQ ID NO 51
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Ser Leu Ser His Cys Ala Gly Tyr Tyr Asn Ser Gly Trp Thr Tyr His
1               5                   10                  15

Asn Pro Ser Leu Lys Ser
            20

<210> SEQ ID NO 52
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Phe Gly Gly Asp Val Leu Val Tyr His Asp Trp Pro Lys Pro Ala Trp
1               5                   10                  15

Val Asp Leu

<210> SEQ ID NO 53
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Thr Gly Asn Ile Asn Asn Phe Val Ser
1               5

<210> SEQ ID NO 54
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Ser Leu Ala Gly Asn Trp Asp Val Val
1               5                   10

<210> SEQ ID NO 55
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

```
Ala Cys Asn Ser Phe Trp Gly
1               5
```

<210> SEQ ID NO 56
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

```
Ser Leu Ser His Cys Ala Ser Tyr Trp Asn Arg Gly Trp Thr Tyr His
1               5                   10                  15

Asn Pro Ser Leu Lys Ser
            20
```

<210> SEQ ID NO 57
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

```
Phe Gly Gly Glu Val Leu Arg Tyr Thr Asp Trp Pro Lys Pro Ala Trp
1               5                   10                  15

Val Asp Leu
```

<210> SEQ ID NO 58
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

```
Thr Gly Thr Ser Asn Asn Phe Val Ser
1               5
```

<210> SEQ ID NO 59
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

```
Asp Val Asn Lys Arg Pro Ser
1               5
```

<210> SEQ ID NO 60
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

```
Ala Arg His Arg His His Asp Val Phe Met Leu Val Pro Ile Ala Gly
1               5                   10                  15

Trp Phe Asp Val
```

<210> SEQ ID NO 61
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Gly Cys Asp Tyr Phe Trp Gly
1               5

<210> SEQ ID NO 62
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Glu Thr Tyr Ser Lys Ile Ala
1               5

<210> SEQ ID NO 63
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Phe Asp Gly Glu Val Leu Val Tyr Asn Asp Trp Pro Lys Pro Ala Trp
1               5                   10                  15

Val Asp Leu

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Thr Gly His Tyr Tyr Trp Gly
1               5

<210> SEQ ID NO 65
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

His Ile His Tyr Thr Thr Ala Val Leu His Asn Pro Ser Leu Lys Ser
1               5                   10                  15

<210> SEQ ID NO 66
<211> LENGTH: 19
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 66

Ser Gly Gly Asp Ile Leu Tyr Tyr Tyr Glu Trp Gln Lys Pro His Trp
1               5                   10                  15

Phe Ser Pro

<210> SEQ ID NO 67
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Asn Gly Thr Ser Ser Asp Ile Gly Gly Trp Asn Phe Val Ser
1               5                   10

<210> SEQ ID NO 68
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Glu Val Asn Lys Arg Pro Ser
1               5

<210> SEQ ID NO 69
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ser Ser Leu Phe Gly Arg Trp Asp Val Val
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Gly Thr Asp Trp Gly Glu Asn Asp Phe His Tyr Gly
1               5                   10

<210> SEQ ID NO 71
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Ser Ile His Trp Arg Gly Arg Thr Thr His Tyr Lys Thr Ser Phe Arg
```

Ser

<210> SEQ ID NO 72
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

His Lys Tyr His Asp Ile Phe Arg Val Val Pro Val Ala Gly Trp Phe
1               5                   10                  15

Asp Pro

<210> SEQ ID NO 73
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Arg Ala Ser Gln Asn Val Lys Asn Asn Leu Ala
1               5                   10

<210> SEQ ID NO 74
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Asp Ala Ser Ser Arg Ala Gly
1               5

<210> SEQ ID NO 75
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Gln Gln Tyr Glu Glu Trp Pro Arg Thr
1               5

<210> SEQ ID NO 76
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 76

Gly Gly Glu Trp Gly Asp Ser Asp Tyr His Trp Gly
1               5                   10

<210> SEQ ID NO 77
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Ser Ile His Trp Arg Gly Thr Thr His Tyr Asn Ala Pro Phe Arg Gly
1               5                   10                  15

<210> SEQ ID NO 78
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

His Lys Tyr His Asp Ile Val Met Val Val Pro Ile Ala Gly Trp Phe
1               5                   10                  15

Asp Pro

<210> SEQ ID NO 79
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Arg Ala Ser Gln Ser Val Lys Asn Asn Leu Ala
1               5                   10

<210> SEQ ID NO 80
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asp Thr Ser Ser Arg Ala Ser
1               5

<210> SEQ ID NO 81
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Gly Gly Glu Trp Gly Asp Lys Asp Tyr His Trp Gly
1               5                   10

<210> SEQ ID NO 82
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82
```

-continued

Ser Ile His Trp Arg Gly Thr Thr His Tyr Lys Glu Ser Leu Arg Arg
1               5                   10                  15

<210> SEQ ID NO 83
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

His Arg His His Asp Val Phe Met Leu Val Pro Ile Ala Gly Trp Phe
1               5                   10                  15

Asp Val

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Arg Ala Ser Gln Asn Ile Asn Lys Asn Leu Ala
1               5                   10

<210> SEQ ID NO 85
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 85

Ser Asp His Ser Trp Thr
1               5

<210> SEQ ID NO 86
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Asp Ile His Tyr Asn Gly Ala Thr Thr Tyr Asn Pro Ser Leu Arg Ser
1               5                   10                  15

<210> SEQ ID NO 87
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 87

Asn Ala Ile Arg Ile Tyr Gly Val Val Ala Leu Gly Glu Trp Phe His
1               5                   10                  15

Tyr Gly Met Asp Val
            20

<210> SEQ ID NO 88
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 88

Ser Gly Ala Pro Leu Thr Ser Arg Phe Thr Tyr
1               5                   10

<210> SEQ ID NO 89
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Ser Ser Gln Arg Ser Ser
1               5

<210> SEQ ID NO 90
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Gln Ser Ser Asp Thr Ser Asp Ser Tyr Lys Met
1               5                   10

<210> SEQ ID NO 91
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Asp Val His Tyr Asn Gly Asp Asn Thr Tyr Asn Pro Ser Leu Arg Gly
1               5                   10                  15

<210> SEQ ID NO 92
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Asn Val Ile Arg Val Phe Gly Val Ile Ser Leu Gly Glu Trp Phe His
1               5                   10                  15

Tyr Gly Met Asp Val
            20

<210> SEQ ID NO 93
<211> LENGTH: 11
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 93

Ser Gly Pro Pro Leu Ala Ser Arg Tyr Thr Tyr
1               5                   10

<210> SEQ ID NO 94
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Arg Asp Arg Gln Phe Pro Ser
1               5

<210> SEQ ID NO 95
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gln Ser Ser Asp Ile Asn Asp Ser Tyr Lys Met
1               5                   10

<210> SEQ ID NO 96
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Asp Val His Tyr Asn Gly Asp Thr Thr Tyr Asn Pro Ser Leu Arg Gly
1               5                   10                  15

<210> SEQ ID NO 97
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Ser Gly Ala Ala Leu Thr Ser Arg Phe Thr Tyr
1               5                   10

<210> SEQ ID NO 98
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Arg Thr Ser Gln Arg Ser Ser
1               5

-continued

```
<210> SEQ ID NO 99
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Asp Ile His Tyr Gly Gly Asp Ile Thr Tyr Asn Pro Ser Leu Arg Ser
1               5                   10                  15

<210> SEQ ID NO 100
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Asn Val Ile Arg Val Phe Gly Val Ile Ala Leu Gly Glu Trp Phe His
1               5                   10                  15

Tyr Gly Met Asp Val
            20

<210> SEQ ID NO 101
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Ser Gly Pro Pro Leu Ala Ser Arg Tyr Cys Tyr
1               5                   10

<210> SEQ ID NO 102
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Arg Asp Arg Gln Phe Ser Ser
1               5

<210> SEQ ID NO 103
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103

Gln Ser Ser Asp Thr Ser Asp Ser Phe Lys Met
1               5                   10

<210> SEQ ID NO 104
<211> LENGTH: 11
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 104

Ser Gly Pro Pro Leu Ala Thr Arg Tyr Cys Tyr
1               5                   10

<210> SEQ ID NO 105
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 105

Asp Ile His Tyr Asn Gly Asp Lys Thr Tyr Asn Pro Ser Leu Arg Gly
1               5                   10                  15

<210> SEQ ID NO 106
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ser Leu Ser His Cys Ala Gly Tyr Tyr Asn Ser Gly Trp Thr Tyr
1               5                   10                  15

<210> SEQ ID NO 107
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gln Ser Ser Asp Asn Ser Asp Ser Phe Lys Met
1               5                   10

<210> SEQ ID NO 108
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 108

Asp Tyr Ala Met Ala
1               5

<210> SEQ ID NO 109
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Phe Met Arg Gly Trp Ala Tyr Gly Gly Ser Ala Gln Phe Ala Ala Phe
1               5                   10                  15

Ala Val Gly

<210> SEQ ID NO 110
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Glu Gln Arg Asn Lys Asp Tyr Arg Tyr Gly Gln Glu Gly Phe Gly Tyr
1               5                   10                  15

Ser Tyr Gly Met Asp Val
            20

<210> SEQ ID NO 111
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Arg Ala Ser His Phe Ile Ala Asn Tyr Val Asn
1               5                   10

<210> SEQ ID NO 112
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Glu Ser Ser Thr Leu Gln Arg
1               5

<210> SEQ ID NO 113
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Gln Gln Ser His Ser Pro Pro Val Thr
1               5

<210> SEQ ID NO 114
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Phe Ile Arg Gly Trp Ala Tyr Gly Gln Ala Ala Gln Tyr Gly Lys Ser
1               5                   10                  15

Ala Ser Gly

<210> SEQ ID NO 115
<211> LENGTH: 22
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 115

Glu Gln Arg Gly Gly Asp Gly Arg Tyr Ser Gly Asp Gly Phe Gly Tyr
1               5                   10                  15

Pro Tyr Gly Met Asp Val
            20

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gln Ser Trp Thr Leu Asn Arg
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Gln Ser His Ser Pro Pro Leu Ser
1               5

<210> SEQ ID NO 118
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Phe Ile Arg Gly Trp Ala Tyr Gly Gln Ser Ala Gln Tyr Gly Lys Ser
1               5                   10                  15

Ala Ser Gly

<210> SEQ ID NO 119
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Glu Gln Arg Gly Ala Asn Gly Arg Tyr Gly Gly Asp Gly Phe Gly Tyr
1               5                   10                  15

Ser Tyr Gly Met Asp Val
            20

<210> SEQ ID NO 120
<211> LENGTH: 7
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 120

Glu Ser Ser Thr Leu Asn Arg
1               5

<210> SEQ ID NO 121
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Gln Gln Ser His Ser Pro Pro Val Ser
1               5

<210> SEQ ID NO 122
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

His Tyr Gly Gly Asp
1               5

<210> SEQ ID NO 123
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Gly Ala Ser Ile Ser Asp
1               5

<210> SEQ ID NO 124
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Tyr Val His Lys Ser Gly Asp Thr Asn
1               5

<210> SEQ ID NO 125
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gly Asp Ser Met Asn Asn
1               5
```

<210> SEQ ID NO 126
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Tyr Ile Ser Asp Arg Glu Ser Ala Thr
1               5

<210> SEQ ID NO 127
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Gly Gly Ser Ile Ser Asn
1               5

<210> SEQ ID NO 128
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Tyr Ile Ser Asp Arg Glu Thr Thr Thr
1               5

<210> SEQ ID NO 129
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Asn Gly Ser Val Ser Gly
1               5

<210> SEQ ID NO 130
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Tyr Phe Ser Asp Thr Asp Arg Ser Glu
1               5

<210> SEQ ID NO 131
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 131

Gly Thr Leu Val Arg Asp
1               5

<210> SEQ ID NO 132
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Tyr Val His Asp Ser Gly Asp Thr Asn
1               5

<210> SEQ ID NO 133
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Gly Ala Ser Ile Asn Asp
1               5

<210> SEQ ID NO 134
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Tyr Val His His Ser Gly Asp Thr Asn
1               5

<210> SEQ ID NO 135
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Gly Glu Ser Thr Gly Ala Cys Thr
1               5

<210> SEQ ID NO 136
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Ser Leu Ser His Cys Gln Ser Phe Trp Gly Ser Gly Trp Thr Phe
1               5                   10                  15

<210> SEQ ID NO 137
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 137

Gly Asp Ser Thr Ala Ala Cys Asp
1               5

<210> SEQ ID NO 138
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Gly Leu Ser His Cys Ala Gly Tyr Tyr Asn Thr Gly Trp Thr Tyr
1               5                   10                  15

<210> SEQ ID NO 139
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139

Gly Asp Ser Thr Ala Ala Cys Asn
1               5

<210> SEQ ID NO 140

<400> SEQUENCE: 140

000

<210> SEQ ID NO 141
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

Gly Asp Ser Thr Ala Gly Cys Asp
1               5

<210> SEQ ID NO 142
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

Gly Glu Ser Ile Asn Thr Gly His
1               5

<210> SEQ ID NO 143
<211> LENGTH: 9
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 143

His Ile His Tyr Thr Thr Ala Val Leu
1               5

<210> SEQ ID NO 144
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

Gly Gly Ser Met Arg Gly Thr Asp Trp Gly Glu Asn Asp
1               5                   10

<210> SEQ ID NO 145
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 145

Ser Ile His Trp Arg Gly Arg Thr Thr His
1               5                   10

<210> SEQ ID NO 146
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Gly Ser Ile Arg Gly Gly Glu Trp Gly Asp Ser Asp
1               5                   10

<210> SEQ ID NO 147
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Ser Ile His Trp Arg Gly Thr Thr His
1               5

<210> SEQ ID NO 148
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Gly Asp Ser Ile Arg Gly Gly Glu Trp Gly Asp Lys Asp
1               5                   10
```

```
<210> SEQ ID NO 149
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gln Asp Ser Arg Pro Ser Asp His
1               5

<210> SEQ ID NO 150
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

His Tyr Asn Gly Ala
1               5

<210> SEQ ID NO 151
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Asn Asp Ser Arg Pro Ser Asp His
1               5

<210> SEQ ID NO 152
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Gly Asp Ser Arg Pro Ser Asp His
1               5

<210> SEQ ID NO 153
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 153

His Tyr Asn Gly Asp
1               5

<210> SEQ ID NO 154
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 154
```

```
Gly Phe Tyr Phe Pro Asp Tyr
1               5

<210> SEQ ID NO 155
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 155

Arg Gly Trp Ala Tyr Gly Gly Ser
1               5

<210> SEQ ID NO 156
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 156

Asp Phe Tyr Phe Pro Asp Tyr
1               5

<210> SEQ ID NO 157
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 157

Arg Gly Trp Ala Tyr Gly Gln Ala
1               5

<210> SEQ ID NO 158
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 158

Asp Phe Tyr Phe Pro Asp Tyr
1               5

<210> SEQ ID NO 159
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 159

Arg Gly Trp Ala Tyr Gly Gln Ser
1               5

<210> SEQ ID NO 160
<211> LENGTH: 8
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 160

Gly Ala Ser Ile Ser Asp Ser Tyr
1               5

<210> SEQ ID NO 161
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 161

Val His Lys Ser Gly Asp Thr
1               5

<210> SEQ ID NO 162
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 162

Ala Arg Thr Leu His Gly Arg Arg Ile Tyr Gly Ile Val Ala Phe Asn
1               5                   10                  15

Glu Trp Phe Thr Tyr Phe Tyr Met Asp Val
            20                  25

<210> SEQ ID NO 163
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ser Leu Gly Ser Arg Ala
1               5

<210> SEQ ID NO 164
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Asn Asn Gln
1

<210> SEQ ID NO 165
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 165
```

Gly Asp Ser Met Asn Asn Tyr Tyr
1               5

<210> SEQ ID NO 166
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 166

Ile Ser Asp Arg Glu Ser Ala
1               5

<210> SEQ ID NO 167
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 167

Ala Thr Ala Arg Arg Gly Gln Arg Ile Tyr Gly Val Val Ser Phe Gly
1               5                   10                  15

Glu Phe Phe Tyr Tyr Tyr Ser Met Asp Val
            20                  25

<210> SEQ ID NO 168
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 168

Ala Leu Gly Ser Arg Ala
1               5

<210> SEQ ID NO 169
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 169

Gly Gly Ser Ile Ser Asn Tyr Tyr
1               5

<210> SEQ ID NO 170
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 170

Ile Ser Asp Arg Glu Thr Thr
1               5

<210> SEQ ID NO 171
<211> LENGTH: 26

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 171

Ala Thr Ala Arg Arg Gly Gln Arg Ile Tyr Gly Val Val Ser Phe Gly
1               5                   10                  15

Glu Phe Phe Tyr Tyr Tyr Tyr Met Asp Val
            20                  25

<210> SEQ ID NO 172
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 172

Asn Gly Ser Val Ser Gly Arg Phe
1               5

<210> SEQ ID NO 173
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 173

Phe Ser Asp Thr Asp Arg Ser
1               5

<210> SEQ ID NO 174
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Ala Arg Ala Gln Gln Gly Lys Arg Ile Tyr Gly Ile Val Ser Phe Gly
1               5                   10                  15

Glu Leu Phe Tyr Tyr Tyr Tyr Met Asp Ala
            20                  25

<210> SEQ ID NO 175
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Ser Arg Gly Ser Arg Ala
1               5

<210> SEQ ID NO 176
<211> LENGTH: 26
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 176

Ala Arg Ala Gln Gln Gly Lys Arg Ile Tyr Gly Ile Val Ser Phe Gly
1               5                   10                  15

Glu Phe Phe Tyr Tyr Tyr Tyr Met Asp Ala
            20                  25

<210> SEQ ID NO 177
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 177

Gly Thr Leu Val Arg Asp Asn Tyr
1               5

<210> SEQ ID NO 178
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 178

Val His Asp Ser Gly Asp Thr
1               5

<210> SEQ ID NO 179
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 179

Ala Thr Thr Lys His Gly Arg Arg Ile Tyr Gly Val Val Ala Phe Lys
1               5                   10                  15

Glu Trp Phe Thr Tyr Phe Tyr Met Asp Val
            20                  25

<210> SEQ ID NO 180
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 180

Ser Ile Gly Ser Arg Ala
1               5

<210> SEQ ID NO 181
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 181

Gly Ala Ser Ile Asn Asp Ala Tyr
1               5

<210> SEQ ID NO 182
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Val His His Ser Gly Asp Thr
1               5

<210> SEQ ID NO 183
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Ala Arg Ala Leu His Gly Lys Arg Ile Tyr Gly Ile Val Ala Leu Gly
1               5                   10                  15

Glu Leu Phe Thr Tyr Phe Tyr Met Asp Val
            20                  25

<210> SEQ ID NO 184
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Ser Leu Gly Ser Arg Ser
1               5

<210> SEQ ID NO 185
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 185

Asn Asn Asn
1

<210> SEQ ID NO 186
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Gly Glu Ser Thr Gly Ala Cys Thr Tyr Phe
1               5                   10
```

```
<210> SEQ ID NO 187
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Leu Ser His Cys Gln Ser Phe Trp Gly Ser Gly Trp Thr
1               5                   10

<210> SEQ ID NO 188
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Ala Arg Phe Asp Gly Glu Val Leu Val Tyr Asn His Trp Pro Lys Pro
1               5                   10                  15

Ala Trp Val Asp Leu
            20

<210> SEQ ID NO 189
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 189

Ala Thr Asn Phe
1

<210> SEQ ID NO 190
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gly Val Asp
1

<210> SEQ ID NO 191
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Gly Asp Ser Thr Ala Ala Cys Asp Tyr Phe
1               5                   10

<210> SEQ ID NO 192
<211> LENGTH: 13
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 192

Leu Ser His Cys Ala Gly Tyr Tyr Asn Thr Gly Trp Thr
1               5                   10

<210> SEQ ID NO 193
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 193

Ala Arg Phe Asp Gly Glu Val Leu Val Tyr His Asp Trp Pro Lys Pro
1               5                   10                  15

Ala Trp Val Asp Leu
            20

<210> SEQ ID NO 194
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Ser Asn Arg Phe
1

<210> SEQ ID NO 195
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gly Val Asn
1

<210> SEQ ID NO 196
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Leu Ser His Cys Ala Gly Tyr Tyr Asn Ser Gly Trp Thr
1               5                   10

<210> SEQ ID NO 197
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 197

Ala Arg Phe Gly Gly Asp Val Leu Val Tyr His Asp Trp Pro Lys Pro
1               5                   10                  15

Ala Trp Val Asp Leu
            20

<210> SEQ ID NO 198
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 198

Ile Asn Asn Phe
1

<210> SEQ ID NO 199
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 199

Gly Asp Ser Thr Ala Ala Cys Asn Ser Phe
1               5                   10

<210> SEQ ID NO 200
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 200

Leu Ser His Cys Ala Ser Tyr Trp Asn Arg Gly Trp Thr
1               5                   10

<210> SEQ ID NO 201
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 201

Ala Arg Phe Gly Gly Glu Val Leu Arg Tyr Thr Asp Trp Pro Lys Pro
1               5                   10                  15

Ala Trp Val Asp Leu
            20

<210> SEQ ID NO 202
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 202

Ser Asn Asn Phe
1

<210> SEQ ID NO 203

<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 203

Gly Asp Ser Thr Ala Gly Cys Asp Tyr Phe
1               5                   10

<210> SEQ ID NO 204
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 204

Leu Ser His Cys Ala Gly Tyr Tyr Asn Thr Gly Trp Thr
1               5                   10

<210> SEQ ID NO 205
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 205

Ala Arg Phe Asp Gly Glu Val Leu Val Tyr Asn Asp Trp Pro Lys Pro
1               5                   10                  15

Ala Trp Val Asp Leu
            20

<210> SEQ ID NO 206
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 206

Gly Glu Ser Ile Asn Thr Gly His Tyr Tyr
1               5                   10

<210> SEQ ID NO 207
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 207

Ile His Tyr Thr Thr Ala Val
1               5

<210> SEQ ID NO 208
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 208

Val Arg Ser Gly Gly Asp Ile Leu Tyr Tyr Tyr Glu Trp Gln Lys Pro
1               5                   10                  15

His Trp Phe Ser Pro
            20

<210> SEQ ID NO 209
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 209

Ser Ser Asp Ile Gly Gly Trp Asn Phe
1               5

<210> SEQ ID NO 210
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 210

Glu Val Asn
1

<210> SEQ ID NO 211
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 211

Gly Gly Ser Met Arg Gly Thr Asp Trp Gly Glu Asn Asp Phe His
1               5                   10                  15

<210> SEQ ID NO 212
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 212

Ile His Trp Arg Gly Arg Thr Thr
1               5

<210> SEQ ID NO 213
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 213

Ala Arg His Lys Tyr His Asp Ile Phe Arg Val Val Pro Val Ala Gly
1               5                   10                  15
```

Trp Phe Asp Pro
          20

<210> SEQ ID NO 214
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 214

Gln Asn Val Lys Asn Asn
1               5

<210> SEQ ID NO 215
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 215

Asp Ala Ser
1

<210> SEQ ID NO 216
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 216

Gly Gly Ser Ile Arg Gly Gly Glu Trp Gly Asp Ser Asp Tyr His
1               5                   10                  15

<210> SEQ ID NO 217
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 217

Ile His Trp Arg Gly Thr Thr
1               5

<210> SEQ ID NO 218
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 218

Val Lys His Lys Tyr His Asp Ile Val Met Val Val Pro Ile Ala Gly
1               5                   10                  15

Trp Phe Asp Pro
          20

<210> SEQ ID NO 219
<211> LENGTH: 6

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 219

Gln Ser Val Lys Asn Asn
1               5

<210> SEQ ID NO 220
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 220

Asp Thr Ser
1

<210> SEQ ID NO 221
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 221

Gly Asp Ser Ile Arg Gly Gly Glu Trp Gly Asp Lys Asp Tyr His
1               5                   10                  15

<210> SEQ ID NO 222

<400> SEQUENCE: 222

000

<210> SEQ ID NO 223
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 223

Gln Asn Ile Asn Lys Asn
1               5

<210> SEQ ID NO 224
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 224

Glu Thr Tyr
1

<210> SEQ ID NO 225
<211> LENGTH: 9
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 225

Gln Asp Ser Arg Pro Ser Asp His Ser
1               5

<210> SEQ ID NO 226
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 226

Ile His Tyr Asn Gly Ala Thr
1               5

<210> SEQ ID NO 227
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 227

Pro Leu Thr Ser Arg Phe
1               5

<210> SEQ ID NO 228
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 228

Arg Ser Ser
1

<210> SEQ ID NO 229
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 229

Asn Asp Ser Arg Pro Ser Asp His Ser
1               5

<210> SEQ ID NO 230
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 230

Gly Asp Ser Arg Pro Ser Asp His Ser
1               5
```

```
<210> SEQ ID NO 231
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 231

Val His Tyr Asn Gly Asp Asn
1               5

<210> SEQ ID NO 232
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 232

Pro Leu Ala Ser Arg Tyr
1               5

<210> SEQ ID NO 233
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 233

Arg Asp Arg
1

<210> SEQ ID NO 234
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 234

Val His Tyr Asn Gly Asp Thr
1               5

<210> SEQ ID NO 235
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 235

Ala Leu Thr Ser Arg Phe
1               5

<210> SEQ ID NO 236
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 236

Ile His Tyr Gly Gly Asp Ile
1               5

<210> SEQ ID NO 237
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 237

Pro Leu Ala Thr Arg Tyr
1               5

<210> SEQ ID NO 238
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 238

Ile His Tyr Asn Gly Asp Lys
1               5

<210> SEQ ID NO 239
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 239

Gly Phe Tyr Phe Pro Asp Tyr Ala
1               5

<210> SEQ ID NO 240
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 240

Met Arg Gly Trp Ala Tyr Gly Gly Ser Ala
1               5                   10

<210> SEQ ID NO 241
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 241

His Phe Ile Ala Asn Tyr
1               5

<210> SEQ ID NO 242
<211> LENGTH: 3
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 242

Glu Ser Ser
1

<210> SEQ ID NO 243
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 243

Asp Phe Tyr Phe Pro Asp Tyr Ala
1               5

<210> SEQ ID NO 244
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 244

Ile Arg Gly Trp Ala Tyr Gly Gln Ala Ala
1               5                   10

<210> SEQ ID NO 245
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 245

Gln Ser Trp
1

<210> SEQ ID NO 246
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Ile Arg Gly Trp Ala Tyr Gly Gln Ser Ala
1               5                   10

<210> SEQ ID NO 247
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 247

Glu Ser Ser
1
```

<210> SEQ ID NO 248
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 248

Val Ser Gly Ala Ser Ile Ser Asp Ser Tyr
1               5                   10

<210> SEQ ID NO 249
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 249

Val His Lys Ser Gly Asp Thr Asn Tyr Ser Pro Ser Leu Lys Ser Arg
1               5                   10                  15

<210> SEQ ID NO 250
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 250

Thr Leu His Gly Arg Arg Ile Tyr Gly Ile Val Ala Phe Asn Glu Trp
1               5                   10                  15

Phe Thr Tyr Phe Tyr Met Asp
            20

<210> SEQ ID NO 251
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 251

Glu Lys Ser Leu Gly Ser Arg Ala
1               5

<210> SEQ ID NO 252
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 252

Asn Asn Gln Asp Arg Pro Ser Gly Ile Pro Glu Arg
1               5                   10

<210> SEQ ID NO 253
<211> LENGTH: 9
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 253

Trp Asp Ser Arg Val Pro Thr Lys Trp
1               5

<210> SEQ ID NO 254
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 254

Val His Lys Ser Gly Asp Thr Asn Tyr Asn Pro Ser Leu Lys Ser Arg
1               5                   10                  15

<210> SEQ ID NO 255
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 255

Val Ser Gly Asp Ser Met Asn Asn Tyr Tyr
1               5                   10

<210> SEQ ID NO 256
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 256

Ile Ser Asp Arg Glu Ser Ala Thr Tyr Asn Pro Ser Leu Asn Ser Arg
1               5                   10                  15

<210> SEQ ID NO 257
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 257

Ala Arg Arg Gly Gln Arg Ile Tyr Gly Val Val Ser Phe Gly Glu Phe
1               5                   10                  15

Phe Tyr Tyr Tyr Ser Met Asp
            20

<210> SEQ ID NO 258
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 258
```

Arg Gln Ala Leu Gly Ser Arg Ala
1               5

<210> SEQ ID NO 259
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 259

Trp Asp Ser Arg Ser Gly Phe Ser Trp
1               5

<210> SEQ ID NO 260
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 260

Val Ser Gly Gly Ser Ile Ser Asn Tyr Tyr
1               5                   10

<210> SEQ ID NO 261
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 261

Ile Ser Asp Arg Glu Thr Thr Thr Tyr Asn Pro Ser Leu Asn Ser Arg
1               5                   10                  15

<210> SEQ ID NO 262
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 262

Ala Arg Arg Gly Gln Arg Ile Tyr Gly Val Val Ser Phe Gly Glu Phe
1               5                   10                  15

Phe Tyr Tyr Tyr Tyr Met Asp
            20

<210> SEQ ID NO 263
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Val Ser Asn Gly Ser Val Ser Gly Arg Phe
1               5                   10

<210> SEQ ID NO 264
<211> LENGTH: 16

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Phe Ser Asp Thr Asp Arg Ser Glu Tyr Asn Pro Ser Leu Arg Ser Arg
1               5                   10                  15

<210> SEQ ID NO 265
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Ala Gln Gln Gly Lys Arg Ile Tyr Gly Ile Val Ser Phe Gly Glu Leu
1               5                   10                  15

Phe Tyr Tyr Tyr Tyr Met Asp
            20

<210> SEQ ID NO 266
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 266

Glu Arg Ser Arg Gly Ser Arg Ala
1               5

<210> SEQ ID NO 267
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 267

Asn Asn Gln Asp Arg Pro Ala Gly Val Ser Glu Arg
1               5                   10

<210> SEQ ID NO 268
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 268

Trp Asp Ser Arg Ser Pro Ile Ser Trp
1               5

<210> SEQ ID NO 269
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 269

Val Ser Gly Ala Ser Ile Asn Asp Ala Tyr
1               5                   10

<210> SEQ ID NO 270
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 270

Val His His Ser Gly Asp Thr Asn Tyr Asn Pro Ser Leu Lys Arg Arg
1               5                   10                  15

<210> SEQ ID NO 271
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 271

Ala Leu His Gly Lys Arg Ile Tyr Gly Ile Val Ala Leu Gly Glu Leu
1               5                   10                  15

Phe Thr Tyr Phe Tyr Met Asp
            20

<210> SEQ ID NO 272
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 272

Lys Glu Ser Ile Gly Ser Arg Ala
1               5

<210> SEQ ID NO 273
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 273

Asn Asn Gln Asp Arg Pro Ala Gly Val Pro Glu Arg
1               5                   10

<210> SEQ ID NO 274
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 274

Tyr Asp Ala Arg Gly Gly Thr Asn Trp
1               5
```

```
<210> SEQ ID NO 275
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 275

Val Ser Gly Thr Leu Val Arg Asp Asn Tyr
1               5                   10

<210> SEQ ID NO 276
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 276

Val His Asp Ser Gly Asp Thr Asn Tyr Asn Pro Ser Leu Lys Ser Arg
1               5                   10                  15

<210> SEQ ID NO 277
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 277

Thr Lys His Gly Arg Arg Ile Tyr Gly Val Val Ala Phe Lys Glu Trp
1               5                   10                  15

Phe Thr Tyr Phe Tyr Met Asp
            20

<210> SEQ ID NO 278
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 278

Glu Glu Ser Leu Gly Ser Arg Ser
1               5

<210> SEQ ID NO 279
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 279

Asn Asn Asn Asp Arg Pro Ser Gly Ile Pro Asp Arg
1               5                   10

<210> SEQ ID NO 280
<211> LENGTH: 9
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 280

Trp Asp Ser Arg Arg Pro Thr Asn Trp
1               5

<210> SEQ ID NO 281
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 281

Val Ser Gly Glu Ser Thr Gly Ala Cys Thr Tyr Phe
1               5                   10

<210> SEQ ID NO 282
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 282

Leu Ser His Cys Gln Ser Phe Trp Gly Ser Gly Trp Thr Phe His Asn
1               5                   10                  15

Pro Ser Leu Lys Ser Arg
            20

<210> SEQ ID NO 283
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 283

Phe Asp Gly Glu Val Leu Val Tyr Asn His Trp Pro Lys Pro Ala Trp
1               5                   10                  15

Val Asp

<210> SEQ ID NO 284
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 284

Gly Thr Ala Thr Asn Phe
1               5

<210> SEQ ID NO 285
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 285
```

```
Gly Val Asp Lys Arg Pro Pro Gly Val Pro Asp Arg
1               5                   10
```

<210> SEQ ID NO 286
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 286

```
Leu Val Gly Asn Trp Asp Val
1               5
```

<210> SEQ ID NO 287
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 287

```
Val Ser Gly Asp Ser Thr Ala Ala Cys Asp Tyr Phe
1               5                   10
```

<210> SEQ ID NO 288
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 288

```
Leu Ser His Cys Ala Gly Tyr Tyr Asn Thr Gly Trp Thr Tyr His Asn
1               5                   10                  15

Pro Ser Leu Lys Ser Arg
            20
```

<210> SEQ ID NO 289
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 289

```
Phe Asp Gly Glu Val Leu Val Tyr His Asp Trp Pro Lys Pro Ala Trp
1               5                   10                  15

Val Asp
```

<210> SEQ ID NO 290
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 290

```
Gly Thr Ser Asn Arg Phe
1               5
```

```
<210> SEQ ID NO 291
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 291

Gly Val Asn Lys Arg Pro Ser Gly Val Pro Asp Arg
1               5                   10

<210> SEQ ID NO 292
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 292

Leu Ser His Cys Ala Gly Tyr Tyr Asn Ser Gly Trp Thr Tyr His Asn
1               5                   10                  15

Pro Ser Leu Lys Ser Arg
            20

<210> SEQ ID NO 293
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 293

Phe Gly Gly Asp Val Leu Val Tyr His Asp Trp Pro Lys Pro Ala Trp
1               5                   10                  15

Val Asp

<210> SEQ ID NO 294
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 294

Gly Asn Ile Asn Asn Phe
1               5

<210> SEQ ID NO 295
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 295

Gly Val Asn Lys Arg Pro Ser Gly Val Pro Asp Arg
1               5                   10

<210> SEQ ID NO 296
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 296

Leu Ala Gly Asn Trp Asp Val
1               5

<210> SEQ ID NO 297
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 297

Val Ser Gly Asp Ser Thr Ala Ala Cys Asn Ser Phe
1               5                   10

<210> SEQ ID NO 298
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 298

Leu Ser His Cys Ala Ser Tyr Trp Asn Arg Gly Trp Thr Tyr His Asn
1               5                   10                  15

Pro Ser Leu Lys Ser Arg
            20

<210> SEQ ID NO 299
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 299

Phe Gly Gly Glu Val Leu Arg Tyr Thr Asp Trp Pro Lys Pro Ala Trp
1               5                   10                  15

Val Asp

<210> SEQ ID NO 300
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 300

Gly Thr Ser Asn Asn Phe
1               5

<210> SEQ ID NO 301
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 301

Asp Val Asn Lys Arg Pro Ser Gly Val Pro Asp Arg
1               5                   10

<210> SEQ ID NO 302
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 302

Val Ser Gly Asp Ser Thr Ala Gly Cys Asp Tyr Phe
1               5                   10

<210> SEQ ID NO 303
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 303

Phe Asp Gly Glu Val Leu Val Tyr Asn Asp Trp Pro Lys Pro Ala Trp
1               5                   10                  15

Val Asp

<210> SEQ ID NO 304
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 304

Val Ser Gly Glu Ser Ile Asn Thr Gly His Tyr Tyr
1               5                   10

<210> SEQ ID NO 305
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 305

Ile His Tyr Thr Thr Ala Val Leu His Asn Pro Ser Leu Lys Ser Arg
1               5                   10                  15

<210> SEQ ID NO 306
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 306

Ser Gly Gly Asp Ile Leu Tyr Tyr Tyr Glu Trp Gln Lys Pro His Trp
1               5                   10                  15

Phe Ser
```

```
<210> SEQ ID NO 307
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 307

Gly Thr Ser Ser Asp Ile Gly Gly Trp Asn Phe
1               5                   10

<210> SEQ ID NO 308
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 308

Glu Val Asn Lys Arg Pro Ser Gly Val Pro Gly Arg
1               5                   10

<210> SEQ ID NO 309
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 309

Leu Phe Gly Arg Trp Asp Val
1               5

<210> SEQ ID NO 310
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 310

Val Ser Gly Gly Ser Met Arg Gly Thr Asp Trp Gly Glu Asn Asp Phe
1               5                   10                  15

His

<210> SEQ ID NO 311
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 311

Ile His Trp Arg Gly Arg Thr Thr His Tyr Lys Thr Ser Phe Arg Ser
1               5                   10                  15

Arg

<210> SEQ ID NO 312
<211> LENGTH: 17
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 312

His Lys Tyr His Asp Ile Phe Arg Val Val Pro Val Ala Gly Trp Phe
1               5                   10                  15

Asp

<210> SEQ ID NO 313
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 313

Ala Ser Gln Asn Val Lys Asn Asn
1               5

<210> SEQ ID NO 314
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 314

Asp Ala Ser Ser Arg Ala Gly Gly Ile Pro Asp Arg
1               5                   10

<210> SEQ ID NO 315
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 315

Tyr Glu Glu Trp Pro Arg
1               5

<210> SEQ ID NO 316
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 316

Ala Ser Gly Gly Ser Ile Arg Gly Gly Glu Trp Gly Asp Ser Asp Tyr
1               5                   10                  15

His

<210> SEQ ID NO 317
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 317
```

```
Ile His Trp Arg Gly Thr Thr His Tyr Asn Ala Pro Phe Arg Gly Arg
1               5                   10                  15
```

<210> SEQ ID NO 318
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 318

```
His Lys Tyr His Asp Ile Val Met Val Val Pro Ile Ala Gly Trp Phe
1               5                   10                  15

Asp
```

<210> SEQ ID NO 319
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 319

```
Ala Ser Gln Ser Val Lys Asn Asn
1               5
```

<210> SEQ ID NO 320
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 320

```
Asp Thr Ser Ser Arg Ala Ser Gly Ile Pro Ala Arg
1               5                   10
```

<210> SEQ ID NO 321
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 321

```
Val Ser Gly Asp Ser Ile Arg Gly Gly Glu Trp Gly Asp Lys Asp Tyr
1               5                   10                  15

His
```

<210> SEQ ID NO 322
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 322

```
Ile His Trp Arg Gly Thr Thr His Tyr Lys Glu Ser Leu Arg Arg
1               5                   10                  15
```

```
<210> SEQ ID NO 323
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 323

His Arg His His Asp Val Phe Met Leu Val Pro Ile Ala Gly Trp Phe
1               5                   10                  15

Asp

<210> SEQ ID NO 324
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 324

Ala Ser Gln Asn Ile Asn Lys Asn
1               5

<210> SEQ ID NO 325
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 325

Glu Thr Tyr Ser Lys Ile Ala Ala Phe Pro Ala Arg
1               5                   10

<210> SEQ ID NO 326
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 326

Val Ser Gln Asp Ser Arg Pro Ser Asp His Ser
1               5                   10

<210> SEQ ID NO 327
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 327

Ile His Tyr Asn Gly Ala Thr Thr Tyr Asn Pro Ser Leu Arg Ser Arg
1               5                   10                  15

<210> SEQ ID NO 328
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 328

Asn Ala Ile Arg Ile Tyr Gly Val Val Ala Leu Gly Glu Trp Phe His
1               5                   10                  15

Tyr Gly Met Asp
            20

<210> SEQ ID NO 329
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 329

Gly Ala Pro Leu Thr Ser Arg Phe
1               5

<210> SEQ ID NO 330
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 330

Arg Ser Ser Gln Arg Ser Ser Gly Trp Ser Gly Arg
1               5                   10

<210> SEQ ID NO 331
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 331

Ser Asp Thr Ser Asp Ser Tyr Lys
1               5

<210> SEQ ID NO 332
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 332

Val Ser Asn Asp Ser Arg Pro Ser Asp His Ser
1               5                   10

<210> SEQ ID NO 333
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 333

Val Phe Gly Asp Ser Arg Pro Ser Asp His Ser
1               5                   10

```
<210> SEQ ID NO 334
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 334

Val His Tyr Asn Gly Asp Asn Thr Tyr Asn Pro Ser Leu Arg Gly Arg
1               5                   10                  15

<210> SEQ ID NO 335
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 335

Asn Val Ile Arg Val Phe Gly Val Ile Ser Leu Gly Glu Trp Phe His
1               5                   10                  15

Tyr Gly Met Asp
            20

<210> SEQ ID NO 336
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 336

Gly Pro Pro Leu Ala Ser Arg Tyr
1               5

<210> SEQ ID NO 337
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 337

Arg Asp Arg Gln Phe Pro Ser Gly Val Ser Gly Arg
1               5                   10

<210> SEQ ID NO 338
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 338

Ser Asp Thr Ser Asp Ser Tyr Lys
1               5

<210> SEQ ID NO 339
<211> LENGTH: 16
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 339

Val His Tyr Asn Gly Asp Thr Thr Tyr Asn Pro Ser Leu Arg Gly Arg
1               5                   10                  15

<210> SEQ ID NO 340
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 340

Gly Ala Ala Leu Thr Ser Arg Phe
1               5

<210> SEQ ID NO 341
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 341

Arg Thr Ser Gln Arg Ser Ser Gly Trp Ser Gly Arg
1               5                   10

<210> SEQ ID NO 342
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 342

Ile Ser Gly Asp Ser Arg Pro Ser Asp His Ser
1               5                   10

<210> SEQ ID NO 343
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 343

Ile His Tyr Gly Gly Asp Ile Thr Tyr Asn Pro Ser Leu Arg Ser Arg
1               5                   10                  15

<210> SEQ ID NO 344
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 344

Asn Val Ile Arg Val Phe Gly Val Ile Ala Leu Gly Glu Trp Phe His
1               5                   10                  15

Tyr Gly Met Asp

```
<210> SEQ ID NO 345
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 345

Arg Asp Arg Gln Phe Ser Ser Gly Met Ser Gly Arg
1               5                   10

<210> SEQ ID NO 346
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 346

Ser Asp Ile Asn Asp Ser Tyr Lys
1               5

<210> SEQ ID NO 347
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 347

Arg Asp Arg Gln Phe Ser Ser Gly Ile Ser Gly Arg
1               5                   10

<210> SEQ ID NO 348
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 348

Ser Asp Thr Ser Asp Ser Phe Lys
1               5

<210> SEQ ID NO 349
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 349

Gly Pro Pro Leu Ala Thr Arg Tyr
1               5

<210> SEQ ID NO 350
<211> LENGTH: 12
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 350

Arg Asp Arg Gln Phe Ser Ser Gly Val Ser Gly Arg
1               5                   10

<210> SEQ ID NO 351
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 351

Ile His Tyr Asn Gly Asp Lys Thr Tyr Asn Pro Ser Leu Arg Gly Arg
1               5                   10                  15

<210> SEQ ID NO 352
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 352

Ser Asp Asn Ser Asp Ser Phe Lys
1               5

<210> SEQ ID NO 353
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 353

Ala Ser Gly Phe Tyr Phe Pro Asp Tyr Ala
1               5                   10

<210> SEQ ID NO 354
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 354

Met Arg Gly Trp Ala Tyr Gly Gly Ser Ala Gln Phe Ala Ala Phe Ala
1               5                   10                  15

Val Gly Lys

<210> SEQ ID NO 355
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 355

Glu Gln Arg Asn Lys Asp Tyr Arg Tyr Gly Gln Glu Gly Phe Gly Tyr
1               5                   10                  15

```
Ser Tyr Gly Met Asp
            20

<210> SEQ ID NO 356
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 356

Ala Ser His Phe Ile Ala Asn Tyr
1               5

<210> SEQ ID NO 357
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 357

Glu Ser Ser Thr Leu Gln Arg Gly Val Pro Ser Arg
1               5                   10

<210> SEQ ID NO 358
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 358

Ser His Ser Pro Pro Val
1               5

<210> SEQ ID NO 359
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 359

Ala Phe Asp Phe Tyr Phe Pro Asp Tyr Ala
1               5                   10

<210> SEQ ID NO 360
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 360

Ile Arg Gly Trp Ala Tyr Gly Gln Ala Ala Gln Tyr Gly Lys Ser Ala
1               5                   10                  15

Ser Gly Arg

<210> SEQ ID NO 361
<211> LENGTH: 21
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 361

Glu Gln Arg Gly Gly Asp Gly Arg Tyr Ser Gly Asp Gly Phe Gly Tyr
1               5                   10                  15

Pro Tyr Gly Met Asp
            20

<210> SEQ ID NO 362
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 362

Gln Ser Trp Thr Leu Asn Arg Gly Ile Pro Ser Arg
1               5                   10

<210> SEQ ID NO 363
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 363

Ser His Ser Pro Pro Leu
1               5

<210> SEQ ID NO 364
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 364

Ile Arg Gly Trp Ala Tyr Gly Gln Ser Ala Gln Tyr Gly Lys Ser Ala
1               5                   10                  15

Ser Gly Arg

<210> SEQ ID NO 365
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 365

Glu Gln Arg Gly Ala Asn Gly Arg Tyr Gly Gly Asp Gly Phe Gly Tyr
1               5                   10                  15

Ser Tyr Gly Met Asp
            20

<210> SEQ ID NO 366
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 366

Glu Ser Ser Thr Leu Asn Arg Gly Val Pro Ser Arg
1               5                   10

<210> SEQ ID NO 367

<400> SEQUENCE: 367

000

<210> SEQ ID NO 368

<400> SEQUENCE: 368

000

<210> SEQ ID NO 369

<400> SEQUENCE: 369

000

<210> SEQ ID NO 370

<400> SEQUENCE: 370

000

<210> SEQ ID NO 371

<400> SEQUENCE: 371

000

<210> SEQ ID NO 372

<400> SEQUENCE: 372

000

<210> SEQ ID NO 373

<400> SEQUENCE: 373

000

<210> SEQ ID NO 374

<400> SEQUENCE: 374

000

<210> SEQ ID NO 375

<400> SEQUENCE: 375

000

<210> SEQ ID NO 376

<400> SEQUENCE: 376

000

<210> SEQ ID NO 377

<400> SEQUENCE: 377

000

<210> SEQ ID NO 378

<400> SEQUENCE: 378

000

<210> SEQ ID NO 379

<400> SEQUENCE: 379

000

<210> SEQ ID NO 380

<400> SEQUENCE: 380

000

<210> SEQ ID NO 381

<400> SEQUENCE: 381

000

<210> SEQ ID NO 382

<400> SEQUENCE: 382

000

<210> SEQ ID NO 383

<400> SEQUENCE: 383

000

<210> SEQ ID NO 384

<400> SEQUENCE: 384

000

<210> SEQ ID NO 385

<400> SEQUENCE: 385

000

<210> SEQ ID NO 386

<400> SEQUENCE: 386

000

<210> SEQ ID NO 387

<400> SEQUENCE: 387

000

<210> SEQ ID NO 388

<210> SEQ ID NO 388
<400> SEQUENCE: 388
000

<210> SEQ ID NO 389
<400> SEQUENCE: 389
000

<210> SEQ ID NO 390
<400> SEQUENCE: 390
000

<210> SEQ ID NO 391
<400> SEQUENCE: 391
000

<210> SEQ ID NO 392
<400> SEQUENCE: 392
000

<210> SEQ ID NO 393
<400> SEQUENCE: 393
000

<210> SEQ ID NO 394
<400> SEQUENCE: 394
000

<210> SEQ ID NO 395
<400> SEQUENCE: 395
000

<210> SEQ ID NO 396
<400> SEQUENCE: 396
000

<210> SEQ ID NO 397
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 397

Ala Gln Gln Gly Lys Arg Ile Tyr Gly Ile Val Ser Phe Gly Glu Phe
1               5                   10                  15

Phe Tyr Tyr Tyr Tyr Met Asp
            20

```
<210> SEQ ID NO 398
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 398

Arg Thr Ser
1

<210> SEQ ID NO 399
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 399

Asp Val Asn
1

<210> SEQ ID NO 400
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 400

Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
            20                  25                  30

Tyr Trp Ser Trp Ile Arg Arg Ser Pro Gly Lys Gly Leu Glu Trp Ile
        35                  40                  45

Gly Tyr Val His Lys Ser Gly Asp Thr Asn Tyr Ser Pro Ser Leu Lys
    50                  55                  60

Ser Arg Val Asn Leu Ser Leu Asp Thr Ser Lys Asn Gln Val Ser Leu
65                  70                  75                  80

Ser Leu Val Ala Ala Thr Ala Ala Asp Ser Gly Lys Tyr Tyr Cys Ala
                85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Asn Gly Thr Gln Val
        115                 120                 125

Thr Val Ser Ser
    130

<210> SEQ ID NO 401
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 401

Ser Asp Ile Ser Val Ala Pro Gly Glu Thr Ala Arg Ile Ser Cys Gly
1               5                   10                  15
```

```
Glu Lys Ser Leu Gly Ser Arg Ala Val Gln Trp Tyr Gln His Arg Ala
             20                  25                  30

Gly Gln Ala Pro Ser Leu Ile Ile Tyr Asn Asn Gln Asp Arg Pro Ser
         35                  40                  45

Gly Ile Pro Glu Arg Phe Ser Gly Ser Pro Asp Ser Pro Phe Gly Thr
     50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Val Pro Thr Lys Trp Val Phe
                 85                  90                  95

Gly Gly Gly Thr Thr Leu Thr Val Leu
            100                 105

<210> SEQ ID NO 402
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 402

Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
             20                  25                  30

Tyr Trp Ser Trp Ile Arg Arg Ser Pro Gly Lys Gly Leu Glu Trp Ile
         35                  40                  45

Gly Tyr Val His Lys Ser Gly Asp Thr Asn Tyr Asn Pro Ser Leu Lys
     50                  55                  60

Ser Arg Val His Leu Ser Leu Asp Thr Ser Lys Asn Gln Val Ser Leu
65                  70                  75                  80

Ser Leu Thr Gly Val Thr Ala Ala Asp Ser Gly Lys Tyr Tyr Cys Ala
                 85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Thr Gly Thr Gln Val
        115                 120                 125

Thr Val Ser Ser
        130

<210> SEQ ID NO 403
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 403

Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln His Arg Ala
             20                  25                  30

Gly Gln Ala Pro Ser Leu Ile Ile Tyr Asn Asn Gln Asp Arg Pro Ser
         35                  40                  45

Gly Ile Pro Glu Arg Phe Ser Gly Ser Pro Asp Phe Arg Pro Gly Thr
     50                  55                  60
```

```
Thr Ala Thr Leu Thr Ile Thr Ser Val Glu Ala Gly Asp Glu Ala Asp
 65                  70                  75                  80

Tyr Tyr Cys His Ile Trp Asp Ser Arg Val Pro Thr Lys Trp Val Phe
                 85                  90                  95

Gly Gly Gly Thr Thr Leu Thr Val Leu
            100                 105

<210> SEQ ID NO 404
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 404

Ser Asp Ile Ser Val Ala Pro Gly Glu Thr Ala Arg Ile Ser Cys Gly
 1               5                  10                  15

Glu Lys Ser Leu Gly Ser Arg Ala Val Gln Trp Tyr Gln His Arg Ala
                20                  25                  30

Gly Gln Ala Pro Ser Leu Ile Ile Tyr Asn Asn Gln Asp Arg Pro Ser
             35                  40                  45

Gly Ile Pro Glu Arg Phe Ser Gly Ser Pro Asp Ser Arg Pro Gly Thr
         50                  55                  60

Thr Ala Thr Leu Thr Ile Thr Ser Val Glu Ala Gly Asp Glu Ala Asp
 65                  70                  75                  80

Tyr Tyr Cys His Ile Trp Asp Ser Arg Val Pro Thr Lys Trp Val Phe
                 85                  90                  95

Gly Gly Gly Thr Thr Leu Thr Val Leu
            100                 105

<210> SEQ ID NO 405
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 405

Gln Val Gln Leu Gln Glu Ser Gly Pro Gly Leu Val Lys Pro Ser Glu
 1               5                  10                  15

Thr Leu Ser Val Thr Cys Ser Val Ser Gly Asp Ser Met Asn Asn Tyr
                20                  25                  30

Tyr Trp Thr Trp Ile Arg Gln Ser Pro Gly Lys Gly Leu Glu Trp Ile
             35                  40                  45

Gly Tyr Ile Ser Asp Arg Glu Ser Ala Thr Tyr Asn Pro Ser Leu Asn
         50                  55                  60

Ser Arg Val Val Ile Ser Arg Asp Thr Ser Lys Asn Gln Leu Ser Leu
 65                  70                  75                  80

Lys Leu Asn Ser Val Thr Pro Ala Asp Thr Ala Val Tyr Tyr Cys Ala
                 85                  90                  95

Thr Ala Arg Arg Gly Gln Arg Ile Tyr Gly Val Val Ser Phe Gly Glu
            100                 105                 110

Phe Phe Tyr Tyr Tyr Ser Met Asp Val Trp Gly Lys Gly Thr Thr Val
        115                 120                 125

Thr Val Ser Ser
    130
```

<210> SEQ ID NO 406
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 406

Ser Tyr Val Arg Pro Leu Ser Val Ala Leu Gly Glu Thr Ala Arg Ile
1               5                   10                  15

Ser Cys Gly Arg Gln Ala Leu Gly Ser Arg Ala Val Gln Trp Tyr Gln
                20                  25                  30

His Arg Pro Gly Gln Ala Pro Ile Leu Leu Ile Tyr Asn Asn Gln Asp
            35                  40                  45

Arg Pro Ser Gly Ile Pro Glu Arg Phe Ser Gly Thr Pro Asp Ile Asn
        50                  55                  60

Phe Gly Thr Arg Ala Thr Leu Thr Ile Ser Gly Val Glu Ala Gly Asp
65                  70                  75                  80

Glu Ala Asp Tyr Tyr Cys His Met Trp Asp Ser Arg Ser Gly Phe Ser
                85                  90                  95

Trp Ser Phe Gly Gly Ala Thr Arg Leu Thr Val Leu
            100                 105

<210> SEQ ID NO 407
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 407

Gln Val Gln Leu Gln Glu Ser Gly Pro Gly Leu Val Arg Pro Ser Glu
1               5                   10                  15

Thr Leu Ser Val Thr Cys Ile Val Ser Gly Gly Ser Ile Ser Asn Tyr
                20                  25                  30

Tyr Trp Thr Trp Ile Arg Gln Ser Pro Gly Lys Gly Leu Glu Trp Ile
            35                  40                  45

Gly Tyr Ile Ser Asp Arg Glu Thr Thr Thr Tyr Asn Pro Ser Leu Asn
        50                  55                  60

Ser Arg Ala Val Ile Ser Arg Asp Thr Ser Lys Asn Gln Leu Ser Leu
65                  70                  75                  80

Gln Leu Arg Ser Val Thr Thr Ala Asp Thr Ala Ile Tyr Phe Cys Ala
                85                  90                  95

Thr Ala Arg Arg Gly Gln Arg Ile Tyr Gly Val Val Ser Phe Gly Glu
            100                 105                 110

Phe Phe Tyr Tyr Tyr Tyr Met Asp Val Trp Gly Lys Gly Thr Ala Val
        115                 120                 125

Thr Val Ser Ser
        130

<210> SEQ ID NO 408
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 408

Ser Tyr Val Ser Pro Leu Ser Val Ala Leu Gly Glu Thr Ala Arg Ile
1               5                   10                  15

Ser Cys Gly Arg Gln Ala Leu Gly Ser Arg Ala Val Gln Trp Tyr Gln
                20                  25                  30

His Lys Pro Gly Gln Ala Pro Ile Leu Leu Ile Tyr Asn Asn Gln Asp
            35                  40                  45

Arg Pro Ser Gly Ile Pro Glu Arg Phe Ser Gly Thr Pro Asp Ile Asn
50                  55                  60

Phe Gly Thr Thr Ala Thr Leu Thr Ile Ser Gly Val Glu Val Gly Asp
65                  70                  75                  80

Glu Ala Asp Tyr Tyr Cys His Met Trp Asp Ser Arg Ser Gly Phe Ser
                85                  90                  95

Trp Ser Phe Gly Gly Ala Thr Arg Leu Thr Val
                100                 105

<210> SEQ ID NO 409
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 409

Gln Val His Leu Gln Glu Ser Gly Pro Gly Leu Val Thr Pro Ser Glu
1               5                   10                  15

Thr Leu Ser Leu Thr Cys Thr Val Ser Asn Gly Ser Val Ser Gly Arg
                20                  25                  30

Phe Trp Ser Trp Ile Arg Gln Ser Pro Gly Arg Gly Leu Glu Trp Ile
            35                  40                  45

Gly Tyr Phe Ser Asp Thr Asp Arg Ser Glu Tyr Asn Pro Ser Leu Arg
50                  55                  60

Ser Arg Leu Thr Leu Ser Val Asp Arg Ser Lys Asn Gln Leu Ser Leu
65                  70                  75                  80

Arg Leu Lys Ser Val Thr Ala Ala Asp Ser Ala Thr Tyr Tyr Cys Ala
                85                  90                  95

Arg Ala Gln Gln Gly Lys Arg Ile Tyr Gly Ile Val Ser Phe Gly Glu
                100                 105                 110

Phe Phe Tyr Tyr Tyr Tyr Met Asp Ala Trp Gly Lys Gly Thr Pro Val
            115                 120                 125

Thr Val Ser Ser
    130

<210> SEQ ID NO 410
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 410

Ser Leu Asn Pro Leu Ser Leu Ala Pro Gly Ala Thr Ala Lys Ile Pro
1               5                   10                  15

Cys Gly Glu Arg Ser Arg Gly Ser Arg Ala Val Gln Trp Tyr Gln Gln
                20                  25                  30

Lys Pro Gly Gln Ala Pro Thr Leu Ile Ile Tyr Asn Asn Gln Asp Arg

```
                35                  40                  45
Pro Ala Gly Val Ser Glu Arg Phe Ser Gly Asn Pro Asp Val Ala Ile
            50                  55                  60
Gly Val Thr Ala Thr Leu Thr Ile Ser Arg Val Glu Val Gly Asp Glu
65                  70                  75                  80
Ala Asp Tyr Tyr Cys His Tyr Trp Asp Ser Arg Ser Pro Ile Ser Trp
                85                  90                  95
Ile Phe Gly Gly Gly Thr Gln Leu Thr Val Leu
            100                 105

<210> SEQ ID NO 411
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 411

Gln Val His Leu Gln Glu Ser Gly Pro Gly Leu Val Thr Pro Ser Glu
1               5                   10                  15
Thr Leu Ser Leu Thr Cys Thr Val Ser Asn Gly Ser Val Ser Gly Arg
            20                  25                  30
Phe Trp Ser Trp Ile Arg Gln Ser Pro Gly Arg Gly Leu Glu Trp Ile
        35                  40                  45
Gly Tyr Phe Ser Asp Thr Asp Arg Ser Glu Tyr Asn Pro Ser Leu Arg
    50                  55                  60
Ser Arg Leu Thr Leu Ser Val Asp Arg Ser Lys Asn Gln Leu Ser Leu
65                  70                  75                  80
Lys Leu Lys Ser Val Thr Ala Ala Asp Ser Ala Thr Tyr Tyr Cys Ala
                85                  90                  95
Arg Ala Gln Gln Gly Lys Arg Ile Tyr Gly Ile Val Ser Phe Gly Glu
            100                 105                 110
Leu Phe Tyr Tyr Tyr Tyr Met Asp Ala Trp Gly Lys Gly Thr Pro Val
        115                 120                 125
Thr Val Ser Ser
    130

<210> SEQ ID NO 412
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 412

Ser Leu Asn Pro Leu Ser Leu Ala Pro Gly Ala Thr Ala Lys Ile Pro
1               5                   10                  15
Cys Gly Glu Arg Ser Arg Gly Ser Arg Ala Val Gln Trp Tyr Gln Gln
            20                  25                  30
Lys Pro Gly Gln Ala Pro Thr Leu Ile Ile Tyr Asn Asn Gln Asp Arg
        35                  40                  45
Pro Ala Gly Val Ser Glu Arg Phe Ser Gly Asn Pro Asp Val Ala Ile
    50                  55                  60
Gly Val Thr Ala Thr Leu Thr Ile Ser Arg Val Glu Val Gly Asp Glu
65                  70                  75                  80
Gly Asp Tyr Tyr Cys His Tyr Trp Asp Ser Arg Ser Pro Ile Ser Trp
```

Ile Phe Ala Gly Gly Thr Gln Leu Thr Val Leu
            100                 105

<210> SEQ ID NO 413
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 413

Gln Val His Leu Gln Glu Ser Gly Pro Gly Leu Val Lys Pro Ser Glu
1               5                   10                  15

Thr Leu Ser Leu Thr Cys Asn Val Ser Gly Thr Leu Val Arg Asp Asn
            20                  25                  30

Tyr Trp Ser Trp Ile Arg Gln Pro Leu Gly Lys Gln Pro Glu Trp Ile
        35                  40                  45

Gly Tyr Val His Asp Ser Gly Asp Thr Asn Tyr Asn Pro Ser Leu Lys
    50                  55                  60

Ser Arg Val His Leu Ser Leu Asp Lys Ser Lys Asn Leu Val Ser Leu
65                  70                  75                  80

Arg Leu Thr Gly Val Thr Ala Ala Asp Ser Ala Ile Tyr Tyr Cys Ala
                85                  90                  95

Thr Thr Lys His Gly Arg Arg Ile Tyr Gly Val Val Ala Phe Lys Glu
            100                 105                 110

Trp Phe Thr Tyr Phe Tyr Met Asp Val Trp Gly Lys Gly Thr Ser Val
        115                 120                 125

Thr Val Ser Ser
    130

<210> SEQ ID NO 414
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 414

Thr Phe Val Ser Val Ala Pro Gly Gln Thr Ala Arg Ile Thr Cys Gly
1               5                   10                  15

Glu Glu Ser Leu Gly Ser Arg Ser Val Ile Trp Tyr Gln Gln Arg Pro
            20                  25                  30

Gly Gln Ala Pro Ser Leu Ile Ile Tyr Asn Asn Asn Asp Arg Pro Ser
        35                  40                  45

Gly Ile Pro Asp Arg Phe Ser Gly Ser Pro Gly Ser Thr Phe Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Arg Pro Thr Asn Trp Val Phe
                85                  90                  95

Gly Glu Gly Thr Thr Leu Ile Val Leu
            100                 105

<210> SEQ ID NO 415
<211> LENGTH: 132
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 415

```
Gln Leu His Leu Gln Glu Ser Gly Pro Gly Leu Val Lys Pro Pro Glu
1               5                   10                  15

Thr Leu Ser Leu Thr Cys Ser Val Ser Gly Ala Ser Ile Asn Asp Ala
            20                  25                  30

Tyr Trp Ser Trp Ile Arg Gln Ser Pro Gly Lys Arg Pro Glu Trp Val
        35                  40                  45

Gly Tyr Val His His Ser Gly Asp Thr Asn Tyr Asn Pro Ser Leu Lys
    50                  55                  60

Arg Arg Val Thr Phe Ser Leu Asp Thr Ala Lys Asn Glu Val Ser Leu
65                  70                  75                  80

Lys Leu Val Asp Leu Thr Ala Ala Asp Ser Ala Thr Tyr Phe Cys Ala
                85                  90                  95

Arg Ala Leu His Gly Lys Arg Ile Tyr Gly Ile Val Ala Leu Gly Glu
            100                 105                 110

Leu Phe Thr Tyr Phe Tyr Met Asp Val Trp Gly Lys Gly Thr Ala Val
        115                 120                 125

Thr Val Ser Ser
    130
```

<210> SEQ ID NO 416
<211> LENGTH: 105
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 416

```
Ser Ser Met Ser Val Ser Pro Gly Glu Thr Ala Lys Ile Ser Cys Gly
1               5                   10                  15

Lys Glu Ser Ile Gly Ser Arg Ala Val Gln Trp Tyr Gln Gln Lys Pro
            20                  25                  30

Gly Gln Pro Pro Ser Leu Ile Ile Tyr Asn Asn Gln Asp Arg Pro Ala
        35                  40                  45

Gly Val Pro Glu Arg Phe Ser Ala Ser Pro Asp Phe Arg Pro Gly Thr
    50                  55                  60

Thr Ala Thr Leu Thr Ile Thr Asn Val Asp Ala Glu Asp Glu Ala Asp
65                  70                  75                  80

Tyr Tyr Cys His Ile Tyr Asp Ala Arg Gly Gly Thr Asn Trp Val Phe
                85                  90                  95

Asp Arg Gly Thr Thr Leu Thr Val Leu
            100                 105
```

<210> SEQ ID NO 417
<211> LENGTH: 135
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 417

```
Gln Ser Gln Leu Gln Glu Ser Gly Pro Arg Leu Val Glu Ala Ser Glu
1               5                   10                  15
```

```
Thr Leu Ser Leu Thr Cys Asn Val Ser Gly Glu Ser Thr Gly Ala Cys
            20                  25                  30

Thr Tyr Phe Trp Gly Trp Val Arg Gln Ala Pro Gly Lys Gly Leu Glu
            35                  40                  45

Trp Ile Gly Ser Leu Ser His Cys Gln Ser Phe Trp Gly Ser Gly Trp
        50                  55                  60

Thr Phe His Asn Pro Ser Leu Lys Ser Arg Leu Thr Ile Ser Leu Asp
65                  70                  75                  80

Thr Pro Lys Asn Gln Val Phe Leu Lys Leu Thr Ser Leu Thr Ala Ala
                85                  90                  95

Asp Thr Ala Thr Tyr Tyr Cys Ala Arg Phe Asp Gly Glu Val Leu Val
            100                 105                 110

Tyr Asn His Trp Pro Lys Pro Ala Trp Val Asp Leu Trp Gly Arg Gly
        115                 120                 125

Ile Pro Val Thr Val Ser Ser
        130                 135

<210> SEQ ID NO 418
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 418

Gln Ser Ala Leu Thr Gln Pro Pro Ser Ala Ser Gly Ser Pro Gly Gln
1               5                   10                  15

Ser Ile Thr Ile Ser Cys Asn Gly Thr Ala Thr Asn Phe Val Ser Trp
            20                  25                  30

Tyr Gln Gln Phe Pro Asp Lys Ala Pro Lys Leu Ile Ile Phe Gly Val
            35                  40                  45

Asp Lys Arg Pro Pro Gly Val Pro Asp Arg Phe Ser Gly Ser Arg Ser
        50                  55                  60

Gly Thr Thr Ala Ser Leu Thr Val Ser Arg Leu Gln Thr Asp Asp Glu
65                  70                  75                  80

Ala Val Tyr Tyr Cys Gly Ser Leu Val Gly Asn Trp Asp Val Ile Phe
                85                  90                  95

Gly Gly Gly Thr Thr Leu Thr Val Leu
            100                 105

<210> SEQ ID NO 419
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 419

Gln Pro Gln Leu Gln Glu Ser Gly Pro Gly Leu Val Glu Ala Ser Glu
1               5                   10                  15

Thr Leu Ser Leu Thr Cys Thr Val Ser Gly Asp Ser Thr Ala Ala Cys
            20                  25                  30

Asp Tyr Phe Trp Gly Trp Val Arg Gln Pro Pro Gly Lys Gly Leu Glu
            35                  40                  45

Trp Ile Gly Gly Leu Ser His Cys Ala Gly Tyr Tyr Asn Thr Gly Trp
        50                  55                  60
```

Thr Tyr His Asn Pro Ser Leu Lys Ser Arg Leu Thr Ile Ser Leu Asp
65                  70                  75                  80

Thr Pro Lys Asn Gln Val Phe Leu Lys Leu Asn Ser Val Thr Ala Ala
                85                  90                  95

Asp Thr Ala Ile Tyr Tyr Cys Ala Arg Phe Asp Gly Glu Val Leu Val
            100                 105                 110

Tyr His Asp Trp Pro Lys Pro Ala Trp Val Asp Leu Trp Gly Arg Gly
        115                 120                 125

Thr Leu Val Thr Val Ser Ser
        130                 135

<210> SEQ ID NO 420
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 420

Gln Ser Ala Leu Thr Gln Pro Pro Ser Ala Ser Gly Ser Pro Gly Gln
1               5                   10                  15

Ser Ile Ser Ile Ser Cys Thr Gly Thr Ser Asn Arg Phe Val Ser Trp
            20                  25                  30

Tyr Gln Gln His Pro Gly Lys Ala Pro Lys Leu Val Ile Tyr Gly Val
        35                  40                  45

Asn Lys Arg Pro Ser Gly Val Pro Asp Arg Phe Ser Gly Ser Lys Ser
50                  55                  60

Gly Asn Thr Ala Ser Leu Thr Val Ser Gly Leu Gln Thr Asp Asp Glu
65                  70                  75                  80

Ala Val Tyr Tyr Cys Ser Ser Leu Val Gly Asn Trp Asp Val Ile Phe
            85                  90                  95

Gly Gly Gly Thr Lys Leu Thr Val Leu
            100                 105

<210> SEQ ID NO 421
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 421

Gln Leu Gln Met Gln Glu Ser Gly Pro Gly Leu Val Lys Pro Ser Glu
1               5                   10                  15

Thr Leu Ser Leu Ser Cys Thr Val Ser Gly Asp Ser Ile Arg Gly Gly
            20                  25                  30

Glu Trp Gly Asp Lys Asp Tyr His Trp Gly Trp Val Arg His Ser Ala
        35                  40                  45

Gly Lys Gly Leu Glu Trp Ile Gly Ser Ile His Trp Arg Gly Thr Thr
50                  55                  60

His Tyr Lys Glu Ser Leu Arg Arg Val Ser Met Ser Ile Asp Thr
65                  70                  75                  80

Ser Arg Asn Trp Phe Ser Leu Arg Leu Ala Ser Val Thr Ala Ala Asp
            85                  90                  95

Thr Ala Val Tyr Phe Cys Ala Arg His Arg His His Asp Val Phe Met
            100                 105                 110

Leu Val Pro Ile Ala Gly Trp Phe Asp Val Trp Gly Pro Gly Val Gln
            115                 120                 125

Val Thr Val Ser Ser
    130

<210> SEQ ID NO 422
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 422

Glu Ile Val Met Thr Gln Ser Pro Asp Thr Leu Ser Val Ser Pro Gly
1               5                   10                  15

Glu Thr Val Thr Leu Ser Cys Arg Ala Ser Gln Asn Ile Asn Lys Asn
            20                  25                  30

Leu Ala Trp Tyr Gln Tyr Lys Pro Gly Gln Ser Pro Arg Leu Val Ile
        35                  40                  45

Phe Glu Thr Tyr Ser Lys Ile Ala Ala Phe Pro Ala Arg Phe Val Ala
    50                  55                  60

Ser Gly Ser Gly Thr Glu Phe Thr Leu Thr Ile Asn Asn Met Gln Ser
65                  70                  75                  80

Glu Asp Val Ala Val Tyr Tyr Cys Gln Gln Tyr Glu Glu Trp Pro Arg
                85                  90                  95

Thr Phe Gly Gln Gly Thr Lys Val Asp Ile Lys
            100                 105

<210> SEQ ID NO 423
<211> LENGTH: 134
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 423

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Met Arg Gly Thr
            20                  25                  30

Asp Trp Gly Glu Asn Asp Phe His Tyr Gly Trp Ile Arg Gln Ser Ser
        35                  40                  45

Ala Lys Gly Leu Glu Trp Ile Gly Ser Ile His Trp Arg Gly Arg Thr
    50                  55                  60

Thr His Tyr Lys Thr Ser Phe Arg Ser Arg Ala Thr Leu Ser Ile Asp
65                  70                  75                  80

Thr Ser Asn Asn Arg Phe Ser Leu Thr Phe Ser Phe Val Thr Ala Ala
                85                  90                  95

Asp Thr Ala Val Tyr Tyr Cys Ala Arg His Lys Tyr His Asp Ile Phe
            100                 105                 110

Arg Val Val Pro Val Ala Gly Trp Phe Asp Pro Trp Gly Gln Gly Leu
        115                 120                 125

Leu Val Thr Val Ser Ser
    130

<210> SEQ ID NO 424

```
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 424

Glu Ile Val Met Thr Gln Ser Pro Pro Thr Leu Ser Val Ser Pro Gly
1               5                   10                  15

Glu Thr Ala Thr Leu Ser Cys Arg Ala Ser Gln Asn Val Lys Asn Asn
            20                  25                  30

Leu Ala Trp Tyr Gln Leu Lys Pro Gly Gln Ala Pro Arg Leu Leu Ile
        35                  40                  45

Phe Asp Ala Ser Ser Arg Ala Gly Gly Ile Pro Asp Arg Phe Ser Gly
    50                  55                  60

Ser Gly Tyr Gly Thr Asp Phe Thr Leu Thr Val Asn Ser Val Gln Ser
65                  70                  75                  80

Glu Asp Phe Gly Asp Tyr Phe Cys Gln Gln Tyr Glu Glu Trp Pro Arg
                85                  90                  95

Thr Phe Gly Gln Gly Thr Lys Val Asp Ile Lys
            100                 105

<210> SEQ ID NO 425
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 425

Glu Val His Leu Glu Glu Ser Gly Pro Gly Leu Val Arg Pro Ser Glu
1               5                   10                  15

Thr Leu Ser Leu Thr Cys Thr Ala Ser Gly Gly Ser Ile Arg Gly Gly
            20                  25                  30

Glu Trp Gly Asp Ser Asp Tyr His Trp Gly Trp Val Arg His Ser Pro
        35                  40                  45

Glu Lys Gly Leu Glu Trp Ile Gly Ser Ile His Trp Arg Gly Thr Thr
    50                  55                  60

His Tyr Asn Ala Pro Phe Arg Gly Arg Gly Arg Leu Ser Ile Asp Leu
65                  70                  75                  80

Ser Arg Asn Gln Phe Ser Leu Arg Leu Thr Ser Val Thr Ala Glu Asp
                85                  90                  95

Thr Ala Val Tyr Tyr Cys Val Lys His Lys Tyr His Asp Ile Val Met
            100                 105                 110

Val Val Pro Ile Ala Gly Trp Phe Asp Pro Trp Gly Gln Gly Leu Gln
        115                 120                 125

Val Thr Val Ser Ser
        130

<210> SEQ ID NO 426
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 426
```

Glu Ile Met Met Thr Gln Ser Pro Ala Ile Leu Ser Val Ser Pro Gly
1               5                   10                  15

Asp Arg Ala Thr Leu Ser Cys Arg Ala Ser Gln Ser Val Lys Asn Asn
            20                  25                  30

Leu Ala Trp Tyr Gln Lys Arg Pro Gly Gln Ala Pro Arg Leu Leu Ile
        35                  40                  45

Phe Asp Thr Ser Ser Arg Ala Ser Gly Ile Pro Ala Arg Phe Ser Gly
    50                  55                  60

Gly Gly Ser Gly Thr Glu Phe Thr Leu Thr Val Asn Ser Met Gln Ser
65                  70                  75                  80

Glu Asp Phe Ala Thr Tyr Tyr Cys Gln Gln Tyr Glu Glu Trp Pro Arg
                85                  90                  95

Thr Phe Gly Gln Gly Thr Lys Val Glu Ile Lys
            100                 105

<210> SEQ ID NO 427
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 427

Gln Pro Gln Leu Gln Glu Ser Gly Pro Gly Leu Val Glu Ala Ser Glu
1               5                   10                  15

Thr Leu Ser Leu Thr Cys Thr Val Ser Gly Asp Ser Thr Ala Ala Cys
            20                  25                  30

Asp Tyr Phe Trp Gly Trp Val Arg Gln Pro Pro Gly Lys Gly Leu Glu
        35                  40                  45

Trp Ile Gly Ser Leu Ser His Cys Ala Gly Tyr Tyr Asn Ser Gly Trp
    50                  55                  60

Thr Tyr His Asn Pro Ser Leu Lys Ser Arg Leu Thr Ile Ser Leu Asp
65                  70                  75                  80

Thr Pro Lys Asn Gln Val Phe Leu Lys Leu Asn Ser Val Thr Ala Ala
                85                  90                  95

Asp Thr Ala Ile Tyr Tyr Cys Ala Arg Phe Gly Gly Asp Val Leu Val
            100                 105                 110

Tyr His Asp Trp Pro Lys Pro Ala Trp Val Asp Leu Trp Gly Arg Gly
        115                 120                 125

Val Leu Val Thr Val Ser Ser
        130                 135

<210> SEQ ID NO 428
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 428

Gln Ser Ala Leu Thr Gln Pro Pro Ser Ala Ser Gly Ser Pro Gly Gln
1               5                   10                  15

Ser Ile Thr Ile Ser Cys Thr Gly Asn Ile Asn Asn Phe Val Ser Trp
            20                  25                  30

Tyr Gln Gln His Pro Gly Lys Ala Pro Lys Leu Val Ile Tyr Gly Val
        35                  40                  45

Asn Lys Arg Pro Ser Gly Val Pro Asp Arg Phe Ser Gly Ser Lys Ser
            50                  55                  60

Gly Asn Ala Ala Ser Leu Thr Val Ser Gly Leu Gln Thr Asp Asp Glu
65                  70                  75                  80

Ala Val Tyr Tyr Cys Gly Ser Leu Ala Gly Asn Trp Asp Val Val Phe
                85                  90                  95

Gly Gly Gly Thr Lys Leu Thr Val Leu
            100                 105

<210> SEQ ID NO 429
<211> LENGTH: 135
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 429

Gln Pro Gln Leu Gln Glu Ser Gly Pro Thr Leu Val Glu Ala Ser Glu
1               5                   10                  15

Thr Leu Ser Leu Thr Cys Ala Val Ser Gly Asp Ser Thr Ala Ala Cys
            20                  25                  30

Asn Ser Phe Trp Gly Trp Val Arg Gln Pro Pro Gly Lys Gly Leu Glu
        35                  40                  45

Trp Val Gly Ser Leu Ser His Cys Ala Ser Tyr Trp Asn Arg Gly Trp
    50                  55                  60

Thr Tyr His Asn Pro Ser Leu Lys Ser Arg Leu Thr Leu Ala Leu Asp
65                  70                  75                  80

Thr Pro Lys Asn Leu Val Phe Leu Lys Leu Asn Ser Val Thr Ala Ala
                85                  90                  95

Asp Thr Ala Thr Tyr Tyr Cys Ala Arg Phe Gly Gly Glu Val Leu Arg
            100                 105                 110

Tyr Thr Asp Trp Pro Lys Pro Ala Trp Val Asp Leu Trp Gly Arg Gly
        115                 120                 125

Thr Leu Val Thr Val Ser Ser
    130                 135

<210> SEQ ID NO 430
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 430

Gln Ser Ala Leu Thr Gln Pro Pro Ser Ala Ser Gly Ser Pro Gly Gln
1               5                   10                  15

Ser Ile Thr Ile Ser Cys Thr Gly Thr Ser Asn Asn Phe Val Ser Trp
            20                  25                  30

Tyr Gln Gln His Ala Gly Lys Ala Pro Lys Leu Val Ile Tyr Asp Val
        35                  40                  45

Asn Lys Arg Pro Ser Gly Val Pro Asp Arg Phe Ser Gly Ser Lys Ser
    50                  55                  60

Gly Asn Thr Ala Ser Leu Thr Val Ser Gly Leu Gln Thr Asp Asp Glu
65                  70                  75                  80

Ala Val Tyr Tyr Cys Gly Ser Leu Val Gly Asn Trp Asp Val Ile Phe
                85                  90                  95

```
Gly Gly Gly Thr Lys Leu Thr Val Leu
        100                 105
```

<210> SEQ ID NO 431
<211> LENGTH: 135
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 431

```
Gln Pro Gln Leu Gln Glu Ser Gly Pro Gly Leu Val Glu Ala Ser Glu
1               5                   10                  15

Thr Leu Ser Leu Thr Cys Thr Val Ser Gly Asp Ser Thr Ala Gly Cys
            20                  25                  30

Asp Tyr Phe Trp Gly Trp Val Arg Gln Pro Pro Gly Lys Gly Leu Glu
        35                  40                  45

Trp Ile Gly Gly Leu Ser His Cys Ala Gly Tyr Tyr Asn Thr Gly Trp
    50                  55                  60

Thr Tyr His Asn Pro Ser Leu Lys Ser Arg Leu Thr Ile Ser Leu Asp
65                  70                  75                  80

Thr Pro Lys Asn Gln Val Phe Leu Lys Leu Asn Ser Val Thr Ala Ala
                85                  90                  95

Asp Thr Ala Ile Tyr Tyr Cys Ala Arg Phe Asp Gly Glu Val Leu Val
            100                 105                 110

Tyr Asn Asp Trp Pro Lys Pro Ala Trp Val Asp Leu Trp Gly Arg Gly
        115                 120                 125

Thr Leu Val Thr Val Ser Ser
        130                 135
```

<210> SEQ ID NO 432
<211> LENGTH: 105
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 432

```
Gln Ser Ala Leu Thr Gln Pro Pro Ser Ala Ser Gly Ser Pro Gly Gln
1               5                   10                  15

Ser Ile Thr Ile Ser Cys Thr Gly Thr Ser Asn Asn Phe Val Ser Trp
            20                  25                  30

Tyr Gln Gln His Pro Ala Lys Ala Pro Lys Leu Val Ile Tyr Gly Val
        35                  40                  45

Asn Lys Arg Pro Ser Gly Val Pro Asp Arg Phe Ser Gly Ser Lys Ser
    50                  55                  60

Gly Asn Thr Ala Ser Leu Thr Val Ser Gly Leu Gln Thr Asp Asp Glu
65                  70                  75                  80

Ala Val Tyr Tyr Cys Gly Ser Leu Val Gly Asn Trp Asp Val Ile Phe
                85                  90                  95

Gly Gly Gly Thr Lys Leu Thr Val Leu
        100                 105
```

<210> SEQ ID NO 433
<211> LENGTH: 129
<212> TYPE: PRT
<213> ORGANISM: Artificial Sequence
<220> FEATURE:

<223> OTHER INFORMATION: Description of Artificial Sequence: Synthetic
    polypeptide

<400> SEQUENCE: 433

Gln Val Gln Leu Gln Glu Ser Gly Pro Gly Leu Val Lys Pro Ala Glu
1               5                   10                  15

Thr Leu Ser Leu Thr Cys Ser Val Ser Gly Glu Ser Ile Asn Thr Gly
            20                  25                  30

His Tyr Tyr Trp Gly Trp Val Arg Gln Val Pro Gly Lys Gly Leu Glu
        35                  40                  45

Trp Ile Gly His Ile His Tyr Thr Thr Ala Val Leu His Asn Pro Ser
    50                  55                  60

Leu Lys Ser Arg Leu Thr Ile Lys Ile Tyr Thr Leu Arg Asn Gln Ile
65                  70                  75                  80

Thr Leu Arg Leu Ser Asn Val Thr Ala Ala Asp Thr Ala Val Tyr His
                85                  90                  95

Cys Val Arg Ser Gly Gly Asp Ile Leu Tyr Tyr Tyr Glu Trp Gln Lys
            100                 105                 110

Pro His Trp Phe Ser Pro Trp Gly Pro Gly Ile His Val Thr Val Ser
        115                 120                 125

Ser

<210> SEQ ID NO 434
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 434

Gln Ser Ala Leu Thr Gln Pro Pro Ser Ala Ser Gly Ser Leu Gly Gln
1               5                   10                  15

Ser Val Thr Ile Ser Cys Asn Gly Thr Ser Ser Asp Ile Gly Gly Trp
            20                  25                  30

Asn Phe Val Ser Trp Tyr Gln Gln Phe Pro Gly Arg Ala Pro Arg Leu
        35                  40                  45

Ile Ile Phe Glu Val Asn Lys Arg Pro Ser Gly Val Pro Gly Arg Phe
    50                  55                  60

Ser Gly Ser Lys Ser Gly Asn Ser Ala Ser Leu Thr Val Ser Gly Leu
65                  70                  75                  80

Gln Ser Asp Asp Glu Gly Gln Tyr Phe Cys Ser Ser Leu Phe Gly Arg
                85                  90                  95

Trp Asp Val Val Phe Gly Gly Gly Thr Lys Leu Thr Val Leu
            100                 105                 110

<210> SEQ ID NO 435
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 435

Gln Val Gln Leu Arg Glu Ser Gly Pro Gly Leu Val Lys Pro Ser Glu
1               5                   10                  15

Thr Leu Ser Leu Ser Cys Thr Val Ser Gln Asp Ser Arg Pro Ser Asp
            20                  25                  30

His Ser Trp Thr Trp Val Arg Gln Ser Pro Gly Lys Ala Leu Glu Trp
            35                  40                  45

Ile Gly Asp Ile His Tyr Asn Gly Ala Thr Thr Tyr Asn Pro Ser Leu
    50                  55                  60

Arg Ser Arg Val Arg Ile Glu Leu Asp Gln Ser Ile Pro Arg Phe Ser
65                  70                  75                  80

Leu Lys Met Thr Ser Met Thr Ala Ala Asp Thr Gly Met Tyr Tyr Cys
                85                  90                  95

Ala Arg Asn Ala Ile Arg Ile Tyr Gly Val Val Ala Leu Gly Glu Trp
            100                 105                 110

Phe His Tyr Gly Met Asp Val Trp Gly Gln Gly Thr Ala Val Thr Val
            115                 120                 125

Ser Ser
    130

<210> SEQ ID NO 436
<211> LENGTH: 110
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 436

Trp Ala Ser Ser Glu Leu Thr Gln Pro Pro Ser Val Ser Val Ser Pro
1               5                   10                  15

Gly Gln Thr Ala Arg Ile Thr Cys Ser Gly Ala Pro Leu Thr Ser Arg
            20                  25                  30

Phe Thr Tyr Trp Tyr Arg Gln Lys Pro Gly Gln Ala Pro Val Leu Ile
            35                  40                  45

Ile Ser Arg Ser Ser Gln Arg Ser Ser Gly Trp Ser Gly Arg Phe Ser
    50                  55                  60

Ala Ser Trp Ser Gly Thr Thr Val Thr Leu Thr Ile Arg Gly Val Gln
65                  70                  75                  80

Ala Asp Asp Glu Ala Asp Tyr Tyr Cys Gln Ser Ser Asp Thr Ser Asp
                85                  90                  95

Ser Tyr Lys Met Phe Gly Gly Gly Thr Lys Leu Thr Val Leu
            100                 105                 110

<210> SEQ ID NO 437
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 437

Gln Val Gln Leu Arg Glu Ser Gly Pro Gly Leu Val Lys Pro Ser Glu
1               5                   10                  15

Thr Leu Ser Leu Ser Cys Thr Val Ser Asn Asp Ser Arg Pro Ser Asp
            20                  25                  30

His Ser Trp Thr Trp Val Arg Gln Ser Pro Gly Lys Ala Leu Glu Trp
            35                  40                  45

Ile Gly Asp Ile His Tyr Asn Gly Ala Thr Thr Tyr Asn Pro Ser Leu
    50                  55                  60

Arg Ser Arg Val Arg Ile Glu Leu Asp Gln Ser Ile Pro Arg Phe Ser
65                  70                  75                  80

```
Leu Lys Met Thr Ser Met Thr Ala Ala Asp Thr Gly Met Tyr Tyr Cys
                85                  90                  95

Ala Arg Asn Ala Ile Arg Ile Tyr Gly Val Val Ala Leu Gly Glu Trp
            100                 105                 110

Phe His Tyr Gly Met Asp Val Trp Gly Gln Gly Thr Ala Val Thr Val
        115                 120                 125

Ser Ser
    130

<210> SEQ ID NO 438
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 438

Ser Ser Glu Leu Thr Gln Pro Pro Ser Val Ser Val Ser Pro Gly Gln
1               5                   10                  15

Thr Ala Arg Ile Thr Cys Ser Gly Ala Pro Leu Thr Ser Arg Phe Thr
            20                  25                  30

Tyr Trp Tyr Arg Gln Lys Pro Gly Gln Ala Pro Val Leu Ile Ile Ser
        35                  40                  45

Arg Ser Ser Gln Arg Ser Ser Gly Trp Ser Gly Arg Phe Ser Ala Ser
50                  55                  60

Trp Ser Gly Thr Thr Val Thr Leu Thr Ile Arg Gly Val Gln Ala Asp
65                  70                  75                  80

Asp Glu Ala Asp Tyr Tyr Cys Gln Ser Ser Asp Thr Ser Asp Ser Tyr
                85                  90                  95

Lys Met Phe Gly Gly Gly Thr Lys Leu Thr Val Leu
            100                 105

<210> SEQ ID NO 439
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 439

Glu Val Gln Leu Arg Glu Ser Gly Pro Arg Leu Val Lys Pro Ser Glu
1               5                   10                  15

Thr Leu Ser Leu Ser Cys Asp Val Phe Gly Asp Ser Arg Pro Ser Asp
            20                  25                  30

His Ser Trp Thr Trp Val Arg Gln Pro Pro Gly Lys Ala Leu Glu Trp
        35                  40                  45

Ile Gly Asp Val His Tyr Asn Gly Asp Asn Thr Tyr Asn Pro Ser Leu
    50                  55                  60

Arg Gly Arg Val Lys Ile Asp Val Asp Arg Ser Thr His Arg Phe Ser
65                  70                  75                  80

Leu Thr Leu Lys Ser Leu Thr Ala Ala Asp Thr Gly Ile Tyr Phe Cys
                85                  90                  95

Ala Arg Asn Val Ile Arg Val Phe Gly Val Ile Ser Leu Gly Glu Trp
            100                 105                 110

Phe His Tyr Gly Met Asp Val Trp Gly Pro Gly Thr Ala Val Ile Val
        115                 120                 125
```

Ser Ser
    130

<210> SEQ ID NO 440
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 440

Ser Ser Glu Leu Thr Gln Ala Pro Ser Val Ser Val Ser Pro Gly Gln
1               5                   10                  15

Thr Ala Thr Ile Ala Cys Ser Gly Pro Pro Leu Ala Ser Arg Tyr Thr
            20                  25                  30

Tyr Trp Tyr Arg Gln Lys Pro Gly Gln Ala Pro Val Leu Ile Ile Phe
        35                  40                  45

Arg Asp Arg Gln Phe Pro Ser Gly Val Ser Gly Arg Phe Ser Ala Ser
50                  55                  60

Lys Ser Gly Thr Thr Ala Thr Leu Thr Ile Arg Asp Val Gln Val Glu
65                  70                  75                  80

Asp Glu Gly Asp Tyr Tyr Cys Gln Ser Ser Asp Thr Ser Asp Ser Tyr
                85                  90                  95

Lys Met Phe Gly Gly Gly Thr Thr Leu Thr Val Leu
            100                 105

<210> SEQ ID NO 441
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 441

Glu Val Gln Leu Arg Glu Ser Gly Pro Gly Leu Val Lys Pro Ser Glu
1               5                   10                  15

Thr Leu Ser Leu Ser Cys Asp Val Phe Gly Asp Ser Arg Pro Ser Asp
            20                  25                  30

His Ser Trp Thr Trp Val Arg Gln Pro Pro Gly Lys Ala Leu Glu Trp
        35                  40                  45

Ile Gly Asp Val His Tyr Asn Gly Asp Thr Thr Tyr Asn Pro Ser Leu
50                  55                  60

Arg Gly Arg Val Lys Ile Asp Val Asp Arg Ser Thr His Arg Phe Ser
65                  70                  75                  80

Leu Thr Leu Asn Ser Leu Thr Ala Ala Asp Thr Gly Ile Tyr Phe Cys
                85                  90                  95

Ala Arg Asn Val Ile Arg Val Phe Gly Val Ile Ser Leu Gly Glu Trp
            100                 105                 110

Phe His Tyr Gly Met Asp Val Trp Gly Gln Gly Thr Ala Val Thr Val
        115                 120                 125

Ser Ser
    130

<210> SEQ ID NO 442
<211> LENGTH: 108
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 442

Ser Ser Glu Leu Thr Gln Ala Pro Ser Val Ser Val Ser Pro Gly Gln
1               5                   10                  15

Thr Ala Thr Ile Ala Cys Ser Gly Pro Pro Leu Ala Ser Arg Tyr Thr
            20                  25                  30

Tyr Trp Tyr Arg Gln Lys Pro Gly Gln Ala Pro Val Leu Ile Ile Phe
        35                  40                  45

Arg Asp Arg Gln Phe Pro Ser Gly Val Ser Gly Arg Phe Ser Ala Ser
50                  55                  60

Lys Ser Gly Thr Thr Ala Thr Leu Thr Ile Arg Asp Val Gln Val Glu
65                  70                  75                  80

Asp Glu Gly Asp Tyr Tyr Cys Gln Ser Ser Asp Thr Ser Asp Ser Tyr
                85                  90                  95

Lys Met Phe Gly Gly Gly Thr Thr Leu Thr Val Leu
            100                 105

<210> SEQ ID NO 443
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 443

Gln Val Gln Leu Arg Glu Ser Gly Pro Gly Leu Val Lys Pro Ser Glu
1               5                   10                  15

Thr Leu Ser Leu Thr Cys Thr Val Ser Asn Asp Ser Arg Pro Ser Asp
            20                  25                  30

His Ser Trp Thr Trp Val Arg Gln Ser Pro Gly Lys Ala Leu Glu Trp
        35                  40                  45

Ile Gly Asp Ile His Tyr Asn Gly Ala Thr Thr Tyr Asn Pro Ser Leu
50                  55                  60

Arg Ser Arg Val Arg Ile Glu Leu Asp Gln Ser Ile Pro Arg Phe Ser
65                  70                  75                  80

Leu Lys Met Thr Ser Met Thr Ala Ala Asp Thr Gly Met Tyr Tyr Cys
                85                  90                  95

Ala Arg Asn Ala Ile Arg Ile Tyr Gly Val Val Ala Leu Gly Glu Trp
            100                 105                 110

Phe His Tyr Gly Met Asp Val Trp Gly Gln Gly Thr Ala Val Thr Val
        115                 120                 125

Ser Ser
    130

<210> SEQ ID NO 444
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 444

Ser Ser Glu Leu Thr Gln Pro Pro Ser Val Ser Val Ser Pro Gly Gln
1               5                   10                  15
```

```
Thr Ala Lys Ile Thr Cys Ser Gly Ala Ala Leu Thr Ser Arg Phe Thr
            20                  25                  30

Tyr Trp Tyr Arg Gln Lys Pro Gly Gln Ala Pro Val Leu Ile Ile Ser
        35                  40                  45

Arg Thr Ser Gln Arg Ser Ser Gly Trp Ser Gly Arg Phe Ser Ala Ser
 50                  55                  60

Trp Ser Gly Thr Thr Val Thr Leu Thr Ile Arg Gly Val Gln Ala Asp
 65                  70                  75                  80

Asp Glu Gly Asp Tyr Tyr Cys Gln Ser Ser Asp Thr Ser Asp Ser Tyr
                85                  90                  95

Lys Met Phe Gly Gly Gly Thr Lys Leu Thr Val Leu
            100                 105

<210> SEQ ID NO 445
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 445

Glu Val Gln Leu Arg Glu Ser Gly Pro Gly Leu Val Lys Pro Ser Gly
 1               5                  10                  15

Asn Met Ala Leu Thr Cys Thr Ile Ser Gly Asp Ser Arg Pro Ser Asp
            20                  25                  30

His Ser Trp Thr Trp Val Arg Gln Ser Pro Gly Lys Ala Leu Glu Trp
        35                  40                  45

Ile Gly Asp Ile His Tyr Gly Gly Asp Ile Thr Tyr Asn Pro Ser Leu
 50                  55                  60

Arg Ser Arg Val Lys Leu Glu Val Asp Thr Ser Thr Asn Arg Phe Phe
 65                  70                  75                  80

Leu Lys Met Thr Ser Leu Thr Val Ala Asp Thr Gly Ile Tyr Phe Cys
                85                  90                  95

Ala Arg Asn Val Ile Arg Val Phe Gly Val Ile Ala Leu Gly Glu Trp
            100                 105                 110

Phe His Tyr Gly Met Asp Val Trp Gly Gln Gly Thr Ala Ile Thr Val
        115                 120                 125

Ser Pro
    130

<210> SEQ ID NO 446
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 446

Ser Ser Glu Leu Thr Gln Thr Pro Ser Val Thr Val Ser Pro Gly Glu
 1               5                  10                  15

Thr Ala Arg Ile Ala Cys Ser Gly Pro Pro Leu Ala Ser Arg Tyr Cys
            20                  25                  30

Tyr Trp Tyr Arg Gln Lys Pro Gly Gln Ala Pro Val Leu Ile Ile Phe
        35                  40                  45

Arg Asp Arg Gln Phe Ser Ser Gly Met Ser Gly Arg Phe Ala Ser Ser
 50                  55                  60
```

His Ser Gly Thr Thr Val Thr Leu Thr Ile Arg Asp Val Arg Val Glu
65                  70                  75                  80

Asp Glu Ala Asp Tyr Tyr Cys Gln Ser Ser Asp Ile Asn Asp Ser Tyr
                85                  90                  95

Lys Met Phe Gly Gly Gly Thr Lys Val Thr Val Leu
            100                 105

<210> SEQ ID NO 447
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 447

Glu Val Gln Leu Arg Glu Ser Gly Pro Gly Leu Val Lys Pro Ser Gly
1               5                   10                  15

Asn Met Ala Leu Thr Cys Thr Ile Ser Gly Asp Ser Arg Pro Ser Asp
            20                  25                  30

His Ser Trp Thr Trp Val Arg Gln Ser Pro Gly Lys Thr Leu Glu Trp
        35                  40                  45

Ile Gly Asp Ile His Tyr Gly Gly Asp Ile Thr Tyr Asn Pro Ser Leu
    50                  55                  60

Arg Ser Arg Val Lys Leu Glu Val Asp Thr Ser Ser Asn Arg Phe Phe
65                  70                  75                  80

Leu Lys Met Thr Ser Leu Thr Val Ala Asp Thr Gly Ile Tyr Phe Cys
                85                  90                  95

Ala Arg Asn Val Ile Arg Val Phe Gly Val Ile Ala Leu Gly Glu Trp
            100                 105                 110

Phe His Tyr Gly Met Asp Val Trp Gly Gln Gly Thr Ala Ile Thr Val
        115                 120                 125

Ser Pro
    130

<210> SEQ ID NO 448
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 448

Ser Ser Glu Leu Thr Gln Thr Ala Ser Val Thr Val Ser Pro Gly Glu
1               5                   10                  15

Thr Ala Arg Ile Ala Cys Ser Gly Pro Pro Leu Ala Ser Arg Tyr Cys
            20                  25                  30

Tyr Trp Tyr Arg Gln Lys Pro Gly Gln Ala Pro Val Leu Ile Ile Phe
        35                  40                  45

Arg Asp Arg Gln Phe Ser Gly Ile Ser Gly Arg Phe Ser Ser Ser
    50                  55                  60

Gln Ser Gly Thr Thr Val Thr Leu Thr Ile Arg Asp Val Arg Val Glu
65                  70                  75                  80

Asp Glu Ala Asp Tyr Tyr Cys Gln Ser Ser Asp Thr Ser Asp Ser Phe
                85                  90                  95

Lys Met Phe Gly Gly Gly Thr Lys Leu Thr Val Leu
            100                 105

<210> SEQ ID NO 449
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 449

Gln Val Gln Leu Arg Glu Ser Gly Pro Gly Leu Val Lys Pro Ser Gly
1               5                   10                  15

Asn Met Ala Leu Thr Cys Thr Ile Ser Gly Asp Ser Arg Pro Ser Asp
            20                  25                  30

His Ser Trp Thr Trp Val Arg Gln Ser Pro Gly Lys Ala Leu Glu Trp
        35                  40                  45

Ile Gly Asp Ile His Tyr Gly Asp Ile Thr Tyr Asn Pro Ser Leu
    50                  55                  60

Arg Ser Arg Val Glu Leu Glu Val Asp Arg Ser Thr Asn Arg Phe Phe
65                  70                  75                  80

Leu Lys Met Thr Ser Leu Ser Val Ala Asp Thr Gly Met Tyr Phe Cys
                85                  90                  95

Ala Arg Asn Val Ile Arg Val Phe Gly Val Ile Ala Leu Gly Glu Trp
            100                 105                 110

Phe His Tyr Gly Met Asp Val Trp Gly Gln Gly Thr Ala Ile Thr Val
        115                 120                 125

Ser Pro
    130

<210> SEQ ID NO 450
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 450

Ser Ser Glu Leu Thr Gln Ala Pro Ser Val Thr Val Ser Pro Gly Asp
1               5                   10                  15

Thr Ala Arg Ile Ala Cys Ser Gly Pro Pro Leu Ala Thr Arg Tyr Cys
            20                  25                  30

Tyr Trp Tyr Arg Gln Lys Ser Gly Gln Ala Pro Val Leu Ile Ile Phe
        35                  40                  45

Arg Asp Arg Gln Phe Ser Gly Val Ser Gly Arg Phe Ser Ser Ser
    50                  55                  60

Gln Ser Gly Ser Thr Val Thr Leu Thr Ile Arg Asp Val Arg Val Glu
65                  70                  75                  80

Asp Glu Ala Asp Tyr Tyr Cys Gln Ser Ser Asp Thr Ser Asp Ser Tyr
                85                  90                  95

Lys Met Phe Gly Gly Gly Thr Lys Leu Thr Val Leu
            100                 105

<210> SEQ ID NO 451
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 451

Gln Val Gln Leu Arg Glu Ser Gly Pro Gly Leu Val Lys Pro Ser Glu
1               5                   10                  15

Thr Leu Ser Leu Ser Cys Asp Val Phe Gly Asp Ser Arg Pro Ser Asp
            20                  25                  30

His Ser Trp Thr Trp Val Arg Gln Pro Pro Gly Lys Ala Leu Glu Trp
        35                  40                  45

Ile Gly Asp Ile His Tyr Asn Gly Asp Lys Thr Tyr Asn Pro Ser Leu
    50                  55                  60

Arg Gly Arg Val Lys Ile Asp Val Asp Arg Ser Thr His Arg Phe Ser
65                  70                  75                  80

Leu Thr Leu Asn Ser Leu Thr Ala Ala Asp Thr Gly Met Tyr Phe Cys
                85                  90                  95

Ala Arg Asn Val Ile Arg Val Phe Gly Val Ile Ser Leu Gly Glu Trp
            100                 105                 110

Phe His Tyr Gly Met Asp Val Trp Gly Pro Gly Thr Ala Val Thr Val
        115                 120                 125

<210> SEQ ID NO 452
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 452

Ser Ser Glu Leu Thr Gln Ala Pro Ser Val Ser Val Ser Pro Gly Gln
1               5                   10                  15

Thr Ala Arg Ile Ala Cys Ser Gly Pro Pro Leu Ala Ser Arg Tyr Thr
            20                  25                  30

Tyr Trp Tyr Arg Gln Lys Pro Gly Gln Ala Pro Val Leu Ile Ile Phe
        35                  40                  45

Arg Asp Arg Gln Phe Pro Ser Gly Val Ser Gly Arg Phe Ser Ala Ser
    50                  55                  60

Lys Ser Gly Thr Thr Gly Thr Leu Thr Ile Arg Asp Val Gln Ala Glu
65                  70                  75                  80

Asp Glu Gly Asp Tyr Tyr Cys Gln Ser Ser Asp Thr Ser Asp Ser Tyr
                85                  90                  95

Lys Met Phe Gly Gly Gly Thr Thr Leu Thr Val Leu
            100                 105

<210> SEQ ID NO 453
<211> LENGTH: 130
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 453

Gln Val Gln Leu Arg Glu Ser Gly Pro Gly Leu Val Lys Pro Ser Gly
1               5                   10                  15

Asn Met Ala Leu Thr Cys Thr Ile Ser Gly Asp Ser Arg Pro Ser Asp
            20                  25                  30

His Ser Trp Thr Trp Val Arg Gln Ser Pro Gly Lys Ala Leu Glu Trp
        35                  40                  45

Ile Gly Asp Ile His Tyr Gly Gly Asp Ile Thr Tyr Asn Pro Ser Leu

```
                    50                  55                  60

Arg Ser Arg Val Lys Leu Glu Val Asp Thr Ser Ser Asn Arg Phe Phe
 65                  70                  75                  80

Leu Lys Met Thr Ser Leu Thr Val Ala Asp Thr Gly Ile Tyr Phe Cys
                     85                  90                  95

Ala Arg Asn Val Ile Arg Val Phe Gly Val Ile Ala Leu Gly Glu Trp
                    100                 105                 110

Phe His Tyr Gly Met Asp Val Trp Gly Gln Gly Thr Ala Ile Thr Val
            115                 120                 125

Ser Pro
    130

<210> SEQ ID NO 454
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 454

Ser Ser Glu Leu Thr Gln Ala Pro Ser Val Thr Leu Ser Pro Gly Glu
  1               5                  10                  15

Thr Ala Arg Ile Ala Cys Ser Gly Pro Pro Leu Ala Ser Arg Tyr Cys
                 20                  25                  30

Tyr Trp Tyr Arg Gln Lys Pro Gly Gln Ala Pro Val Leu Ile Ile Phe
             35                  40                  45

Arg Asp Arg Gln Phe Ser Ser Gly Ile Ser Gly Arg Phe Ser Ser Ser
 50                  55                  60

Gln Ser Gly Thr Thr Val Thr Leu Thr Ile Arg Asp Val Arg Val Glu
 65                  70                  75                  80

Asp Glu Ala Asp Tyr Tyr Cys Gln Ser Ser Asp Asn Ser Asp Ser Phe
                 85                  90                  95

Lys Met Phe Gly Gly Gly Thr Lys Leu Thr Val Leu
            100                 105

<210> SEQ ID NO 455
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 455

Ala Glu Gln Leu Val Glu Ser Gly Gly Gly Leu Val Pro Pro Gly Arg
  1               5                  10                  15

Ser Leu Arg Leu Ser Cys Ser Ala Ser Gly Phe Tyr Phe Pro Asp Tyr
                 20                  25                  30

Ala Met Ala Trp Val Arg Gln Ala Pro Gly Gln Gly Leu Gln Trp Val
             35                  40                  45

Gly Phe Met Arg Gly Trp Ala Tyr Gly Gly Ser Ala Gln Phe Ala Ala
             50                  55                  60

Phe Ala Val Gly Lys Phe Ala Ile Ser Arg Asp Asp Gly Arg Asn Val
 65                  70                  75                  80

Val Tyr Leu Asp Val Lys Asn Pro Thr Phe Glu Asp Thr Gly Val Tyr
                 85                  90                  95

Phe Cys Ala Arg Glu Gln Arg Asn Lys Asp Tyr Arg Tyr Gly Gln Glu
```

```
                    100                 105                 110
Gly Phe Gly Tyr Ser Tyr Gly Met Asp Val Trp Gly Arg Gly Thr Thr
            115                 120                 125
Val Val Val Ser Thr
        130

<210> SEQ ID NO 456
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 456

Asp Ile His Met Thr Gln Ser Pro Val Ser Leu Ser Ala Ser Val Gly
1               5                   10                  15

Asp Arg Val Thr Ile Thr Cys Arg Ala Ser His Phe Ile Ala Asn Tyr
            20                  25                  30

Val Asn Trp Tyr Gln Gln Lys Pro Gly Lys Ala Pro Thr Leu Leu Ile
        35                  40                  45

Phe Glu Ser Ser Thr Leu Gln Arg Gly Val Pro Ser Arg Phe Ser Ala
    50                  55                  60

Tyr Gly Asp Gly Thr Glu Phe Thr Leu Ser Ile Asn Thr Leu Gln Pro
65                  70                  75                  80

Glu Asp Phe Ala Ser Tyr Ile Cys Gln Gln Ser His Ser Pro Pro Val
                85                  90                  95

Thr Phe Gly Ala Gly Thr Arg Val Asp Gln Lys
            100                 105

<210> SEQ ID NO 457
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 457

Glu Glu Arg Leu Val Glu Ser Gly Gly Gly Leu Val Pro Pro Gly Arg
1               5                   10                  15

Ser Leu Arg Leu Ser Cys Ser Ala Phe Asp Phe Tyr Phe Pro Asp Tyr
            20                  25                  30

Ala Met Ala Trp Val Arg Gln Ala Pro Gly Lys Gly Leu Glu Trp Ile
        35                  40                  45

Gly Phe Ile Arg Gly Trp Ala Tyr Gln Ala Gln Tyr Gly Lys
    50                  55                  60

Ser Ala Ser Gly Arg Met Thr Ile Ser Arg Asp Asp Ser Arg Arg Val
65                  70                  75                  80

Val Tyr Leu Asp Ile Lys Ser Pro Ile Glu Asp Thr Gly Ala Tyr
                85                  90                  95

Phe Cys Ala Arg Glu Gln Arg Gly Gly Asp Gly Arg Tyr Ser Gly Asp
            100                 105                 110

Gly Phe Gly Tyr Pro Tyr Gly Met Asp Val Trp Gly Arg Gly Thr Met
        115                 120                 125

Val Thr Val Ser Ala
    130
```

<210> SEQ ID NO 458
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 458

```
Asp Ile Leu Met Thr Gln Ser Pro Val Ser Leu Ser Ala Ser Ile Gly
1               5                   10                  15

Glu Arg Ile Thr Ile Thr Cys Arg Ala Ser His Phe Ile Ala Asn Tyr
            20                  25                  30

Val Asn Trp Tyr Gln Gln Arg Pro Gly Lys Ala Pro Lys Leu Leu Ile
        35                  40                  45

Phe Gln Ser Trp Thr Leu Asn Arg Gly Ile Pro Ser Arg Phe Ser Gly
    50                  55                  60

Tyr Gly Asp Gly Thr Glu Phe Thr Leu Ser Ile Ser Ala Leu Gln Ser
65                  70                  75                  80

Glu Asp Phe Gly Thr Tyr Ile Cys Gln Gln Ser His Ser Pro Pro Leu
                85                  90                  95

Ser Phe Gly Gly Gly Thr Arg Val Asp Gln Thr
            100                 105
```

<210> SEQ ID NO 459
<211> LENGTH: 133
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 459

```
Glu Glu Arg Leu Val Glu Ser Gly Gly Gly Leu Val Pro Pro Gly Arg
1               5                   10                  15

Ser Leu Arg Leu Ser Cys Ser Ala Phe Asp Phe Tyr Phe Pro Asp Tyr
            20                  25                  30

Ala Met Ala Trp Val Arg Gln Ala Pro Gly Arg Ala Leu Glu Trp Ile
        35                  40                  45

Gly Phe Ile Arg Gly Trp Ala Tyr Gly Gln Ser Ala Gln Tyr Gly Lys
    50                  55                  60

Ser Ala Ser Gly Arg Met Thr Ile Ser Arg Asp Asp Ser Arg Arg Val
65                  70                  75                  80

Val Tyr Leu Asp Ile Lys Ser Pro Thr His Glu Asp Thr Gly Val Tyr
                85                  90                  95

Phe Cys Ala Arg Glu Gln Arg Gly Ala Asn Gly Arg Tyr Gly Gly Asp
                100                 105                 110

Gly Phe Gly Tyr Ser Tyr Gly Met Asp Val Trp Gly Arg Gly Thr Met
        115                 120                 125

Val Ser Val Ser Ala
    130
```

<210> SEQ ID NO 460
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 460

Asp Ile Gln Met Thr Gln Ser Pro Phe Thr Leu Ser Ala Ser Val Gly
1               5                   10                  15

Glu Arg Val Thr Ile Thr Cys Arg Ala Ser His Phe Ile Ala Asn Tyr
            20                  25                  30

Val Asn Trp Tyr Gln Gln Arg Pro Gly Arg Ala Pro Lys Leu Leu Ile
        35                  40                  45

Phe Glu Ser Ser Thr Leu Asn Arg Gly Val Pro Ser Arg Phe Ser Gly
50                  55                  60

Ser Gly Asp Gly Thr Glu Phe Thr Leu Ser Ile Ser Ala Leu Gln Ser
65                  70                  75                  80

Glu Asp Phe Ala Thr Tyr Ile Cys Gln Gln Ser His Ser Pro Pro Val
                85                  90                  95

Ser Phe Gly Gly Gly Thr Arg Val Asp Gln Thr
            100                 105

<210> SEQ ID NO 461
<211> LENGTH: 26
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 461

Ala Arg Ala Arg Arg Gly Gln Arg Ile Tyr Gly Val Val Ser Phe Gly
1               5                   10                  15

Glu Phe Phe Tyr Tyr Tyr Ser Met Asp Val
            20                  25

<210> SEQ ID NO 462
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 462

Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
            20                  25                  30

Tyr Trp Ser Trp Ile Arg Arg Ser Pro Gly Lys Gly Leu Glu Trp Ile
        35                  40                  45

Gly Tyr Val His Lys Ser Gly Asp Thr Asn Tyr Asn Pro Ser Leu Lys
50                  55                  60

Ser Arg Val His Leu Ser Leu Asp Thr Ser Lys Asn Gln Val Ser Leu
65                  70                  75                  80

Ser Leu Thr Gly Val Thr Ala Ala Asp Ser Gly Lys Tyr Tyr Cys Ala
                85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Thr Gly Thr Gln Val
        115                 120                 125

Thr Val Ser Ser
    130

<210> SEQ ID NO 463

```
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 463

Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln His Arg Ala
            20                  25                  30

Gly Gln Ala Pro Ser Leu Ile Ile Tyr Asn Asn Gln Asp Arg Pro Ser
        35                  40                  45

Gly Ile Pro Glu Arg Phe Ser Gly Ser Pro Asp Ser Arg Pro Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Val Pro Thr Lys Trp Val Phe
                85                  90                  95

Gly Gly Gly Thr Thr Leu Thr Val Leu
            100                 105

<210> SEQ ID NO 464
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 464

Gln Met Gln Leu Gln Glu Ser Gly Pro Gly Leu Val Lys Pro Ser Glu
1               5                   10                  15

Thr Leu Ser Leu Thr Cys Ser Val Ser Gly Ala Ser Ile Ser Asp Ser
            20                  25                  30

Tyr Trp Ser Trp Ile Arg Gln Pro Pro Gly Lys Gly Leu Glu Trp Ile
        35                  40                  45

Gly Tyr Val His Lys Ser Gly Asp Thr Asn Tyr Ser Pro Ser Leu Lys
    50                  55                  60

Ser Arg Val Asn Leu Ser Leu Asp Thr Ser Lys Asn Gln Val Ser Leu
65                  70                  75                  80

Ser Leu Ser Ala Ala Thr Ala Ala Asp Ser Gly Val Tyr Tyr Cys Ala
                85                  90                  95

Arg Thr Leu His Gly Arg Arg Ile Tyr Gly Ile Val Ala Phe Asn Glu
            100                 105                 110

Trp Phe Thr Tyr Phe Tyr Met Asp Val Trp Gly Asn Gly Thr Gln Val
        115                 120                 125

Thr Val Ser Ser
    130

<210> SEQ ID NO 465
<211> LENGTH: 105
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 465
```

```
Ser Asp Ile Ser Val Ala Pro Gly Glu Thr Ala Arg Ile Ser Cys Gly
1               5                   10                  15

Glu Lys Ser Leu Gly Ser Arg Ala Val Gln Trp Tyr Gln Gln Arg Ala
            20                  25                  30

Gly Gln Ala Pro Ser Leu Ile Ile Tyr Asn Asn Gln Asp Arg Pro Ser
        35                  40                  45

Gly Ile Pro Glu Arg Phe Ser Gly Ser Pro Asp Ser Gly Phe Gly Thr
    50                  55                  60

Thr Ala Thr Leu Thr Ile Thr Ser Val Glu Ala Gly Asp Glu Ala Asp
65                  70                  75                  80

Tyr Tyr Cys His Ile Trp Asp Ser Arg Val Pro Thr Lys Trp Val Phe
                85                  90                  95

Gly Gly Gly Thr Thr Leu Thr Val Leu
            100                 105

<210> SEQ ID NO 466
<211> LENGTH: 132
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 466

Gln Val Gln Leu Gln Glu Ser Gly Pro Gly Leu Val Lys Pro Ser Glu
1               5                   10                  15

Thr Leu Ser Val Thr Cys Ser Val Ser Gly Asp Ser Met Asn Asn Tyr
            20                  25                  30

Tyr Trp Thr Trp Ile Arg Gln Ser Pro Gly Lys Gly Leu Glu Trp Ile
        35                  40                  45

Gly Tyr Ile Ser Asp Arg Glu Ser Ala Thr Tyr Asn Pro Ser Leu Asn
    50                  55                  60

Ser Arg Val Thr Ile Ser Arg Asp Thr Ser Lys Asn Gln Phe Ser Leu
65                  70                  75                  80

Lys Leu Asn Ser Val Thr Pro Ala Asp Thr Ala Val Tyr Tyr Cys Ala
                85                  90                  95

Arg Ala Arg Arg Gly Gln Arg Ile Tyr Gly Val Val Ser Phe Gly Glu
            100                 105                 110

Phe Phe Tyr Tyr Tyr Ser Met Asp Val Trp Gly Lys Gly Thr Thr Val
        115                 120                 125

Thr Val Ser Ser
    130

<210> SEQ ID NO 467
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 467

Ser Pro Val Arg Pro Leu Ser Val Ala Leu Gly Glu Thr Ala Arg Ile
1               5                   10                  15

Ser Cys Gly Arg Gln Ala Leu Gly Ser Arg Ala Val Gln Trp Tyr Gln
            20                  25                  30

His Arg Pro Gly Gln Ala Pro Ile Leu Leu Ile Tyr Asn Asn Gln Asp
        35                  40                  45
```

```
Arg Pro Ser Gly Ile Pro Glu Arg Phe Ser Gly Thr Pro Asp Ile Asn
     50                  55                  60

Phe Gly Thr Arg Ala Thr Leu Thr Ile Ser Gly Val Glu Ala Gly Asp
65              70                  75                  80

Glu Ala Asp Tyr Tyr Cys His Met Trp Asp Ser Arg Ser Gly Phe Ser
                85                  90                  95

Trp Ser Phe Gly Gly Ala Thr Arg Leu Thr Val Leu
            100                 105

<210> SEQ ID NO 468
<211> LENGTH: 4
<212> TYPE: PRT
<213> ORGANISM: Human immunodeficiency virus 1

<400> SEQUENCE: 468

Lys Leu Ile Cys
1
```

METHODS OF IDENTIFYING HIV PATIENTS SENSITIVE TO THERAPY WITH GP120 V3 GLYCAN-DIRECTED ANTIBODIES

CROSS-REFERENCE TO RELATED APPLICATIONS

This application claims the benefit under 35 U.S.C. § 119(e) of U.S. provisional application No. 62/850,994, filed on May 21, 2019, which is hereby incorporated herein by reference in its entirety for all purposes.

SEQUENCE LISTING

The instant application contains a Sequence Listing which has been submitted electronically in ASCII format and is hereby incorporated by reference in its entirety. Said ASCII copy, created on Apr. 27, 2020, is named 1289PC_SL.txt and is 199,543 bytes in size.

BACKGROUND

Human immunodeficiency virus (HIV) infection and related diseases are a major public health problem worldwide. Most currently approved therapies for HIV infection target the viral reverse transcriptase, protease enzymes, and integrase but resistance of HIV to these existing drugs, long term toxicity, and lack of patient adherence to daily dosing regimens have proven to be problems associated with these therapies. Therefore, it is important to discover and develop new HIV drugs.

WO 2009/066702, WO 2012/030904, WO 2014/063059, WO 2016/149698, WO 2017/106346; WO 2018/075564 and WO 2018/125813, McCoy, *Retrovirology* (2018) 15:70; Sok and Burton, *Nat Immunol.* 2018 19(11):1179-1188; Possas, et al., *Expert Opin Ther Pat.* 2018 July; 28(7):551-560; and Stephenson and Barouch, *Curr HIV/AIDS Rep* (2016) 13:31-37 describe human anti-HIV antibodies derived from memory B cells of HIV-infected donors, which target the V3 glycan region of gp120, and are capable of inhibiting infection by HIV-1 species from a plurality of clades. The therapeutic use of the antibodies may be limited due to the need to identify patients infected with HIV-1 species that can be targeted by HIV gp120 V3 glycan region antibodies.

SUMMARY

Provided are methods of identifying patients most likely to benefit from therapy with an antibody targeting the V3 glycan region of HIV gp120.

Accordingly, in one aspect, provided are methods treating or preventing HIV in a human subject in need thereof, the method comprising: a) Identifying a human subject who is infected with an HIV or a population of HIV expressing a gp120 comprising the following amino acid residues: a glycosylated asparagine at the position corresponding to amino acid residue position 332 (N332glycan), an aspartate at the position corresponding to amino acid residue position 325 (D325), and one or more amino acid residues selected from the group consisting of: a threonine at the position corresponding to amino acid residue position 63 (T63), a leucine at the position corresponding to amino acid residue position 179 (L179), a threonine at the position corresponding to amino acid residue position 320 (T320), and a histidine at the position corresponding to amino acid residue position 330 (H330), wherein the amino acid positions are with reference to SEQ ID NO: 4; and b) Administering to the subject an effective amount of an antibody or antigen-binding fragment thereof that competes with or comprises VH and VL regions that bind to an epitope of gp120 within the third variable loop (V3) and/or high mannose patch comprising a N332 oligomannose glycan. In some embodiments, the method entails identifying a subject infected with an HIV or a population of HIV expressing a gp120 comprising the following amino acid residues: i. N332glycan, D325 and T63; ii. N332glycan, D325 and L179; iii. N332glycan, D325 and T320; iv. N332glycan, D325 and H330; v. N332glycan, D325, T63 and L179; vi. N332glycan, D325, T63 and T320; vii. N332glycan, D325, T63 and H330; viii. N332glycan, D325, L179 and T320; ix. N332glycan, D325, L179 and H330; x. N332glycan, D325, T320 and H330; xi. N332glycan, D325, T63, T320 and H330; xii. N332glycan, D325, T63, L179 and T320; xiii. N332glycan, D325, T63, L179 and H330; xiv. N332glycan, D325, L179, T320 and H330; or xv. N332glycan, D325, T63, L179, T320 and H330, wherein the amino acid positions are with reference to SEQ ID NO: 4. In some embodiments, the method entails identifying a subject infected with an HIV or a population of HIV expressing a gp120 comprising the following amino acid residues: i. N332glycan, D325 and T63; ii. N332glycan, D325 and L179; iii. N332glycan, D325 and T320; or iv. N332glycan, D325 and H330, wherein the amino acid positions are with reference to SEQ ID NO: 4. In some embodiments, the method entails identifying a subject infected with an HIV or a population of HIV expressing a gp120 comprising the following amino acid residues: i. N332glycan, D325, T63 and L179; ii. N332glycan, D325, T63 and T320; iii. N332glycan, D325, T63 and H330; iv. N332glycan, D325, L179 and T320; v. N332glycan, D325, L179 and H330; or vi. N332glycan, D325, T320 and H330, wherein the amino acid positions are with reference to SEQ ID NO: 4. In some embodiments, the method entails identifying a subject infected with an HIV or a population of HIV expressing a gp120 comprising the following amino acid residues: i. N332glycan, D325, L179, T320 and H330; ii. N332glycan, D325, T63, T320 and H330; iii. N332glycan, D325, T63, L179 and T320; or iv. N332glycan, D325, T63, L179 and H330, wherein the amino acid positions are with reference to SEQ ID NO: 4. In some embodiments, the method entails identifying a subject infected with an HIV or a population of HIV expressing a gp120 comprising the following amino acid residues: i. N332glycan, D325, T63 and H330; ii. N332glycan, D325, T320 and H330; iii. N332glycan, D325, L179, T320 and H330; or iv. N332glycan, D325, T63, L179, T320 and H330, wherein the amino acid positions are with reference to SEQ ID NO: 4. In some embodiments, the subject is infected with an HIV or a population of HIV expressing a gp120 further comprising one or more of the following amino acid residues: a glycan at amino acid residue 301 (glycan301); a lysine at amino acid residue 677 (K677); an amino acid residue other than tryptophan (e.g., A, C, D, E, F, G, H, I, K, L, M, N, P, Q, R, S, T, V or Y) at position 17 (not_W17); an amino acid residue other than arginine (e.g., A, C, D, E, F, G, H, I, K, L, M, N, P, Q, S, T, V, W or Y) at position 747 (not_R747); an insertion_321.01 (e.g., an insertion of any amino acid (e.g., A, C, D, E, F, G, H, I, K, L, M, N, P, Q, R, S, T, V, W or Y) between position G321 and K322); a glutamic acid at position 429 (E429); a glutamine at position 442 (Q442); an arginine at position 335 (R335); an isoleucine at position 165 (I165); a serine at position 393 (S393); an isoleucine at position 307 (I307); a glycan at position 295 (295 glycan); and/or an asparagine at position 300 (N300), wherein the amino acid positions are with reference to SEQ ID NO: 4. In some embodiments, at least 90%, e.g., at least 91%, at least 92%, at least 93%, at least 94%, at least 95%, at least 96%, at least 97%, at least 98%, at least 99%, or 100%, of the HIV species in the population of HIV comprise the recited amino acid residues. In some embodiments, the administered antibody or antigen-binding fragment thereof competes with or comprises VH and VL regions from an antibody selected from the group consisting of GS-9722 (elipovimab), GS-9721, PGT-121, PGT-121.66, PGT-121.414, PGT-122, PGT-123, PGT-124, PGT-125, PGT-126, PGT-128, PGT-130, PGT-133, PGT-134, PGT-135, PGT-136, PGT-137, PGT-138, PGT-139, 10-1074, 10-1074-J, VRC24, 2G12, BG18, 354BG8, 354BG18, 354BG42, 354BG33, 354BG129, 354BG188, 354BG411, 354BG426, DH270.1, DH270.6, PGDM12, VRC41.01, PGDM21, PCDN-33A, BF520.1 and VRC29.03. In some embodiments, the antibody or antigen-binding fragment thereof competes with or comprises VH and VL regions from an antibody selected from the group consisting of GS-9722, GS-9721, PGT-121, PGT-121.66, PGT-121.414, PGT-124, PGT-134, GS-2872, 10-1074, 10-1074-J, PGT-122 and PGT-123. In some embodiments, the methods comprise administering an antibody comprising an Fc region comprising one or more amino acid substitutions that extend serum half-life. In some embodiments, the methods comprise administering an antibody comprising an Fc region comprising the following amino acids at the indicated positions (EU index numbering): i. Tyrosine at position 252, threonine at position 254 and glutamic acid at position 256 (YTE); or ii. Leucine at position 428 and serine at position 434 (LS). In some embodiments, the methods comprise administering an antibody comprising an Fc region comprising the following amino acids at the indicated positions (EU index numbering): i. Aspartate at position 239 and glutamate at position 332 (DE); ii. Aspartate at position 239, glutamate at position 332 and leucine at position 330 (DEL); iii. Aspartate at position 239, glutamate at position 332, alanine at position 236 (DEA); or iv. Aspartate at position 239, glutamate at position 332, alanine at position 236 and leucine at position 330 (DEAL). In some embodiments, the methods comprise administering an antigen binding fragment. In some embodiments, the antigen binding fragment is selected from the group consisting of scFv, Fab, Fab2, Fab', F(ab')2, Fv, and a diabody. In some embodiments, the antibody is one or more arms of a multi-specific antibody, e.g., a bi-specific antibody. In some embodiments, the human subject is acutely infected with HIV. In some embodiments, the antibody is administered to a human subject having an HIV infection of Fiebig stage IV or earlier, e.g., Fiebig stage III, Fiebig stage II or Fiebig stage I. In some embodiments, the antibody is administered to a human subject who has not seroconverted. In some embodiments, the human subject is recently infected with HIV, e.g., within 1, 2, 3 or 4 weeks, or prior to detection, seroconversion or manifestation of symptoms. In some embodiments, the antibody is administered to a human subject having an HIV infection of Fiebig stage V or Fiebig stage VI. In some embodiments, the human subject is chronically infected with HIV. In some embodiments, the human subject is infected with HIV clade B viruses. In some embodiments, the human subject is infected with HIV clade B viruses and the methods entail identifying a subject infected with an HIV or a population of HIV expressing a gp120 comprising the following amino acid residues: i. N332glycan, D325, T63 and H330; ii. N332glycan, D325, L179, T320 and H330; or iii. N332glycan, D325, T63, L179, T320 and H330. In some embodiments, the human subject is infected with HIV clade A viruses. In some embodiments, the human subject is infected with HIV clade C viruses. In some embodiments, the methods further comprise administering to the subject one or more additional therapeutic agents for treating an HIV infection. In some embodiments, the subject is not receiving antiretroviral therapy (ART) or ART is discontinued prior to administration of the antibody. In some embodiments, ART is discontinued after one or more administrations of the antibody or antigen-binding fragment thereof. In some embodiments, the methods further comprise administering one or more antiretroviral therapy (ART) agents to the subject. In some embodiments, the methods further comprise administering to the subject a second antibody or antigen-binding fragment thereof that binds to an epitope or region of gp120 selected from the group consisting of: second variable loop (V2) and/or Env trimer apex; CD4 binding site (CD4bs); gp120/gp41 interface; or silent face of gp120. In some embodiments, the second antibody or antigen-binding fragment thereof binds to an epitope or region of gp120 in the second variable loop (V2) and/or Env trimer apex and competes with or comprises VH and VL regions from an antibody selected from the group consisting of PG9, PG16, PGC14, PGG14, PGT-142, PGT-143, PGT-144, PGT-145, CH01, CH59, PGDM1400, CAP256, CAP256-VRC26.08, CAP256-VRC26.09, CAP256-VRC26.25, PCT64-24E and VRC38.01. In some embodiments, the second antibody or antigen-binding fragment thereof binds to an epitope or region of gp120 in the CD4 binding site (CD4bs) and competes with or comprises VH and VL regions from an antibody selected from the group consisting of b12, F105, VRC01, VRC07, VRC07-523, VRC03, VRC06, VRC06b01 VRC08, VRC0801, NIH45-46, GS-9723, GS-5423, 3BNC117, 3BNC60, VRC-PG04, PGV04; CH103, 44-VRC13.01, 1NC9, 12A12, N6, N6LS (VRC-HIVMAB091-00-AB), N49-P7, NC-Cow1, IOMA, CH235 and CH235.12, N49P6, N49P7, N49P11, N49P9 and N60P25. In some embodiments, the second antibody or antigen-binding fragment thereof binds to an epitope or region of gp120 in the gp120/gp41 interface and competes with or comprises VH and VL regions from an antibody selected from the group consisting of PGT-151, CAP248-2B, 35O22, 8ANC195, ACS202, VRC34 and VRC34.01. In some embodiments, the second antibody or antigen-binding fragment thereof binds to an epitope or region of the gp120 silent face and competes with or comprises VH and VL regions from antibody VRC-PG05. In some embodiments, the second antibody or antigen-binding fragment thereof binds to an epitope or region of gp41 in the membrane proximal region (MPER) and competes with or comprises VH and VL regions from an antibody selected from the group consisting of 10E8, 10E8v4, 10E8-5R-100cF, 4E10, DH511.11P, 2F5, 7b2, and LN01. In some embodiments, the second antibody or antigen-binding fragment thereof binds to an epitope or region of the gp41 fusion peptide and competes with or comprises VH and VL regions from an antibody selected from the group consisting of VRC34 and ACS202. In some embodiments, the methods further comprise administering to the subject a TLR agonist. In some embodiments, the TLR agonist is a TLR2 agonist, a TLR3 agonist, a TLR7 agonist, a TLR8 agonist or a TLR9 agonist. In some embodiments, the TLR7 agonist is selected from the group consisting of vesatolimod, imiquimod, and resiquimod. In some embodiments, the methods comprise multiple administrations of the antibody or antigen-binding fragment thereof, optionally with a TLR agonist, at predetermined intervals. In some embodiments, after one or more administrations of the antibody or antigen-binding fragment thereof, the subject does not exhibit symptoms of HIV or AIDS in the absence of anti-retroviral treatment (ART) for at least 6 months, at least 1 year, at least 2 years, at least 3 years, at least 4 years, at least 5 years or longer. In some embodiments, after one or more administrations of the antibody, the subject has an HIV viral load copies/ml blood of less than 500, e.g., less than 400, less than 300, less than 200, less than 100, less than 50, in the absence of anti-retroviral treatment (ART) for at least 6 months, at least 1 year, at least 2 years, at least 3 years, or more.

In another aspect, provided are methods of identifying a human subject infected with an HIV or a population of HIV sensitive to an antibody or antigen-binding fragment thereof that competes with or comprises VH and VL regions that bind to an epitope of gp120 within the third variable loop (V3) and/or high mannose patch comprising a N332 oligomannose glycan. In some embodiments, the methods comprise identifying in a biological sample from the human subject a gp120 comprising the following amino acid residues: a glycosylated asparagine at the position corresponding to amino acid residue position 332 (N332glycan), an aspartate at the position corresponding to amino acid residue position 325 (D325), and one or more amino acid residues selected from the group consisting of: a threonine at the position corresponding to amino acid residue position 63 (T63), a leucine at the position corresponding to amino acid residue position 179 (L179), a threonine at the position corresponding to amino acid residue position 320 (T320), and a histidine at the position corresponding to amino acid residue position 330 (H330), wherein the amino acid positions are with reference to SEQ ID NO: 4. In some embodiments, the method entails identifying a subject infected with an HIV or a population of HIV expressing a gp120 comprising the following amino acid residues: i. N332glycan, D325 and T63; ii. N332glycan, D325 and L179; iii. N332glycan, D325 and T320; iv. N332glycan, D325 and H330; v. N332glycan, D325, T63 and L179; vi. N332glycan, D325, T63 and T320; vii. N332glycan, D325, T63 and H330; viii. N332glycan, D325, L179 and T320; ix. N332glycan, D325, L179 and H330; x. N332glycan, D325, T320 and H330; xi. N332glycan, D325, T63, T320 and H330; xii. N332glycan, D325, T63, L179 and T320; xiii. N332glycan, D325, T63, L179 and H330; xiv. N332glycan, D325, L179, T320 and H330; or xv. N332glycan, D325, T63, L179, T320 and H330, wherein the amino acid positions are with reference to SEQ ID NO: 4. In some embodiments, the method entails identifying a subject infected with an HIV or a population of HIV expressing a gp120 comprising the following amino acid residues: i. N332glycan, D325 and T63; ii. N332glycan, D325 and L179; iii. N332glycan, D325 and T320; or iv. N332glycan, D325 and H330, wherein the amino acid positions are with reference to SEQ ID NO: 4. In some embodiments, the method entails identifying a subject infected with an HIV or a population of HIV expressing a gp120 comprising the following amino acid residues: i. N332glycan, D325, T63 and L179; ii. N332glycan, D325, T63 and T320; iii. N332glycan, D325, T63 and H330; iv. N332glycan, D325, L179 and T320; v. N332glycan, D325, L179 and H330; or vi. N332glycan, D325, T320 and H330, wherein the amino acid positions are with reference to SEQ ID NO: 4. In some embodiments, the method entails identifying a subject infected with an HIV or a population of HIV expressing a gp120 comprising the following amino acid residues: i. N332glycan, D325, L179, T320 and H330; ii. N332glycan, D325, T63, T320 and H330; iii. N332glycan, D325, T63, L179 and T320; or iv. N332glycan, D325, T63, L179 and H330, wherein the amino acid positions are with reference to SEQ ID NO: 4. In some embodiments, the method entails identifying a subject infected with an HIV or a population of HIV expressing a gp120 comprising the following amino acid residues: i. N332glycan, D325, T63 and H330; ii. N332glycan, D325, T320 and H330; iii. N332glycan, D325, L179, T320 and H330; or iv. N332glycan, D325, T63, L179, T320 and H330, wherein the amino acid positions are with reference to SEQ ID NO: 4. In some embodiments, the subject is infected with an HIV or a population of HIV expressing a gp120 further comprising one or more of the following amino acid residues: a glycan at amino acid residue 301 (glycan301); a lysine at amino acid residue 677 (K677); an amino acid residue other than tryptophan (e.g., A, C, D, E, F, G, H, I, K, L, M, N, P, Q, R, S, T, V or Y) at position 17 (not_W17); an amino acid residue other than arginine (e.g., A, C, D, E, F, G, H, I, K, L, M, N, P, Q, S, T, V, W or Y) at position 747 (not_R747); an insertion_321.01 (e.g., an insertion of any amino acid (e.g., A, C, D, E, F, G, H, I, K, L, M, N, P, Q, R, S, T, V, W or Y) between position G321 and K322); a glutamic acid at position 429 (E429); a glutamine at position 442 (Q442); an arginine at position 335 (R335); an isoleucine at position 165 (I165); a serine at position 393 (S393); an isoleucine at position 307 (I307); a glycan at position 295 (295 glycan); and/or an asparagine at position 300 (N300), wherein the amino acid positions are with reference to SEQ ID NO: 4. In some embodiments, the antibody or antigen-binding fragment thereof competes with or comprises VH and VL regions from an antibody selected from the group consisting of GS-9722, GS-9721, PGT-121, PGT-121.66, PGT-121.414, PGT-122, PGT-123, PGT-124, PGT-125, PGT-126, PGT-128, PGT-130, PGT-133, PGT-134, PGT-135, PGT-136, PGT-137, PGT-138, PGT-139, 10-1074, 10-1074-J, VRC24, 2G12, BG18, 354BG8, 354BG18, 354BG42, 354BG33, 354BG129, 354BG188, 354BG411, 354BG426, DH270.1, DH270.6, PGDM12, VRC41.01, PGDM21, PCDN-33A, BF520.1 and VRC29.03. In some embodiments, the antibody or antigen-binding fragment thereof competes with or comprises VH and VL regions from an antibody selected from the group consisting of GS-9722, GS-9721, PGT-121, PGT-121.66, PGT-121.414, PGT-124, PGT-134, GS-2872, 10-1074, 10-1074-J, PGT-122 and PGT-123. In some embodiments, the human subject is acutely infected with HIV. In some embodiments, the antibody is administered to a human subject having an HIV infection of Fiebig stage IV or earlier. In some embodiments, the antibody is administered to a human subject who has not seroconverted. In some embodiments, the human subject is recently infected with HIV. In some embodiments, the antibody is administered to a human subject having an HIV infection of Fiebig stage V or Fiebig stage VI. In some embodiments, the human subject is chronically infected with HIV. In some embodiments, the human subject is infected with HIV clade B viruses. In some embodiments, the human subject is infected with HIV clade B viruses and the methods entail identifying a subject infected with an HIV or a population of HIV expressing a gp120 comprising the following amino acid residues: i. N332glycan, D325, T63 and H330; ii. N332glycan, D325, L179, T320 and H330; or iii. N332glycan, D325, T63, L179, T320 and H330. In some embodiments, the human subject is infected with HIV clade A viruses. In some embodiments, the human subject is infected with HIV clade C viruses.

With respect to further embodiments of the methods described herein, in some embodiments, the gp120 amino acids are identified in one or more gp120 polypeptide sequences expressed from an HIV or a population of HIV isolated from the subject. In some embodiments, the gp120 amino acids are identified in one or more gp120 polynucleotide sequences encoding a gp120 polypeptide from an HIV or a population of HIV isolated from the subject. In various embodiments, the methods entail performing next generation sequencing (NGS) on polynucleotide sequences encoding gp120 from a population of HIV. In some embodiments, the gp120 variants are detected to a frequency level of about 1%, e.g., to a frequency level of about 0.5%, of the virus population. In some embodiments, the gp120 amino acids are identified in one or more biological samples from the subject, wherein the one or more biological sample are obtained from blood, peripheral blood mononuclear cells (PBMCs), serum, plasma, semen or lymph nodes. In some embodiments, the methods entail identifying a population of HIV RNA in a serum or plasma sample. In some embodiments, the methods further comprise the step of obtaining one or more biological samples from the subject. In some embodiments, two or more biological samples are obtained from the subject. In some embodiments, two or more biological samples are obtained from the same tissue or fluid at two or more different time points. In some embodiments, two or more biological samples are obtained from different tissues or fluids, or from different anatomical locations.

Definitions

The words "a" and "an" denote one or more, unless specifically noted.

By "about" is meant a quantity, level, value, number, frequency, percentage, dimension, size, amount, weight or length that varies by as much as 30, 25, 20, 15, 10, 9, 8, 7, 6, 5, 4, 3, 2 or 1% to a reference quantity, level, value, number, frequency, percentage, dimension, size, amount, weight or length. In any embodiment discussed in the context of a numerical value used in conjunction with the term "about," it is specifically contemplated that the term about can be omitted.

Unless the context requires otherwise, throughout the present specification and claims, the word "comprise" and variations thereof, such as, "comprises" and "comprising" are to be construed in an open, inclusive sense, that is as "including, but not limited to". Where the terms "comprise" or "comprising" are used herein, it is understood that the disclosure further includes embodiments wherein these terms are replaced with "consist of" or "consist essentially of" or "consisting of" or "consisting essentially of."

By "consisting of" is meant including, and limited to, whatever follows the phrase "consisting of" Thus, the phrase "consisting of" indicates that the listed elements are required or mandatory, and that no other elements may be present.

By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

Reference throughout this specification to "one embodiment" or "an embodiment" means that a particular feature, structure or characteristic described in connection with the embodiment is included in at least one embodiment described herein. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

An "increased" or "enhanced" amount is typically a "statistically significant" amount, and may include an increase that is 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 2.1, 2.2, 2.3, 2.4, etc.) an amount or level described herein. It may also include an increase of at least 10%, at least 20%, at least 30%, at least 40%, at least 50%, at least 60%, at least 70%, at least 80%, at least 90%, at least 100%, at least 150%, at least 200%, at least 500%, or at least 1000% of an amount or level described herein.

A "decreased" or "reduced" or "lesser" amount is typically a "statistically significant" amount, and may include a decrease that is about 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein. It may also include a decrease of at least 10%, at least 20%, at least 30%, at least 40%, at least 50%, at least 60%, at least 70%, at least 80%, or at least 90%, at least 100%, at least 150%, at least 200%, at least 500%, or at least 1000% of an amount or level described herein.

A "composition" can comprise an active agent, e.g., a contrast agent and a carrier, inert or active, e.g., a pharmaceutically acceptable carrier, diluent or excipient. A composition may be a pharmaceutical composition. In particular embodiments, the compositions are sterile, substantially free of endotoxins or non-toxic to recipients at the dosage or concentration employed.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent or emulsifier which has been approved by the United States Food and Drug Administration as being acceptable for use in humans or domestic animals.

A "biological sample" or "sample" refers to any fluid, cellular or solid tissue sample from a subject that has or is suspected of having detectable HIV.

A "subject," "individual" or "patient" refers to any mammal, including humans and non-human primates. In particular embodiments, the mammal is human.

The term "buffer" as used herein denotes a pharmaceutically acceptable excipient, which stabilizes the pH of a pharmaceutical preparation. Suitable buffers are well known in the art. Suitable pharmaceutically acceptable buffers include but are not limited to acetate-buffers, histidine-buffers, citrate-buffers, succinate-buffers, tris-buffers and phosphate-buffers. In certain embodiments, the concentration of the buffer is from about 0.01 mM to about 1000 mM, about 0.1 mM to about 1000 mM, about 0.1 mM to about 500 mM, about 0.1 to about 200 mM, about 0.1 to about 100 mM, about 1 mM to about 1000 mM, about 1 mM to about 500 mM, about 1 mM to about 200 mM, about 1 mM to about 100 mM, about 1 mM to about 50 mM, about 2 mM to about 60 mM, about 4 mM to about 60 mM, or about 4 mM to about 40 mM, about 5 mM to about 20 mM, or about 5 mM to about 25 mM.

"Optional" or "optionally" means that the subsequently described event of circumstances may or may not occur, and that the description includes instances where said event or circumstance occurs and instances in which it does not.

"Pharmaceutical composition" refers to a formulation of a compound and a medium generally accepted in the art for the delivery of the biologically active compound to mammals, e.g., humans. Such a medium may include any pharmaceutically acceptable carriers, diluents or excipients therefore.

"Effective amount" or "therapeutically effective amount" refers to that amount of an antibody or antigen-binding fragment thereof that, when administered alone or in combination with another therapeutic agent to a cell, tissue, or subject is sufficient to effect treatment or a beneficial result in the subject. The amount which constitutes an "effective amount" will vary depending on the antibody or antigen-binding fragment thereof and its specific use, and potentially also the condition and its severity, the manner of administration, and the age of the subject to be treated, but can be determined routinely by one of ordinary skill in the art having regard to his own knowledge and to this disclosure. A therapeutically effective dose further refers to that amount of the antibody or antigen-binding fragment thereof sufficient to treat, prevent or ameliorate an infection or disease condition or the progression of an infection or disease, and that amount sufficient to effect an increase in rate of treatment, healing, prevention or amelioration of such conditions. When applied to an individual antibody or antigen-binding fragment thereof administered alone, a therapeutically effective dose refers to that active ingredient alone. When applied to a combination, a therapeutically effective dose refers to combined amounts of the active ingredients that result in the therapeutic effect, whether administered in combination, serially or simultaneously.

"Treat," "treating" or "treatment" as used herein covers the treatment of the disease, injury, or condition of interest, e.g., HIV-1 infection, in a subject, e.g., a mammal, such as a human, having the disease or condition of interest, and includes: (i) inhibiting progression of the disease, injury, or condition, i.e., arresting its development; (ii) reducing or relieving the disease, injury, or condition, i.e., causing regression of the disease or condition; or (iii) relieving the symptoms resulting from the disease, injury, or condition. As used herein, the terms "disease," "disorder," and "condition" may be used interchangeably. As used herein, "inhibition," "treatment," "treating," and "ameliorating" are used interchangeably and refer to, e.g., stasis of symptoms, prolongation of survival, partial or full amelioration of symptoms, and partial or full eradication of a condition, disease or disorder.

As used herein, "prevent" or "prevention" includes (i) preventing or inhibiting the disease, injury, or condition from occurring in a subject, in particular, when such subject is predisposed to the condition but has not yet been diagnosed as having it; or (ii) reducing the likelihood that the disease, injury, or condition will occur in the subject.

As used herein, the term "antibody" means an isolated or recombinant binding agent that comprises the necessary variable region sequences to specifically bind an antigenic epitope. Therefore, an antibody is any form of antibody or fragment thereof that exhibits the desired biological activity, e.g., binding the specific target antigen. Thus, it is used in the broadest sense and specifically covers monoclonal antibodies (including full-length monoclonal antibodies), polyclonal antibodies, human antibodies, humanized antibodies, chimeric antibodies, nanobodies, diabodies, multispecific antibodies (e.g., bispecific antibodies), and antibody fragments including but not limited to scFv, Fab, and Fab2, so long as they exhibit the desired biological activity.

The term "human antibody" refers to antibodies containing sequences of human origin, except for possible non-human CDR regions, and does not imply that the full structure of an Ig molecule be present, only that the antibody has minimal immunogenic effect in a human.

"Antibody fragments" comprise a portion of an intact antibody, for example, the antigen-binding or variable region of the intact antibody. Examples of antibody fragments include Fab, Fab', F(ab')2, and Fv fragments; diabodies; linear antibodies (e.g., Zapata et al., Protein Eng. 8(10): 1057-1062 (1995)); single-chain antibody molecules (e.g., scFv); and multispecific antibodies formed from antibody fragments. Papain digestion of antibodies produces two identical antigen-binding fragments, called "Fab" fragments, each with a single antigen-binding site, and a residual "Fc" fragment, a designation reflecting the ability to crystallize readily. Pepsin treatment yields an F(ab')2 fragment that has two antigen combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRS of each variable domain typically interact to define an antigen-binding site on the surface of the VH-VL dimer. Generally, the six CDRs collectively confer antigen-binding specificity to the antibody, although there are examples of antigen-binding specificity being maintained when one or more of the six CDRs are deleted or modified, e.g., by altering the amino acid sequence of the one or more CDRs, e.g., by amino acid insertion, deletion or substitution. In addition, even a single variable domain (or half of an Fv comprising only three CDRs specific for an antigen) has the ability to recognize and bind antigen, although at a lower affinity than the entire binding site. Residues other than those present in the CDRs may also be important for or play a role in antigen binding and/or specificity as shown for PGT121 and closely related somatic variants which interact with the gp120 antigen using residues in light chain framework 3 (Julien et al. Science 342:1477-83 (2013); Julien et al. PLOS Pathog. 9: e1003342 (2013)) These residues in part arise from an unusual three amino acid insertion which extends an otherwise short surface loop in PGT121 and related somatic variants (e.g. PGT122, PGT123, PGT124, PGT133, PGT134, 10-1074) that contacts both the N332 linked glycan and protein residues on HIV Env, effectively forming an additional (e.g. a fourth) complementarity determining region (CDR) loop in the PGT121 light chain between LC CDRs 2 and 3.

The term "hypervariable region" refers to the amino acid residues of an antibody that are typically responsible for antigen-binding. The hypervariable region generally comprises amino acid residues from a "complementarity determining region" or "CDR" (e.g., around about residues 24-34 (L1), 50-56 (L2) and 89-97 (L3) in the VL, and around about 31-35 (H1), 50-65 (H2) and 95-102 (H3) in the VH when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the VL, and 26-32 (H1), 52-56 (H2) and 95-101 (H3) in the VH when numbered in accordance with the Chothia numbering system; Chothia and Lesk, J. Mol. Biol. 196:901-917 (1987)); and/or those residues from a "hypervariable loop" VCDR (e.g., residues 27-38 (L1), 56-65 (L2) and 105-120 (L3) in the VL, and 27-38 (H1), 56-65 (H2) and 105-120 (H3) in the VH when numbered in accordance with the IMGT numbering system; Lefranc, M. P. et al. Nucl. Acids Res. 27:209-212 (1999), Ruiz, M. e al. Nucl. Acids Res. 28:219-221 (2000)). Optionally, the antibody has symmetrical insertions at one or more of the following points 28, 36 (L1), 63, 74-75 (L2) and 123 (L3) in the VL, and 28, 36 (H1), 63, 74-75 (H2) and 123 (H3) in the VH when numbered in accordance with AHo; Honneger, A. and Plunkthun, A. J. Mol. Biol. 309:657-670 (2001)).

The "Fab" fragment is a region on an antibody that binds to antigens. It is composed of one constant and one variable domain of each of the heavy and light chain. These domains shape the paratope—the antigen-binding site—at the amino terminal end of the monomer. The two variable domains bind the epitope on their specific antigens. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa and lambda, based on the amino acid sequences of their variable or constant domains. Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2.

"Single-chain Fv" or "scFv" or "sFv" antibody fragments comprise the VH and VL domains of antibody, wherein these domains are present in a single polypeptide chain. In some embodiments, the Fv polypeptide further comprises a polypeptide linker between the VH and VL domains, which enables the sFv to form the desired structure for antigen-binding.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al, Proc. Natl. Acad. Sci. USA, 90:6444-6448 (1993).

An "isolated" antibody or antigen-binding fragment thereof is one that has been identified and separated and/or recovered from a component of its natural environment. Contaminant components of its natural environment are materials that would interfere with diagnostic or therapeutic uses for the antibody, and may include enzymes, hormones, and other proteinaceous or nonproteinaceous solutes. In some embodiments, the antibody will be purified (1) to greater than 95% by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

An antibody or antigen-binding fragment thereof that "specifically binds to" or is "specific for" a particular polypeptide or an epitope on a particular polypeptide is one that binds to that particular polypeptide or epitope on a particular polypeptide without substantially binding to any other polypeptide or polypeptide epitope. In some embodiments, the antibody of the present disclosure specifically binds to an antigen, e.g., an HIV-1 gp120 polypeptide, with dissociation constant Kd equal to or lower than 100 nM, optionally lower than 10 nM, optionally lower than 1 nM, optionally lower than 0.5 nM, optionally lower than 0.1 nM, optionally lower than 0.01 nM, or optionally lower than 0.005 nM, in the form of monoclonal antibody, scFv, Fab, or other form of antibody measured at a temperature of about 4° C., 25° C., 37° C., or 42° C. Affinities of antibodies can be readily determined using conventional techniques, for example, those described by Scatchard et al. (Ann. N. Y. Acad. Sci. USA 51: 660 (1949), ELISA assays, biolayer interferometry (BLI) assays, and surface plasmon resonance (SPR) assays). Binding properties of an antibody to antigens, cells or tissues thereof may generally be determined and assessed using immunodetection methods including, for example, immunofluorescence-based assays, such as immuno-histochemistry (IHC) and/or fluorescence-activated cell sorting (FACS).

As used herein, an antibody that "internalizes" is one that is taken up by (i.e., enters) the cell upon binding to an antigen on a mammalian cell {e.g., a cell surface polypeptide or receptor). The internalizing antibody will of course include antibody fragments, human or chimeric antibody, and antibody conjugates. For certain therapeutic applications, internalization in vivo is contemplated. The number of antibody molecules internalized will be sufficient or adequate to kill a cell or inhibit its growth, especially an infected cell. Depending on the potency of the antibody or antibody conjugate, in some instances, the uptake of a single antibody molecule into the cell is sufficient to kill the target cell to which the antibody binds. For example, certain toxins are highly potent in killing such that internalization of one molecule of the toxin conjugated to the antibody is sufficient to kill the infected cell.

The term "antagonist" antibody is used in the broadest sense, and includes an antibody that partially or fully blocks, inhibits, or neutralizes a biological activity of an epitope, polypeptide, or cell that it specifically binds. Methods for identifying antagonist antibodies may comprise contacting a polypeptide or cell specifically bound by a candidate antagonist antibody with the candidate antagonist antibody and measuring a detectable change in one or more biological activities normally associated with the polypeptide or cell.

An "antibody that inhibits the growth of infected cells" or a "growth inhibitory" antibody is one that binds to and results in measurable growth inhibition of infected cells expressing or capable of expressing an HIV1 epitope bound by an antibody. Preferred growth inhibitory antibodies inhibit growth of infected cells by greater than 20%, preferably from about 20% to about 50%, and even more preferably, by greater than 50% (e.g., from about 50% to about 100%) as compared to the appropriate control, the control typically being infected cells not treated with the antibody being tested. Growth inhibition can be measured at an antibody concentration of about 0.1 to about 30 μg/ml or about 0.5 nM to about 200 nM in cell culture, where the growth inhibition is determined 1-10 days after exposure of the infected cells to the antibody. Growth inhibition of infected cells in vivo can be determined in various ways known in the art. The antibody is growth inhibitory in vivo if administration of the antibody at about 1 μg/kg to about 100 mg/kg body weight results in reduction the percent of infected cells or total number of infected cells within about 5 days to 3 months from the first administration of the antibody, preferably within about 5 to 30 days.

An antibody that "induces apoptosis" is one which induces programmed cell death as determined by binding of annexin V, fragmentation of DNA, cell shrinkage, dilation of endoplasmic reticulum, cell fragmentation, and/or formation of membrane vesicles (called apoptotic bodies). Preferably the cell is an infected cell. Various methods are available for evaluating the cellular events associated with apoptosis. For example, phosphatidyl serine (PS) translocation can be measured by annexin binding; DNA fragmentation can be evaluated through DNA laddering; and nuclear/chromatin condensation along with DNA fragmentation can be evaluated by any increase in hypodiploid cells. Preferably, the antibody that induces apoptosis is one that results in about 2- to 50-fold, preferably about 5- to 50-fold, and most preferably about 10- to 50-fold, induction of annexin binding relative to untreated cell in an annexin binding assay.

Antibody "effector functions" refer to those biological activities attributable to the Fc region (a native sequence Fc region or amino acid sequence variant Fc region) of an antibody, and vary with the antibody isotype. Examples of antibody effector functions include: Clq binding and complement dependent cytotoxicity; Fc receptor binding; antibody-dependent cell-mediated cytotoxicity (ADCC); phagocytosis (e.g., antibody-dependent cell-mediated phagocytosis (ADCP)); down regulation of cell surface receptors (e.g., B cell receptor); and B cell activation.

"Antibody-dependent cell-mediated cytotoxicity" or "ADCC" refers to a form of cytotoxicity in which secreted or exogenously administered Ig bound to Fc receptors (FcRs) present on certain cytotoxic cells (e.g., Natural Killer (NK) cells, neutrophils, and macrophages) enable these cytotoxic effector cells to bind specifically to an antigen-bearing target cell and subsequently kill the target cell with cytotoxins. The antibodies "arm" the cytotoxic cells and are required for such killing. The primary cells for mediating ACC, NK cells, express FcγRIII only, whereas monocytes express FcγRI, FcγRII and FcγRIII. FcR expression on hematopoietic cells is summarized in Table 4 on page 464 of Ravetch and Kinet, Annu. Rev. Immunol 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the antibody or antigen-binding fragment thereof may be assessed in vivo, e.g., in an animal model such as that disclosed in Clynes et al., Proc. Natl. Acad. Sci. (USA) 95:652-656 (1998).

"Fc receptor" or "FcR" describes a receptor that binds to the Fc region of an antibody. In certain embodiments, the FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof, and FcγRIIC, which includes the FcγRIIB extracellular domain fused to an activating cytoplasmic region. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see review M. in Daeron, Annu. Rev. Immunol. 15:203-234 (1997)). FcRs are reviewed in Ravetch and Kinet, Annu. Rev. Immunol 9:457-92 (1991); Capel et al, Immunomethods 4:25-34 (1994); and de Haas et al, J. Lab. Clin. Med. 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al, J. Immunol. 117:587 (1976) and Kim et al, J. Immunol. 24:249 (1994)), and which plays a role in salvaging IgG from lysosomal degradation by FcRn dependent recycling following endocytosis. FcRn binding following pinocytosis in endothelial cells has been shown to be important for sustaining the prolonged pharmacokinetic half-life of antibodies. Assessment of pH dependent human FcRn binding of antibodies in vitro may be performed to provide a prediction of potential for favorable clinical pharmacokinetics (Datta-Mannan and Wroblewski, Drug Metab. Dispos. 42:1867-1872 (2014)).

"Human effector cells" are leukocytes that express one or more FcRs and perform effector functions. Preferably, the cells express at least FcγRIII and perform ADCC effector function. Examples of human leukocytes that mediate ADCC include PBMC, NK cells, monocytes, cytotoxic T cells and neutrophils; with PBMCs and NK cells being preferred. The effector cells may be isolated from a native source, e.g., from blood.

"Complement dependent cytotoxicity" or "CDC" refers to the lysis of a target cell in the presence of complement. Activation of the classical complement pathway is initiated by the binding of the first component of the complement system (Clq) to antibodies (of the appropriate subclass) that are bound to their cognate antigen. To assess complement activation, a CDC assay, e.g., as described in Gazzano-Santoro et al, J. Immunol. Methods 202: 163 (1996), may be performed.

A "neutralizing antibody" is one that can neutralize the ability of that pathogen to initiate and/or perpetuate an infection in a host and/or in target cells in vitro. Described herein are neutralizing monoclonal human antibodies and antigen-binding fragments thereof, wherein the antibody recognizes an antigen from HIV, e.g., a gp120 polypeptide. In certain embodiments, a "neutralizing antibody" may inhibit the entry of HIV-1 virus, e.g., SF162 and/or JR-CSF, with a neutralization index>1.5 or >2.0 (Kostrikis L G et al./Virol. 1996; 70(1): 445-458). By "broadly neutralizing antibodies" are meant antibodies that neutralize more than one HIV-1 virus species (from diverse clades and different strains within a clade) in a neutralization assay. A broad neutralizing antibody may neutralize at least 2, 3, 4, 5, 6, 7, 8, 9 or more different strains of HIV-1, the strains belonging to the same or different clades. In particular embodiments, a broad neutralizing antibody may neutralize multiple HIV-1 species belonging to at least 2, 3, 4, 5, or 6 different clades. In certain embodiments, the inhibitory concentration of the monoclonal antibody may be less than about 0.0001 μg/ml, less than about 0.001 μg/ml, less than about 0.01 μg/ml, less than about 0.1 μg/ml, less than about 0.5 μg/ml, less than about 1.0 μg/ml, less than about 5 μg/ml, less than about 10

μg/ml, less than about 25 μg/ml, less than about 50 μg/ml, or less than about 100 μg/ml to neutralize about 50% of the input virus in the neutralization assay.

HIV viruses are divided into specific groups, M, N, O and P, of which M is the "major" group and responsible for majority of HIV/AIDS globally. Based on their genetic sequence, Group M is further subdivided into subtypes (also called clades) with prevalence in distinct geographical locations.

A Group M "subtype" or "clade" is a subtype of HIV-1 group M defined by genetic sequence data. Examples of Group M subtypes include Subtypes A-K. Some of the subtypes are known to be more virulent or are resistant to different medications. There are also "circulating recombinant forms" or CRFs derived from recombination between viruses of different subtypes, which are each given a number. CRF12_BF, for example, is a recombination between subtypes B and F. Subtype A is common in West Africa. Subtype B is the dominant form in Europe, the Americas, Japan, Thailand, and Australia. Subtype C is the dominant form in Southern Africa, Eastern Africa, India, Nepal, and parts of China. Subtype D is generally only seen in Eastern and central Africa. Subtype E has never been identified as a nonrecombinant, only recombined with subtype A as CRF01_AE. Subtype F has been found in central Africa, South America and Eastern Europe. Subtype G (and the CRF02_AG) have been found in Africa and central Europe. Subtype H is limited to central Africa. Subtype I was originally used to describe a strain that is now accounted for as CRF04_cpx, with the cpx for a "complex" recombination of several subtypes. Subtype J is primarily found in North, Central and West Africa, and the Caribbean Subtype K is limited to the Democratic Republic of Congo and Cameroon. These subtypes are sometimes further split into sub-subtypes such as A1 and A2 or F1 and F2. In 2015, the strain CRF19, a recombinant of subtype A, subtype D and subtype G, with a subtype D protease was found to be strongly associated with rapid progression to AIDS in Cuba.

"HIV tropism" refers to the specificity of an HIV virus for a particular host cell, determined in part by the interaction of viral surface structures with receptors present on the surface of the host cell. HIV tropism of a patient's virus may be measured, e.g. by sequencing analysis or by the TROFILE® assay (monogrambio.com) (see, e.g., Lee, et al, AIDS Res Hum Retroviruses. (2013) 29(6):979-84).

HIV can infect a variety of cells such as CD4+ helper T cells and macrophages that express the CD4 molecule on their surface. HIV-1 entry to macrophages and T helper cells is mediated not only through interaction of the virion envelope glycoprotein, (e.g., gp120) with the CD4 molecule on the target cells but also with its chemokine coreceptors. Macrophage (M-tropic) strains of HIV-1, or non-syncitia-inducing strains (NSI) use the beta-chemokine receptor CCR5 for entry and are thus able to replicate in macrophages and CD4+ T-cells. These strains are called R5 viruses. This CCR5 coreceptor is used by almost all primary HIV-1 isolates regardless of viral genetic subtype. T-tropic isolates, or syncitia-inducing (SI) strains replicate in primary CD4+ T-cells as well as in macrophages and use the alpha-chemokine receptor, CSCR4, for entry. These strains are called X4 viruses. Viruses that use only the CCR5 receptor are termed R5, those that only use CXCR4 are termed X4, and those that use both, X4R5 or dual/mixed-tropism. However, the use of a coreceptor alone does not explain viral tropism, as not all R5 viruses are able to use CCR5 on macrophages for a productive infection.

Also described herein are "non-neutralizing antibodies," which in certain embodiments are antibodies that bind to one or more strains of virus but do not neutralize the virus. However, in terms of Fc-mediated killing, the non-neutralizing antibody could still eliminate cells expressing viral antigens that are bound but not neutralized by the antibody. Thus, in certain embodiments, an antibody can bind a viral antigen and eliminate virally infected cells without neutralizing the virus.

The term "nucleic acid molecule" refers to a polymeric form of nucleotides and includes both sense and anti-sense strands of RNA, cDNA, genomic DNA, and synthetic forms and mixed polymers of the above. In particular embodiments, a nucleotide refers to a ribonucleotide, deoxynucleotide or a modified form of either type of nucleotide, and combinations thereof. The terms also include, but is not limited to, single- and double-stranded forms of DNA. In addition, a polynucleotide, e.g., a cDNA or mRNA, may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analogue, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hairpinned, circular and padlocked conformations. A reference to a nucleic acid sequence encompasses its complement unless otherwise specified. Thus, a reference to a nucleic acid molecule having a particular sequence should be understood to encompass its complementary strand, with its complementary sequence. The term also includes codon-optimized nucleic acids.

The term "operably linked" refers to two or more nucleic acid sequence elements that are usually physically linked and are in a functional relationship with each other. For instance, a promoter is operably linked to a coding sequence if the promoter is able to initiate or regulate the transcription or expression of a coding sequence, in which case, the coding sequence should be understood as being "under the control of" the promoter.

A "substitution," as used herein, denotes the replacement of one or more amino acids or nucleotides by different amino acids or nucleotides, respectively.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an antibody or fragment thereof" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to A polynucleotide "variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences described herein and evaluating one or more biological activities of the encoded polypeptide as described herein and/or using any of a number of techniques well known in the art.

A polypeptide "variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences of the invention and evaluating one or more biological activities of the polypeptide as described herein and/or using any of a number of techniques well known in the art.

The term "variant" may also refer to any naturally occurring or engineered molecule comprising one or more nucleotide or amino acid mutations. In one embodiment, the molecule is an antibody. For example, somatic variants may encompass all related naturally occurring antibodies that are part of or derived from the same B-cell lineage. Engineered variants may encompass all single mutations or combinatorial mutations made to an antibody.

Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the polypeptide sequences of the disclosed antibodies and antigen-binding fragments thereof, or corresponding DNA sequences that encode said polypeptides without appreciable loss of their biological utility or activity.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Alignment of sequences for comparison may be conducted using the Megalign program in the Lasergene suite of bioinformatics software (DNASTAR, Inc., Madison, WI), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J. (1990) Unified Approach to Alignment and Phylogenes pp. 626-645 Methods in Enzymology vol. 183, Academic Press, Inc., San Diego, CA; Higgins, D. G. and Sharp, P. M. (1989) CABIOS 5: 151-153; Myers, E. W. and Muller W. (1988) CABIOS 4:11-17; Robinson, E. D. (1971) Comb. Theor 77: 105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, CA; Wilbur, W. J. and Lipman, D. J. (1983) Proc. Natl. Acad., Sci. USA 80:726-730.

Alternatively, alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, WI), or by inspection.

One example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides described herein. Software for performing BLAST analyses is publicly available through the National Center for Biotechnology Information.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a word length (W) of 11, and expectation (E) of 10, and the BLOSUM62 scoring matrix (see Henikoff and Henikoff (1989) Proc. Natl. Acad. Sci. USA 89: 10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

"Homology" refers to the percentage of residues in the polynucleotide or polypeptide sequence variant that are identical to the non-variant sequence after aligning the sequences and introducing gaps, if necessary, to achieve the maximum percent homology.

"Binding affinity" may refer to a binding dissociate constant (Kd) or an apparent affinity (e.g., EC50) value.

DETAILED DESCRIPTION

1. Introduction

Figure 1:
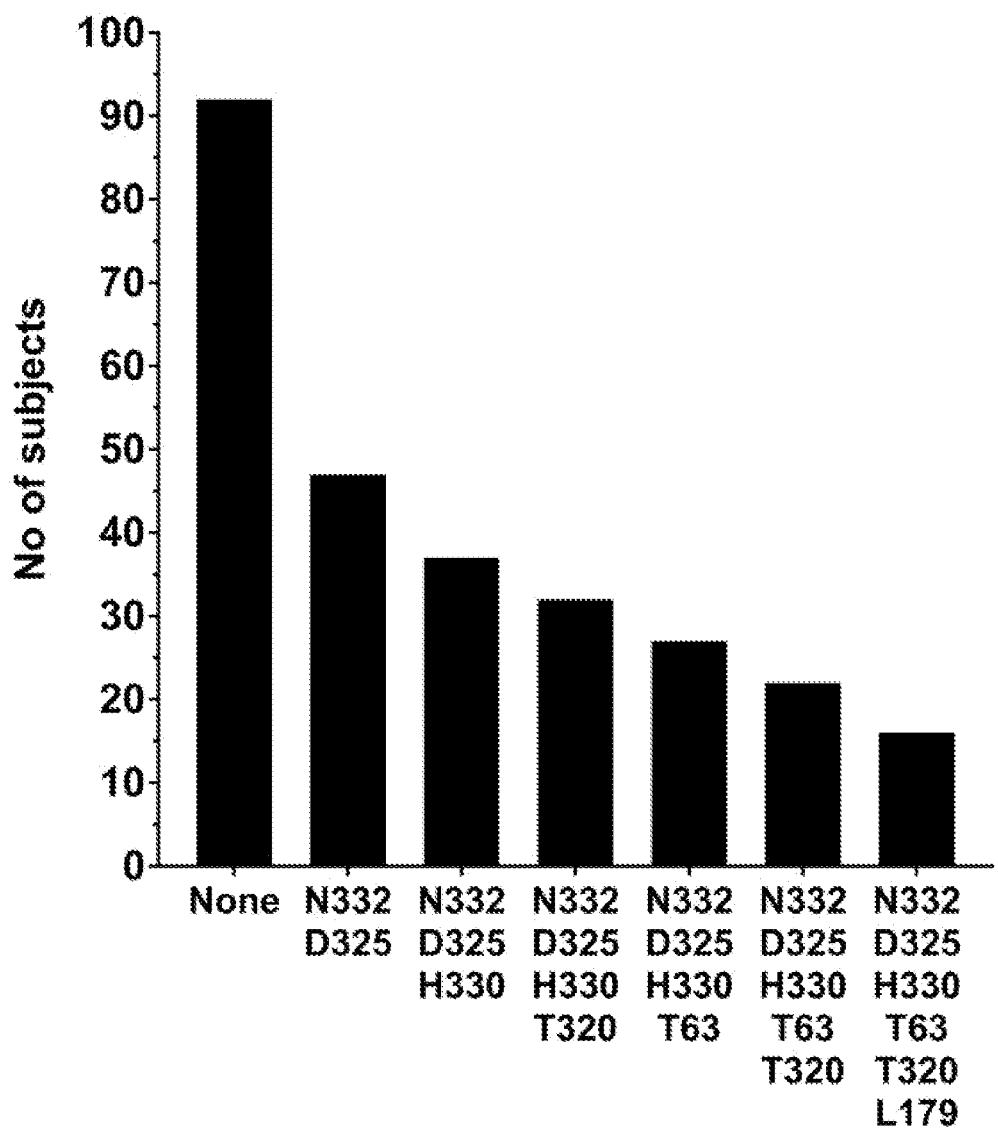
FIG. 1 illustrates the number of screened subjects from the Zurich Primary HIV Infection Cohort Study with a genotype predicting sensitivity to GS-9722 (elipovimab). Pre-ART plasma samples from 92 individuals were analyzed in the GenoSure HIV Envelope RNA Assay. "None," indicates all screened individuals without selection for specific amino acids in the HIV envelope gene. Amino acid positions indicated for each category.

The present methods are based, in part, on the unexpected discovery of HIV-infected patient populations who are responsive to the administration of an anti-HIV gp120 V3-glycan directed antibody or antigen-binding fragment thereof, in the absence of co-administration of additional anti-HIV antibodies directed against other HIV antigens (e.g., gp41) or non-overlapping epitopes of the same HIV antigen (e.g., directed against gp120 in the region of the CD4 binding site or V2 apex region). Such patients are infected with a species of HIV having a gp120 protein that is bound by a V3-glycan directed antibody or antigen-binding fragment thereof.

Generally, the methods entail identifying a human subject who is infected with an HIV or a population of HIV expressing a gp120 comprising: a glycosylated asparagine at the position corresponding to amino acid residue position 332 (N332glycan), an aspartate at the position corresponding to amino acid residue position 325 (D325), and one or more amino acid of: a threonine at the position corresponding to amino acid residue position 63 (T63), a leucine at the position corresponding to amino acid residue position 179 (L179), a threonine at the position corresponding to amino acid residue position 320 (T320), and a histidine at the position corresponding to amino acid residue position 330 (H330), wherein the amino acid positions are with reference to SEQ ID NO: 4 (i.e., residues 1-511 of NCBI Ref Seq No. NP_057856.1). In various embodiments, the glycan is an oligomannose.

2. Identification of Subjects Responsive to Treatment with an Anti-HIV gp120 V3-Glycan Directed Antibody or Antigen-Binding Fragment Thereof.

In some embodiments, the patient is identified by receiving a report of the HIV species infecting the patient that identifies the HIV gp120 amino acids residues present at the designated amino acid positions of interest, e.g., at positions 332 and 325, and one or more amino acid positions from the group consisting of: 63, 179, 320 and 330, wherein the amino acid positions are with reference to SEQ ID NO: 4. In some embodiments, the patient is identified by conducting one or more assays (e.g., polynucleotide or polypeptide sequencing) to determine the amino acid sequence(s) of the gp120 or the amino acid residues present at the designated amino acid positions of interest of the gp120 protein(s) of the HIV species infecting the patient. Identification of the full length or partial sequences of the gp120 proteins obtained from the subject can be determined at the polynucleotide or polypeptide level. In some embodiments, the amino acids present at the gp120 residue positions of interest are determined at the polypeptide level.

In various embodiments, the methods entail identifying a subject infected with an HIV or a population of HIV expressing a gp120 comprising N332glycan, D325 and T63, wherein the amino acid positions are with reference to SEQ ID NO: 4.

In various embodiments, the methods entail identifying a subject infected with an HIV or a population of HIV expressing a gp120 comprising N332glycan, D325 and L179, wherein the amino acid positions are with reference to SEQ ID NO: 4.

In various embodiments, the methods entail identifying a subject infected with an HIV or a population of HIV expressing a gp120 comprising N332glycan, D325 and T320, wherein the amino acid positions are with reference to SEQ ID NO: 4.

In various embodiments, the methods entail identifying a subject infected with an HIV or a population of HIV expressing a gp120 comprising N332glycan, D325 and H330, wherein the amino acid positions are with reference to SEQ ID NO: 4.

In various embodiments, the methods entail identifying a subject infected with an HIV or a population of HIV expressing a gp120 comprising N332glycan, D325, T63 and L179, wherein the amino acid positions are with reference to SEQ ID NO: 4.

In various embodiments, the methods entail identifying a subject infected with an HIV or a population of HIV expressing a gp120 comprising N332glycan, D325, T63 and T320, wherein the amino acid positions are with reference to SEQ ID NO: 4.

In some embodiments, the subject is infected with HIV clade B viruses. In various embodiments, the methods entail identifying a subject infected with an HIV or a population of HIV expressing a gp120 comprising N332glycan, D325, T63 and H330, wherein the amino acid positions are with reference to SEQ ID NO: 4. In various embodiments, the methods entail identifying a subject infected with an HIV or a population of HIV expressing a gp120 comprising N332glycan, D325, T63, L179, T320 and H330, wherein the amino acid positions are with reference to SEQ ID NO: 4.

In various embodiments, the methods entail identifying a subject infected with an HIV or a population of HIV expressing a gp120 comprising N332glycan, D325, T320 and H330, wherein the amino acid positions are with reference to SEQ ID NO: 4.

In various embodiments, the methods entail identifying a subject infected with an HIV or a population of HIV expressing a gp120 comprising N332glycan, D325, L179, T320 and H330, wherein the amino acid positions are with reference to SEQ ID NO: 4. In some embodiments, the subject is infected with HIV clade A and/or HIV clade C viruses. In some embodiments, the subject is infected with HIV clade A, clade B and/or HIV clade C viruses.

In various embodiments, the methods entail identifying a subject infected with an HIV or a population of HIV expressing a gp120 comprising N332glycan, D325, T63, L179 and T320, wherein the amino acid positions are with reference to SEQ ID NO: 4.

In various embodiments, the methods entail identifying a subject infected with an HIV or a population of HIV expressing a gp120 comprising N332glycan, D325, T63, L179 and H330, wherein the amino acid positions are with reference to SEQ ID NO: 4.

In some embodiments, the subject is infected with an HIV or a population of HIV expressing a gp120 further comprising one or more of the following amino acid residues: a glycan at amino acid residue 301 (glycan301); a lysine at amino acid residue 677 (K677); an amino acid residue other than tryptophan (Trp, W) (e.g., alanine (Ala, A); cysteine (Cys, C); aspartate or aspartic acid (Asp, D); glutamate or glutamic acid (Glu, E); phenylalanine (Phe, F); glycine (Gly, G); histidine (His, H); isoleucine (Ile, I); lysine (Lys, K); leucine (Leu, L); methionine (Met, M); asparagine (Asn, N); proline (Pro, P); glutamine (Gln, Q); arginine (Arg, R); serine (Ser, S); Threonine (Thr, T); valine (Val, V) or tyrosine (Tyr, Y)) at position 17 (not_W17); an amino acid residue other than arginine (e.g., A, C, D, E, F, G, H, I, K, L, M, N, P, Q, S, T, V, W or Y) at position 747 (not_R747); an insertion_321.01 (e.g., an insertion of any amino acid (e.g., A, C, D, E, F, G, H, I, K, L, M, N, P, Q, R, S, T, V, W or Y) between position G321 and K322); a glutamic acid at position 429 (E429); a glutamine at position 442 (Q442); an arginine at position 335 (R335); an isoleucine at position 165 (I165); a serine at position 393 (S393); an isoleucine at position 307 (I307); a glycan at position 295 (295 glycan); and/or an asparagine at position 300 (N300), wherein the amino acid positions are with reference to SEQ ID NO: 4.

gp120

Envelope glycoprotein gp120 (or gp120) is a 120 kDa glycoprotein that is part of the outer layer of HIV. It presents itself as viral membrane spikes consisting of three molecules of gp120 linked together and anchored to the membrane by gp41 protein. Gp120 is essential for viral infection as it facilitates HIV entry into the host cell through its interaction with cell surface receptors. These receptors include DC-SIGN, Heparan Sulfate Proteoglycan, and the CD4 receptor. Binding to CD4 on helper T-cells induces the start of a cascade of conformational changes in gp120 and gp41 that lead to the fusion of the virus with the host cell membrane.

Gp120 is encoded by the HIV env gene. The env gene encodes a gene product of around 850 amino acids. The primary env product is the protein gp160, which gets cleaved to gp120 (about 480 amino acids) and gp41 (about 345 amino acids) in the endoplasmic reticulum by the cellular protease furin.

The V3 glycan site on gp120 is formed partly by a section of the CCR5 coreceptor site and partly by the surrounding camouflaging glycans (so-called "high mannose patch") (Sok, et al., *Immunity* (2016) 45, 31-45). Broadly neutralizing antibodies (bnAbs) to the V3 glycan site are the most common of all Abs found in HIV infection (Walker, et al., *PLoS Pathog.* (2010) 6:e1001028 (2010); Landais, et al., *PLoS Pathog.* (2016) 12:e1005369; Georgiev, et al. *Science* (2013) 340:751-756). A consensus sequence of the V3 region of gp120 (Milich et al., *J Virol.*, 67(9):5623-5634 (1993) is provided below:

```
                                              (SEQ ID NO: 1)
CTRPNNNTRKSIHIGPGRAFYTTGEIIGDIRQAHC.
```

The amino acid sequence of an exemplary gp160 polypeptide of HIV clone WITO is provided below (the V3 hypervariable loop is boldened and the N332 potential N-linked glycosylation site is boldened and underlined):

```
                                              (SEQ ID NO: 2)
MKVMGTKKNYQHLWRWGIMLLGMLMMSSAAEQLWVTVYYGVPVWREANTT

LFCASDAKAYDTEVHNVWATHACVPTDPNPQEVVMGNVTEDFNMWKNNMV

EQMHEDIISLWDQSLKPCVKLTPLCVTLHCTNVTISSTNGSTANVIMREE

MKNCSFNTTTVIRDKIQKEYALFYKLDIVPIEGKNTNTSYRLINCNTSVI

TQACPKVSFEPIPIHYCAPAGFAILKCNNKTFNGKGPCRNVSTVQCTHGI

KPVVSTQLLLNGSLAEEDIIIRSENFTNNGKNIIVQLKEPVKINCTRPGN

NTRRSINIGPGRAFYATGAIIGDIRKAHCNISTEQWNNTLTQIVDKLREQ

FGNKTIIFNQSSGGDPEVVMHTFNCGGEFFYCNSTQLFNSTWFNNGTSTW

NSTADNITLPCRIKQVINMWQEVGKAMYAPPIRGQIDCSSNITGLILTRD

GGSNSSQNETFRPGGGNMKDNWRSELYKYKVVKIEPLGIAPTRAKRRVVQ
```

-continued
```
REKRAVTLGAVFLGFLGAAGSTMGAASLTLIVQARLLLSGIVQQQSNLLR

AIEAQQHMLQLTVWGIKQLQARVLAIERYLKDQQLLGIWGCSGKLICTTT

VPWNTSWSNKSYDYIWNNMTWMQWEREIDNYTGFIYTLIEESQNQQEKNE

LELLELDKWASLWNWFNITNWLWYIKLFIMIIGGLVGLRIVCAVLSIVNR

VRQGYSPLSFQTRLPNPRGPDRPEETEGEGGERDRDRSARLVNGFLAIIW

DDLRSLCLFSYHRLRDLLLIVARVVEILGRRGWEILKYWWNLLKYWSQEL

KNSAVSLLNVTAIAVAEGTDRVIEIVQRAVRAILHIPTRIRQGFERALL
```

The amino acid sequence of an exemplary gp160 polypeptide of HIV clone identified in NCBI Ref Seq No. NP_057856.1 is provided below (the V3 hypervariable loop is boldened and the N332 potential N-linked glycosylation site is boldened and underlined):

(SEQ ID NO: 3)

MRVKEKYQHLWRWGWRWGTMLLGMLMICSATEKLWVTVYYGVPVWKEATT

TLFCASDAKAYDTEVHNVWATHACVPTDPNPQEVVLVNVTENFNMWKNDM

VEQMHEDIISLWDQSLKPCVKLTPLCVSLKCTDLKNDTNTNSSSGRMIME

KGEIKNCSFNISTSIRGKVQKEYAFFYKLDIIPIDNDTTSYKLTSCNTSV

ITQACPKVSFEPIPIHYCAPAGFAILKCNNKTFNGTGPCTNVSTVQCTHG

IRPVVSTQLLLNGSLAEEEVVIRSVNFTDNAKTIIVQLNTSVEINCTRPN

NNTRKRIRIQRGPGRAFVTIGKIGNMRQAHC<u>N</u>ISRAKWNNTLKQIASKLR

EQFGNNKTIIFKQSSGGDPEIVTHSFNCGGEFFYCNSTQLFNSTWFNSTW

STEGSNNTEGSDTITLPCRIKQIINMWQKVGKAMYAPPISGQIRCSSNIT

GLLLTRDGGNSNNESEIFRPGGGDMRDNWRSELYKYKVVKIEPLGVAPTK

AKRRVVQREKRAVGIGALFLGFLGAAGSTMGAASMTLTVQARQLLSGIVQ

QQNNLLRAIEAQQHLLQLTVWGIKQLQARILAVERYLKDQQLLGIWGCSG

KLICTTAVPWNASWSNKSLEQIWNHTTWMEWDREINNYTSLIHSLIEESQ

NQQEKNEQELLELDKWASLWNWFNITNWLWYIKLFIMIVGGLVGLRIVFA

VLSIVNRVRQGYSPLSFQTHLPTPRGPDRPEGIEEEGGERDRDRSIRLVN

GSLALIWDDLRSLCLFSYHRLRDLLLIVTRIVELLGRRGWEALKYWWNLL

QYWSQELKNSAVSLLNATAIAVAEGTDRVIEVVQGACRAIRHIPRRIRQG

LERILL

The amino acid sequence of an exemplary gp120 polypeptide of HXB2 subtype B HIV-1 isolate (GenBank Accession No. K0345; corresponding to residues 1-511 of NCBI Ref Seq No. NP_057856.1) is provided below (the V3 hypervariable loop is boldened and the N332 potential N-linked glycosylation site is boldened and underlined; signal peptide is underlined):

(SEQ ID NO: 4)

<u>MRVKEKYQHLWRWGWRWGTMLLGMLMI</u>CSATEKLWVTVYYGVPVWKEATT

TLFCASDAKAYDTEVHNVWATHACVPTDPNPQEVVLVNVTENFNMWKNDM

VEQMHEDIISLWDQSLKPCVKLTPLCVSLKCTDLKNDTNTNSSSGRMIME

KGEIKNCSFNISTSIRGKVQKEYAFFYKLDIIPIDNDTTSYKLTSCNTSV

ITQACPKVSFEPIPIHYCAPAGFAILKCNNKTFNGTGPCTNVSTVQCTHG

-continued

IRPVVSTQLLLNGSLAEEEVVIRSVNFTDNAKTIIVQLNTSVEINCTRPN

NNTRKRIRIQRGPGRAFVTIGKIGNMRQARC<u>N</u>ISRAKWNNTLKQIASKLR

EQFGNNKTIIFKQSSGGDPEIVTHSFNCGGEFFYCNSTQLFNSTWFNSTW

STEGSNNTEGSDTITLPCRIKQIINMWQKVGKAMYAPPISGQIRCSSNIT

GLLLTRDGGNSNNESEIFRPGGGDMRDNWRSELYKYKVVKIEPLGVAPTK

AKRRVVQREKR

The amino acid sequence of an exemplary gp120 polypeptide is provided below:

(SEQ ID NO: 5)

AEQLWVTVYYGVPVWREANTTLFCASDAKAYDTEVHNVWATHACVPTDPN

PQEVVMGNVTEDFNMWKNNMVEQMHEDIISLWDQSLKPCVKLTPLCVTLH

CTNVTISSTNGSTANVTMREEMKNCSFNTTTVIRDKIQKEYALFYKLDIV

PIEGKNTNTSYRLINCNTSVITQACPKVSFEPIPIHYCAPAGFAILKCNN

KTFNGKGPCRNVSTVQCTHGIKPVVSTQLLLNGSLAEEDIIIRSENFTNN

GKNIIVQLKEPVKINCTRPGNNTRRSINIGPGRAFYATGAIIGDIRKAHC

<u>N</u>ISTEQWNNTLTQIVDKLREQFGNKTIIFNQSSGGDPEVVMHTFNCGGEF

FYCNSTQLFNSTWFNNGTSTWNSTADNITLPCRIKQVINMWQEVGKAMYA

PPIRGQIDCSSNITGLILTRDGGSNSSQNETFRPGGGNMKDNWRSELYKY

KVVKIEPLGIAPTRAKRRVVQREKR.

The amino acid sequence of another exemplary gp120 polypeptide (see, bioafrica.net/proteomics/ENV-GP120prot.html) is provided below:

(SEQ ID NO: 6)

TEKLWVTVYY GVPVWKEATT TLFCASDAKA YDTEVHNVWA

THACVPTDPN PQEVVLVNVT ENFNMWKNDM VEQMHEDIIS

LWDQSLKPCV KLTPLCVSLK CTDLKNDTNT NSSSGRMIME

KGEIKNCSFN ISTSIRGKVQ KEYAFFYKLD IIPIDNDTTS

YKLTSCNTSV ITQACPKVSF EPIPIHYCAP AGFAILKCNN

KTFNGTGPCT NVSTVQCTHG IRPVVSTQLL LNGSLAEEEV

VIRSVNFTDN AKTIIVQLNT SVEINCTRPN NNTRKRIRIQ

RGPGRAPVTI GKIGNMRQAH CNISRAKWNN TLKQIASKLR

EQFGNNKTII FKQSSGGDPE IVTHSFNCGG EFFYCNSTQL

FNSTWFNSTW STEGSNNTEG SDTITLPCRI KQIINMWQKV

GKAMYAPPIS GQIRCSSNIT GLLLTRDGGN SNNESEIFRP

GGGDMRDNWR SELYKYKVVK IEPLGVAPTK AKRRVVQREK R

Genomic diversity among independent human immunodeficiency virus type 1 (HIV-1) isolates, to a lesser degree among sequential isolates from the same patients, and even within a single patient isolate is a well-known feature of HIV-1. Although this sequence heterogeneity is distributed throughout the genome, most of the heterogeneity is located in the env gene. Comparison of predicted amino acid sequences from several different isolates has shown that sequence heterogeneity is clustered in five variable regions (designated V1 through V5) of the surface glycoprotein, gp120. The V3 region, although only 35 amino acids long, exhibits considerable sequence variability. Interestingly, despite this variability, the V3 region includes determinants that mediate interactions with CD4+ cells. The increase in gp120 variability results in higher levels of viral replication, suggesting an increase in viral fitness in individuals infected by diverse HIV-1 variants. Variability in potential N-linked glycosylation sites (PNGSs) also result in increased viral fitness. PNGSs allow for the binding of long-chain carbohydrates to the high variable regions of gp120. Thus, the number of PNGSs in env might affect the fitness of the virus by providing more or less sensitivity to neutralizing antibodies.

Biological Sample

The HIV gp120 amino acid residues of interest are determined from HIV present or suspected to be present in a biological sample from the subject. The biological sample can be from a solid tissue or biological fluid of the subject known or suspected to contain HIV. In various embodiments, the biological sample comprises or is from blood, peripheral blood mononuclear cells (PBMCs), serum, plasma, semen or lymph nodes. In some embodiments, the biological sample comprises or is from bile, blood, blood plasma, serum, breast milk, feces, pus, saliva, sebum, semen, sweat, tears, urine, or vomit. In patients whose virus levels are suppressed, e.g., by antiretroviral (ART) therapy, the biological sample comprises solid tissue or biological fluid of the subject known or suspected to contain an HIV reservoir, e.g., solid tissues and/or biological fluids comprising latently HIV-infected CD4+ T cells (including memory and non-memory effector CD4+ T cells), hematopoietic progenitors of CD4+ T cells, γδT cells (including memory and non-memory effector γδT cells), natural killer (NK) cells, myeloid cells (including monocytes and macrophages), hematopoietic progenitors of myeloid cells and follicular dendritic cells. Anatomical reservoirs that may harbor latently HIV-infected cells include lymphoid tissues, the brain and the central nervous system, the gastrointestinal tract and the gut-associated lymphoid tissue (GALT), genital tract, lungs and skin. Tissues and cells found to harbor latently HIV infected cells and HIV reservoirs are described, e.g., in Kuo, et al., *Curr Opin HIV AIDS*. (2018) 13(2):137-142; Mzingwane, et al., *Rev Med Virol*. (2017) March; 27(2), doi: 10.1002/rmv.1924 (PMID 28128885); Churchill, et al., *Nat Rev Microbiol*. (2016) 14(1):55-60; Barton, et al., *Trends Microbiol*. (2016) 24(5):345-355, which are hereby incorporated herein by reference in their entireties for all purposes.

In some embodiments, multiple biological samples are evaluated from a single patient. For example, in some embodiments two or more biological samples from two or more different tissues or two or more different anatomical reservoirs are evaluated from a single patient.

Stage of Infection

In various embodiments, the human subject is an adult, a juvenile or an infant. The subject may be symptomatic (e.g., viremic) or asymptomatic (e.g., acutely infected or ART suppressed). In some embodiments, the human subject is acutely infected or recently infected with HIV. In certain embodiments, the subject has not seroconverted. In some embodiments, the human subject is chronically infected with HIV. The subject many or may not be receiving a regimen of antiretroviral therapy (ART).

Patients can be categorized into Fiebig stages I-VI, which are based on a sequential gain in positive HIV-1 clinical diagnostic assays (viral RNA measured by PCR, p24 and p31 viral antigens measured by enzyme-linked immunosorbent assay (ELISA). p24 antigen is a viral core protein that transiently appears in the blood during the ramp-up phase once HIV-1 RNA levels rise above 10,000 copies/mL and before the development of detectable HIV antibodies. In Fiebig stage I, during ramp-up viremia, only HIV-1 RNA in the blood can be detected. Fiebig stage II commences about 7 days later, when results of tests to detect p24 antigen become positive. In Fiebig stage III, within about 5 days after p24 antigen test results become positive, IgM anti-HIV-1 antibodies can be detected with sufficiently sensitive enzyme immunoassays (EIAs) (e.g., third-generation EIAs). Stage III typically occurs 1-2 weeks after the onset of acute retroviral symptoms. Fiebig stage IV represents the development of an indeterminate Western blot test and occurs about 3 days after EIA tests show positive results. Conversion to a clearly positive Western blot test, Fiebig stage V, generally occurs after another 7 days, or about 1 month after initial infection. Fiebig stages of HIV infection are described, e.g., in Fiebig, et al., AIDS. (2003) 17(13):1871-9; Cohen, et al., *J Infect Dis*. (2010) 202 Suppl 2:S270-7; and McMichael, et al., *Nature Reviews Immunology* (2010) 10:11-23, which are hereby incorporated herein by reference in their entireties for all purposes. In some embodiments, the biological sample evaluated is from a human subject having an HIV infection of Fiebig stage IV or earlier, e.g., Fiebig stage I, Fiebig stage II, Fiebig stage III or Fiebig stage IV. In some embodiments, the biological sample evaluated is from a human subject having an HIV infection of an HIV infection of Fiebig stage V or Fiebig stage VI.

In some embodiments, the methods further comprise the step of obtaining the biological sample from the subject. In some embodiments, the methods entail receiving a report of the HIV gp120 amino acids residues present at the designated positions of interest, e.g., at 332 and 325, and one or more amino acid positions from the group consisting of: 63, 179, 320 and 330, wherein the amino acid positions are with reference to SEQ ID NO: 4.

Determining gp120 Amino Acids of Interest

Determination of the amino acid residues at HIV gp120 sequences of a subject at the designated positions of interest, e.g., at 332 and 325, and one or more amino acid positions from the group consisting of: 63, 179, 320 and 330, wherein the amino acid positions are with reference to SEQ ID NO: 4, can be done at the polynucleotide or polypeptide level. At the level of the polynucleotide, HIV RNA or proviral DNA isolated from one or more biological samples can be sequenced using methods known in the art. In some embodiments, HIV RNA or proviral DNA isolated from two or more biological samples of a subject are sequenced. In some embodiments, the two or more biological samples are obtained from different tissue sources (e.g., blood, peripheral blood mononuclear cells, lymph nodes and/or semen). In some embodiments, the two or more biological samples are obtained at different time points, e.g., 1, 2, 3, 4, 5, 6, 7 or 8 weeks apart, 3, 4, 5, 6, 7, 8, 9, 10, 11 or 12 months apart.

As appropriate, primers that anneal to and amplify the HIV env coding sequence, and particularly the V3 variable region of gp120, can be used. In some embodiments, nested sets of primers can be used. In various embodiments, the RNA is sequenced directly or reverse-transcriptase polymerase chain reaction (RT-PCR) can be performed. In some embodiments, Sanger sequencing can be performed, e.g., when sequencing to determine amino acid residues in the V3 region, or when sequencing a sample from a patient in an early Fiebig stage of disease, e.g., prior to Fiebig stage III, e.g., Fiebig stages I or II. In various embodiments, single genome amplification (SGA) and sequencing is performed.

Methods for single genome amplification (SGA) and sequencing of plasma HIV virion RNA, are described, e.g., in Salazar-Gonzalez, et al. (2008) *J Virol* 82:3952-3970; and Keele, et al., *Proc Natl Acad Sci USA*. (2008) 105(21):7552-7. Application of SGA to determining amino acid sequence variance in HIV gp120 sequences, and which can be employed in the herein described methods, is described, e.g., in Bar, et al., *N Engl J Med*. (2016) 375(21):2037-2050; and Mendoza, et al., *Nature*. (2018) 561(7724):479-484. In various embodiments, high throughput, Next Generation Sequencing (NGS), massively parallel or deep sequencing techniques are employed to sequence gp120, including at least the V3 variable region, from a population of HIV species in one or more biological samples from a single patient or subject. In such cases, multiple nucleic acid sequences encoding at least the V3 variable region of gp120 are sequenced and aligned. In some embodiments, the full-length of gp120 is sequenced. Illustrative platforms for performing NGS sequencing that can be used for determining the gp120 sequences of HIV species in one or more biological samples from a patient include Illumina (Solexa) (illumina.com), Ion torrent: Proton/PGM sequencing (thermofisher.com), SOLiD (thermofisher.com), and Single Molecule, Real-Time (SMRT) Sequencing (Pacific Biosciences, pacb.com). Methods for isolating and sequencing HIV gp120, including at least the V3 glycan region, from patients, and which can be applied in the present methods, are described in, e.g., Shioda, et al., *J Virol*. (1997) 71(7): 4871-81; Colón, et al., *J Virol Antivir Res*. (2015) 4(3). pii: 143 (PMID: 27358904); Kafando, et al., *PLoS One*. (2017) 12(12):e0189999; Hebberecht, et al., *PLoS One*. (2018) 13(4):e0195679, Andrews, et al., *Sci Rep*. (2018) 8(1):5743 and Landais, et al. *Immunity*. (2017) 47(5):990-1003. As appropriate, shorter sequence reads of the nucleic acid sequences ("contigs") can be assembled into longer sequences, including at least the V3 variable region of gp120. Methods of contig assembly of HIV genomic sequences that can be applied in the present methods are described, e.g., in Huang, et al., *Bioinformation*. (2018) 14(8):449-454; Hiener, et al., *J Vis Exp*. (2018) October 16; (140). doi: 10.3791/58016; and Wymant, et al., *Virus Evol*. (2018) May 18; 4(1):vey007. doi: 10.1093/ve/vey007.

In some embodiments, at least 90%, at least 91%, at least 92%, at least 93%, at least 94%, at least 95%, at least 96%, at least 97%, at least 98%, at least 99%, or 100%, of the sequenced V3 variable region of gp120 in a population of HIV obtained from one or more biological samples in a single patient comprise an amino acid sequence comprising a glycosylated asparagine at the position corresponding to amino acid residue position 332 (N332glycan), an aspartate at the position corresponding to amino acid residue position 325 (D325), and one or more of a threonine at the position corresponding to amino acid residue position 63 (T63), a leucine at the position corresponding to amino acid residue position 179 (L179), a threonine at the position corresponding to amino acid residue position 320 (T320), and a histidine at the position corresponding to amino acid residue position 330 (H330), wherein the amino acid positions are with reference to SEQ ID NO: 4. As used herein, numbering of a given amino acid polymer or nucleic acid polymer "corresponds to", is "corresponding to" or is "relative to" the numbering of a selected or reference amino acid polymer or nucleic acid polymer when the position of any given polymer component (e.g., amino acid, nucleotide, also referred to generically as a "residue") is designated by reference to the same or to an equivalent position (e.g., based on an optimal alignment or a consensus sequence) in the selected amino acid or nucleic acid polymer, rather than by the actual numerical position of the component in the given polymer. In some embodiments, HIV gp120 variants are detected to a frequency level about 1% (e.g., 1% mutant or variant frequency) of the virus population. In some embodiments, HIV gp120 variants are detected to a frequency level of about 0.5% of the virus population. As a rule of thumb, reliable detection of variants at 1% frequency will require HIV RNA levels of at least 1000 copies/mL. See, e.g., Casadellà, et al., *Virus Research* 239 (2017) 69-81; Noguera-Julian, et al., *J Infect Dis*. (2017) 216 (suppl 9):S829-S833 and Lee, et al., *Sci Rep*. (2020) 10(1): 1634.

3. Administration of an Anti-HIV gp120 V3-Glycan Directed Antibody or Antigen-Binding Fragment Thereof In certain embodiments, the methods entail administration of an anti-HIV antibody or antigen-binding fragment thereof, or antigen binding molecule, that targets the V3 glycan binding region of gp120.

HIV-1 is the main family of HIV and accounts for 95% of all infections worldwide. HIV-2 is mainly seen in a few West African countries.

HIV viruses are divided into specific groups, M, N, O and P, of which M is the "major" group and responsible for majority of HIV/AIDS globally. Based on their genetic sequence, Group M is further subdivided into subtypes (also called clades) with prevalence in distinct geographical locations.

A Group M "subtype" or "clade" is a subtype of HIV-1 group M defined by genetic sequence data. Examples of Group M subtypes include Subtypes A-K. Some of the subtypes are known to be more virulent or are resistant to different medications. There are also "circulating recombinant forms" or CRFs derived from recombination between viruses of different subtypes, which are each given a number. CRF12_BF, for example, is a recombination between subtypes B and F. Subtype A is common in West Africa. Subtype B is the dominant form in Europe, the Americas, Japan, Thailand, and Australia. Subtype C is the dominant form in Southern Africa, Eastern Africa, India, Nepal, and parts of China. Subtype D is generally only seen in Eastern and central Africa. Subtype E has never been identified as a nonrecombinant, only recombined with subtype A as CRF01_AE. Subtype F has been found in central Africa, South America and Eastern Europe. Subtype G (and the CRF02_AG) have been found in Africa and central Europe. Subtype H is limited to central Africa. Subtype I was originally used to describe a strain that is now accounted for as CRF04_cpx, with the cpx for a "complex" recombination of several subtypes. Subtype J is primarily found in North, Central and West Africa, and the Caribbean Subtype K is limited to the Democratic Republic of Congo and Cameroon. These subtypes are sometimes further split into sub-subtypes such as A1 and A2 or F1 and F2. In 2015, the strain CRF19, a recombinant of subtype A, subtype D, and subtype G, with a subtype D protease was found to be strongly associated with rapid progression to AIDS in Cuba.

This disclosure provides, inter alia, methods entailing administration of human anti-HIV neutralizing antibodies (e.g., broadly neutralizing Abs) that target the V3-Glycan region of the gp120 polypeptide on the surface of HIV-infected cells. Neutralizing antibodies against viral envelope proteins provide adaptive immune defense against HIV-1 exposure by blocking the infection of susceptible cells. Broad neutralization indicates that the antibodies can neutralize HIV-1 isolates from different clades. Thus, the anti- HIV gp120 V3 glycan directed antibodies or antigen-binding fragments described herein have cross-clade binding activity.

Antibodies and Antigen-Binding Fragments Thereof Directed to the V3 Glycan Region of HIV gp120

In certain embodiments of the methods described herein, the subject is administered an antibody or antigen-binding fragment thereof, or an antigen-binding molecule that binds to HIV gp120 protein within the V3 Glycan region, e.g., an epitope or region of gp120 third variable loop (V3) and/or high mannose patch comprising a N332 oligomannose glycan. In certain embodiments, the administered antibody or antigen-binding fragment thereof, or an antigen-binding molecule binds to HIV-1 antigens expressed on a cell surface and eliminates or kills the infected cell.

In certain embodiments, the administered antibody or antigen-binding fragment thereof, or an antigen-binding molecule, is or is derived from human neutralizing antibodies (e.g., monoclonal) that target HIV-1. A "neutralizing antibody" is one that can neutralize the ability of HIV to initiate and/or perpetuate an infection in a host and/or in target cells in vitro. The disclosure provides neutralizing monoclonal human antibodies, wherein the antibody recognizes an antigen from HIV, e.g., a gp120 polypeptide. In certain embodiments, a "neutralizing antibody" may inhibit the entry of HIV-1 virus, e.g., SF162 and/or JR-CSF, with a neutralization index>1.5 or >2.0 (Kostrikis L G et al., *J. Virol.*, 70(1): 445-458 (1996)).

In some embodiments, the administered antibody or antigen-binding fragment thereof, or an antigen-binding molecule, is or is derived from human broadly neutralizing antibodies (e.g., monoclonal) that target HIV-1. By "broadly neutralizing antibodies" are meant antibodies that neutralize more than one HIV-1 virus species (from diverse clades and different strains within a clade) in a neutralization assay. A broad neutralizing antibody may neutralize at least 2, 3, 4, 5, 6, 7, 8, 9 or more different strains of HIV-1, the strains belonging to the same or different clades. In particular embodiments, a broad neutralizing antibody may neutralize multiple HIV-1 species belonging to at least 2, 3, 4, 5, or 6 different clades. In certain embodiments, the inhibitory concentration of the anti-HIV gp120 V3 glycan directed antibody or antigen-binding fragment may be less than about 0.0001 µg/ml, less than about 0.001 µg/ml, less than about 0.01 µg/ml, less than about 0.1 µg/ml, less than about 0.5 µg/ml, less than about 1.0 µg/ml, less than about 5 µg/ml, less than about 10 µg/ml, less than about 25 µg/ml, less than about 50 µg/ml, or less than about 100 µg/ml to neutralize about 50% of the input virus in the neutralization assay.

Illustrative broadly neutralizing antibodies that bind to gp120 in the third variable loop (V3) and/or high mannose patch comprising a N332 oligomannose glycan and which can be used in the herein described methods include without limitation GS-9722 (elipovimab), GS-9721, PGT-121, PGT-121.66, PGT-121.414, PGT-122, PGT-123, PGT-124, PGT-125, PGT-126, PGT-128, PGT-130, PGT-133, PGT-134, PGT-135, PGT-136, PGT-137, PGT-138, PGT-139, 10-1074, 10-1074-J, VRC24, 2G12, BG18, 354BG8, 354BG18, 354BG42, 354BG33, 354BG129, 354BG188, 354BG411, 354BG426, DH270.1, DH270.6, PGDM12, VRC41.01, PGDM21, PCDN-33A, BF520.1 and VRC29.03. Additional broadly neutralizing antibodies that bind to gp120 in the third variable loop (V3) and/or high mannose patch comprising a N332 oligomannose glycan and which can be used in the herein described methods are described, e.g., in WO 2012/030904; WO 2014/063059; WO 2016/149698; WO 2017/106346; WO 2018/075564; WO 2018/125813; WO 2018/237148, WO 2019/226829, WO 2020/023827, WO2020/056145 and Kerwin, et al., *J Pharm Sci.* 2020 January; 109(1):233-246, which are hereby incorporated herein by reference in their entireties for all purposes.

Illustrative sequences of complementarity determining regions (CDRs) of the antibody or antigen-binding fragments, targeting HIV gp120 V3 glycan region, are provided in Tables A1-A4. Illustrative sequences of the VH and VL of the antibody or antigen-binding fragments, targeting HIV gp120 V3 glycan region, are provided in Table B.

TABLE A1

CDRs (Kabat) for Anti-HIV gp120 V3 Glycan-Directed Antibodies or Antigen-Binding Fragments Thereof

| Ab Name | VH-CDR1 | VH-CDR2 | VH-CDR3 | VL-CDR1 | VL-CDR2 | VL-CDR3 |
|---|---|---|---|---|---|---|
| 1 | DSYWS SEQ ID NO: 7 | YVHKSGDTNYSPSLKS SEQ ID NO: 8 | TLHGRRIYGIVAFNEW FTYFYMDV SEQ ID NO: 9 | GEKSLGSRAVQ SEQ ID NO: 10 | NNQDRPS SEQ ID NO: 11 | HIWDSRVPTK WV SEQ ID NO: 12 |
| 2 | DSYWS SEQ ID NO: 7 | YVHKSGDTNYNPSLKS SEQ ID NO: 13 | TLHGRRIYGIVAFNEW FTYFYMDV SEQ ID NO: 9 | GEKSLGSRAVQ SEQ ID NO: 10 | NNQDRPS SEQ ID NO: 11 | HIWDSRVPTK WV SEQ ID NO: 12 |
| 3 | NYYWT SEQ ID NO: 14 | YISDRESATYNPSLNS SEQ ID NO: 15 | ARRGQRIYGVVSFGEF FYYYSMDV SEQ ID NO: 16 | GRQALGSRAVQ SEQ ID NO: 17 | NNQDRPS SEQ ID NO: 11 | HMWDSRSGFS WS SEQ ID NO: 18 |
| 4 | NYYWT SEQ ID NO: 14 | YISDRETTTYNPSLNS SEQ ID NO: 19 | ARRGQRIYGVVSFGEF FYYYYMDV SEQ ID NO: 20 | GRQALGSRAVQ SEQ ID NO: 17 | NNQDRPS SEQ ID NO: 11 | HMWDSRSGFS WS SEQ ID NO: 18 |
| 5 | GRFWS SEQ ID NO: 21 | YFSDTDRSEYNPSLRS SEQ ID NO: 22 | AQQGKRIYGIVSFGEF FYYYYMDA SEQ ID NO: 23 | GERSRGSRAVQ SEQ ID NO: 24 | NNQDRPA SEQ ID NO: 25 | HYWDSRSPIS WI SEQ ID NO: 26 |

TABLE A1-continued

CDRs (Kabat) for Anti-HIV gp120 V3 Glycan-Directed Antibodies or Antigen-Binding F TABLE A1-continued CDRs (Kabat) for Anti-HIV gp120 V3 Glycan-Directed Antibodies or Antigen-Binding Fragments Thereof

| Ab Name | VH-CDR1 | VH-CDR2 | VH-CDR3 | VL-CDR1 | VL-CDR2 | VL-CDR3 |
|---|---|---|---|---|---|---|
| 22 | SDHSWT SEQ ID NO: 85 | DIHYGGDITYNPSLRS SEQ ID NO: 99 | NVIRVFGVIALGEWFH YGMDV SEQ ID NO: 100 | SGPPLASRYCY SEQ ID NO: 101 | RDRQFSS SEQ ID NO: 102 | QSSDINDSYK M SEQ ID NO: 95 |
| 23 | SDHSWT SEQ ID NO: 85 | DIHYGGDITYNPSLRS SEQ ID NO: 99 | NVIRVFGVIALGEWFH YGMDV SEQ ID NO: 100 | SGPPLASRYCY SEQ ID NO: 101 | RDRQFSS SEQ ID NO: 102 | QSSDTSDSFK M SEQ ID NO: 103 |
| 24 | SDHSWT SEQ ID NO: 85 | DIHYGGDITYNPSLRS SEQ ID NO: 99 | NVIRVFGVIALGEWFH YGMDV SEQ ID NO: 100 | SGPPLATRYCY SEQ ID NO: 104 | RDRQFSS SEQ ID NO: 102 | QSSDTSDSYK M SEQ ID NO: 90 |
| 25 | SDHSWT SEQ ID NO: 85 | DIHYNGDKTYNPSLRG SEQ ID NO: 105 | NVIRVFGVISLGEWFH YGMDV SEQ ID NO: 92 | SGPPLASRYTY SEQ ID NO: 93 | RDRQFPS SEQ ID NO: 94 | QSSDTSDSYK M SEQ ID NO: 90 |
| 26 | SDHSWT SEQ ID NO: 85 | DIHYGGDITYNPSLRS SEQ ID NO: 99 | NVIRVFGVIALGEWFH YGMDV SEQ ID NO: 100 | SGPPLASRYCY SEQ ID NO: 101 | RDRQFSS SEQ ID NO: 102 | QSSDNSDSFK M SEQ ID NO: 107 |
| 27 | DYAMA SEQ ID NO: 108 | FMRGWAYGGSAQFAAF AVG SEQ ID NO: 109 | EQRNKDYRYGQEGFGY SYGMDV SEQ ID NO: 110 | RASHFIANYVN SEQ ID NO: 111 | ESSTLQR SEQ ID NO: 112 | QQSHSPPVT SEQ ID NO: 113 |
| 28 | DYAMA SEQ ID NO: 108 | FIRGWAYGQAAQYGKS ASG SEQ ID NO: 114 | EQRGGDGRYSGDGFGY PYGMDV SEQ ID NO: 115 | RASHFIANYVN SEQ ID NO: 111 | QSWTLNR SEQ ID NO: 116 | QQSHSPPLS SEQ ID NO: 117 |
| 29 | DYAMA SEQ ID NO: 108 | FIRGWAYGQSAQYGKS ASG SEQ ID NO: 118 | EQRGANGRYGGDGFGY SYGMDV SEQ ID NO: 119 | RASHFIANYVN SEQ ID NO: 111 | ESSTLNR SEQ ID NO: 120 | QQSHSPPVS SEQ ID NO: 121 |

TABLE A2

CDRs (Chothia) for Anti-HIV gp120 V3 Glycan-Directed Antibodies or Antigen-Binding Fragments Thereof

| Ab Name | VH-CDR1 | VH-CDR2 | VH-CDR3 | VL-CDR1 | VL-CDR2 | VL-CDR3 |
|---|---|---|---|---|---|---|
| 30 | GASISD SEQ ID NO: 123 | YVHKSGDTN SEQ ID NO: 124 | TLHGRRIYGIVAFNEWF TYFYMDV SEQ ID NO: 9 | GEKSLGSRAVQ SEQ ID NO: 10 | NNQDRPS SEQ ID NO: 11 | HIWDSRVPTK WV SEQ ID NO: 12 |
| 31 | GDSMNN SEQ ID NO: 125 | YISDRESAT SEQ ID NO: 126 | ARRGQRIYGVVSFGEFF YYYSMDV SEQ ID NO: 16 | GRQALGSRAVQ SEQ ID NO: 17 | NNQDRPS SEQ ID NO: 11 | HMWDSRSGFS WS SEQ ID NO: 18 |
| 32 | GGSISN SEQ ID NO: 127 | YISDRETTT SEQ ID NO: 128 | ARRGQRIYGVVSFGEFF YYYYMDV SEQ ID NO: 20 | GRQALGSRAVQ SEQ ID NO:17 | NNQDRPS SEQ ID NO: 11 | HMWDSRSGFS WS SEQ ID NO: 18 |
| 33 | NGSVSG SEQ ID NO: 129 | YFSDTDRSE SEQ ID NO: 130 | AQQGKRIYGIVSFGEFF YYYYMDA SEQ ID NO: 23 | GERSRGSRAVQ SEQ ID NO: 24 | NNQDRPA SEQ ID NO: 25 | HYWDSRSPIS WI SEQ ID NO: 26 |
| 34 | NGSVSG SEQ ID NO: 129 | YFSDTDRSE SEQ ID NO: 130 | AQQGKRIYGIVSFGELF YYYYMDA SEQ ID NO: 27 | GERSRGSRAVQ SEQ ID NO: 24 | NNQDRPA SEQ ID NO: 25 | HYWDSRSPIS WI SEQ ID NO: 26 |

TABLE A2-continued

CDRs (Chothia) for Anti-HIV gp120 V3 Glycan-Directed Antibodies or Antigen-Binding Fragments Thereof

| Ab Name | VH-CDR1 | VH-CDR2 | VH-CDR3 | VL-CDR1 | VL-CDR2 | VL-CDR3 |
|---|---|---|---|---|---|---|
| 35 | GTLVRD SEQ ID NO: 131 | YVHDSGDTN SEQ ID NO: 132 | TKHGRRIYGVVAFKEWF TYFYMDV SEQ ID NO: 30 | GEESLGSRSVI SEQ ID NO: 31 | NNNDRPS SEQ ID NO: 32 | HIWDSRRPTN WV SEQ ID NO: 33 |
| 36 | GASIND SEQ ID NO: 133 | YVHHSGDTN SEQ ID NO: 134 | ALHGKRIYGIVALGELF TYFYMDV SEQ ID NO: 36 | GKESIGSRAVQ SEQ ID NO: 37 | NNQDRPA SEQ ID NO: 25 | HIYDARGGTN WV SEQ ID NO: 38 |
| 37 | GESTGACT SEQ ID NO: 135 | SLSHCQSFWGSGW TF SEQ ID NO: 136 | FDGEVLVYNHWPKPAWV DL SEQ ID NO: 41 | NGTATNFVS SEQ ID NO: 42 | GVDKRP P SEQ ID NO: 43 | GSLVGNWDVI SEQ ID NO: 44 |
| 38 | GDSTAACD SEQ ID NO: 137 | GLSHCAGYYNTGW TY SEQ ID NO: 138 | FDGEVLVYHDWPKPAWV DL SEQ ID NO: 47 | TGTSNRFVS SEQ ID NO: 48 | GVNKRP S SEQ ID NO: 49 | SSLVGNWDVI SEQ ID NO: 50 |
| 39 | GDSTAACD SEQ ID NO: 137 | SLSHCAGYYNSGW TY SEQ ID NO: 106 | FGGDVLVYHDWPKPAWV DL SEQ ID NO: 52 | TGNINNFVS SEQ ID NO: 53 | GVNKRP S SEQ ID NO: 49 | GSLAGNWDVV SEQ ID NO: 54 |
| 40 | GDSTAACN SEQ ID NO: 139 | SLSHCASYWNRGW TYHNPSLKS SEQ ID NO: 56 | FGGEVLRYTDWPKPAWV DL SEQ ID NO: 57 | TGTSNNFVS SEQ ID NO: 58 | DVNKRP S SEQ ID NO: 59 | GSLVGNWDVI SEQ ID NO: 44 |
| 41 | GDSTAGCD SEQ ID NO: 141 | GLSHCAGYYNTGW TY SEQ ID NO: 138 | FDGEVLVYNDWPKPAWV DL SEQ ID NO: 63 | TGTSNNFVS SEQ ID NO: 58 | GVNKRP S SEQ ID NO: 49 | GSLVGNWDVI SEQ ID NO: 44 |
| 42 | GESINTGH SEQ ID NO: 142 | HIHYTTAVL SEQ ID NO: 143 | SGGDILYYYEWQKPHWF SP SEQ ID NO: 66 | NGTSSDIGGWNF VS SEQ ID NO: 67 | EVNKRP S SEQ ID NO: 68 | SSLFGRWDVV SEQ ID NO: 69 |
| 43 | GGSMRGTDWGEN D SEQ ID NO: 144 | SIHWRGRTTH SEQ ID NO: 145 | HKYHDIFRVVPVAGWFD P SEQ ID NO: 72 | RASQNVKNNLA SEQ ID NO: 73 | DASSRA G SEQ ID NO: 74 | QQYEEWPRT SEQ ID NO: 75 |
| 44 | GGSIRGGEWGDS D SEQ ID NO: 146 | SIHWRGTTH SEQ ID NO: 147 | HKYHDIVMVVPIAGWFD P SEQ ID NO: 78 | RASQSVKNNLA SEQ ID NO: 79 | DTSSRA S SEQ ID NO: 80 | QQYEEWPRT SEQ ID NO: 75 |
| 45 | GDSIRGGEWGDK D SEQ ID NO: 148 | SIHWRGTTH SEQ ID NO: 147 | HRHHDVFMLVPIAGWFD V SEQ ID NO: 83 | RASQNINKNLA SEQ ID NO: 84 | ETYSKI A SEQ ID NO: 62 | QQYEEWPRT SEQ ID NO: 75 |
| 46 | QDSRPSDH SEQ ID NO: 149 | HYNGA SEQ ID NO: 150 | NAIRIYGVVALGEWFHY GMDV SEQ ID NO: 87 | SGAPLTSRFTY SEQ ID NO: 88 | RSSQRS S SEQ ID NO: 89 | QSSDTSDSYK M SEQ ID NO: 90 |
| 47 | NDSRPSDH SEQ ID NO: 151 | HYNGA SEQ ID NO: 150 | NAIRIYGVVALGEWFHY GMDV SEQ ID NO: 87 | SGAPLTSRFTY SEQ ID NO: 88 | RSSQRS S SEQ ID NO: 89 | QSSDTSDSYK M SEQ ID NO: 90 |
| 48 | GDSRPSDH SEQ ID NO: 152 | HYNGD SEQ ID NO: 153 | NVIRVFGVISLGEWFHY GMDV SEQ ID NO: 92 | SGPPLASRYTY SEQ ID NO: 93 | RDRQFP S SEQ ID NO: 94 | QSSDTSDSYK M SEQ ID NO: 90 |
| 49 | NDSRPSDH SEQ ID NO: 151 | HYNGA SEQ ID NO: 150 | NAIRIYGVVALGEWFHY GMDV SEQ ID NO: 87 | SGAALTSRFTY SEQ ID NO: 97 | RTSQRS S SEQ ID NO: 98 | QSSDTSDSYK M SEQ ID NO: 90 |

TABLE A2-continued

CDRs (Chothia) for Anti-HIV gp120 V3 Glycan-Directed Antibodies or Antigen-Binding Fragments Thereof

| Ab Name | VH-CDR1 | VH-CDR2 | VH-CDR3 | VL-CDR1 | VL-CDR2 | VL-CDR3 |
|---|---|---|---|---|---|---|
| 50 | GDSRPSDH SEQ ID NO: 152 | HYGGD SEQ ID NO: 122 | NVIRVFGVIALGEWFHY GMDV SEQ ID NO: 100 | SGPPLASRYCY SEQ ID NO: 101 | RDRQFS SEQ ID NO: 102 | QSSDINDSYK M SEQ ID NO: 95 |
| 51 | GDSRPSDH SEQ ID NO: 152 | HYGGD SEQ ID NO: 122 | NVIRVFGVIALGEWFHY GMDV SEQ ID NO: 100 | SGPPLASRYCY SEQ ID NO: 101 | RDRQFS SEQ ID NO: 102 | QSSDTSDSFK M SEQ ID NO: 103 |
| 52 | GDSRPSDH SEQ ID NO: 152 | HYGGD SEQ ID NO: 122 | NVIRVFGVIALGEWFHY GMDV SEQ ID NO: 100 | SGPPLATRYCY SEQ ID NO: 104 | RDRQFS SEQ ID NO: 102 | QSSDTSDSYK M SEQ ID NO: 90 |
| 53 | GDSRPSDH SEQ ID NO: 152 | HYGGD SEQ ID NO: 122 | NVIRVFGVIALGEWFHY GMDV SEQ ID NO: 100 | SGPPLASRYCY SEQ ID NO: 101 | RDRQFS SEQ ID NO: 102 | QSSDNSDSFK M SEQ ID NO: 107 |
| 54 | GFYFPDY SEQ ID NO: 154 | RGWAYGGS SEQ ID NO: 155 | EQRNKDYRYGQEGFGYS YGMDV SEQ ID NO: 110 | RASHFIANYVN SEQ ID NO: 111 | ESSTLQ R SEQ ID NO: 112 | QQSHSPPVT SEQ ID NO: 113 |
| 55 | DFYFPDY SEQ ID NO: 156 | RGWAYGQA SEQ ID NO: 157 | EQRGGDGRYSGDGFGYP YGMDV SEQ ID NO: 115 | RASHFIANYVN SEQ ID NO: 111 | QSWTLN R SEQ ID NO: 116 | QQSHSPPLS SEQ ID NO: 117 |
| 56 | DFYFPDY SEQ ID NO: 158 | RGWAYGQS SEQ ID NO: 159 | EQRGANGRYGGDGFGYS YGMDV SEQ ID NO: 119 | RASHFIANYVN SEQ ID NO: 111 | ESSTLN R SEQ ID NO: 120 | QQSHSPPVS SEQ ID NO: 121 |

TABLE A3

CDRs (IMGT) for Anti-HIV gp120 V3 Glycan-Directed Antibodies or Antigen-Binding Fragments Thereof

| Ab Name | VH-CDR1 | VH-CDR2 | VH-CDR3 | VL-CDR1 | VL-CDR2 | VL-CDR3 |
|---|---|---|---|---|---|---|
| 57 | GASISDSY SEQ ID NO: 160 | VHKSGDT SEQ ID NO: 161 | ARTLHGRRIYGIVAFNEWFTYFYM DV SEQ ID NO: 162 | SLGSRA SEQ ID NO: 163 | NNQ V SEQ ID NO: 164 | HIWDSRVPTKW V SEQ ID NO: 12 |
| 58 | GDSMNNYY SEQ ID NO: 165 | ISDRESA SEQ ID NO: 166 | ATARRGQRIYGVVSFGEFFYYYSM DV SEQ ID NO: 167 | ALGSRA SEQ ID NO: 168 | NNQ SEQ ID NO: 164 | HMWDSRSGFSW S SEQ ID NO: 18 |
| 180 | GDSMNNYY SEQ ID NO: 165 | ISDRESA SEQ ID NO: 166 | ARARRGQRIYGVVSFGEFFYYYSM DV SEQ ID NO: 461 | ALGSRA SEQ ID NO: 168 | NNQ SEQ ID NO: 164 | HMWDSRSGFSW S SEQ ID NO: 18 |
| 59 | GGSISNYY SEQ ID NO: 169 | ISDRETT SEQ ID NO: 170 | ATARRGQRIYGVVSFGEFFYYYM DV SEQ ID NO: 171 | ALGSRA SEQ ID NO: 168 | NNQ SEQ ID NO: 164 | HMWDSRSGFSW S SEQ ID NO: 18 |
| 60 | NGSVSGRF SEQ ID NO: 172 | FSDTDRS SEQ ID NO: 173 | ARAQQGKRIYGIVSFGELFYYYM DA SEQ ID NO: 174 | SRGSRA SEQ ID NO: 175 | NNQ SEQ ID NO: 164 | HYWDSRSPISW I SEQ ID NO: 26 |
| 61 | NGSVSGRF SEQ ID | FSDTDRS SEQ ID | ARAQQGKRIYGIVSFGEFFYYYM DA | SRGSRA SEQ ID | NNQ SEQ ID | HYWDSRSPISW I |

TABLE A3-continued

CDRs (IMGT) for Anti-HIV gp120 V3 Glycan-Directed Antibodies or Antigen-Binding Fragments Thereof

| Ab Name | VH-CDR1 | VH-CDR2 | VH-CDR3 | VL-CDR1 | VL-CDR2 | VL-CDR3 |
|---|---|---|---|---|---|---|
| | NO: 172 | NO: 173 | SEQ ID NO: 176 | NO: 175 | NO: 164 | SEQ ID NO: 26 |
| 62 | GTLVRDNY SEQ ID NO: 177 | VHDSGDT SEQ ID NO: 178 | ATTKHGRRIYGVVAFKEWFTYFYMDV SEQ ID NO: 179 | SIGSRA SEQ ID NO: 180 | NNQ SEQ ID NO: 164 | HIYDARGGTNWV SEQ ID NO: 38 |
| 63 | GASINDAY SEQ ID NO: 181 | VHHSGDT SEQ ID NO: 182 | ARALHGKRIYGIVALGELFTYFYMDV SEQ ID NO: 183 | SLGSRS SEQ ID NO: 184 | NNN SEQ ID NO: 185 | HIWDSRRPTNWV SEQ ID NO: 33 |
| 64 | GESTGACTYF SEQ ID NO: 186 | LSHCQSFWGSGWT SEQ ID NO: 187 | ARFDGEVLVYNHWPKPAWVDL SEQ ID NO: 188 | ATNF SEQ ID NO: 189 | GVD SEQ ID NO: 190 | GSLVGNWDVI SEQ ID NO: 44 |
| 65 | GDSTAACDYF SEQ ID NO: 191 | LSHCAGYYNTGWT SEQ ID NO: 192 | ARFDGEVLVYHDWPKPAWVDL SEQ ID NO: 193 | SNRF SEQ ID NO: 194 | GVN SEQ ID NO: 195 | SSLVGNWDVI SEQ ID NO: 50 |
| 66 | GDSTAACDYF SEQ ID NO: 191 | LSHCAGYYNSGWT SEQ ID NO: 196 | ARFGGDVLVYHDWPKPAWVDL SEQ ID NO: 197 | INNF SEQ ID NO: 198 | GVN SEQ ID NO: 195 | GSLAGNWDVV SEQ ID NO: 54 |
| 67 | GDSTAACNSF SEQ ID NO: 199 | LSHCASYWNRGWT SEQ ID NO: 200 | ARFGGEVLRYTDWPKPAWVDL SEQ ID NO: 201 | SNNF SEQ ID NO: 202 | DVN SEQ ID NO: 399 | GSLVGNWDVI SEQ ID NO: 44 |
| 68 | GDSTAGCDYF SEQ ID NO: 203 | LSHCAGYYNTGWT SEQ ID NO: 204 | ARFDGEVLVYNDWPKPAWVDL SEQ ID NO: 205 | SNNF SEQ ID NO: 202 | GVN SEQ ID NO: 195 | GSLVGNWDVI SEQ ID NO: 44 |
| 69 | GESINTGHYY SEQ ID NO: 206 | IHYTTAV SEQ ID NO: 207 | VRSGGDILYYYEWQKPHWFSP SEQ ID NO: 208 | SSDIGGWNF SEQ ID NO: 209 | EVN SEQ ID NO: 210 | SSLFGRWDVV SEQ ID NO: 69 |
| 70 | GGSMRGTDWGENDFH SEQ ID NO: 211 | IHWRGRTT SEQ ID NO: 212 | ARHKYHDIFRVVPVAGWFDP SEQ ID NO: 213 | QNVKNN SEQ ID NO: 214 | DAS SEQ ID NO: 215 | QQYEEWPRT SEQ ID NO: 75 |
| 71 | GGSIRGGEWGDSDYH SEQ ID NO: 216 | IHWRGTT SEQ ID NO: 217 | VKHKYHDIVMVVPIAGWFDP SEQ ID NO: 218 | QSVKNN SEQ ID NO: 219 | DTS SEQ ID NO: 220 | QQYEEWPRT SEQ ID NO: 75 |
| 72 | GDSIRGGEWGDKDYH SEQ ID NO: 221 | IHWRGTT SEQ ID NO: 217 | ARHRHHDVFMLVPIAGWFDV SEQ ID NO: 60 | QNINKN SEQ ID NO: 223 | ETY SEQ ID NO: 224 | QQYEEWPRT SEQ ID NO: 75 |
| 73 | QDSRPSDHS SEQ ID NO: 225 | IHYNGAT SEQ ID NO: 226 | NAIRIYGVVALGEWFHYGMDV SEQ ID NO: 87 | PLTSRF SEQ ID NO: 227 | RSS SEQ ID NO: 228 | QSSDTSDSYKM SEQ ID NO: 90 |
| 74 | NDSRPSDHS SEQ ID NO: 229 | IHYNGAT SEQ ID NO: 226 | NAIRIYGVVALGEWFHYGMDV SEQ ID NO: 87 | PLTSRF SEQ ID NO: 227 | RSS SEQ ID NO: 228 | QSSDTSDSYKM SEQ ID NO: 90 |
| 75 | GDSRPSDHS SEQ ID NO: 230 | VHYNGDN SEQ ID NO: 231 | NVIRVFGVISLGEWFHYGMDV SEQ ID NO: 92 | PLASRY SEQ ID NO: 232 | RDR SEQ ID NO: 233 | QSSDTSDSYKM SEQ ID NO: 90 |
| 76 | GDSRPSDHS SEQ ID NO: 230 | VHYNGDT SEQ ID NO: 234 | NVIRVFGVISLGEWFHYGMDV SEQ ID NO: 92 | PLASRY SEQ ID NO: 232 | RDR SEQ ID NO: 233 | QSSDTSDSYKM SEQ ID NO: 90 |

TABLE A3-continued

CDRs (IMGT) for Anti-HIV gp120 V3 Glycan-Directed Antibodies or Antigen-Binding Fragments Thereof

| Ab Name | VH-CDR1 | VH-CDR2 | VH-CDR3 | VL-CDR1 | VL-CDR2 | VL-CDR3 |
|---|---|---|---|---|---|---|
| 77 | NDSRPSDHS SEQ ID NO: 229 | IHYNGAT SEQ ID NO: 226 | NAIRIYGVVALGEWFHYGMDV SEQ ID NO: 87 | ALTSRF SEQ ID NO: 235 | RTS SEQ ID NO: 398 | QSSDTSDSYKM SEQ ID NO: 90 |
| 78 | GDSRPSDHS SEQ ID NO: 230 | IHYGGDI SEQ ID NO: 236 | NVIRVFGVIALGEWFHYGMDV SEQ ID NO: 100 | PLASRY SEQ ID NO: 232 | RDR SEQ ID NO: 233 | QSSDINDSYKM SEQ ID NO: 95 |
| 79 | GDSRPSDHS SEQ ID NO: 230 | IHYGGDI SEQ ID NO: 236 | NVIRVFGVIALGEWFHYGMDV SEQ ID NO: 100 | PLASRY SEQ ID NO: 232 | RDR SEQ ID NO: 233 | QSSDTSDSFKM SEQ ID NO: 103 |
| 80 | GDSRPSDHS SEQ ID NO: 230 | IHYGGDI SEQ ID NO: 236 | NVIRVFGVIALGEWFHYGMDV SEQ ID NO: 100 | PLATRY SEQ ID NO: 237 | RDR SEQ ID NO: 233 | QSSDTSDSYKM SEQ ID NO: 90 |
| 81 | GDSRPSDHS SEQ ID NO: 230 | IHYNGDK SEQ ID NO: 238 | NVIRVFGVISLGEWFHYGMDV SEQ ID NO: 92 | PLASRY SEQ ID NO: 232 | RDR SEQ ID NO: 233 | QSSDTSDSYKM SEQ ID NO: 90 |
| 82 | GDSRPSDHS SEQ ID NO: 230 | IHYGGDI SEQ ID NO: 236 | NVIRVFGVIALGEWFHYGMDV SEQ ID NO: 100 | PLASRY SEQ ID NO: 232 | RDR SEQ ID NO: 233 | QSSDNSDSFKM SEQ ID NO: 107 |
| 83 | GFYFPDYA SEQ ID NO: 239 | MRGWAYGGSA SEQ ID NO: 240 | EQRNKDYRYGQEGFGYSYGMDV SEQ ID NO: 110 | HFIANY SEQ ID NO: 241 | ESS SEQ ID NO: 242 | QQSHSPPVT SEQ ID NO: 113 |
| 84 | DFYFPDYA SEQ ID NO: 243 | IRGWAYGQAA SEQ ID NO: 244 | EQRGGDGRYSGDGFGYPYGMDV SEQ ID NO: 115 | HFIANY SEQ ID NO: 241 | QSW SEQ ID NO: 245 | QQSHSPPLS SEQ ID NO: 117 |
| 85 | DFYFPDYA SEQ ID NO: 243 | IRGWAYGQSA SEQ ID NO: 246 | EQRGANGRYGGDGFGYSYGMDV SEQ ID NO: 119 | HFIANY SEQ ID NO: 241 | ESS SEQ ID NO: 247 | QQSHSPPVS SEQ ID NO: 121 |

TABLE A4

CDRs (Honegger) for Anti-HIV gp120 V3 Glycan-Directed Antibodies or Antigen-Binding Fragments Thereof

| Ab Name | VH-CDR1 | VH-CDR2 | VH-CDR3 | VL-CDR1 | VL-CDR2 | VL-CDR3 |
|---|---|---|---|---|---|---|
| 86 | VSGASISDSY SEQ ID NO: 248 | VHKSGDTNYSPSLKSR SEQ ID NO: 249 | TLHGRRIYGIVAFNEWFTYFYMD SEQ ID NO: 250 | EKSLGSRA SEQ ID NO: 251 | NNQDRPSGIPER SEQ ID NO: 252 | WDSRVPTKW SEQ ID NO: 253 |
| 87 | VSGASISDSY SEQ ID NO: 248 | VHKSGDTNYNPSLKS SEQ ID NO: 254 | TLHGRRIYGIVAFNEWFTYFYMD SEQ ID NO: 250 | EKSLGSRA SEQ ID NO: 251 | NNQDRPSGIPER SEQ ID NO: 252 | WDSRVPTKW SEQ ID NO: 253 |
| 88 | VSGDSMNNYY SEQ ID NO: 255 | ISDRESATYNPSLNSR SEQ ID NO: 256 | ARRGQRIYGVVSFGEFFYYYSMD SEQ ID NO: 257 | RQALGSRA SEQ ID NO: 258 | NNQDRPSGIPER SEQ ID NO: 252 | WDSRSGFSW SEQ ID NO: 259 |
| 89 | VSGGSISNYY SEQ ID NO: 260 | ISDRETTTYNPSLNSR SEQ ID NO: 261 | ARRGQRIYGVVSFGEFFYYYYMD SEQ ID NO: 262 | RQALGSRA SEQ ID NO: 258 | NNQDRPSGIPER SEQ ID NO: 252 | WDSRSGFSW SEQ ID NO: 259 |

TABLE A4-continued

CDRs (Honegger) for Anti-HIV gp120 V3 Glycan-Directed Antibodies or Antigen-Binding Fragments Thereof

| Ab Name | VH-CDR1 | VH-CDR2 | VH-CDR3 | VL-CDR1 | VL-CDR2 | VL-CDR3 |
|---|---|---|---|---|---|---|
| 90 | VSNGSVSGRF SEQ ID NO: 263 | FSDTDRSEYNPSLRS R SEQ ID NO: 264 | AQQGKRIYGIV SFGELFYYYYM D SEQ ID NO: 265 | ERSRGSRA SEQ ID NO: 266 | NNQDRPAGVSER SEQ ID NO: 267 | WDSRSPISW SEQ ID NO: 268 |
| 91 | VSNGSVSGRF SEQ ID NO: 263 | FSDTDRSEYNPSLRS R SEQ ID NO: 264 | AQQGKRIYGIV SFGEFFYYYYM D SEQ ID NO: 397 | ERSRGSRA SEQ ID NO: 266 | NNQDRPAGVSER SEQ ID NO: 267 | WDSRSPISW SEQ ID NO: 268 |
| 92 | VSGASINDAY SEQ ID NO: 269 | VHHSGDTNYNPSLKR R SEQ ID NO: 270 | ALHGKRIYGIV ALGELFTYFYM D SEQ ID NO: 271 | KESIGSRA SEQ ID NO: 272 | NNQDRPAGVPER SEQ ID NO: 273 | YDARGGTNW SEQ ID NO: 274 |
| 93 | VSGTLVRDNY SEQ ID NO: 275 | VHDSGDTNYNPSLKS R SEQ ID NO: 276 | TKHGRRIYGVV AFKEWFTYFYM D SEQ ID NO: 277 | EESLGSRS SEQ ID NO: 278 | NNNDRPSGIPDR SEQ ID NO: 279 | WDSRRPTNW SEQ ID NO: 280 |
| 94 | VSGESTGACTYF SEQ ID NO: 281 | LSHCQSFWGSGWTFH NPSLKSR SEQ ID NO: 282 | FDGEVLVYNHW PKPAWVD SEQ ID NO: 283 | GTATNF SEQ ID NO: 284 | GVDKRPPGVPDR SEQ ID NO: 285 | LVGNWDV SEQ ID NO: 286 |
| 95 | VSGDSTAACDYF SEQ ID NO: 287 | LSHCAGYYNTGWTYH NPSLKSR SEQ ID NO: 288 | FDGEVLVYHDW PKPAWVD SEQ ID NO: 289 | GTSNRF SEQ ID NO: 290 | GVNKRPSGVPDR SEQ ID NO: 291 | LVGNWDV SEQ ID NO: 286 |
| 96 | VSGDSTAACDYF SEQ ID NO: 287 | LSHCAGYYNSGWTYH NPSLKSR SEQ ID NO: 292 | FGGDVLVYHDW PKPAWVD SEQ ID NO: 293 | GNINNF SEQ ID NO: 294 | GVNKRPSGVPDR SEQ ID NO: 295 | LAGNWDV SEQ ID NO: 296 |
| 97 | VSGDSTAACNSF SEQ ID NO: 297 | LSHCASYWNRGWTYH NPSLKSR SEQ ID NO: 298 | FGGEVLRYTDW PKPAWVD SEQ ID NO: 299 | GTSNNF SEQ ID NO: 300 | DVNKRPSGVPDR SEQ ID NO: 301 | LVGNWDV SEQ ID NO: 286 |
| 98 | VSGDSTAGCDYF SEQ ID NO: 302 | LSHCAGYYNTGWTYH NPSLKSR SEQ ID NO: 288 | FDGEVLVYNDW PKPAWVD SEQ ID NO: 303 | GTSNNF SEQ ID NO: 300 | GVNKRPSGVPDR SEQ ID NO: 295 | LVGNWDV SEQ ID NO: 286 |
| 99 | VSGESINTGHYY SEQ ID NO: 304 | IHYTTAVLHNPSLKS R SEQ ID NO: 305 | SGGDILYYYEW QKPHWFS SEQ ID NO: 306 | GTSSDIGGWN F SEQ ID NO: 307 | EVNKRPSGVPGR SEQ ID NO: 308 | LFGRWDV SEQ ID NO: 309 |
| 100 | VSGGSMRGTDWG ENDFH SEQ ID NO: 310 | IHWRGRITHYKTSFR SR SEQ ID NO: 311 | HKYHDIFRVVP VAGWFD SEQ ID NO: 312 | ASQNVKNN SEQ ID NO: 313 | DASSRAGGIPDR SEQ ID NO: 314 | YEEWPR SEQ ID NO: 315 |
| 101 | ASGGSIRGGEWG DSDYH SEQ ID NO: 316 | IHWRGTTHYNAPFRG R SEQ ID NO: 317 | HKYHDIVMVVP IAGWFD SEQ ID NO: 318 | ASQSVKNN SEQ ID NO: 319 | DTSSRASGIPAR SEQ ID NO: 320 | YEEWPR SEQ ID NO: 315 |
| 102 | VSGDSIRGGEWG DKDYH SEQ ID NO: 321 | IHWRGTTHYKESLRR R SEQ ID NO: 322 | HRHHDVFMLVP IAGWFD SEQ ID NO: 323 | ASQNINKN SEQ ID NO: 324 | ETYSKIAAFPAR SEQ ID NO: 325 | YEEWPR SEQ ID NO: 315 |

TABLE A4-continued

CDRs (Honegger) for Anti-HIV gp120 V3 Glycan-Directed Antibodies or Antigen-Binding Fragments Thereof

| Ab Name | VH-CDR1 | VH-CDR2 | VH-CDR3 | VL-CDR1 | VL-CDR2 | VL-CDR3 |
|---|---|---|---|---|---|---|
| 103 | VSQDSRPSDHS SEQ ID NO: 326 | IHYNGATTYNPSLRSR SEQ ID NO: 327 | NAIRIYGVVALGEWFHYGMD SEQ ID NO: 328 | GAPLTSRF SEQ ID NO: 329 | RSSQRSSGWSGR SEQ ID NO: 330 | SDTSDSYK SEQ ID NO: 331 |
| 104 | VSNDSRPSDHS SEQ ID NO: 332 | IHYNGATTYNPSLRSR SEQ ID NO: 327 | NAIRIYGVVALGEWFHYGMD SEQ ID NO: 328 | GAPLTSRF SEQ ID NO: 329 | RSSQRSSGWSGR SEQ ID NO: 330 | SDTSDSYK SEQ ID NO: 331 |
| 105 | VFGDSRPSDHS SEQ ID NO: 333 | VHYNGDNTYNPSLRGR SEQ ID NO: 334 | NVIRVFGVISLGEWFHYGMD SEQ ID NO: 335 | GPPLASRY SEQ ID NO: 336 | RDRQFPSGVSGR SEQ ID NO: 337 | SDTSDSYK SEQ ID NO: 338 |
| 106 | VFGDSRPSDHS SEQ ID NO: 333 | VHYNGDTTYNPSLRGR SEQ ID NO: 339 | NVIRVFGVISLGEWFHYGMD SEQ ID NO: 335 | GPPLASRY SEQ ID NO: 336 | RDRQFPSGVSGR SEQ ID NO: 337 | SDTSDSYK SEQ ID NO: 338 |
| 107 | VSNDSRPSDHS SEQ ID NO: 332 | IHYNGATTYNPSLRSR SEQ ID NO: 327 | NAIRIYGVVALGEWFHYGMD SEQ ID NO: 328 | GAALTSRF SEQ ID NO: 340 | RTSQRSSGWSGR SEQ ID NO: 341 | SDTSDSYK SEQ ID NO: 338 |
| 108 | ISGDSRPSDHS SEQ ID NO: 342 | IHYGGDITYNPSLRSR SEQ ID NO: 343 | NVIRVFGVIALGEWFHYGMD SEQ ID NO: 344 | GPPLASRY SEQ ID NO: 336 | RDRQFSSGMSGR SEQ ID NO: 345 | SDINDSYK SEQ ID NO: 346 |
| 109 | ISGDSRPSDHS SEQ ID NO: 342 | IHYGGDITYNPSLRSR SEQ ID NO: 343 | NVIRVFGVIALGEWFHYGMD SEQ ID NO: 344 | GPPLASRY SEQ ID NO: 336 | RDRQFSSGISGR SEQ ID NO: 347 | SDTSDSFK SEQ ID NO: 348 |
| 110 | ISGDSRPSDHS SEQ ID NO: 342 | IHYGGDITYNPSLRSR SEQ ID NO: 343 | NVIRVFGVIALGEWFHYGMD SEQ ID NO: 344 | GPPLATRY SEQ ID NO: 349 | RDRQFSSGVSGR SEQ ID NO: 350 | SDTSDSYK SEQ ID NO: 338 |
| 111 | VFGDSRPSDHS SEQ ID NO: 333 | IHYNGDKTYNPSLRGR SEQ ID NO: 351 | NVIRVFGVISLGEWFHYGMD SEQ ID NO: 335 | GPPLASRY SEQ ID NO: 336 | RDRQFPSGVSGR SEQ ID NO: 337 | SDTSDSYK SEQ ID NO: 338 |
| 112 | ISGDSRPSDHS SEQ ID NO: 342 | IHYGGDITYNPSLRSR SEQ ID NO: 343 | NVIRVFGVIALGEWFHYGMD SEQ ID NO: 344 | GPPLASRY SEQ ID NO: 336 | RDRQFSSGISGR SEQ ID NO: 347 | SDNSDSFK SEQ ID NO: 352 |
| 113 | ASGFYFPDYA SEQ ID NO: 353 | MRGWAYGGSAQFAAFAVGK SEQ ID NO: 354 | EQRNKDYRYGQEGFGYSYGMD SEQ ID NO: 355 | ASHFIANY SEQ ID NO: 356 | ESSTLQRGVPSR SEQ ID NO: 357 | SHSPPV SEQ ID NO: 358 |
| 114 | AFDFYFPDYA SEQ ID NO: 359 | IRGWAYGQAAQYGKSASGR SEQ ID NO: 360 | EQRGGDGRYSGDGFGYPYGMD SEQ ID NO: 361 | ASHFIANY SEQ ID NO: 356 | QSWTLNRGIPSR SEQ ID NO: 362 | SHSPPL SEQ ID NO: 363 |
| 115 | AFDFYFPDYA SEQ ID NO: 359 | IRGWAYGQSAQYGKSASGR SEQ ID NO: 364 | EQRGANGRYGGDGFGYSYGMD SEQ ID NO: 365 | ASHFIANY SEQ ID NO: 356 | ESSTLNRGVPSR SEQ ID NO: 366 | SHSPPV SEQ ID NO: 358 |

TABLE B

VH/VL for Anti-HIV gp120 V3 Glycan-Directed Antibodies or Antigen-Binding Fragments Thereof

| Ab Name | SEQ ID NO | VH | SEQ ID NO | VL |
|---|---|---|---|---|
| 150 | 400 | QMQLQESGPGLVKPSETLSLTCSVSGASISDSYWSWI RRSPGKGLEWIGYVHKSGDTNYSPSLKSRVNLSLDTS KNQVSLSLVAATAADSGKYYCARTLHGRRIYGIVAFN EWFTYFYMDVWGNGTQVTVSS | 401 | SDISVAPGETARISCGEKSLGSRAVQWYQHRA GQAPSLIIYNNQDRPSGIPERFSGSPDSPFGT TATLTITSVEAGDEADYYCHIWDSRVPTKWVF GGGTTLTVL |
| 151 | 402 | QMQLQESGPGLVKPSETLSLTCSVSGASISDSYWSWI RRSPGKGLEWIGYVHKSGDTNYNPSLKSRVHLSLDTS KNQVSLSLTGVTAADSGKYYCARTLHGRRIYGIVAFN EWFTYFYMDVWGTGTQVTVSS | 403 | SDISVAPGETARISCGEKSLGSRAVQWYQHRA GQAPSLIIYNNQDRPSGIPERFSGSPDFRPGT TATLTITSVEAGDEADYYCHIWDSRVPTKWVF GGGTTLTVL |
| 181 | 462 | QMQLQESGPGLVKPSETLSLTCSVSGASISDSYWSWI RRSPGKGLEWIGYVHKSGDTNYNPSLKSRVHLSLDTS KNQVSLSLTGVTAADSGKYYCARTLHGRRIYGIVAFN EWFTYFYMDVWGTGTQVTVSS | 463 | SDISVAPGETARISCGEKSLGSRAVQWYQHRA GQAPSLIIYNNQDRPSGIPERFSGSPDSRPGT TATLTITSVEAGDEADYYCHIWDSRVPTKWVF GGGTTLTVL |
| 182 | 464 | QMQLQESGPGLVKPSETLSLTCSVSGASISDSYWSWI RQPPGKGLEWIGYVHKSGDTNYSPSLKSRVNLSLDTS KNQVSLSLSAATAADSGVYYCARTLHGRRIYGIVAFN EWFTYFYMDVWGNGTQVTVSS | 465 | SDISVAPGETARISCGEKSLGSRAVQWYQQRA GQAPSLIIYNNQDRPSGIPERFSGSPDSGFGT TATLTITSVEAGDEADYYCHIWDSRVPTKWVF GGGTTLTVL |
| 152 | 402 | QMQLQESGPGLVKPSETLSLTCSVSGASISDSYWSWI RRSPGKGLEWIGYVHKSGDTNYNPSLKSRVHLSLDTS KNQVSLSLTGVTAADSGKYYCARTLHGRRIYGIVAFN EWFTYFYMDVWGTGTQVTVSS | 404 | SDISVAPGETARISCGEKSLGSRAVQWYQHRA GQAPSLIIYNNQDRPSGIPERFSGSPDSRPGT TATLTITSVEAGDEADYYCHIWDSRVPTKWVF GGGTTLTVL |
| 153 | 405 | QVQLQESGPGLVKPSETLSVTCSVSGDSMNNYYWTWI RQSPGKGLEWIGYISDRESATYNPSLNSRVVISRDTS KNQLSLKLNSVTPADTAVYYCATARRGQRIYGVVSFG EFFYYYSMDVWGKGTTVTSS | 406 | SYVRPLSVALGETARISCGRQALGSRAVQWYQ HRPGQAPILLIYNNQDRPSGIPERFSGTPDIN FGTRATLTISGVEAGDEADYYCHMWDSRSGFS WSFGGATRLTVL |
| 183 | 466 | QVQLQESGPGLVKPSETLSVTCSVSGDSMNNYYWTWI RQSPGKGLEWIGYISDRESATYNPSLNSRVTISRDTS KNQFSLKLNSVTPADTAVYYCARARRGQRIYGVVSFG EFFYYYSMDVWGKGTTVTSS | 467 | SPVRPLSVALGETARISCGRQALGSRAVQWYQ HRPGQAPILLIYNNQDRPSGIPERFSGTPDIN FGTRATLTISGVEAGDEADYYCHMWDSRSGFS WSFGGATRLTVL |
| 154 | 407 | QVQLQESGPGLVRPSETLSVICIVSGGSISNYYWTWI RQSPGKGLEWIGYISDRETTTYNPSLNSRAVISRDTS KNQLSLQLRSVTTADTAIYFCATARRGQRIYGVVSFG EFFYYYYMDVWGKGTAVTSS | 408 | SYVSPLSVALGETARISCGRQALGSRAVQWYQ HKPGQAPILLIYNNQDRPSGIPERFSGTPDIN FGTTATLTISGVEVGDEADYYCHMWDSRSGFS WSFGGATRLTV |
| 155 | 409 | QVHLQESGPGLVTPSETLSLICTVSNGSVSGRFWSWI RQSPGRGLEWIGYFSDTDRSEYNPSLRSRLTLSVDRS KNQLSLRLKSVTAADSATYYCARAQQGKRIYGIVSFG EFFYYYYMDAWGKGTPVTSS | 410 | SLNPLSLAPGATAKIPCGERSRGSRAVQWYQQ KPGQAPTLIIYNNQDRPAGVSERFSGNPDVAI GVTATLTISRVEVGDEADYYCHYWDSRSPISW IFGGGTQLTVL |
| 156 | 411 | QVHLQESGPGLVTPSETLSLICTVSNGSVSGRFWSWI RQSPGRGLEWIGYFSDTDRSEYNPSLRSRLTLSVDRS KNQLSLKLKSVTAADSATYYCARAQQGKRIYGIVSFG ELFYYYYMDAWGKGTPVTSS | 412 | SLNPLSLAPGATAKIPCGERSRGSRAVQWYQQ KPGQAPTLIIYNNQDRPAGVSERFSGNPDVAI GVTATLTISRVEVGDEGDYYCHYWDSRSPISW IFAGGTQLTVL |
| 157 | 413 | QVHLQESGPGLVKPSETLSLTCNVSGTLVRDNYWSWI RQPLGKQPEWIGYVHDSGDTNYNPSLKSRVHLSLDKS KNLVSLRLTGVTAADSAIYYCATTKHGRRIYGVVAFK EWFTYFYMDVWGKGTSVTSS | 414 | TFVSVAPGQTARITCGEESLGSRSVIWYQQRP GQAPSLIIYNNNDRPSGIPDRFSGSPGSTFGT TATLTITSVEAGDEADYYCHIWDSRRPTNWVF GEGTTLIVL |
| 158 | 415 | QLHLQESGPGLVKPPETLSLTCSVSGASINDAYWSWI RQSPGKRPEWVGYVHHSGDTNYNPSLKRRVTFSLDTA KNEVSLKLVDLTAADSATYFCARALHGKRIYGIVALG ELFTYFYMDVWGKGTAVTSS | 416 | SSMSVSPGETAKISCGKESIGSRAVQWYQQKP GQPPSLIIYNNQDRPAGVPERFSASPDFRPGT TATLTITNVDAEDEADYYCHIYDARGGTNWVF DRGTTLTVL |
| 159 | 417 | QSQLQESGPRLVEASETLSLTCNVSGESTGACTYFWG WVRQAPGKGLEWIGSLSHCQSFWGSGWTFHNPSLKSR LTISLDTPKNQVFLKLTSLTAADTATYYCARFDGEVL VYNHWPKPAWVDLWGRGIPVTVSS | 418 | QSALTQPPSASGSPGQSITISCNGTATNFVSW YQQFPDKAPKLIIFGVDKRPPGVPDRFSGSRS GTTASLTVSRLQTDDEAVYYCGSLVGNWDVIF GGGTTLTVL |
| 160 | 419 | QPQLQESGPGLVEASETLSLTCTVSGDSTAACDYFWG WVRQPPGKGLEWIGGLSHCAGYYNTGWTYHNPSLKSR LTISLDTPKNQVFLKLNSVTAADTAIYYCARFDGEVL VYHDWPKPAWVDLWGRGTLVTVSS | 420 | QSALTQPPSASGSPGQSISISCTGTSNRFVSW YQQHPGKAPKLVIYGVNKRPSGVPDRFSGSKS GNTASLTVSGLQTDDEAVYYCSSLVGNWDVIF GGGTKLTVL |
| 161 | 421 | QLQMQESGPGLVKPSETLSLSCTVSGDSIRGGEWGDK DYHWGWVRHSAGKGLEWIGSIHWRGITHYKESLRRRV | 422 | EIVMTQSPDTLSVSPGETVTLSCRASQNINKN LAWYQYKPGQSPRLVIFETYSKIAAPPARFVA |

TABLE B-continued

VH/VL for Anti-HIV gp120 V3 Glycan-Directed Antibodies or Antigen-Binding Fragments Thereof

| Ab Name | SEQ ID NO | VH | SEQ ID NO | VL |
|---|---|---|---|---|
| | | SMSIDTSRNWFSLRLASVTAADTAVYFCARHRHHDVFMLVPIAGWFDVWGPGVQVTVSS | | SGSGTEFTLTINNMQSEDVAVYYCQQYEEWPRTFGQGTKVDIK |
| 162 | 423 | QLQLQESGPGLVKPSETLSLICTVSGGSMRGTDWGENDFHYGWIRQSSAKGLEWIGSIHWRGRTTHYKTSFRSRAILSIDTSNNRFSLTFSFVTAADTAVYYCARHKYHDIFRVVPVAGWFDPWGQGLLVTVSS | 424 | EIVMTQSPPTLSVSPGETATLSCRASQNVKNNLAWYQLKPGQAPRLLIFDASSRAGGIPDRFSGSGYGTDFTLIVNSVQSEDFGDYFCQQYEEWPRTFGQGTKVDIK |
| 163 | 425 | EVHLEESGPGLVRPSETLSLICTASGGSIRGGEWGDSDYHWGVRHSPEKGLEWIGSIHWRGITHYNAPFRGRGRLSIDLSRNQFSLRLTSVTAEDTAVYYCVKHKYHDIVMVVPIAGWFDPWGQGLQVTVSS | 426 | EIMMTQSPAILSVSPGDRATLSCRASQSVKNNLAWYQKRPGQAPRLLIFDTSSRASGIPARFSGGGSGTEFTLTVNSMQSEDFATYYCQQYEEWPRTFGQGTKVEIK |
| 164 | 427 | QPQLQESGPGLVEASETLSLTCTVSGDSTAACDYFWGWVRQPPGKGLEWIGSLSHCAGYYNSGWTYHNPSLKSRLTISLDTPKNQVFLKLNSVTAADTAIYYCARFGGDVLVYHDWPKPAWVDLWGRGVLVTVSS | 428 | QSALTQPPSASGSPGQSITISCTGNINNFVSWYQQHPGKAPKLVIYGVNKRPSGVPDRFSGSKSGNAASLTVSGLQTDDEAVYYCGSLAGNWDVVFGGGTKLTVL |
| 165 | 429 | QPQLQESGPTLVEASETLSLTCAVSGDSTAACNSFWGWVRQPPGKGLEWVGSLSHCASYWNRGWTYHNPSLKSRLTLALDTPKNLVFLKLNSVTAADTATYYCARFGGEVLRYTDWPKPAWVDLWGRGTLVTVSS | 430 | QSALTQPPSASGSPGQSITISCTGTSNNFVSWYQQHAGKAPKLVIYDVNKRPSGVPDRFSGSKSGNTASLTVSGLQTDDEAVYYCGSLVGNWDVIFGGGTKLTVL |
| 166 | 431 | QPQLQESGPGLVEASETLSLTCTVSGDSTAGCDYFWGWVRQPPGKGLEWIGGLSHCAGYYNTGWTYHNPSLKSRLTISLDTPKNQVFLKLNSVTAADTAIYYCARFDGEVLVYNDWPKPAWVDLWGRGTLVTVSS | 432 | QSALTQPPSASGSPGQSITISCTGTSNNFVSWYQQHPAKAPKLVIYGVNKRPSGVPDRFSGSKSGNTASLTVSGLQTDDEAVYYCGSLVGNWDVIFGGGTKLTVL |
| 167 | 433 | QVQLQESGPGLVKPAETLSLTCSVSGESINTGHYYWGWVRQVPGKGLEWIGHIHYTTAVLHNPSLKSRLTIKIYTLRNQITLRLSNVTAADTAVYHCVRSGGDILYYYEWQKPHWFSPWGPGIHVTVSS | 434 | QSALTQPPSASGSLGQSVTISCNGTSSDIGGWNFVSWYQQFPGRAPRLIIFEVNKRPSGVPGRFSGSKSGNSASLTVSGLQSDDEGQYFCSSLFGRWDVVFGGGTKLTVL |
| 168 | 435 | QVQLRESGPGLVKPSETLSLSCTVSQDSRPSDHSWTWVRQSPGKALEWIGDIHYNGATTYNPSLRSRVRIELDQSIPRFSLKMTSMTAADTGMYYCARNAIRIYGVVALGEWFHYGMDVWGQGTAVTVSS | 436 | WASSELTQPPSVSVSPGQTARITCSGAPLTSRFTYWYRQKPGQAPVLIISRSSQRSSGWSGRFSASWSGTTVTLTIRGVQADDEADYYCQSSDTSDSYKMFGGGTKLTVL |
| 169 | 437 | QVQLRESGPGLVKPSETLSLSCTVSNDSRPSDHSWTWVRQSPGKALEWIGDIHYNGATTYNPSLRSRVRIELDQSIPRFSLKMTSMTAADTGMYYCARNAIRIYGVVALGEWFHYGMDVWGQGTAVTVSS | 438 | SSELTQPPSVSVSPGQTARITCSGAPLTSRFTYWYRQKPGQAPVLIISRSSQRSSGWSGRFSASWSGTTVTLTIRGVQADDEADYYCQSSDTSDSYKMFGGGTKLTVL |
| 170 | 439 | EVQLRESGPRLVKPSETLSLSCDVFGDSRPSDHSWTWVRQPPGKALEWIGDVHYNGDNTYNPSLRGRVKIDVDRSTHRFSLTLKSLTAADTGIYFCARNVIRVFGVISLGEWFHYGMDVWGPGTAVIVSS | 440 | SSELTQAPSVSVSPGQTATIACSGPPLASRYTYWYRQKPGQAPVLIIFRDRQFPSGVSRFSASKSGTTATLTIRDVQVEDEGDYYCQSSDTSDSYKMFGGGTTLTVL |
| 171 | 441 | EVQLRESGPGLVKPSETLSLSCDVFGDSRPSDHSWTWVRQPPGKALEWIGDVHYNGDTTYNPSLRGRVKIDVDRSTHRFSLTLNSLTAADTGIYFCARNVIRVFGVISLGEWFHYGMDVWGQGTAVTVSS | 442 | SSELTQAPSVSVSPGQTATIACSGPPLASRYTYWYRQKPGQAPVLIIFRDRQFPSGVSRFSASKSGTTATLTIRDVQVEDEGDYYCQSSDTSDSYKMFGGGTTLTVL |
| 172 | 443 | QVQLRESGPGLVKPSETLSLICTVSNDSRPSDHSWTWVRQSPGKALEWIGDIHYNGATTYNPSLRSRVRIELDQSIPRFSLKMTSMTAADTGMYYCARNAIRIYGVVALGEWFHYGMDVWGQGTAVTVSS | 444 | SSELTQPPSVSVSPGQTAKITCSGAALTSRFTYWYRQKPGQAPVLIISRTSQRSSGWSGRFSASWSGTTVTLTIRGVQADDEGDYYCQSSDTSDSYKMFGGGTKLTVL |
| 173 | 445 | EVQLRESGPGLVKPSGNMALTCTISGDSRPSDHSWTWVRQSPGKALEWIGDIHYGGDITYNPSLRSRVKLEVDTSTNRFFLKMTSLTVADTGIYFCARNVIRVFGVIALGEWFHYGMDVWGQGTAITVSP | 446 | SSELTQTPSVTVSPGETARIACSGPPLASRYCYWYRQKPGQAPVLIIFRDRQFSSGMSGRFASSHSGTTVTLTIRDVRVEDEADYYCQSSDINDSYKMFGGGTKVTVL |
| 174 | 447 | EVQLRESGPGLVKPSGNMALTCTISGDSRPSDHSWTWVRQSPGKTLEWIGDIHYGGDITYNPSLRSRVKLEVDTSSNRFFLKMTSLTVADTGIYFCARNVIRVFGVIALGEWFHYGMDVWGQGTAITVSP | 448 | SSELTQASVTVSPGETARIACSGPPLASRYCYWYRQKPGQAPVLIIFRDRQFSSGISRFSSSQSGTTVTLTIRDVRVEDEADYYCQSSDTSDSFKMFGGGTKLTVL |
| 175 | 449 | QVQLRESGPGLVKPSGNMALTCTISGDSRPSDHSWTWVRQSPGKALEWIGDIHYGGDITYNPSLRSRVELEVDRSTNRFFLKMTSLSVADTGMYFCARNVIRVFGVIALGEWFHYGMDVWGQGTAITVSP | 450 | SSELTQAPSVTVSPGDTARIACSGPPLATRYCYWYRQKSGQAPVLIIFRDRQFSSGVSRFSSSQSGSTVTLTIRDVRVEDEADYYCQSSDTSDSYKMFGGGTKLTVL |

TABLE B-continued

VH/VL for Anti-HIV gp120 V3 Glycan-Directed Antibodies or Antigen-Binding Fragments Thereof

| Ab Name | SEQ ID NO | VH | SEQ ID NO | VL |
|---|---|---|---|---|
| 176 | 451 | QVQLRESGPGLVKPSETLSLSCDVFGDSRPSDHSWTW VRQPPGKALEWIGDIHYNGDKTYNPSLRGRVKIDVDR STHRFSLTLNSLTAADTGMYFCARNVIRVFGVISLGE WFHYGMDVWGPGTAVTV | 452 | SSELTQAPSVSVSPGQTARIACSGPPLASRYT YWYRQKPGQAPVLIIFRDRQFPSGVSGRFSAS KSGTTGILTIRDVQAEDEGDYYCQSSDTSDSY KMFGGGTTLTVL |
| 177 | 453 | QVQLRESGPGLVKPSGNMALTCTISGDSRPSDHSWTW VRQSPGKALEWIGDIHYGGDITYNPSLRSRVKLEVDT SSNRFFLKMTSLTVADTGIYFCARNVIRVFGVIALGE WFHYGMDVWGQGTAITVSP | 454 | SSELTQAPSVTLSPGETARIACSGPPLASRYC YWYRQKPGQAPVLIIFRDRQFSSGISGRFSSS QSGTTVTLTIRDVRVEDEADYYCQSSDNSDSF KMFGGGTKLTVL |
| 178 | 455 | AEQLVESGGGLVPPGRSLRLSCSASGFYFPDYAMAWV RQAPGQGLQWVGFMRGWAYGGSAQFAAFAVGKFAISR DDGRNVVYLDVKNPTFEDTGVYFCAREQRNKDYRYGQ EGFGYSYGMDVWGRGTTVVVST | 456 | DIHMTQSPVSLSASVGDRVTITCRASHFIANY VNWYQQKPGKAPTLLIFESSTLQRGVPSRFSA YGDGTEFTLSINTLQPEDFASYICQQSHSPPV TFGAGTRVDQK |
| 179 | 457 | EERLVESGGGLVPPGRSLRLSCSAFDFYFPDYAMAWV RQAPGKGLEWIGFIRGWAYGQAAQYGKSASGRMTISR DDSRRVVYLDIKSPIEEDTGAYFCAREQRGGDGRYSG DGFGYPYGMDVWGRGTMVTVSA | 458 | DILMTQSPVSLSASIGERITITCRASHFIANY VNWYQQRPGKAPKLLIFQSWTLNRGIPSRFSG YGDGTEFTLSISALQSEDFGTYICQQSHSPPL SFGGGTRVDQT |
| 180 | 459 | EERLVESGGGLVPPGRSLRLSCSAFDFYFPDYAMAWV RQAPGRALEWIGFIRGWAYGQSAQYGKSASGRMTISR DDSRRVVYLDIKSPTHEDTGVYFCAREQRGANGRYGG DGFGYSYGMDVWGRGTMVSVSA | 460 | DIQMTQSPFTLSASVGERVTITCRASHFIANY VNWYQQRPGRAPKLLIFESSTLNRGVPSRFSG SGDGTEFTLSISALQSEDFATYICQQSHSPPV SFGGGTRVDQT |

In some embodiments, the anti-HIV gp120 V3 glycan-directed antibody or antigen-binding fragment thereof comprises a VH comprising a VH-CDR1, a VH-CDR2, and a VH-CDR3; and a VL comprising a VL-CDR1, a VL-CDR2, and a second VH-CDR3; wherein the VH-CDR1, the VH-CDR2, the VH-CDR3 the VL-CDR1, the VL-CDR2, and the VH-CDR3 comprise the sequences set forth in: SEQ ID NOs.: 7, 8, 9, 10, 11 and 12; SEQ ID NOs.: 7, 13, 9, 10, 11 and 12; SEQ ID NOs.: 14, 15, 16, 17, 11 and 18; SEQ ID NOs.: 14, 19, 20, 17, 11 and 18; SEQ ID NOs.: 21, 22, 23, 24, 25 and 26; SEQ ID NOs.: 21, 22, 27, 24, 25 and 26; SEQ ID NOs.: 28, 29, 30, 31, 32 and 33; SEQ ID NOs.: 34, 35, 36, 37, 25 and 38; SEQ ID NOs.: 39, 40, 41, 42, 43 and 44; SEQ ID NOs.: 45, 46, 47, 48, 49 and 50; SEQ ID NOs.: 45, 51, 52, 53, 49 and 54; SEQ ID NOs.: 55, 56, 57, 58, 59 and 44; SEQ ID NOs.: 61, 46, 63, 58, 49 and 44; SEQ ID NOs.: 64, 65, 66, 67, 68 and 69; SEQ ID NOs.: 70, 71, 72, 73, 74 and 75; SEQ ID NOs.: 76, 77, 78, 79, 80 and 75; SEQ ID NOs.: 81, 82, 83, 84, 85 and 75; SEQ ID NOs.: 85, 86, 87, 88, 89 and 90; SEQ ID NOs.: 85, 91, 92, 93, 94 and 90; SEQ ID NOs.: 85, 96, 92, 93, 94 and 90; SEQ ID NOs.: 85, 86, 87, 97, 98 and 90; SEQ ID NOs.: 85, 99, 100, 101, 102 and 95; SEQ ID NOs.: 85, 99, 100, 101, 102 and 103; SEQ ID NOs.: 85, 99, 100, 104, 102 and 90; SEQ ID NOs.: 85, 105, 92, 93, 94 and 90; SEQ ID NOs.: 85, 99, 100, 101, 102 and 107; SEQ ID NOs.: 108, 109, 110, 111, 112, 113; SEQ ID NOs.: 108, 114, 115, 111, 116 and 117; or SEQ ID NOs.: 108, 118, 119, 111, 120 and 121 (CDRs according to Kabat).

In some embodiments, the anti-HIV gp120 V3 glycan-directed antibody or antigen-binding fragment thereof comprises a VH comprising a VH-CDR1, a VH-CDR2, and a VH-CDR3; and a VL comprising a VL-CDR1, a VL-CDR2, and a second VH-CDR3; wherein the VH-CDR1, the VH-CDR2, the VH-CDR3 the VL-CDR1, the VL-CDR2, and the VH-CDR3 comprise the sequences set forth in: SEQ ID NOs.: 123, 124, 9, 10, 11 and 12; SEQ ID NOs.: 125, 126, 16, 17, 11 and 18; SEQ ID NOs.: 127, 128, 20, 17, 11 and 18; SEQ ID NOs.: 129, 130, 23, 24, 25 and 26; SEQ ID NOs.: 129, 130, 27, 24, 25 and 26; SEQ ID NOs.: 131, 132, 30, 31, 32 and 33; SEQ ID NOs.: 133, 134, 36, 37, 25 and 38; SEQ ID NOs.: 135, 136, 41, 42, 43 and 44; SEQ ID NOs.: 137, 138, 47, 48, 49 and 50; SEQ ID NOs.: 137, 138, 52, 53, 49 and 54; SEQ ID NOs.: 139, 56, 57, 58, 59 and 44; SEQ ID NOs.: 141, 138, 63, 58, 49 and 44; SEQ ID NOs.: 142, 143, 66, 67, 68 and 69; SEQ ID NOs.: 144, 145, 72, 73, 74 and 75; SEQ ID NOs.: 146, 147, 78, 79, 80 and 75; SEQ ID NOs.: 146, 147, 83, 84, 85 and 75; SEQ ID NOs.: 149, 150, 87, 88, 89 and 90; SEQ ID NOs.: 151, 150, 87, 88, 89 and 90; SEQ ID NOs.: 152, 153, 92, 93, 94 and 90; SEQ ID NOs.: 151, 150, 87, 97, 98 and 90; SEQ ID NOs.: 152, 153, 100, 101, 102 and 95; SEQ ID NOs.: 152, 153, 100, 101, 102 and 103; SEQ ID NOs.: 152, 153, 100, 104, 102 and 90; SEQ ID NOs.: 152, 153, 100, 101, 102 and 107; SEQ ID NOs.: 154, 155, 110, 111, 116 and 117; SEQ ID NOs.: 156, 157, 115, 111, 116 and 117; or SEQ ID NOs.: 158, 159, 119, 111, 120 and 121 (CDRs according to Chothia).

In some embodiments, the anti-HIV gp120 V3 glycan-directed antibody or antigen-binding fragment thereof comprises a VH comprising a VH-CDR1, a VH-CDR2, and a VH-CDR3; and a VL comprising a VL-CDR1, a VL-CDR2, and a second VH-CDR3; wherein the VH-CDR1, the VH-CDR2, the VH-CDR3 the VL-CDR1, the VL-CDR2, and the VH-CDR3 comprise the sequences set forth in: SEQ ID NOs.: 160, 161, 162, 163, 164 and 12; SEQ ID NOs.: 165, 166, 167, 168, 164 and 18; SEQ ID NOs.: 165, 166, 461, 168, 164 and 18; SEQ ID NOs.: 169, 170, 171, 168, 164 and 18; SEQ ID NOs.: 172, 173, 174, 175, 164 and 26; SEQ ID NOs.: 172, 173, 176, 175, 164 and 26; SEQ ID NOs.: 177, 178, 179, 180, 164 and 38; SEQ ID NOs.: 181, 182, 183, 184, 185 and 33; SEQ ID NOs.: 186, 187, 188, 189, 190 and 44; SEQ ID NOs.: 191, 192, 193, 194, 195 and 50; SEQ ID NOs.: 191, 196, 197, 198, 195 and 54; SEQ ID NOs.: 199, 200, 201, 202, 399 and 44; SEQ ID NOs.: 203, 204, 205, 202, 195 and 44; SEQ ID NOs.: 206, 207, 208, 209, 210 and 69; 211, 212, 213, 214, 215 and 75; SEQ ID NOs.: 216, 217, 218, 219, 220 and 75; SEQ ID NOs.: 221, 217, 83, 223, 224 and 75; SEQ ID NOs.: 225, 226, 87, 227, 228 and 90; SEQ ID NOs.: 229, 226, 87, 227, 228 and 90; SEQ ID NOs.: 230, 231, 92, 232, 233 and 90; SEQ ID NOs.: 230, 234, 92, 232, 233 and 90; SEQ ID NOs.: 229, 226, 87, 235, 398 and 90; SEQ ID NOs.: 230, 236, 100, 232, 233 and 95; SEQ ID NOs.: 230, 236, 100, 232, 233 and 103; SEQ ID NOs.: 230, 236, 100, 237, 233 and 90; SEQ ID NOs.: 230, 238, 92, 232, 233 and 107; SEQ ID NOs.: 239, 240, 110, 241, 242 and 113; SEQ ID NOs.: 243, 244, 115, 241, 245 and 117; or SEQ ID NOs.: 243, 246, 119, 241, 247 and 121 (CDRs according to IMGT).

In some embodiments, the anti-HIV gp120 V3 glycan-directed antibody or antigen-binding fragment thereof comprises a VH comprising a VH-CDR1, a VH-CDR2, and a VH-CDR3; and a VL comprising a VL-CDR1, a VL-CDR2, and a second VH-CDR3; wherein the VH-CDR1, the VH-CDR2, the VH-CDR3 the VL-CDR1, the VL-CDR2, and the VH-CDR3 comprise the sequences set forth in: SEQ ID NOs.: 248, 249, 250, 251, 252 and 253; SEQ ID NOs.: 248, 254, 250, 251 252 and 253; SEQ ID NOs.: 255, 256, 257, 258, 252 and 259; SEQ ID NOs.: 260, 261, 262, 258, 252 and 259; SEQ ID NOs.: 263, 264, 265, 266, 267 and 268; SEQ ID NOs.: 263, 264, 397, 266, 267 and 268; SEQ ID NOs.: 269, 270, 271, 272, 273 and 274; SEQ ID NOs.: 275, 276, 277, 278, 279 and 280; SEQ ID NOs.: 281, 282, 283, 284, 285 and 286; SEQ ID NOs.: 287, 288, 289, 290, 291 and 286; SEQ ID NOs.: 287, 292, 293, 294, 295 and 296; SEQ ID NOs.: 297, 298, 299, 300, 301 and 286; SEQ ID NOs.: 302, 288, 303, 300, 295 and 286; SEQ ID NOs.: 304, 305, 306, 307, 308 and 309; SEQ ID NOs.: 310, 311, 312, 313, 314 and 315; SEQ ID NOs.: 316, 316, 318, 319, 320 and 315; SEQ ID NOs.: 321, 322, 323, 324, 325 and 315; 326, 327, 328, 329, 330 and 331; SEQ ID NOs.: 332, 327, 328, 329, 330 and 331; SEQ ID NOs.: 333, 334, 335, 336, 337 and 338; SEQ ID NOs.: 333, 339, 335, 336, 337 and 338; SEQ ID NOs.: 332, 327, 328, 340, 341 and 338; SEQ ID NOs.: 342, 343, 344, 336, 345 and 346; SEQ ID NOs.: 342, 343, 344, 336, 347 and 348; SEQ ID NOs.: 342, 343, 344, 349, 350 and 338; SEQ ID NOs.: 333, 351, 335, 336, 337 and 338; SEQ ID NOs.: 342, 343, 344, 336, 347 and 352; SEQ ID NOs: 353, 354, 355, 356, 357 and 358; SEQ ID NOs: 359, 360, 361, 356, 362 and 363; or SEQ ID NOs: 359, 364, 365, 356, 366 and 358. (CDRs according to Honegger).

Illustrative embodiments of CDR sequences of an anti-HIV gp120 V3 glycan-directed antibody or antigen-binding fragment thereof, useful in the methods described herein, are provided in Tables A1-A4.

In some embodiments, the anti-HIV gp120 V3 glycan-directed antibody or antigen-binding fragment thereof comprises VH and VL comprising amino acid sequences that are at least 80%, at least 85%, at least 90%, at least 91%, at least 92%, at least 93%, at least 94%, at least 95%, at least 96%, at least 97%, at least 98%, at least 99%, or 100%, identical to the amino acid sequences set forth, respectively, as selected from: SEQ ID NOs.: 400 and 401; SEQ ID NOs.: 402 and 403; SEQ ID NOs.: 402 and 404; SEQ ID NOs.: 462 and 463; SEQ ID NOs.: 464 and 465; SEQ ID NOs.: 405 and 406; SEQ ID NOs.: 466 and 467; SEQ ID NOs.: 407 and 408; SEQ ID NOs.: 409 and 410; SEQ ID NOs.: 411 and 412; SEQ ID NOs.: 413 and 414; SEQ ID NOs.: 415 and 416; SEQ ID NOs.: 417 and 418; SEQ ID NOs.: 419 and 420; SEQ ID NOs.: 421 and 422; SEQ ID NOs.: 423 and 424; SEQ ID NOs.: 425 and 426; SEQ ID NOs.: 427 and 428; SEQ ID NOs.: 429 and 430; SEQ ID NOs.: 431 and 432; SEQ ID NOs.: 433 and 434; SEQ ID NOs.: 435 and 436; SEQ ID NOs.: 437 and 438; SEQ ID NOs.: 439 and 440; SEQ ID NOs.: 441 and 442; SEQ ID NOs.: 443 and 444; SEQ ID NOs.: 445 and 446; SEQ ID NOs.: 447 and 448; SEQ ID NOs.: 449 and 450; SEQ ID NOs.: 451 and 452; SEQ ID NOs.: 453 and 454; SEQ ID NOs.: 455 and 456; SEQ ID NOs.: 457 and 458; or SEQ ID NOs.: 459 and 460. Illustrative embodiments of variable domain VH and VL sequences of an anti-HIV gp120 V3 glycan-directed antibody or antigen-binding fragment thereof, useful in the methods described herein, are provided in Table B.

In some embodiments, the anti-HIV gp120 V3 glycan directed antibody comprises VH and VL amino acid sequences that are at least 80%, at least 85%, at least 90%, at least 91%, at least 92%, at least 93%, at least 94%, at least 95%, at least 96%, at least 97%, at least 98%, or at least 99% identical to the amino acid sequences set forth below, respectively, and comprising one or more of the following amino acids at the indicated positions (position numbering according to Kabat): SEQ ID NOs.: 400 or 402, comprising one or more of: Ser-Ser-Val (SSV) or Thr-Gly-Val (TGV) at positions 82a-82c, Gln (Q) at position 39, Asn (N) at position 60, His (H) at position 68, any one of Lys (K), His (H) or Thr (T) at position 105, Leu (L) at position 2, Ala (A) at position 32, and/or Ala (A) at position 95; and SEQ ID NOs.: 401, 403 or 404 comprising one or more of: Gly (G) at position 67, Tyr (Y), Phe (F) or Thr (T) at position 67a, Arg (R) at position 67b, Pro (P) at position 67c, and/or Lys (K) at position 103. In some embodiments, the anti-HIV gp120 V3 glycan directed antibody comprises VH and VL amino acid sequences that are at least 80%, at least 85%, at least 90%, at least 91%, at least 92%, at least 93%, at least 94%, at least 95%, at least 96%, at least 97%, at least 98%, or at least 99% identical to the amino acid sequences set forth below, respectively, and comprising one or more of the following amino acids at the indicated positions (position numbering according to Kabat): SEQ ID NO.: 400 or 402, comprising one or more of: Thr-Gly-Val (TGV) at positions 82a-82c, Asn (N) at position 60, His (H) at position 68, any one of Lys (K), His (H) and/or Thr (T) at position 105; and SEQ ID NOs.: 401, 403 or 404 comprising one or more of: Gly (G) at position 67, Tyr (Y), Phe (F) or Thr (T) at position 67a, Arg (R) at position 67b, Pro (P) at position 67c.

Fc Mutations that Increase Serum Half-Life

In some embodiments, the Fc region or Fc domain of the anti-HIV gp120 V3 glycan directed antibody comprise amino acid modifications that promote an increased serum half-life of the anti-binding molecule. Mutations that increase the half-life of an antibody have been described. In one embodiment, the Fc region or Fc domain of one or both of the CD3-targeting heavy chain and the HIV antigen-targeting heavy chain comprise a methionine to tyrosine substitution at position 252 (EU numbering), a serine to threonine substitution at position 254 (EU numbering), and a threonine to glutamic acid substitution at position 256 (EU numbering). See, e.g., U.S. Pat. No. 7,658,921. This type of mutant, designated as a "YTE mutant" exhibits a four-fold increased half-life relative to wild-type versions of the same antibody (Dall'Acqua, et al., J Biol Chem, 281: 23514-24 (2006); Robbie, et al., Antimicrob Agents Chemotherap., 57(12):6147-6153 (2013)). In certain embodiments, the Fc region or Fc domain of one or both of the CD3-targeting heavy chain and the HIV antigen-targeting heavy chain comprise an IgG constant domain comprising one, two, three or more amino acid substitutions of amino acid residues at positions 251-257, 285-290, 308-314, 385-389, and 428-436 (EU numbering). Alternatively, M428L and N434S ("LS") substitutions can increase the pharmacokinetic half-life of the multi-specific antigen binding molecule. In other embodiments, the Fc region or Fc domain of one or both of the CD3-targeting heavy chain and the HIV antigen-targeting heavy chain comprise a M428L and N434S substitution (EU numbering). In other embodiments, the Fc region or Fc domain of one or both of the CD3-targeting heavy chain and the HIV antigen-targeting heavy chain comprise T250Q and M428L (EU numbering) mutations. In other embodiments, the Fc region or Fc domain of one or both of the CD3-targeting heavy chain and the HIV antigen-targeting heavy chain comprise H433K and N434F (EU numbering) mutations.

Fc Mutations that Enhance Effector Activity

In some embodiments, the Fc region or Fc domain of the anti-HIV gp120 V3 glycan directed antibody comprise post-translational and/or amino acid modifications that increase effector activity, e.g., have improved FcγIIIa binding and increased antibody-dependent cellular cytotoxicity (ADCC). In some embodiments, the Fc region or Fc domain of the anti-HIV gp120 V3 glycan directed antibody comprises DE modifications (i.e., S239D and I332E by EU numbering) in the Fc region. In some embodiments, the Fc region or Fc domain of the anti-HIV gp120 V3 glycan directed antibody comprises DEL modifications (i.e., S239D, I332E and A330L by EU numbering) in the Fc region. In some embodiments, the Fc region or Fc domain of the anti-HIV gp120 V3 glycan directed antibody comprises DEA modifications (i.e., S239D, I332E and G236A by EU numbering) in the Fc region. In some embodiments, the Fc region or Fc domain of the anti-HIV gp120 V3 glycan directed antibody comprises DEAL modifications (i.e., S239D, I332E, G236A and A330L by EU numbering) in the Fc region. See, e.g., U.S. Pat. Nos. 7,317,091; 7,662,925; 8,039,592; 8,093,357; 8,093,359; 8,383,109; 8,388,955; 8,735,545; 8,858,937; 8,937,158; 9,040,041; 9,353,187; 10,184,000; and 10,584,176. Additional amino acid modifications that increase effector activity, e.g., have improved FcγIIIa binding and increased antibody-dependent cellular cytotoxicity (ADCC) include without limitation (EU numbering) F243L/R292P/Y300L/V305I/P396L; S298A/E333A/K334A; or L234Y/L235Q/G236W/S239M/H268D/D270E/S298A on a first Fc domain and D270E/K326D/A330M/K334E on a second Fc domain. Amino acid mutations that increase C1q binding and complement-dependent cytotoxicity (CDC) include without limitation (EU numbering) S267E/H268F/S324T or K326W/E333S. Fc region mutations that enhance effector activity are reviewed in, e.g., Wang, et al., Protein Cell (2018) 9(1): 63-73; and Saunders, Front Immunol. (2019) 10:1296.

In other embodiments, the anti-HIV gp120 V3 glycan directed antibody or antigen-binding fragment thereof has modified glycosylation, which, e.g., may be introduced post-translationally or through genetic engineering. In some embodiments, the anti-HIV gp120 V3 glycan directed antibody or antigen-binding fragment thereof is afucosylated, e.g., at a glycosylation site present in the antibody or antigen-binding fragment thereof. Most approved monoclonal antibodies are of the IgG1 isotype, where two N-linked biantennary complex-type oligosaccharides are bound to the Fc region. The Fc region exercises the effector function of ADCC through its interaction with leukocyte receptors of the FcγR family. Afucosylated monoclonal antibodies are monoclonal antibodies engineered so that the oligosaccharides in the Fc region of the antibody do not have any fucose sugar units.

In some embodiments, as appropriate, the Fc region or Fc domain of the anti-HIV gp120 V3 glycan directed antibody can comprise post-translational and/or amino acid modifications for increasing serum half-life and enhancing effector activity.

4. Combination Therapies with Two or More Anti-HIV Antibodies

In certain embodiments, this disclosure provides a method for treating or preventing an HIV infection in a human subject having, or at risk of having, the HIV infection. The method comprises administering to the human subject a therapeutically effective amount of an anti-HIV gp120 V3 glycan directed antibody or antigen-binding fragment, as disclosed herein, or a pharmaceutical composition thereof, in combination with a therapeutically effective amount of one or more (e.g., one, two, three, one or two, or one to three) additional therapeutic agents. In one embodiment, a method for treating an HIV infection in a human subject having or at risk of having the infection is provided, the method comprising administering to the human subject a therapeutically effective amount of an antibody or antibodies disclosed herein, or a pharmaceutically acceptable salt thereof, in combination with a therapeutically effective amount of one or more (e.g., one, two, three, one or two, or one to three) additional therapeutic agents.

Antibody Combination Therapy

In some embodiments, the anti-V3-glycan antibody or antigen-binding fragment thereof is co-administered with a second anti-HIV antibody. In some embodiments, the anti-V3-glycan antibody or antigen-binding fragment thereof is co-administered with a second anti-HIV antibody that binds to an epitope or region of gp120 selected from the group consisting of: (i) second variable loop (V2) and/or Env trimer apex; (ii) CD4 binding site (CD4bs); (iii) gp120/gp41 interface; or (v) silent face of gp120. The foregoing epitopes or regions of gp120 bound by broadly neutralizing antibodies are described, e.g., in McCoy, *Retrovirology* (2018) 15:70; Sok and Burton, *Nat Immunol.* 2018 19(11):1179-1188; Possas, et al., *Expert Opin Ther Pat.* 2018 July; 28(7):551-560; and Stephenson and Barouch, *Curr HIV/AIDS Rep* (2016) 13:31-37, which are hereby incorporated herein by reference in their entirety for all purposes.

In some embodiments, the combination therapy entails co-administration of an anti-V3-glycan antibody or antigen-binding fragment thereof and another anti-HIV broadly neutralizing antibody or bNAb (i.e., a neutralizing antibody that neutralizes multiple HIV-1 viral strains). Various bNAbs are known in the art and may be used as a combining therapeutic agent. Additional illustrative bNAbs of use include, those that comprise VH and VL that bind to or compete with an epitope or region of gp120 selected from the group consisting of: (i) second variable loop (V2) and/or Env trimer apex; (ii) CD4 binding site (CD4bs); (iii) gp120/gp41 interface; or (v) silent face of gp120. Illustrative bNAbs for use in anti-HIV antibody combination therapies include those that comprise VH and VL that bind to or compete with 2F5, 4E10, M66.6, CAP206-CH12, 10E8, 10E8v4, 10E8-5R-100cF, DH511.11P, 7b2, and LN01 (all of which bind the MPER of gp41); PG9, PG16, CH01-04 (all of which bind V1V2-glycan), 2G12 (which binds to outer domain glycan); b12, F105, VRC01, VRC07, VRC07-523, VRC03, VRC06, VRC06b01 VRC08, VRC0801, NIH45-46, GS-9723, GS-5423, 3BNC117, 3BNC60, VRC-PG04, PGV04; CH103, 44-VRC13.01, 1NC9, 12A12, N6, N6LS (VRC-HIVMAB091-00-AB), N49-P7, NC-Cow1, IOMA, CH235 and CH235.12, N49P6, N49P7, N49P11, N49P9 and N60P25 (all of which bind to the CD4 binding site).

In some embodiments, the combination therapy includes an antibody that binds to an epitope or region of gp120 in the second variable loop (V2) and/or Env trimer apex and competes with or comprises CDRs and/or VH and VL regions from an antibody selected from the group consisting of PG9, PG16, PGC14, PGG14, PGT-142, PGT-143, PGT-144, PGT-145, CH01, CH59, PGDM1400, CAP256, CAP256-VRC26.08, CAP256-VRC26.09, CAP256-VRC26.25, PCT64-24E and VRC38.01.

In some embodiments, the combination therapy includes an antibody that binds to an epitope or region of gp120 in the CD4 binding site (CD4bs) and competes with or comprises CDRs and/or VH and VL regions from an antibody selected from the group consisting of b12, F105, VRC01, VRC07, VRC07-523, VRC03, VRC06, VRC06b01 VRC08, VRC0801, NIH45-46, GS-9723, GS-5423, 3BNC117, 3BNC60, VRC-PG04, PGV04; CH103, 44-VRC13.01, 1NC9, 12A12, N6, N6LS (VRC-HIVMAB091-00-AB), N49-P7, NC-Cow1, IOMA, CH235 and CH235.12, N49P6, N49P7, N49P11, N49P9 and N60P25.

In some embodiments, the combination therapy includes an antibody that binds to an epitope or region of gp120 in the gp120/gp41 interface and competes with or comprises CDRs and/or VH and VL regions from an antibody selected from the group consisting of PGT-151, CAP248-2B, 35O22, 8ANC195, ACS202, VRC34 and VRC34.01.

In some embodiments, the combination therapy includes an antibody that binds to an epitope or region of the gp120 silent face and competes with or comprises second VH and VL regions from antibody VRC-PG05.

In some embodiments, the combination therapy includes an antibody that binds to an epitope or region of gp41 in the membrane proximal region (MPER) and competes with or comprises second VH and VL regions from an antibody selected from the group consisting of 10E8, 10E8v4, 10E8-5R-100cF, 4E10, DH511.11P, 2F5, 7b2, and LN01. In some embodiments, the combination therapy includes an antibody that binds to an epitope or region of KLIC ("KLIC" disclosed as SEQ ID NO: 468), an immutable site of the transmembrane protein gp41 and competes with or comprises second VH and VL regions from Clone 3 human monoclonal antibody (C13hmAb) (Protheragen). See, e.g., Vanini, et al., AIDS. (1993) 7(2):167-74.

In some embodiments, the combination therapy includes an antibody that binds to and epitope or region of the gp41 fusion peptide and competes with or comprises second VH and VL regions from an antibody selected from the group consisting of VRC34 and ACS202.

In some embodiments, the combination therapy includes a multi-specific, e.g., a bispecific or tri-specific antibody that binds to an HIV antigen. Examples of HIV bispecific and trispecific antibodies include MGD014, B12BiTe, BiIA-SG, TMB-bispecific, SAR-441236, VRC-01/PGDM-1400/10E8v4, 10E8.4/iMab, and 10E8v4/PGT121-VRC01.

Prior to administration, the bNAbs may be improved to have enhanced drug-like-properties, reduced immunogenicity, enhanced ADCC, and suitable pharmacokinetic properties. Such antibodies were shown to bind to the HIV envelope glycoprotein expressed on the surface of virion or infected cells, and mediate both direct neutralization of the virus as well as potent NK, Monocyte and PBMC killing of these cells. This property allows the antibodies to treat HIV infections by neutralizing the virus, and also kill and eliminate latently HIV infected cells in infected individuals, potentially leading to a sterilizing cure for HIV.

In various embodiments, all antibodies administered in a combination anti-HIV antibody therapy can have Fc and/or post-translational modifications that increase serum half-life and/or enhance effector activity, as described above.

In various embodiments, the anti-HIV gp120 V3 glycan directed antibody or antigen-binding fragments, and optionally combined bNAbs, can be in vivo delivered, e.g., expressed in vivo from administered mRNA or engineered B-cells. Examples of in vivo delivered bNAbs include AAV8-VRC07; mRNA encoding anti-HIV antibody VRC01; and engineered B-cells encoding 3BNC117 (Hartweger et al, *J. Exp. Med.* 2019, 1301).

5. Combination Therapies with Other Anti-HIV Therapeutic Agents

In certain embodiments, a method for treating or preventing an HIV infection in a human having or at risk of having the infection is provided, comprising administering to the human a therapeutically effective amount of the anti-HIV gp120 V3 glycan directed antibody or antigen-binding fragments, as disclosed herein, in combination with a therapeutically effective amount of one or more (e.g., one, two, three, one or two, or one to three) additional therapeutic agents. In one embodiment, a method for treating an HIV infection in a human having or at risk of having the infection is provided, comprising administering to the human a therapeutically effective amount of the anti-HIV gp120 V3 glycan directed antibody or antigen-binding fragments, as disclosed herein, in combination with a therapeutically effective amount of one or more (e.g., one, two, three, one or two, or one to three) additional therapeutic agents.

In one embodiment, pharmaceutical compositions comprising the anti-HIV gp120 V3 glycan directed antibody or antigen-binding fragments, as disclosed herein, in combination with one or more (e.g., one, two, three, one or two, or one to three) additional therapeutic agents, and a pharmaceutically acceptable carrier, diluent, or excipient are provided.

In certain embodiments, provided are methods for treating an HIV infection, comprising administering to a patient in need thereof a therapeutically effective amount of the anti-HIV gp120 V3 glycan directed antibody or antigen-binding fragment thereof, as described herein, in combination with a therapeutically effective amount of one or more additional therapeutic agents which are suitable for treating an HIV infection.

In certain embodiments, the anti-HIV gp120 V3 glycan directed antibody or antigen-binding fragment thereof is combined with one, two, three, four, or more additional therapeutic agents. In certain embodiments, the anti-HIV gp120 V3 glycan directed antibody or antigen-binding fragment thereof is combined with two additional therapeutic agents. In other embodiments, the anti-HIV gp120 V3 glycan directed antibody or antigen-binding fragment thereof is combined with three additional therapeutic agents. In further embodiments, the anti-HIV gp120 V3 glycan directed antibody or antigen-binding fragment thereof is combined with four additional therapeutic agents. The one, two, three, four, or more additional therapeutic agents can be different therapeutic agents selected from the same class of therapeutic agents, (e.g., one or more anti-HIV broadly neutralizing antibodies), and/or they can be selected from different classes of therapeutic agents.

Administration of HIV Combination Therapy

In certain embodiments, the anti-HIV gp120 V3 glycan directed antibody or antigen-binding fragment thereof, as described herein, is co-administered with one or more additional therapeutic agents. Co-administration of an anti-HIV gp120 V3 glycan directed antibodies or antigen-binding fragments disclosed herein with one or more additional therapeutic agents generally refers to simultaneous or sequential administration of an anti-HIV gp120 V3 glycan directed antibodies or antigen-binding fragments disclosed herein and one or more additional therapeutic agents, such that therapeutically effective amounts of the anti-HIV gp120 V3 glycan directed antibodies or antigen-binding fragments disclosed herein and the one or more additional therapeutic agents are both present in the body of the patient. When administered sequentially, the combination may be administered in two or more administrations.

Co-administration includes concurrent administration as well as administration of unit dosages of the anti-HIV gp120 V3 glycan directed antibody or antigen-binding fragment thereof, as described herein before or after administration of unit dosages of one or more additional therapeutic agents. For example, the anti-HIV gp120 V3 glycan directed antibody or antigen-binding fragment thereof, as described herein, may be administered within seconds, minutes, hours or days of the administration of the one or more additional therapeutic agents. In some embodiments, a unit dose of an anti-HIV gp120 V3 glycan directed antibodies or antigen-binding fragments disclosed herein is administered first, followed within seconds, minutes, hours or days by administration of a unit dose of one or more additional therapeutic agents. Alternatively, a unit dose of one or more additional therapeutic agents is administered first, followed by administration of a unit dose of an anti-HIV gp120 V3 glycan directed antibodies or antigen-binding fragments disclosed herein within seconds, minutes, hours or days. In other embodiments, a unit dose of an anti-HIV gp120 V3 glycan directed antibodies or antigen-binding fragments disclosed herein is administered first, followed, after a period of hours (e.g., 1-12 hours, 1-24 hours, 1-36 hours, 1-48 hours, 1-60 hours, 1-72 hours), by administration of a unit dose of one or more additional therapeutic agents. In yet other embodiments, a unit dose of one or more additional therapeutic agents is administered first, followed, after a period of hours (e.g., 1-12 hours, 1-24 hours, 1-36 hours, 1-48 hours, 1-60 hours, 1-72 hours), by administration of a unit dose of an anti-HIV gp120 V3 glycan directed antibodies or antigen-binding fragments disclosed herein.

In certain embodiments, an anti-HIV gp120 V3 glycan directed antibodies or antigen-binding fragments disclosed herein is combined with one or more additional therapeutic agents in a unitary dosage form for simultaneous administration to a patient, for example as a solid, liquid or suspension dosage form for oral, intravenous, intramuscular or subcutaneous administration.

In certain embodiments, the anti-HIV gp120 V3 glycan directed antibodies or antigen-binding fragments are formulated as a liquid solution or suspension which may optionally contain one or more other compounds useful for treating HIV. In certain embodiments, the liquid solution or suspension can contain another active ingredient for treating HIV, such as HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, pharmacokinetic enhancers, and combinations thereof.

In certain embodiments, such liquid solutions or suspensions are suitable for once daily, once weekly (i.e., QW), once bi-weekly (i.e. once every other week, or once every two weeks or Q2W), once monthly (i.e., QM) or once bi-monthly dosing (i.e. once every other month, or once every two months or Q2M) dosing or administration intervals. In some embodiments, the anti-HIV gp120 V3 glycan directed antibodies or antigen-binding fragments are administered once daily, once weekly (i.e., QW), once bi-weekly (i.e. once every other week, or once every two weeks or Q2W), once monthly (i.e., QM), once bi-monthly dosing (i.e. once every other month, or once every two months or Q2M), once every three months (i.e., Q3M), once every four months (i.e., Q4M), HIV Combination Therapy In the above embodiments, the additional therapeutic agent may be an anti-HIV agent. HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, HIV Tat or Rev inhibitors, immunomodulators, (e.g., immunostimulators), immunotherapeutic agents, immunomodulators, immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T-cell receptors, TCR-T, autologous T-cell therapies), latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, Fatty acid synthase inhibitor, HIV vif gene modulators, Vif dimerization antagonists, HIV-1 viral infectivity factor inhibitors, TAT protein inhibitors, HIV-1 Nef modulators (e.g., Nef inhibitors), Hck tyrosine kinase modulators, mixed lineage kinase-3 (MLK-3) inhibitors, HIV-1 splicing inhibitors, Rev protein inhibitors, integrin antagonists, nucleoprotein inhibitors, splicing factor modulators, COMM domain containing protein 1 modulators, HIV ribonuclease H inhibitors, retrocyclin modulators, CDK-4 inhibitors, CDK-6 inhibitors, CDK-9 inhibitors, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, proprotein convertase PC9 stimulators, ATP dependent RNA helicase DDX3X inhibitors, reverse transcriptase priming complex inhibitors, G6PD and NADH-oxidase inhibitors, mTOR complex 1 inhibitors, mTOR complex 2 inhibitors, P-Glycoprotein modulators, TAT protein inhibitors, prolylendopeptidase inhibitors, Phospholipase A2 inhibitors, pharmacokinetic enhancers, HIV gene therapy, TNF alpha ligand inhibitors, IFN antagonists, HIV vaccines, and combinations thereof.

In some embodiments, the additional therapeutic agent is selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, HIV capsid inhibitors, HIV Tat or Rev inhibitors, immunomodulators, (e.g., immunostimulators), immunotherapeutic agents, immune-based therapies, PI3K inhibitors, HIV antibodies, and bispecific antibodies, and "antibody-like" therapeutic proteins, and combinations thereof.

HIV Combination Drugs

In certain embodiments, the anti-HIV gp120 V3 glycan directed antibodies or antigen-binding fragments described herein are combined with one, two, three, four or more additional anti-HIV therapeutic agents. Example anti-HIV therapeutic agents that can be combined include without limitation ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY (bictegravir+emtricitabine+tenofovir alafenamide), adefovir; adefovir dipivoxil; cobicistat; emtricitabine; tenofovir; tenofovir alafenamide and elvitegravir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; PEGylated raltegravir; raltegravir and lamivudine; maraviroc; tenofovir+emtricitabine+maraviroc, enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine and lamivudine; cabotegravir+rilpivirine; elpida (elsulfavirine; VM-1500; VM-1500A); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; efavirenz, lamivudine, and emtricitabine; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

Other HIV Drugs

Examples of other drugs for treating HIV that can be combined with an agent of this disclosure include aspernigrin C, acemannan, alisporivir, BanLec, deferiprone, Gamimune, metenkefalin, naltrexone, Prolastin, REP 9, RPI-MN, VSSP, H1viral, SB-728-T, 1,5-dicaffeoylquinic acid, rHIV7-sh1-TAR-CCR5RZ, AAV-eCD4-Ig gene therapy, MazF gene therapy, BlockAide, bevirimat derivatives, ABX-464, AG-1105, APH-0812, bryostatin analogs, BIT-225, CYT-107, CS-TATI-1, fluoro-beta-D-arabinose nucleic acid (FANA)-modified antisense oligonucleotides, FX-101, griffithsin, HGTV-43, HPH-116, HS-10234, hydroxychloroquine, IMB-10035, IMO-3100, IND-02, JL-18008, LADAVRU, MK-1376, MK-2048, MK-4250, MK-8507, MK-8558, MK-8591 (islatravir), NOV-205, OB-002H, ODE-Bn-TFV, M1-TFV, PA-1050040 (PA-040), PC-707, PGN-007, QF-036, S-648414, SCY-635, SB-9200, SCB-719, TR-452, TEV-90110, TEV-90112, TEV-90111, TEV-90113, RN-18, DIACC-1010, Fasnall, Immuglo, 2-CLIPS peptide, HRF-4467, thrombospondin analogs, TBL-1004HI, VG-1177, x1-081, rfhSP-D, [$^{18}$F]-MC-225, URMC-099-C, RES-529, and VIR-576.

HIV Protease Inhibitors

In certain embodiments, the anti-HIV gp120 V3 glycan directed antibodies or antigen-binding fragments described herein are combined with an HIV protease inhibitor. Examples of HIV protease inhibitors include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, AEBL-2, DG-17, GS-1156, TMB-657 (PPL-100), T-169, BL-008, MK-8122, TMB-607, GRL-02031 and TMC-310911.

HIV Ribonuclease H Inhibitors

In certain embodiments, the anti-HIV gp120 V3 glycan directed antibodies or antigen-binding fragments described herein are combined with an HIV ribonuclease H inhibitor. Examples of HIV ribonuclease H inhibitors that can be combined include NSC-727447.

HIV Nef Inhibitors

In certain embodiments, the anti-HIV gp120 V3 glycan directed antibodies or antigen-binding fragments described herein are combined with an HIV Nef inhibitor. Examples of HIV Nef inhibitors that can be combined with include FP-1.

HIV Reverse Transcriptase Inhibitors

In certain embodiments, the anti-HIV gp120 V3 glycan directed antibodies or antigen-binding fragments described herein are combined with a non-nucleoside or non-nucleotide inhibitor. Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, ACC-007, ACC-008, AIC-292, F-18, KM-023, PC-1005, VM-1500A-LAI, PF-3450074, elsulfavirine (sustained release oral, HIV infection), elsulfavirine (long-acting injectable nanosuspension, HIV infection), and elsulfavirine (VM-1500).

In certain embodiments, the anti-HIV gp120 V3 glycan directed antibodies or antigen-binding fragments described herein are combined with an HIV nucleoside or nucleotide inhibitor. Examples of HIV nucleoside or nucleotide inhibitors of reverse transcriptase include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir octadecyloxyethyl ester (AGX-1009), tenofovir disoproxil hemifumarate, VIDEX® and VIDEX EC® (didanosine, ddI), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, rovafovir etalafenamide (GS-9131), GS-9148, MK-8504, MK-8591, MK-858, VM-2500 and KP-1461.

HIV Integrase Inhibitors

In certain embodiments, the anti-HIV gp120 V3 glycan directed antibodies or antigen-binding fragments described herein are combined with an HIV integrase inhibitor.

Examples of HIV integrase inhibitors include elvitegravir, elvitegravir (extended-release microcapsules), curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, PEGylated raltegravir, dolutegravir, JTK-351, bictegravir, AVX-15567, cabotegravir (long-acting injectable), diketo quinolin-4-1 derivatives, integrase-LEDGF inhibitor, ledgins, M-522, M-532, MK-0536, NSC-310217, NSC-371056, NSC-48240, NSC-642710, NSC-699171, NSC-699172, NSC-699173, NSC-699174, stilbenedisulfonic acid, T-169, STP-0404, VM-3500 and cabotegravir.

In certain embodiments, the anti-HIV gp120 V3 glycan directed antibodies or antigen-binding fragments described herein are combined with a HIV non-catalytic site, or allosteric, integrase inhibitor (NCINI). Examples of HIV non-catalytic site, or allosteric, integrase inhibitors (NCINI) include CX-05045, CX-05168, and CX-14442.

HIV Entry Inhibitors

In certain embodiments, the anti-HIV gp120 V3 glycan directed antibodies or antigen-binding fragments described herein are combined with an HIV entry inhibitor. Examples of HIV entry (fusion) inhibitors include AAR-501, LBT-5001, cenicriviroc, CCR5 inhibitors, gp41 inhibitors, CD4 attachment inhibitors, gp120 inhibitors, gp160 inhibitors and CXCR4 inhibitors.

In certain embodiments, the anti-HIV gp120 V3 glycan directed antibodies or antigen-binding fragments described herein are combined with a CCR5 inhibitor. Examples of CCR5 inhibitors include aplaviroc, vicriviroc, maraviroc, maraviroc (long-acting injectable nanoemulsion), cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, thioraviroc and vMIP (Haimipu).

In certain embodiments, the anti-HIV gp120 V3 glycan directed antibodies or antigen-binding fragments described herein are combined with a CXCR4 inhibitor. Examples of CXCR4 inhibitors include plerixafor, ALT-1188, N15 peptide, and vMIP (Haimipu).

In certain embodiments, the anti-HIV gp120 V3 glycan directed antibodies or antigen-binding fragments described herein are combined with a gp41 inhibitor. Examples of gp41 inhibitors include albuvirtide, enfuvirtide, griffithsin (gp41/gp120/gp160 inhibitor), BMS-986197, enfuvirtide biobetter, enfuvirtide biosimilar, HIV-1 fusion inhibitors (P26-Bapc), ITV-1, ITV-2, ITV-3, ITV-4, CPT-31, C13hmAb, PIE-12 trimer and sifuvirtide.

In certain embodiments, the anti-HIV gp120 V3 glycan directed antibodies or antigen-binding fragments described herein are combined with a CD4 attachment inhibitor. Examples of CD4 attachment inhibitors include ibalizumab and CADA analogs In certain embodiments, the anti-HIV gp120 V3 glycan directed antibodies or antigen-binding fragments described herein are combined with a gp120 inhibitor. Examples of gp120 inhibitors include anti-HIV microbicide, Radha-108 (receptol) 3B3-PE38, BanLec, bentonite-based nanomedicine, fostemsavir tromethamine, IQP-0831, VVX-004, and BMS-663068.

In certain embodiments, the anti-HIV gp120 V3 glycan directed antibodies or antigen-binding fragments described herein are combined with a gp160 inhibitor. Examples of gp160 inhibitors that can be combined include fangchinoline.

HIV Maturation Inhibitors

In certain embodiments, the anti-HIV gp120 V3 glycan directed antibodies or antigen-binding fragments described herein are combined with an HIV maturation inhibitor. Examples of HIV maturation inhibitors include BMS-955176, GSK-3640254 and GSK-2838232.

Latency Reversing Agents

In certain embodiments, the anti-HIV gp120 V3 glycan directed antibodies or antigen-binding fragments described herein are combined with an HIV latency reversing agent. Examples of latency reversing agents that can be combined with the one or more multi-specific antigen binding molecules, described herein, include IL-15 receptor agonists (e.g., ALT-803; interleukin-15/Fc fusion protein (e.g., XmAb24306); recombinant interleukin-15 (e.g., AM0015, NIZ-985); pegylated IL-15 (e.g., NKTR-255)); toll-like receptor (TLR) agonists (including TLR7 agonists, e.g., GS-9620 and TLR8 agonists, e.g., GS-9688), histone deacetylase (HDAC) inhibitors, proteasome inhibitors such as velcade, protein kinase C (PKC) activators, Smyd2 inhibitors, BET-bromodomain 4 (BRD4) inhibitors, ionomycin, IAP antagonists (inhibitor of apoptosis proteins, such as APG-1387, LBW-242), SMAC mimetics (including TL32711, LCL161, GDC-0917, HGS1029, AT-406), Debio-1143, PMA, SAHA (suberanilohydroxamic acid, or suberoyl, anilide, and hydroxamic acid), NIZ-985, IL-15 modulating antibodies, (including IL-15, IL-15 fusion proteins and IL-15 receptor agonists, e.g., ALT-803), JQ1, disulfiram, amphotericin B, and ubiquitin inhibitors such as largazole analogs, APH-0812, and GSK-343. Examples of HDAC inhibitors include romidepsin, vorinostat, and panobinostat. Examples of PKC activators include indolactam, prostratin, ingenol B, and DAG-lactones.

Toll-Like Receptor (TLR) Agonists

In certain embodiments, the anti-HIV gp120 V3 glycan directed antibodies or antigen-binding fragments described herein are combined with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793). Example TLR7 agonists that can be co-administered or combined with the one or more multi-specific antigen binding molecules, described herein, include without limitation AL-034, DSP-0509, GS-9620 (vesatolimod), vesatolimod analogs, LHC-165, TMX-101 (imiquimod), GSK-2245035, resiquimod, DSR-6434, DSP-3025, IMO-4200, MCT-465, MEDI-9197, 3M-051, SB-9922, 3M-052, Limtop, TMX-30X, TMX-202, RG-7863, RG-7854, RG-7795, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). An TLR7/TLR8 agonist that can be co-administered is NKTR-262, telratolimod and BDB-001. Example TLR8 agonists that can be co-administered or combined with the one or more multi-specific antigen binding molecules, described herein, include without limitation E-6887, IMO-4200, IMO-8400, IMO-9200, MCT-465, MEDI-9197, motolimod, resiquimod, GS-9688, VTX-1463, VTX-763, 3M-051, 3M-052, and the compounds disclosed in US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics). Example TLR9 agonists that can be co-administered include without limitation AST-008, cobitolimod, CMP-001, IMO-2055, IMO-2125, litenimod, MGN-1601, BB-001, BB-006, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PUL-042. Examples of TLR3 agonist include rintatolimod, poly-ICLC, RIBOXXON®, Apoxxim, RIBOXXIM®, IPH-33, MCT-465, MCT-475, and ND-1.1. Examples of TLR4 agonist include G-100, and GSK-1795091.

Histone Deacetylase (HDAC) Inhibitors

In certain embodiments, the anti-HIV gp120 V3 glycan directed antibodies or antigen-binding fragments described herein are combined with an inhibitor of a histone deacetylase, e.g., histone deacetylase 1, histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include without limitation, abexinostat, ACY-241, AR-42, BEBT-908, belinostat, CKD-581, CS-055 (HBI-8000), CT-101, CUDC-907 (fimepinostat), entinostat, givinostat, mocetinostat, panobinostat, pracinostat, quisinostat (JNJ-26481585), resminostat, ricolinostat, romidepsin, SHP-141, TMB-ADC, valproic acid (VAL-001), vorinostat, tinostamustine, remetinostat, and entinostat.

Cyclin-Dependent Kinase (CDK) Inhibitors or Antagonists

In certain embodiments, the anti-HIV gp120 V3 glycan directed antibodies or antigen-binding fragments described herein are combined with an inhibitor or antagonist of a cyclin-dependent kinase (CDK), e.g., cyclin dependent kinase 4 (CDK4; NCBI Gene ID: 1019), cyclin dependent kinase 6 (CDK6; NCBI Gene ID: 1021), cyclin dependent kinase 9 (CDK9; NCBI Gene ID: 1025). In some embodiments, the CDK4/CDK6/CDK9 inhibitor or antagonist is selected from the group consisting of VS2-370.

Stimulator of Interferon Genes (STING) Agonists

In some embodiments, the anti-HIV gp120 V3 glycan directed antibodies or antigen-binding fragments described herein are combined with an stimulator of interferon genes (STING). In some embodiments, the STING receptor agonist or activator is selected from the group consisting of ADU-S100 (MIW-815), SB-11285, MK-1454, SR-8291, AdVCA0848, GSK-532, SYN-STING, MSA-1, SR-8291, 5,6-dimethylxanthenone-4-acetic acid (DMXAA), cyclic-GAMP (cGAMP) and cyclic-di-AMP.

RIG-I Agonists

In certain embodiments, the anti-HIV gp120 V3 glycan directed antibodies or antigen-binding fragments described herein are combined with an agonist of DExD/H-box helicase 58 (DDX58; a.k.a., RIG-I, RIG1, RIGI, RLR-1, SGMRT2; NCBI Gene ID: 23586). In some embodiments, the agents described herein are combined with a RIG-I modulator such as RGT-100, or NOD2 modulator, such as SB-9200 (a.k.a., GS 9992; inarigivir), and IR-103. An illustrative RIG-I agonist is KIN1148, described by Hemann, et al., J Immunol May 1, 2016, 196 (1 Supplement) 76.1. Additional RIG-I agonists are described, e.g., in Elion, et al., Cancer Res. (2018) 78(21):6183-6195; and Liu, et al., J Virol. (2016) 90(20):9406-19. RIG-I agonists are commercially available, e.g., from Invivogen (invivogen.com).

LAG-3 and TIM-3 Inhibitors

In certain embodiments, the anti-HIV gp120 V3 glycan directed antibodies or antigen-binding fragments described herein are combined with an anti-TIM-3 (a.k.a., hepatitis A virus cellular receptor 2 antibody (HAVCR2; NCBI Gene ID: 84868), such as TSR-022, LY-3321367, MBG-453, INCAGN-2390. In some embodiments, the anti-HIV gp120 V3 glycan directed antibodies or antigen-binding fragments described herein are combined with an anti-LAG-3 (Lymphocyte-activation) (NCBI Gene ID: 3902) antibody, such as relatlimab (ONO-4482), LAG-525, MK-4280, REGN-3767, INCAGN2385.

Capsid Inhibitors

In certain embodiments, the anti-HIV gp120 V3 glycan directed antibodies or antigen-binding fragments described herein are combined with a capsid inhibitor. Examples of capsid inhibitors that can be combined with an agent of this disclosure include capsid polymerization inhibitors or capsid disrupting compounds, HIV nucleocapsid p7 (NCp7) inhibitors such as azodicarbonamide, HIV p24 capsid protein inhibitors, GS-6207, GS-CA1, AVI-621, AVI-101, AVI-201, AVI-301, and AVI-CAN1-15 series, PF-3450074, and compounds described in Intl. Patent Publ. No. WO 2019/087016.

Immune-Based Therapies

In certain embodiments, the anti-HIV gp120 V3 glycan directed antibodies or antigen-binding fragments described herein are combined with an immune-based therapy. Examples of immune-based therapies include toll-like receptor (TLR) modulators such as TLR1, TLR2, TLR3, TLR4, TLR5, TLR6, TLR7, TLR8, TLR9, TLR10, TLR11, TLR12, AND TLR13; programmed cell death protein 1 (PD-1) modulators; programmed death-ligand 1 (PD-L1) modulators; IL-15 modulators (e.g., IL-15 receptor agonists (e.g., ALT-803; interleukin-15/Fc fusion protein (e.g., XmAb24306); recombinant interleukin-15 (e.g., AM0015, NIZ-985); pegylated IL-15 (e.g., NKTR-255)); DermaVir; interleukin-7; plaquenil (hydroxychloroquine); proleukin (aldesleukin, IL-2); interferon alfa; interferon alfa-2b; interferon alfa-n3; pegylated interferon alfa; interferon gamma; hydroxyurea; mycophenolate mofetil (MPA) and its ester derivative mycophenolate mofetil (MMF); ribavirin; polymer polyethyleneimine (PEI); gepon; IL-12; WF-10; VGV-1; MOR-22; BMS-936559; CYT-107, normferon, peginterferon alfa-2a, peginterferon alfa-2b, RPI-MN, STING modulators, RIG-I modulators, NOD2 modulators, SB-9200, and IR-103.

In certain embodiments, the anti-HIV gp120 V3 glycan directed antibodies or antigen-binding fragments described herein are combined with a TLR agonist. Examples of TLR agonists include without limitation: vesatolimod (GS-9620), lefitolimod, tilsotolimod, rintatolimod, DSP-0509, AL-034, G-100, cobitolimod, AST-008, motolimod, GSK-1795091, GSK-2245035, VTX-1463, GS-9688, LHC-165, BDB-001, RG-7854, telratolimod.

Immune Checkpoint Receptor Protein Modulators

In various embodiments, the anti-HIV gp120 V3 glycan directed antibodies or antigen-binding fragments described herein are combined with one or more blockers or inhibitors of inhibitory immune checkpoint proteins or receptors and/or with one or more stimulators, activators or agonists of one or more stimulatory immune checkpoint proteins or receptors. Blockade or inhibition of inhibitory immune checkpoints can positively regulate T-cell or NK cell activation and prevent immune escape of infected cells. Activation or stimulation of stimulatory immune check points can augment the effect of immune checkpoint inhibitors in infective therapeutics. In various embodiments, the immune checkpoint proteins or receptors regulate T cell responses (e.g., reviewed in Xu, et al., J Exp Clin Cancer Res. (2018) 37:110). In various embodiments, the immune checkpoint proteins or receptors regulate NK cell responses (e.g., reviewed in Davis, et al., Semin Immunol. (2017) 31:64-75 and Chiossone, et al., Nat Rev Immunol. (2018) 18(11):671-688).

Examples of immune checkpoint proteins or receptors that can be combined with the anti-HIV gp120 V3 glycan directed antibodies or antigen-binding fragments described herein include without limitation CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160, MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); lymphocyte activating 3 (CD223); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); and SLAM family member 7 (SLAMF7).

In various embodiments, the anti-HIV gp120 V3 glycan directed antibodies or antigen-binding fragments described herein are combined with one or more blockers or inhibitors of one or more T-cell inhibitory immune checkpoint proteins or receptors. Illustrative T-cell inhibitory immune checkpoint proteins or receptors include without limitation CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In various embodiments, the anti-HIV gp120 V3 glycan directed antibodies or antigen-binding fragments described herein are combined with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., J Exp Clin Cancer Res. (2018) 37:110.

In various embodiments, the anti-HIV gp120 V3 glycan directed antibodies or antigen-binding fragments described herein are combined with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor C1 (KLRC1, NKG2A, CD159A); and killer cell lectin like receptor D1 (KLRD1, CD94). In various embodiments, the anti-HIV gp120 V3 glycan directed antibodies or antigen-binding fragments described herein are combined with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., Semin Immunol. (2017) 31:64-75; Fang, et al., Semin Immunol. (2017) 31:37-54; and Chiossone, et al., Nat Rev Immunol. (2018) 18(11):671-688.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4.

Examples of inhibitors of CTLA4 that can be co-administered include without limitation ipilimumab, tremelimumab, BMS-986218, AGEN1181, AGEN1884, BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of PD-L1 (CD274) or PD-1 (PDCD1) that can be co-administered include without limitation pembrolizumab, nivolumab, cemiplimab, pidilizumab, AMP-224, MEDI0680 (AMP-514), spartalizumab, atezolizumab, avelumab, durvalumab, BMS-936559, CK-301, PF-06801591, BGB-A317 (tislelizumab), GLS-010 (WBP-3055), AK-103 (HX-008), AK-105, CS-1003, HLX-10, MGA-012, BI-754091, AGEN-2034, JS-001 (toripalimab), JNJ-63723283, genolimzumab (CBT-501), LZM-009, BCD-100, LY-3300054, SHR-1201, SHR-1210 (camrelizumab), Sym-021, ABBV-181 (budigalimab), PD1-PIK, BAT-1306, (MSB0010718C), CX-072, CBT-502, TSR-042 (dostarlimab), MSB-2311, JTX-4014, BGB-A333, SHR-1316, CS-1001 (WBP-3155, KN-035, IBI-308 (sintilimab), HLX-20, KL-A167, STI-A1014, STI-A1015 (IMC-001), BCD-135, FAZ-053, TQB-2450, MDX1105-01, GS-4224, GS-4416, INCB086550, MAX10181, as well as multispecific inhibitors FPT-155 (CTLA4/PD-L1/CD28), PF-06936308 (PD-1/CTLA4), MGD-013 (PD-1/LAG-3), FS-118 (LAG-3/PD-L1) MGD-019 (PD-1/CTLA4), KN-046 (PD-1/CTLA4), MEDI-5752 (CTLA4/PD-1), RO-7121661 (PD-1/TIM-3), XmAb-20717 (PD-1/CTLA4), AK-104 (CTLA4/PD-1), M7824 (PD-L1/TGFβ-EC domain), CA-170 (PD-L1/VISTA), CDX-527 (CD27/PD-L1), LY-3415244 (TIM3/PDL1), and INBRX-105 (4-1BB/PDL1).

In some embodiments, the small molecule inhibitor of CD274 or PDCD1 is selected from the group consisting of GS-4224, GS-4416, INCB086550 and MAX10181. In some embodiments, the small molecule inhibitor of CTLA4 comprises BPI-002.

In various embodiments, the antibodies or antigen-binding fragments as described herein are combined with anti-TIGIT antibodies, such as BMS-986207, RG-6058, AGEN-1307

TNF Receptor Superfamily (TNFRSF) Member Agonists or Activators

In various embodiments, the anti-HIV gp120 V3 glycan directed antibodies or antigen-binding fragments described herein are combined with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example anti-TNFRSF4 (OX40) antibodies that can be co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Example anti-TNFRSF5 (CD40) antibodies that can be co-administered include without limitation RG7876, SEA-CD40, APX-005M and ABBV-428.

In some embodiments, the anti-TNFRSF7 (CD27) antibody varlilumab (CDX-1127) is co-administered.

Example anti-TNFRSF9 (4-1BB, CD137) antibodies that can be co-administered include without limitation urelumab, utomilumab (PF-05082566), AGEN2373 and ADG-106.

Example anti-TNFRSF18 (GITR) antibodies that can be co-administered include without limitation, MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

Interleukin Receptor Agonists

In certain embodiments, the anti-HIV gp120 V3 glycan directed antibodies or antigen-binding fragments described herein are combined with an interleukin receptor agonist, such as IL-2, IL-7, IL-15, IL-10, IL-12 agonists; examples of IL-2 receptor agonists such as proleukin (aldesleukin, IL-2); pegylated IL-2 (e.g., NKTR-214); modified variants of IL-2 (e.g., THOR-707), bempegaldesleukin, AIC-284, ALKS-4230, CUI-101, Neo-2/15; IL-15 receptor agonists, such as ALT-803, NKTR-255, and hetIL-15, interleukin-15/Fc fusion protein, AM-0015, NIZ-985, SO-C101, IL-15 Synthorin (pegylated IL-15), P-22339, and a IL-15-PD-1 fusion protein N-809; examples of IL-7 include CYT-107.

Examples of additional interleukin receptor agonists that can be combined with the anti-HIV gp120 V3 glycan directed antibodies or antigen-binding fragments described herein include interferon alfa; interferon alfa-2b; interferon alfa-n3; pegylated interferon alfa; interferon gamma; Flt3 agonists such as CDX-301; gepon; normferon, peginterferon alfa-2a, peginterferon alfa-2b, RPI-MN.

Bi- and Tri-Specific Natural Killer (NK)-Cell Engagers

In various embodiments, the anti-HIV gp120 V3 glycan directed antibodies or antigen-binding fragments described herein are combined with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAM6 and SLAM7), killer cell immunoglobulin-like receptors (KIR) (KIR-2DS and KIR-3DS), DNAM-1 and CD137 (4-1BB). Illustrative anti-CD16 bi-specific antibodies, BiKEs or TriKEs that can be co-administered include AFM26 (BCMA/CD16A) and AFM-13 (CD16/CD30). As appropriate, the anti-CD16 binding bi-specific molecules may or may not have an Fc. BiKEs and TriKEs are described, e.g., in Felices, et al., Methods Mol Biol. (2016) 1441:333-346; Fang, et al., Semin Immunol. (2017) 31:37-54. Examples of a trispecific NK cell engager (TRiKE) include OXS-3550, and CD16-IL-15-B7H3 TriKe.

Phosphatidylinositol 3-Kinase (PI3K) Inhibitors

In certain embodiments, the anti-HIV gp120 V3 glycan directed antibodies or antigen-binding fragments described herein are combined with a PI3K inhibitor. Examples of PI3K inhibitors include idelalisib, alpelisib, buparlisib, CAI orotate, copanlisib, duvelisib, gedatolisib, neratinib, panulisib, perifosine, pictilisib, pilaralisib, puquitinib mesylate, rigosertib, rigosertib sodium, sonolisib, taselisib, AMG-319, AZD-8186, BAY-1082439, CLR-1401, CLR-457, CUDC-907, DS-7423, EN-3342, GSK-2126458, GSK-2269577, GSK-2636771, INCB-040093, LY-3023414, MLN-1117, PQR-309, RG-7666, RP-6530, RV-1729, SAR-245409, SAR-260301, SF-1126, TGR-1202, UCB-5857, VS-5584, XL-765, and ZSTK-474.

Alpha-4/Beta-7 Antagonists

In certain embodiments, the anti-HIV gp120 V3 glycan directed antibodies or antigen-binding fragments described herein are combined with an alpha-4/beta-7 antagonist. Examples of Integrin alpha-4/beta-7 antagonists include PTG-100, TRK-170, abrilumab, etrolizumab, carotegrast methyl, and vedolizumab.

Pharmacokinetic Enhancers

In certain embodiments, the anti-HIV gp120 V3 glycan directed antibodies or antigen-binding fragments described herein are combined with a pharmacokinetic enhancer. Examples of pharmacokinetic enhancers include cobicistat and ritonavir.

Additional Therapeutic Agents

Examples of additional therapeutic agents include the compounds disclosed in WO 2004/096286 (Gilead Sciences); WO 2006/015261 (Gilead Sciences); WO 2006/110157 (Gilead Sciences); WO 2012/003497 (Gilead Sciences); WO 2012/003498 (Gilead Sciences); WO 2012/145728 (Gilead Sciences); WO 2013/006738 (Gilead Sciences); WO 2013/159064 (Gilead Sciences); WO 2014/100323 (Gilead Sciences), US 2013/0165489 (University of Pennsylvania), US 2014/0221378 (Japan Tobacco), US 2014/0221380 (Japan Tobacco); WO 2009/062285 (Boehringer Ingelheim); WO 2010/130034 (Boehringer Ingelheim); WO 2013/006792 (Pharma Resources), US 20140221356 (Gilead Sciences), US 20100143301 (Gilead Sciences) and WO 2013/091096 (Boehringer Ingelheim).

HIV Combination Therapy

In a particular embodiment, the anti-HIV gp120 V3 glycan directed antibodies or antigen-binding fragments described herein are combined with one, two, three, four or more additional therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir; raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir; fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; aldesleukin; zalcitabine; tipranavir; amprenavir; delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

It will be appreciated by one of skill in the art that the additional therapeutic agents listed above may be included in more than one of the classes listed above. The particular classes are not intended to limit the functionality of those compounds listed in those classes.

In a specific embodiment, the anti-HIV gp120 V3 glycan directed antibodies or antigen-binding fragments described herein are combined with an HIV nucleoside or nucleotide inhibitor of reverse transcriptase and an HIV non-nucleoside inhibitor of reverse transcriptase. In another specific embodiment, the anti-HIV gp120 V3 glycan directed antibodies or antigen-binding fragments described herein are combined with an HIV nucleoside or nucleotide inhibitor of reverse transcriptase, and an HIV protease inhibiting compound. In an additional embodiment, the anti-HIV gp120 V3 glycan directed antibodies or antigen-binding fragments described herein are combined with an HIV nucleoside or nucleotide inhibitor of reverse transcriptase, an HIV non-nucleoside inhibitor of reverse transcriptase, and a pharmacokinetic enhancer. In certain embodiments, the anti-HIV gp120 V3 glycan directed antibodies or antigen-binding fragments described herein are combined with at least one HIV nucleoside inhibitor of reverse transcriptase, an integrase inhibitor, and a pharmacokinetic enhancer. In another embodiment, the anti-HIV gp120 V3 glycan directed antibodies or antigen-binding fragments described herein are combined with two HIV nucleoside or nucleotide inhibitors of reverse transcriptase.

In a particular embodiment, the anti-HIV gp120 V3 glycan directed antibodies or antigen-binding fragments described herein are combined with abacavir sulfate, tenofovir, tenofovir disoproxil, tenofovir disoproxil fumarate, tenofovir disoproxil hemifumarate, tenofovir alafenamide, or tenofovir alafenamide hemifumarate.

In a particular embodiment, the anti-HIV gp120 V3 glycan directed antibodies or antigen-binding fragments described herein are combined with tenofovir, tenofovir disoproxil, tenofovir disoproxil fumarate, tenofovir alafenamide, or tenofovir alafenamide hemifumarate.

In a particular embodiment, the anti-HIV gp120 V3 glycan directed antibodies or antigen-binding fragments described herein are combined with a first additional therapeutic agent selected from the group consisting of abacavir sulfate, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

In a particular embodiment, the anti-HIV gp120 V3 glycan directed antibodies or antigen-binding fragments described herein are combined with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

In certain embodiments, the anti-HIV gp120 V3 glycan directed antibodies or antigen-binding fragments described herein are combined with one or more additional therapeutic agents in a therapeutically effective dosage amount in the range of e.g., from 1 mg to 50 mg, 75 mg, 100 mg, 150 mg, 200 mg, 250 mg, 300 mg, 400 mg, 500 mg, 1000 mg or 1500 mg of the anti-HIV gp120 V3 glycan directed antibody or antigen-binding fragment. In certain embodiments, the anti-HIV gp120 V3 glycan directed antibodies or antigen-binding fragments described herein are combined with one or more additional therapeutic agents in a therapeutically effective dosage amount in the range of e.g., from about 0.1 mg/kg to about 0.5 mg/kg, 1 mg/kg, 2 mg/kg, 3 mg/kg, 4 mg/kg, 5 mg/kg, 8 mg/kg, 10 mg/kg, 15 mg/kg, 20 mg/kg, 25 mg/kg, 30 mg/kg, 35 mg/kg, 40 mg/kg, 45 mg/kg or 50 mg/kg of the anti-HIV gp120 V3 glycan directed antibody or antigen-binding fragment. In certain embodiments, the anti-HIV gp120 V3 glycan directed antibodies or antigen-binding fragments described herein are combined with one or more additional therapeutic agents in a therapeutically effective dosage amount in the range of e.g., from about 5 mg to about 10 mg, 20 mg, 25 mg, 50 mg, 100 mg, 125 mg, 150 mg, 250 mg, 300 mg, 500 mg, 1000 mg or 1500 mg of the anti-HIV gp120 V3 glycan directed antibody or antigen-binding fragment.

In certain embodiments, the anti-HIV gp120 V3 glycan directed antibodies or antigen-binding fragments described herein are combined with 5-30 mg tenofovir alafenamide fumarate, tenofovir alafenamide hemifumarate, or tenofovir alafenamide, and 200 mg emtricitabine. In certain embodiments, the anti-HIV gp120 V3 glycan directed antibodies or antigen-binding fragments described herein are combined with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, the anti-HIV gp120 V3 glycan directed antibodies or antigen-binding fragments described herein are combined with 10 mg tenofovir alafenamide fumarate, tenofovir alafenamide hemifumarate, or tenofovir alafenamide, and 200 mg emtricitabine. In certain embodiments, the anti-HIV gp120 V3 glycan directed antibodies or antigen-binding fragments described herein are combined with 25 mg tenofovir alafenamide fumarate, tenofovir alafenamide hemifumarate, or tenofovir alafenamide, and 200 mg emtricitabine. In some embodiments, the anti-HIV gp120 V3 glycan directed antibodies or antigen-binding fragments described herein are combined with the agents provided herein in any dosage amount of the anti-HIV gp120 V3 glycan directed antibodies or antigen-binding fragments (e.g., from 1 mg to 500 mg of the anti-HIV gp120 V3 glycan directed antibodies or antigen-binding fragments, as described herein) the same as if each combination of dosages were specifically and individually listed.

In certain embodiments, the anti-HIV gp120 V3 glycan directed antibodies or antigen-binding fragments described herein are combined with 200-400 mg tenofovir disoproxil fumarate, tenofovir disoproxil hemifumarate, or tenofovir disoproxil, and 200 mg emtricitabine. In certain embodiments, the anti-HIV gp120 V3 glycan directed antibodies or antigen-binding fragments described herein are combined with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, the anti-HIV gp120 V3 glycan directed antibodies or antigen-binding fragments described herein are combined with 300 mg tenofovir disoproxil fumarate, tenofovir disoproxil hemifumarate, or tenofovir disoproxil, and 200 mg emtricitabine. The anti-HIV gp120 V3 glycan directed antibodies or antigen-binding fragments may be combined with the agents provided herein in any dosage amount (e.g., from 1 mg to 500 mg of the anti-HIV gp120 V3 glycan directed antibodies or antigen-binding fragments) the same as if each combination of dosages were specifically and individually listed.

Long-Acting HIV Inhibitors

In some embodiments, the anti-HIV gp120 V3 glycan directed antibodies or antigen-binding fragments described herein can be co-administered with a long-acting HIV inhibitor. Examples of drugs that are being developed as long acting HIV inhibitors include without limitation: cabotegravir LA, rilpivirine LA, any integrase LA, VM-1500 LAI, maraviroc (LAI), tenofovir implant, MK-8591 implant, long-acting dolutegravir.

In one embodiment, kits comprise the anti-HIV gp120 V3 glycan directed antibodies or antigen-binding fragments described herein in combination with one or more (e.g., one, two, three, one or two, or one to three) additional therapeutic agents.

HIV Vaccines

In certain embodiments, the anti-HIV gp120 V3 glycan directed antibodies or antigen-binding fragments described herein are combined with an HIV vaccine. Examples of HIV vaccines include peptide vaccines, recombinant subunit protein vaccines, live vector vaccines, DNA vaccines, HIV MAG DNA vaccines, CD4-derived peptide vaccines, vaccine combinations, adenoviral vector vaccines (e.g., Ad5, Ad26 or Ad35), simian adenovirus (chimpanzee, gorilla, rhesus i.e., rhAd), adeno-associated virus vector vaccines, chimpanzee adenoviral vaccines (e.g., ChAdOX1, ChAd68, ChAd3, ChAd63, ChAd83, ChAd155, ChAd157, Pan5, Pan6, Pan7, Pan9), Coxsackieviruses based vaccines, enteric virus based vaccines, Gorilla adenovirus vaccines, lentiviral vector based vaccine, bi-segmented or tri-segmented arenavirus based vaccines (e.g., LCMV, Pichinde), trimer-based HIV-1 vaccine, measles virus based vaccine, flavivirus vector based vaccines, tobacco mosaic virus vector based vaccine, Varicella-zoster virus based vaccine, Human parainfluenza virus 3 (PIV3) based vaccines, poxvirus based vaccine (modified vaccinia virus Ankara (MVA), orthopoxvirus-derived NYVAC, and avipoxvirus-derived ALVAC (canarypox virus) strains); fowlpox virus based vaccine, rhabdovirus-based vaccines, such as Vesicular stomatitis virus (VSV) and marabavirus; recombinant human CMV (rhCMV) based vaccine, alphavirus-based vaccines, such as semliki forest virus, venezuelan equine encephalitis virus and sindbis virus (see, e.g., Lauer, et al., *Clin Vaccine Immunol.* (2017) 24(1): e00298-16); LNP formulated mRNA based therapeutic vaccines; and LNP-formulated self-replicating RNA/self-amplifying RNA vaccines.

Examples of HIV vaccines include without limitation anti-CD40.Env-gp140 vaccine, Ad4-EnvC150, BG505 SOSIP.664 gp140 adjuvanted vaccine, BG505 SOSIP.GT1.1 gp140 adjuvanted vaccine, Chimigen HIV vaccine, ConM SOSIP.v7 gp140, rgp120 (AIDSVAX), ALVAC HIV (vCP1521)/AIDSVAX B/E (gp120) (RV144), monomeric gp120 HIV-1 subtype C vaccine, MPER-656 liposome subunit vaccine, Remune, ITV-1, Contre Vir, Ad5-ENVA-48, DCVax-001 (CDX-2401), Vacc-4x, Vacc-05, VAC-3S, multiclade DNA recombinant adenovirus-5 (rAd5), rAd5 gag-pol env A/B/C vaccine, Pennvax-G, Pennvax-GP, Pennvax-G/MVA-CMDR, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), ChAdV63.HIVconsv, gp140[delta]V2.TV1+MF-59, rVSVIN HIV-1 gag vaccine, SeV-EnvF, SeV-Gag vaccine, AT-20, DNK-4, ad35-Grin/ENV, TBC-M4, HIVAX, HIVAX-2, N123-VRC-34.01 inducing epitope-based HIV vaccine, NYVAC-HIV-PT1, NYVAC-HIV-PT4, DNA-HIV-PT123, rAAV1-PG9DP, GOVX-B11, GOVX-B21, GOVX-055, TVI-HIV-1, Ad-4 (Ad4-env Clade C+Ad4-mGag), Paxvax, EN41-UGR7C, EN41-FPA2, ENOB-HV-11, PreVaxTat, AE-H, MYM-V101, CombiHIVvac, ADVAX, MYM-V201, MVA-CMDR, MagaVax, DNA-Ad5 gag/pol/nef/nev (HVTN505), MVATG-17401, ETV-01, CDX-1401, DNA and Sev vectors vaccine expressing SCaVII, rcAD26.MOS1.HIV-Env, Ad26.Mod.HIV vaccine, Ad26.Mod.HIV+MVA mosaic vaccine+gp140, AGS-004, AVX-101, AVX-201, PEP-6409, SAV-001, ThV-01, TL-01, TUTI-16, VGX-3300, VIR-1111, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines, gag-based DNA vaccine, GI-2010, gp41 HIV-1 vaccine, HIV vaccine (PIKA adjuvant), I i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, recombinant peptide vaccine (HIV infection), NCI, rgp160 HIV vaccine, RNActive HIV vaccine, SCB-703, Tat Oyi vaccine, TBC-M4, therapeutic HIV vaccine, UBI HIV gp120, Vacc-4x+romidepsin, variant gp120 polypeptide vaccine, rAd5 gag-pol env A/B/C vaccine, DNA.HTI and MVA.HTI, VRC-HIVDNA016-00-VP+VRC-HIVADV014-00-VP, INO-6145, JNJ-9220, gp145 C.6980; eOD-GT8 60mer based vaccine, PD-201401, env (A, B, C, A/E)/gag (C) DNA Vaccine, gp120 (A, B, C, A/E) protein vaccine, PDPHV-201401, Ad4-EnvCN54, EnvSeq-1 Envs HIV-1 vaccine (GLA-SE adjuvanted), HIV p24gag prime-boost plasmid DNA vaccine, HIV-1 iglb12 neutralizing VRC-01 antibody-stimulating anti-CD4 vaccine, MVA-BN HIV-1 vaccine regimen, UBI HIV gp120, mRNA based prophylactic vaccines, VPI-211, and TBL-1203HI.

Birth Control (Contraceptive) Combination Therapy

In certain embodiments, the anti-HIV gp120 V3 glycan directed antibodies or antigen-binding fragments described herein are combined with a birth control or contraceptive regimen. Therapeutic agents used for birth control (contraceptive) include cyproterone acetate, desogestrel, dienogest, drospirenone, estradiol valerate, ethinyl Estradiol, ethynodiol, etonogestrel, levomefolate, levonorgestrel, lynestrenol, medroxyprogesterone acetate, mestranol, mifepristone, misoprostol, nomegestrol acetate, norelgestromin, norethindrone, noretynodrel, norgestimate, ormeloxifene, segestersone acetate, ulipristal acetate, and any combinations thereof.

Gene Therapy and Cell Therapy

In certain embodiments, the anti-HIV gp120 V3 glycan directed antibodies or antigen-binding fragments described herein are combined with a gene or cell therapy regimen. Gene therapy and cell therapy include without limitation the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection. Examples of cell therapy include LB-1903, ENOB-HV-01, GOVX-B01, and SupT1 cell based therapy. Examples of dendritic cell therapy include AGS-004. CCR5 gene editing agents include SB-728T. CCR5 gene inhibitors include Cal-1. In some embodiments, C34-CCR5/C34-CXCR4 expressing CD4-positive T-cells are co-administered with the anti-HIV gp120 V3 glycan directed antibodies or antigen-binding fragments. In some embodiments, the anti-HIV gp120 V3 glycan directed antibodies or antigen-binding fragments are co-administered with AGT-103-transduced autologous T-cell therapy or AAV-eCD4-Ig gene therapy.

Gene Editors

In certain embodiments, the anti-HIV gp120 V3 glycan directed antibodies or antigen-binding fragments described herein are combined with a gene editor, e.g., an HIV targeted gene editor. In various embodiments, the genome editing system can be selected from the group consisting of: a CRISPR/Cas9 complex, a zinc finger nuclease complex, a TALEN complex, a homing endonucleases complex, and a meganuclease complex. An illustrative HIV targeting CRISPR/Cas9 system includes without limitation EBT-101.

CAR-T-Cell Therapy

In some embodiments, the anti-HIV gp120 V3 glycan directed antibodies or antigen-binding fragments described herein can be co-administered with a population of immune effector cells engineered to express a chimeric antigen receptor (CAR), wherein the CAR comprises an HIV antigen binding domain. The HIV antigen include an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T-cell or an NK cell. In some embodiments, the T-cell is a CD4+ T-cell, a CD8+ T-cell, or a combination thereof. Cells can be autologous or allogeneic. Examples of HIV CAR-T include convertibleCAR-T, VC-CAR-T, anti-CD4 CART-cell therapy, autologous hematopoietic stem cells genetically engineered to express a CD4 CAR and the C46 peptide.

TCR-T-Cell Therapy

In certain embodiments, the anti-HIV gp120 V3 glycan directed antibodies or antigen-binding fragments described herein are combined with a population of TCR-T-cells. TCR-T-cells are engineered to target HIV derived peptides present on the surface of virus-infected cells.

6. Kits

Further provided are kits for performing the diagnostic and treatment methods, as described herein. In some embodiments, the kit comprises primers for amplifying and sequencing at least the gp120 V3 glycan region of HIV species in a biological sample. In some embodiments, the kit comprises a suite or set of nested primers for amplifying and sequencing at least the gp120 V3 glycan region of HIV species in a biological sample. In some embodiments, the kit comprises a pair of primers or a set of nested primers for amplifying and sequencing the full length gp120. In some embodiments, the kit comprises sample preparation, nucleic acid quantification, amplification and/or sequencing reagents, e.g., nucleic acid isolation reagents to isolate RNA and/or DNA, protein denaturation solvents, buffers, dNTPs, reverse transcriptase enzyme, polymerase enzyme, and/or detection labels. In some embodiments, the kit comprises library preparation reagents, e.g., barcode reagents and/or target specific primers. In some embodiments, the kit comprises an analysis guide and/or software, e.g., to facilitate practicing the diagnostic methods, described herein. In some embodiments, the kit comprises instructions for sequencing at least the gp120 V3 glycan region of HIV species in a biological sample and detecting or identifying HIV species expressing a gp120 comprising: a glycosylated asparagine at the position corresponding to amino acid residue position 332 (N332glycan), an aspartate at the position corresponding to amino acid residue position 325 (D325), and one or more amino acid of: a threonine at the position corresponding to amino acid residue position 63 (T63), a leucine at the position corresponding to amino acid residue position 179 (L179), a threonine at the position corresponding to amino acid residue position 320 (T320), and a histidine at the position corresponding to amino acid residue position 330 (H330), wherein the amino acid positions are with reference to SEQ ID NO: 4 (i.e., residues 1-511 of NCBI Ref Seq No. NP_057856.1), as described herein.

In one embodiment, the kit comprises one or more pharmaceutical packs comprising one or more containers (e.g., vials, ampules, pre-loaded syringes) containing one or more of the ingredients of the pharmaceutical compositions described herein, such as an antibody, or antigen-binding fragment thereof, against the HIV gp120 V3 glycan region, or one or more polynucleotides encoding such antibody or antigen-binding fragment, as provided herein. In some instances, the kits contain a pharmaceutical composition described herein. In some embodiments, the kit comprises one or more containers comprising an antibody, or antigen-binding fragment thereof, against the HIV gp120 V3 glycan region, or one or more polynucleotides encoding such antibody or antigen-binding fragment, in an aqueous solution or in lyophilized form. Optionally associated with such container(s) can be a notice in the form prescribed by a governmental agency regulating the manufacture, use or sale of pharmaceuticals or biological products, which notice reflects approval by the agency of manufacture, use or sale for human administration.

EXAMPLES

The following examples are offered to illustrate, but not to limit the claimed invention.

Example 1

Identification of HIV-Infected Patients Responsive to Therapy with an Anti-HIV gp120 V3-Glycan Directed Antibody or Antigen-Binding Fragment Thereof This Example demonstrates identification of Env genotypes associated with viral susceptibility to neutralization by PGT121 and its derivative, GS-9722 (elipovimab), for pre-screening of HIV-infected subjects for susceptibility to PGT121/GS-9722.

High level of sequence diversity in the HIV envelope gene makes prescreening of subjects in clinical trials for broadly neutralizing antibodies (bNAbs) attractive to increase the likelihood of a high response rate. To identify an Env genotype that is predictive of viral susceptibility to PGT121 and GS-9722, we examined the PGT121 and GS-9722 neutralization data and corresponding Env sequence for 206 clade B Envs.

GS-9722 is a engineered variant of PGT121 that maintains the same neutralization activity as PGT121, as evidenced by a highly statistically significant correlation of PGT121 and GS-9722 neutralization IC50s among 397 HIV strains tested with PGT121 and GS-9722 ($r^2$=0.9698, P<0.0001). We therefore combined the GS-9722 neutralization data obtained on 140 clade B Envs isolated from viremic subjects enrolled in Gilead-sponsored clinical trials, with publicly-available PGT121 neutralization data obtained from the Los Alamos HIV Sequence Database (n=66) to increase the statistical power.

Full length Env amino acid sequences were aligned using ClustalW and manually adjusted upon visual inspection. To identify genotypes associated with sensitivity to neutralization by PGT121/GS-9722, we compared the frequency of amino acids and potential N-linked glycosylation sites (PNGS) at each residue among PGT121/GS-9722-sensitive viruses to the frequency in PGT121/GS-9722-resistant viruses by Fisher's exact test. An N-linked glycosylation motif is N—X—S/T, where X is any residue except proline. Neutralization sensitivity to PGT121/GS-9722 was defined as IC50<1 µg/mL. For residues that were statistically significantly associated with sensitivity to PGT121/GS-9722, the positive predictive value (PPV; i.e., probability Env is sensitive to PGT121/GS-9722 when genotype is present) and sensitivity (i.e., probability that the genotype is present when Env is sensitive to PGT121/GS-9722) were calculated as described below:

TABLE 1

2 × 2 Table Used to Calculate PPV, NPV, Sensitivity and Specificity for Genotypic Determinants of PGT121/GS-9722 Sensitivity

|  | PGT121/GS-9722 sensitive | PGT121/GS-9722 resistant |
|---|---|---|
| Genotype (+) | a | c |
| Genotype (−) | b | d |

$$PPV = \frac{a}{a+c}$$

$$Sensitivity = \frac{a}{a+b}$$

A Mann-Whitney test was also applied to identify determinants of susceptibility independent of the 1 μg/mL cut-off for defining Envs as "susceptible" vs "resistant".

Residues that were statistically associated with susceptibility to PGT121/GS-9722 and/or previously are reported to be associated with PGT121 susceptibility are listed in Table 2, ranked by descending PPV. Of the residues previously reported to confer susceptibility to PGT121, 3071, 295 PNGS and 300 PNGS were not statistically associated with susceptibility to PGT121/GS-9722 in this clade B dataset. We identified many previously unreported residues to be significantly associated with susceptibility to PGT121/GS-9722.

TABLE 2

Individual genotypes associated with susceptibility to PGT121/GS-9722 neutralization among clade B Envs

| Virus genotype[1] | PPV | Sensitivity | Fisher's Exact P value | Mann-Whitney P value |
|---|---|---|---|---|
| K677 | 78.8 | 31.8 | 0.005 | 0.002 |
| not_W17 | 75.3 | 47.3 | 0.0031 | 0.0001 |
| 332 glycan* | 75.1 | 98.4 | 0.0001 | 0.0001 |
| not_R747 | 74.4 | 51.9 | 0.0023 | 0.0075 |
| insertion_321.01 | 73.8 | 45.7 | 0.0118 | 0.0365 |
| E429 | 71.7 | 80.6 | 0.0001 | 0.0001 |
| Q442 | 70.7 | 50.4 | 0.0423 | 0.0155 |
| T63 | 69.6 | 86.8 | 0.0002 | 0.0009 |
| R335 | 69.3 | 47.3 | 0.1092 | 0.0035 |
| H330* | 68.9 | 87.6 | 0.0003 | 0.0009 |
| i165 | 68.3 | 66.7 | 0.0397 | 0.1486 |
| D325* | 67.3 | 89.1 | 0.0037 | 0.0033 |
| T320 | 66.5 | 86.0 | 0.0266 | 0.0193 |
| L179 | 66.0 | 81.4 | 0.0855 | 0.0123 |
| S393 | 65.2 | 82.9 | 0.1529 | 0.0165 |
| 301 glycan* | 64.5 | 98.4 | 0.0158 | 0.0147 |
| i307* | 64.1 | 91.5 | 0.2443 | 0.5291 |
| 295 glycan* | 63.9 | 76.7 | 0.617 | 0.1188 |
| N300* | 61.9 | 74.4 | 0.7423 | 0.0629 |
| no selection | 62.6 | 100 | na | na |

[1]Virus genotype, indicates the presence of specific amino acid residues translated from the HIV envelope gene
*Residue reported in the literature to confer susceptibility to PGT121 neutralization (Julg et al, Sci Transl Med. (2017) 9(408)).

Since an epitope is comprised of more than one residue, combinations of genotypic determinants that were statistically associated with susceptibility to PGT121/GS-9722 were evaluated to see if combining individual genotypic determinants improved the PPV by preferentially enriching true positives over false positives. Consideration was also given to sensitivity since genotypes with low sensitivity will require screening of a larger number of subjects in order to enroll sufficient number of subjects in clinical trials.

The combination genotypes that provided the highest PPV and sensitivity are listed in Table 3 and displayed in FIG. 1. Several combination genotypes that incorporated previously unreported genotypes associated with susceptibility to PGT121/GS-9722 neutralization provided higher PPV than was achievable using only previously described genotypes. The highest PPV obtained was 98.4% (for viruses containing the amino acids N332 glycan/D325/H330/T63/T320/L179), which represents a 57% increase over the positive predictive value of 62.6% with no genotype selection.

TABLE 3

Individual and combination genotypes associated with susceptibility to PGT121/GS-9722 neutralization among clade B Envs

| Virus genotype[1] | PPV | Sensitivity | Fisher's Exact P value | Mann-Whitney P value |
|---|---|---|---|---|
| N332glycan/D325/H330/T63/T320/L179 | 98.4 | 47.3 | 0.0001 | 0.0001 |
| N332glycan/D325/H330/T63/T320 | 93.7 | 57.4 | 0.0001 | 0.0001 |
| N332glycan/D325/H330/T320/L179 | 93.3 | 54.3 | 0.0001 | n.a. |
| N332glycan/D325/H330/T63 | 91.6 | 67.4 | 0.0001 | 0.0001 |
| N332glycan/D325/H330/T320 | 86.1 | 67.4 | 0.0001 | 0.0001 |
| 332PNGS/301PNGS/D325/H330* | 83.9 | 76.7 | 0.0001 | 0.0001 |
| N332glycan/D325/H330* | 83.5 | 78.3 | 0.0001 | 0.0001 |
| N332glycan/D325* | 80.7 | 87.6 | 0.0001 | 0.0001 |
| glycan332 | 75.1 | 98.4 | 0.0001 | 0.0001 |
| glycan301 | 64.5 | 98.4 | 0.0158 | 0.0147 |
| D325 | 67.3 | 89.1 | 0.0037 | 0.0033 |
| H330 | 68.9 | 87.6 | 0.0003 | 0.0009 |
| T63 | 69.6 | 86.8 | 0.0002 | 0.0009 |
| T320 | 66.5 | 86 | 0.0266 | 0.0193 |
| L179 | 66 | 81.4 | 0.0855 | 0.0123 |
| no selection[2] | 62.6 | 100 | n.a. | n.a. |

[1]Virus genotype, indicates the presence of specific amino acid residues translated from the HIV envelope gene
[3]None, indicates 206 subtype B viruses without selection for specific amino acids in the HIV envelope gene
*indicates genotypes comprised of residues previously reported in the literature to be associated with susceptibility to PGT121. See, e.g., Julg et al, Sci Transl Med. (2017) 9(408).

The combination genotypes for PGT121/GS-9722 in Table 3 for clade B were used to determine PPV, sensitivity and prevalence for clade A (Table 4) and clade C (Table 5) using neutralization data and corresponding Env sequence for 66 clade A Envs and 258 clade C Envs. The clade A and clade C datasets were publicly-available data obtained from the Los Alamos HIV Sequence Database. The highest PPV obtained for clade A was 93.8% (for viruses containing the amino acids N332glycan/D325/H330/T320/L179), which represents an 88% increase over the positive predictive value of 50% with no genotype selection. The highest PPV obtained for clade C was 89.3% (for viruses containing the amino acids N332glycan/D325/H330/T320/L179), which represents a 53% increase over the positive predictive value of 58.5% with no genotype selection.

TABLE 4

Individual and combination genotypes associated with susceptibility to PGT121 neutralization among clade A Envs

| Virus genotype[1] | PPV | Sensitivity | Prevalence |
|---|---|---|---|
| N332glycan/D325/H330/T63/T320/L179 | 92.9 | 39.4 | 21.2 |
| N332glycan/D325/H330/T63/T320 | 70.8 | 51.5 | 36.4 |
| N332glycan/D325/H330/T63 | 69.2 | 54.6 | 39.4 |
| N332glycan/D325/H330/T320/L179 | 93.8 | 45.5 | 24.2 |
| N332glycan/D325/H330/T320 | 73.1 | 57.6 | 39.4 |
| N332glycan/D325/H330 | 71.4 | 60.6 | 42.4 |
| N332glycan/D325 | 68.8 | 66.7 | 48.5 |
| glycan332 | 68.4 | 78.8 | 57.6 |
| no selection[2] | 50 | 100 | 100 |

[1]Virus genotype, indicates the presence of specific amino acid residues translated from the HIV envelope gene
[2]None, indicates 66 clade A viruses without selection for specific amino acids in the HIV envelope gene

TABLE 5

Individual and combination genotypes associated with susceptibility to PGT121 neutralization among clade C Envs

| Virus genotype[1] | PPV | Sensitivity | Prevalence |
|---|---|---|---|
| N332glycan/D325/H330/T63/T320/L179 | 81.8 | 6.0 | 4.3 |
| N332glycan/D325/H330/T63/T320 | 85.7 | 8.0 | 5.4 |
| N332glycan/D325/H330/T63 | 86.7 | 8.6 | 5.8 |
| N332glycan/D325/H330/T320/L179 | 89.3 | 44.4 | 29.1 |
| N332glycan/D325/H330/T320 | 88.0 | 62.9 | 41.9 |
| N332glycan/D325/H330 | 86.6 | 72.9 | 49.2 |
| N332glycan/D325 | 81.1 | 82.1 | 59.3 |
| glycan332 | 73.7 | 92.7 | 73.6 |
| no selection[2] | 58.5 | 100 | 100 |

[1]Virus genotype, indicates the presence of specific amino acid residues translated from the HIV envelope gene
[2]None, indicates 258 clade C viruses without selection for specific amino acids in the HIV envelope gene The prevalence of individual amino acids (T63, L179, T320, D325, H330, N332, NotP333 and S/T334) used in the PGT121/GS-9722 combination genotypes were determined for the clade A, clade B and clade C virus sequences (Table 6). All amino acids show prevalence above 60% in clade B, in clade A except for L179 (51.5%), and in clade C except for T63 (10.1%).

TABLE 6

Prevalence of individual amino acids in clade A, clade B and clade C viruses

| Position | Prevalence[1] | | |
|---|---|---|---|
| | clade A | clade B | clade C |
| T63 | 84.8 | 78.2 | 10.1 |
| L179 | 51.5 | 77.2 | 63.2 |

TABLE 6-continued

Prevalence of individual amino acids in clade A, clade B and clade C viruses

| Position | Prevalence[1] | | |
|---|---|---|---|
| | clade A | clade B | clade C |
| T320 | 89.4 | 81.1 | 86 |
| D325 | 80.3 | 83 | 80.2 |
| H330 | 72.7 | 79.6 | 75.2 |
| N332 | 66.7 | 86.9 | 83.7 |
| NotP333 | 100 | 100 | 100 |
| S/T334 | 62.1 | 84 | 77.6 |

[1]Analysis based on the 66 clade A, 206 clade B and 258 clade C viruses from the PGT121/GS-9722 datasets 10-1074 is a broadly neutralizing antibody that targets the V3 glycan region of HIV gp120 and that is related to PGT121/GS-9722. See, e.g., Mouquet, et al., *Proc Natl Acad Sci USA*. 2012 Nov. 20; 109(47):E3268-77 and Walker, et al., *Nature*. 2011 Sep. 22; 477(7365):466-70. The combination genotypes for PGT121/GS-9722 in Table 3 were used to determine PPV, sensitivity and prevalence for 10-1074 using neutralization data and corresponding Env sequence for 315 clade B Envs (Table 7). The 315 clade B dataset consisted of 143 clade B Envs isolated from viremic subjects enrolled in Gilead-sponsored clinical trials and 172 clade B Envs from publicly-available data obtained from the Los Alamos HIV Sequence Database. The highest PPV obtained was 100% (for viruses containing the amino acids N332glycan/D325/H330/T63/T320/L179), which represents a 61% increase over the positive predictive value of 62.2% with no genotype selection.

TABLE 7

Individual and combination genotypes associated with susceptibility to 10-1074 neutralization among clade B Envs

| Virus genotype[1] | PPV | Sensitivity | Prevalence |
|---|---|---|---|
| N332glycan/D325/H330/T63/T320/L179 | 100.0 | 38.8 | 24.1 |
| N332glycan/D325/H330/T63/T320 | 99.0 | 51.5 | 32.4 |
| N332glycan/D325/H330/T63 | 98.5 | 65.8 | 41.6 |
| N332glycan/D325/H330/T320/L179 | 96.8 | 46.4 | 29.8 |
| N332glycan/D325/H330/T320 | 94.4 | 59.7 | 39.4 |
| N332glycan/D325/H330* | 93.6 | 75.0 | 49.8 |
| N332glycan/D325 | 92.2 | 84.7 | 57.1 |
| glycan332 | 86.9 | 98.0 | 70.2 |
| no selection[2] | 62.2 | 100 | 100 |

Figure 2:
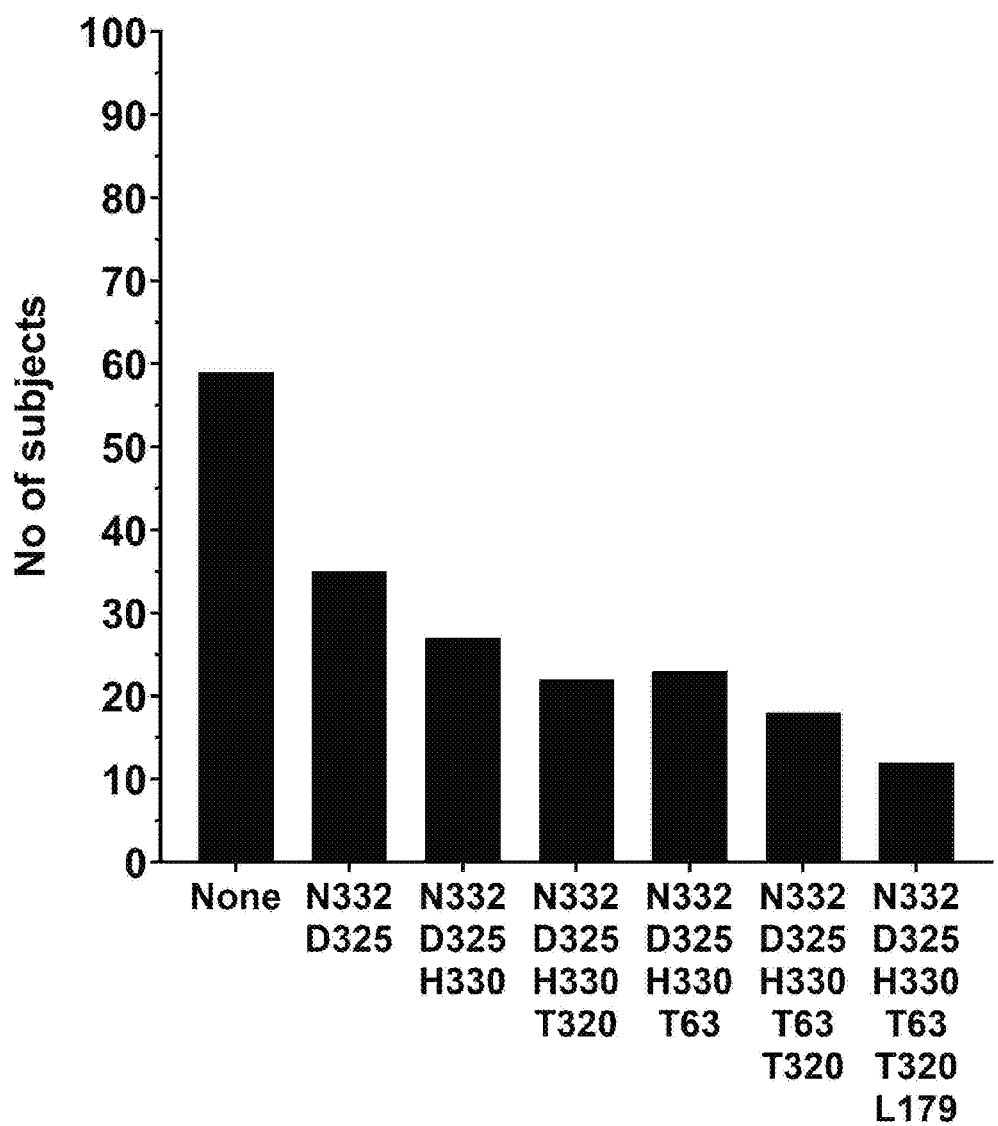
FIG. 2 illustrates the number of screened clade B subjects from the Zurich Primary HIV Infection Cohort Study with a genotype predicting sensitivity to GS-9722. Pre-ART plasma samples from 59 clade B infected individuals were analyzed in the GenoSure HIV Envelope RNA Assay. "None," indicates all screened individuals without selection for specific amino acids in the HIV envelope gene. Amino acid positions indicated for each category.
Figure 3:
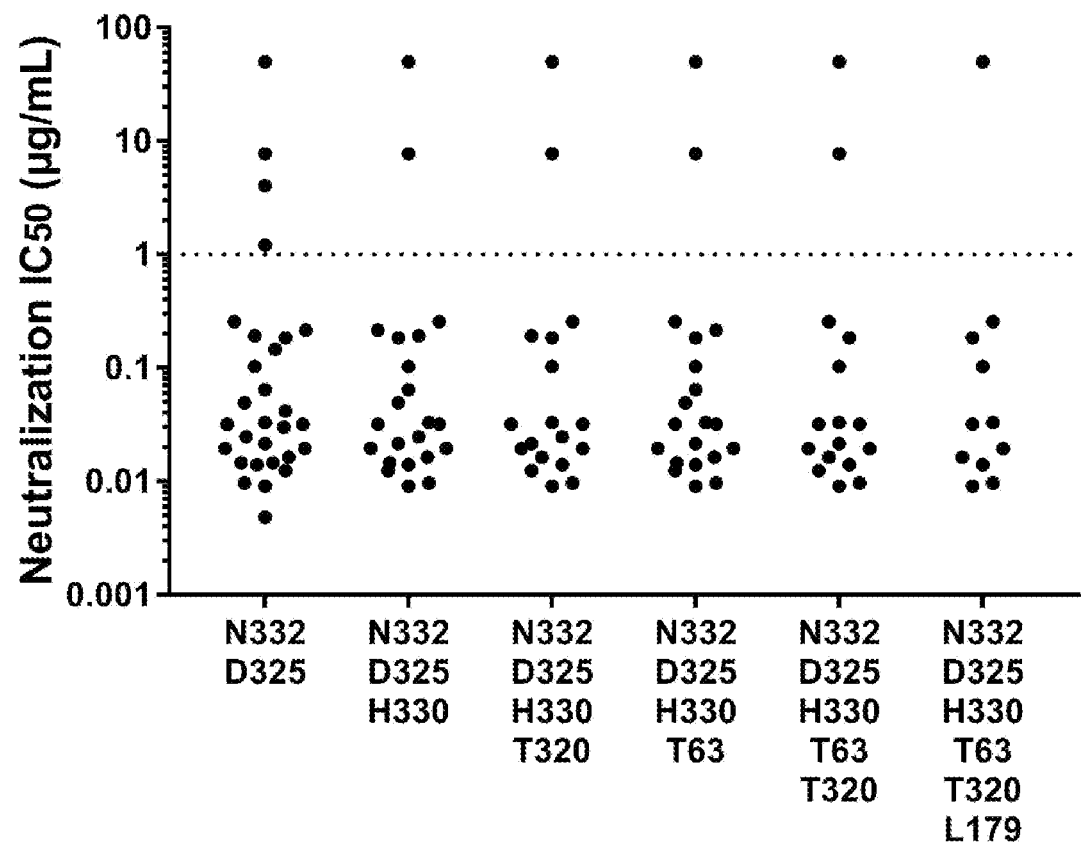
FIG. 3 illustrates the sensitivity to GS-9722 for swarm viruses derived from pre-ART plasma samples from the Zurich Primary HIV Infection Cohort Study. Virus from 29 samples with positive predictive values of 80.7% or higher were analyzed in the PHENOSENSE® HIV Entry Assay (Monogram Biosciences). Amino acid positions indicated for each category.

[1]Virus genotype, indicates the presence of specific amino acid residues translated from the HIV envelope gene
[2]None, indicates 315 clade B viruses without selection for specific amino acids in the HIV envelope gene Subsequently, the highest scoring genotypic algorithms (Table 3) were applied to analyze pre-ART plasma samples from HIV infected individuals from the Zurich Primary HIV Infection Cohort Study (ZPHI) to predict whether they would be sensitive to GS-9722 treatment. A total of 92 individual plasma samples were analyzed in a NGS assay of the HIV envelope gene (GenoSure HIV Envelope RNA Assay, Monogram Biosciences, South San Francisco, CA). Subjects were characterized as positive for a given genotype if the derived virus sequences contained the amino acids specified by the algorithm without sequence variability (zero sequence variability on the specified positions). With these criteria, 47/92, 37/92, 32/92, 27/92, 22/92, and 16/92 subjects were predicted to be sensitivity to GS-9722 (FIG. 1) with corresponding positive predictive values of 80.7%, 83.5%, 86.1%, 91.6%, 93.7%, and 98.4%, respectively (Table 3). For clade B infected subjects (59 of the 92 subjects), 35/59, 27/59, 22/59, 23/59, 18/59, and 12/59 were predicted to be sensitivity to GS-9722 (FIG. 2) with corresponding positive predictive values of 80.7%, 83.5%, 86.1%, 91.6%, 93.7%, and 98.4%, respectively (Table 3).

The 100% conservation (zero sequence variability on the specified positions) of the individual amino acids (T63, L179, T320, D325, H330, N332, NotP333 and S/T334) used in the combination genotypes for GS-9722 sensitivity prediction was determined for pre-ART plasma samples for all subjects (n=92) and for the subset of subjects infected with clade B (n=59), (Table 8).

TABLE 8

100% conservation of individual amino acids in ZPHI subjects

| | 100% conservation (% of subjects) | |
|---|---|---|
| Position | All subjects | Clade B infected subjects |
| T63 | 64 | 75 |
| L179 | 59 | 58 |
| T320 | 86 | 85 |
| D325 | 70 | 73 |
| H330 | 65 | 71 |
| N332 | 76 | 85 |
| NotP333 | 100 | 100 |
| S/T334 | 74 | 85 |

[1]Analysis based on 92 (all subjects) and 59 (clade B subjects) pre-ART plasma samples from ZPHI individuals To confirm the genotypic prediction for sensitivity to GS-9722, virus swarms from pre-ART plasma samples from ZPHI were cloned and evaluated in a GS-9722 neutralization assay (PhenoSense HIV Entry Assay, Monogram Biosciences, South San Francisco, CA). Virus was derived from 29 clade B samples with positive predictive values of 80.7% or higher. The derived viruses were characterized as GS-9722 sensitive when IC50s were 1 μg/ml or below. With these criteria, 25/29, 20/22, 16/18, 18/20, 14/16, and 10/11 viruses were confirmed to be sensitivity to GS-9722 (FIG. 2) with corresponding positive predictive values of 80.7%, 83.5%, 86.1%, 91.6%, 93.7%, and 98.4%, respectively (Table 3).

Figure 4:
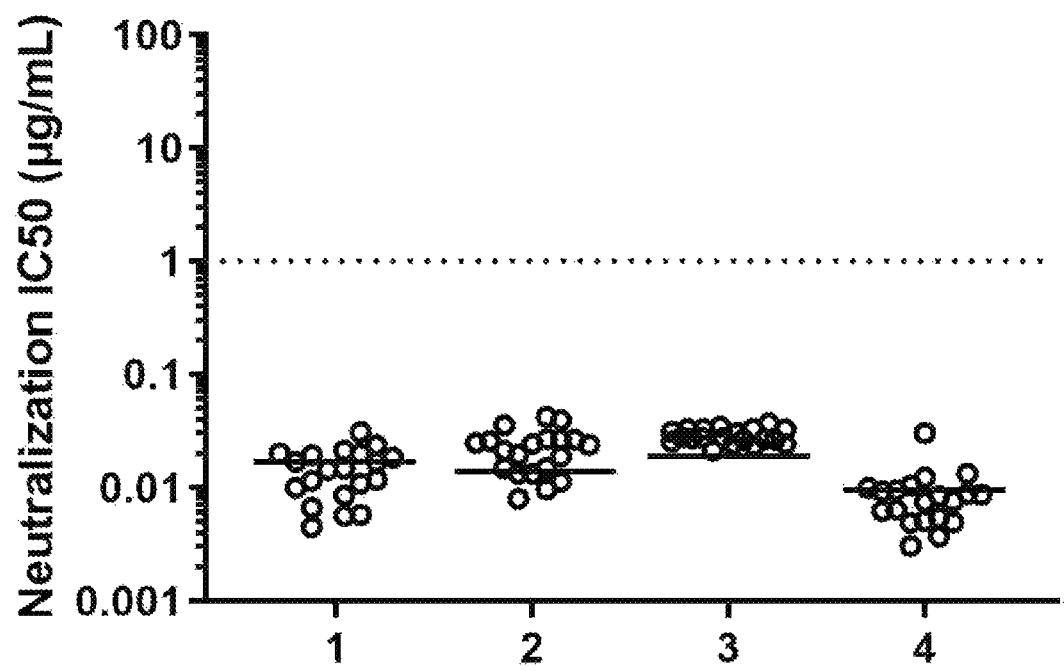
FIG. 4 illustrates the sensitivity to GS-9722 for viruses subcloned from swarm viruses derived from pre-ART plasma samples from the Zurich Primary HIV Infection Cohort Study. Twenty individual viruses from four pre-ART plasma samples, where swarm viruses were predicted sensitive by genotyping and tested sensitive by phenotyping, were analyzed in the PHENOSENSE® HIV Entry Assay (Monogram Biosciences). Solid line indicates IC50 for swarm virus.

To further confirm the genotypic prediction and phenotypic sensitivity to GS-9722, 20 individual viruses from 4 virus swarms from pre-ART plasma samples from ZPHI were subcloned and evaluated in a GS-9722 neutralization assay (PhenoSense HIV Entry Assay, Monogram Biosciences, South San Francisco, CA). All individual viruses were sensitive to GS-9722 with comparable IC50s to the swarm virus (FIG. 4).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of reducing the HIV-1 viral load in a human subject in need thereof, the method comprising:
   a) Identifying a human subject who is infected with HIV-1 clade B;
   b) Identifying in a biological sample from the subject via polynucleotide or polypeptide sequencing an HIV-1 gp120 comprising the following amino acid residues: N332glycan, D325, and one or more amino acid residues selected from the group consisting of T63, L179, T320, and H330, wherein the amino acid positions are with reference to SEQ ID NO: 4, wherein the biological sample is selected from blood, peripheral blood mononuclear cells (PBMCs), serum, plasma, semen or lymph nodes; and
   c) Administering to the subject an effective amount of an antibody or antigen-binding fragment thereof that comprises a VH region comprising a VH-CDR1, a VH-CDR2, and a VH-CDR3; and a VL region comprising a VL-CDR1, a VL-CDR2, and a VL-CDR3, wherein the VH region and the VL region bind to an epitope of the HIV-1 gp120 within the third variable loop (V3); wherein the VH-CDR1, the VH-CDR2, the VH-CDR3 the VL-CDR1, the VL-CDR2, and the VH-CDR3 comprise the sequences set forth, respectively, in:
   i. SEQ ID NOs.: 7, 8, 9, 10, 11 and 12;
   ii. SEQ ID NOs.: 7, 13, 9, 10, 11 and 12;
   iii. SEQ ID NOs.: 14, 15, 16, 17, 11 and 18;
   iv. SEQ ID NOs.: 14, 19, 20, 17, 11 and 18;
   V. SEQ ID NOs.: 21, 22, 23, 24, 25 and 26;
   vi. SEQ ID NOs.: 21, 22, 27, 24, 25 and 26;
   vii. SEQ ID NOs.: 28, 29, 30, 31, 32 and 33; or
   viii. SEQ ID NOs.: 34, 35, 36, 37, 25 and 38.

2. The method of claim 1, comprising identifying a subject infected with a population of HIV-1 expressing a gp120 comprising the following amino acid residues:
   i. N332glycan, D325 and T63;
   ii. N332glycan, D325 and L179;
   iii. N332glycan, D325 and T320;
   iv. N332glycan, D325 and H330;
   V. N332glycan, D325, T63 and L179;
   vi. N332glycan, D325, T63 and T320;
   vii. N332glycan, D325, T63 and H330;
   viii. N332glycan, D325, L179 and T320;
   ix. N332glycan, D325, L179 and H330;
   X. N332glycan, D325, T320 and H330;
   xi. N332glycan, D325, T63, T320 and H330;
   xii. N332glycan, D325, T63, L179 and T320;
   xiii. N332glycan, D325, T63, L179 and H330;
   xiv. N332glycan, D325, L179, T320 and H330; or
   XV. N332glycan, D325, T63, L179, T320 and H330.

3. The method of claim 1, comprising identifying a subject infected with a population of HIV-1 expressing a gp120 comprising the following amino acid residues:
   i. N332glycan, D325 and T63;
   ii. N332glycan, D325 and L179;
   iii. N332glycan, D325 and T320; or
   iv. N332glycan, D325 and H330.

4. The method of claim 1, comprising identifying a subject infected with a population of HIV-1 expressing a gp120 comprising the following amino acid residues:
   i. N332glycan, D325, T63 and L179;
   ii. N332glycan, D325, T63 and T320;
   iii. N332glycan, D325, T63 and H330;
   iv. N332glycan, D325, L179 and T320;
   V. N332glycan, D325, L179 and H330; or
   vi. N332glycan, D325, T320 and H330.

5. The method of claim 1, comprising identifying a subject infected with a population of HIV-1 expressing a gp120 comprising the following amino acid residues:
   i. N332glycan, D325, L179, T320 and H330;
   ii. N332glycan, D325, T63, T320 and H330;
   iii. N332glycan, D325, T63, L179 and T320; or
   iv. N332glycan, D325, T63, L179 and H330.

6. The method of claim 1, comprising identifying a subject infected with a population of HIV-1 expressing a gp120 comprising the following amino acid residues:
   i. N332glycan, D325, T63 and H330;
   ii. N332glycan, D325, T320 and H330;
   iii. N332glycan, D325, L179, T320 and H330; or
   iv. N332glycan, D325, T63, L179, T320 and H330.

7. The method of claim 1, wherein at least 90%, at least 91%, at least 92%, at least 93%, at least 94%, at least 95%, at least 96%, at least 97%, at least 98%, at least 99%, or 100%, of the HIV-1 species in the population of HIV-1 comprise the recited amino acid residues.

8. The method of claim 1, wherein the antibody or antigen-binding fragment thereof comprises VH and VL regions from an antibody selected from the group consisting of GS-9722 (elipovimab), GS-9721, PGT-121, PGT-121.66, PGT-121.414, PGT-124, PGT-134, GS-2872, 10-1074, 10-1074-J, PGT-122 and PGT-123.

9. The method of claim 1, wherein the antibody comprises an Fc region comprising the following amino acids at the indicated positions (EU index numbering):
  i. Tyrosine at position 252, threonine at position 254 and glutamic acid at position 256 (YTE); or
  ii. Leucine at position 428 and serine at position 434 (LS).

10. The method of claim 1, wherein the antibody comprises an Fc region comprising the following amino acids at the indicated positions (EU index numbering):
  i. Aspartate at position 239 and glutamate at position 332 (DE);
  ii. Aspartate at position 239, glutamate at position 332 and leucine at position 330 (DEL);
  iii. Aspartate at position 239, glutamate at position 332, alanine at position 236 (DEA); or
  iv. Aspartate at position 239, glutamate at position 332, alanine at position 236 and leucine at position 330 (DEAL).

11. The method of claim 1, comprising administering an antigen binding fragment.

12. The method of claim 11, wherein the antigen binding fragment is selected from the group consisting of scFv, Fab, Fab2, Fab', F(ab')2, Fv, and a diabody.

13. The method of claim 1, wherein the antibody is a multi-specific antibody.

14. The method of claim 1, wherein the human subject is acutely infected with HIV-1.

15. The method of claim 14, wherein the antibody is administered to a human subject having an HIV-1 infection of Fiebig stage IV or earlier.

16. The method of claim 14, wherein the antibody is administered to a human subject who has not seroconverted.

17. The method of claim 1, wherein the antibody is administered to a human subject having an HIV-1 infection of Fiebig stage V or Fiebig stage VI.

18. The method of claim 1, wherein the human subject is chronically infected with HIV-1.

19. The method of claim 1, further comprising administering to the subject one or more additional therapeutic agents for treating an HIV-1 infection.

20. The method of claim 1, wherein the subject is not receiving antiretroviral therapy (ART) or ART is discontinued prior to administration of the antibody.

21. The method of claim 1, wherein ART is discontinued after one or more administrations of the antibody or antigen-binding fragment thereof.

22. The method of claim 1, further comprising administering one or more antiretroviral therapy (ART) agents to the subject.

23. The method of claim 1, further comprising administering to the subject a TLR agonist.

24. The method of claim 23, wherein the TLR agonist is a TLR2 agonist, a TLR3 agonist, a TLR7 agonist, a TLR8 agonist or a TLR9 agonist.

25. The method of claim 24, wherein the TLR7 agonist is selected from the group consisting of vesatolimod, imiquimod, and resiquimod.

26. The method of claim 1, comprising multiple administrations of the antibody or antigen-binding fragment thereof, optionally with a TLR agonist, at predetermined intervals.

27. The method of claim 1, wherein, after one or more administrations of the antibody or antigen-binding fragment thereof, the subject does not exhibit symptoms of HIV-1 or AIDS in the absence of anti-retroviral treatment (ART) for at least 6 months, at least 1 year, at least 2 years, at least 3 years, or more.

28. The method of claim 1, wherein, after one or more administrations of the antibody, the subject has a viral load copies/ml blood of less than 500, less than 400, less than 300, less than 200, less than 100, less than 50, in the absence of anti-retroviral treatment (ART) for at least 6 months, at least 1 year, at least 2 years, at least 3 years, or more.

29. The method of claim 1, comprising identifying a population of HIV-1 RNA in a serum or plasma sample.

30. The method of claim 1, further comprising the step of obtaining one or more biological samples from the subject.

31. The method of claim 30, wherein two or more biological samples are obtained from the subject.

32. The method of claim 31, wherein the two or more biological samples are obtained from the same tissue or fluid at two or more different time points.

33. The method of claim 31, wherein the two or more biological samples are obtained from different tissues or fluids, or from different anatomical locations.

34. The method of claim 1, wherein the VH region and the VL region comprise amino acid sequences that are at least 95%, at least 96%, at least 97%, at least 98%, at least 99%, or 100%, identical to the VH region and the VL region amino acid sequences set forth, respectively, in:
  SEQ ID NOs.: 400 and 401;
  SEQ ID NOs.: 402 and 403;
  SEQ ID NOs.: 402 and 404;
  SEQ ID NOs.: 464 and 465;
  SEQ ID NOs.: 405 and 406;
  SEQ ID NOs.: 466 and 467;
  SEQ ID NOs.: 407 and 408;
  SEQ ID NOs.: 409 and 410;
  SEQ ID NOs.: 411 and 412;
  SEQ ID NOs.: 413 and 414; or
  SEQ ID NOs.: 415 and 416.

* * * * *